United States Patent
Pananen et al.

(10) Patent No.: US 12,324,897 B2
(45) Date of Patent: Jun. 10, 2025

(54) SMART CONNECTION INTERFACE

(71) Applicant: Medtronic MiniMed, Inc., Northridge, CA (US)

(72) Inventors: Jacob E. Pananen, Santa Monica, CA (US); Afshin Bazargan, Simi Valley, CA (US); Pablo Vazquez, Porter Valley, CA (US); Edmond W. Yu, Chatsworth, CA (US)

(73) Assignee: Medtronic MiniMed, Inc., Northridge (CA)

( * ) Notice: Subject to any disclaimer, the term of this patent is extended or adjusted under 35 U.S.C. 154(b) by 756 days.

(21) Appl. No.: 17/519,472

(22) Filed: Nov. 4, 2021

(65) Prior Publication Data
US 2022/0054738 A1    Feb. 24, 2022

Related U.S. Application Data

(63) Continuation of application No. 14/801,266, filed on Jul. 16, 2015, now Pat. No. 11,185,627.
(Continued)

(51) Int. Cl.
*A61M 5/14* (2006.01)
*A61J 1/14* (2023.01)
(Continued)

(52) U.S. Cl.
CPC .......... *A61M 5/1413* (2013.01); *A61J 1/1418* (2015.05); *A61J 1/1481* (2015.05);
(Continued)

(58) Field of Classification Search
CPC ............ A61M 5/1413; A61M 5/14546; A61M 5/1456; A61M 5/14566;
(Continued)

(56) References Cited

U.S. PATENT DOCUMENTS

| 3,934,430 A | 1/1976 | Fuso |
| 4,755,173 A | 7/1988 | Konopka et al. |

(Continued)

FOREIGN PATENT DOCUMENTS

| CN | 101557847 A | 10/2009 |
| CN | 101631585 A | 1/2010 |

(Continued)

OTHER PUBLICATIONS

US Non-Final Office Action dated Jan. 6, 2022, from U.S. Appl. No. 16/514,495.
(Continued)

*Primary Examiner* — Kami A Bosworth
(74) *Attorney, Agent, or Firm* — Foley & Lardner LLP

(57) ABSTRACT

A method and apparatus for a connection interface between a reservoir or syringe, infusion set tubing, and an infusion pump is provided. The reservoir, a base and a cap are connected to form an integrated unit that is capable of being inserted and secured in an infusion pump housing. The cap and the infusion pump are each provided with at least one sensor or at least one detectable feature, arranged to interact with at least one corresponding detectable feature or sensor on the other of the cap and infusion pump device, to detect one or more of the presence, position or other characteristic of the cap when the cap is aligned or coupled with the infusion pump housing. The detectable feature and sensor may be magnetic, RF, mechanical, optical or any combination.

17 Claims, 64 Drawing Sheets

Related U.S. Application Data

(60) Provisional application No. 62/159,504, filed on May 11, 2015, provisional application No. 62/150,064, filed on Apr. 20, 2015, provisional application No. 62/087,445, filed on Dec. 4, 2014, provisional application No. 62/027,019, filed on Jul. 21, 2014.

(51) Int. Cl.

| | | |
|---|---|---|
| *A61J 1/18* | (2023.01) | |
| *A61M 5/142* | (2006.01) | |
| *A61M 5/145* | (2006.01) | |
| *A61M 5/50* | (2006.01) | |
| *A61M 39/10* | (2006.01) | |
| *A61M 39/12* | (2006.01) | |
| *G01V 3/00* | (2006.01) | |
| *G01V 3/02* | (2006.01) | |
| *G01V 3/08* | (2006.01) | |
| *G01V 15/00* | (2006.01) | |

(52) U.S. Cl.
CPC ............... *A61J 1/18* (2013.01); *A61M 5/142* (2013.01); *A61M 5/1456* (2013.01); *A61M 5/14566* (2013.01); *A61M 5/5086* (2013.01); *A61M 39/10* (2013.01); *A61M 39/1011* (2013.01); *A61M 39/12* (2013.01); *G01V 3/00* (2013.01); *G01V 3/02* (2013.01); *G01V 3/08* (2013.01); *G01V 15/00* (2013.01); *A61J 2205/60* (2013.01); *A61M 2039/1005* (2013.01); *A61M 2039/1016* (2013.01); *A61M 2039/1022* (2013.01); *A61M 2039/1027* (2013.01); *A61M 2039/1033* (2013.01); *A61M 2039/1044* (2013.01); *A61M 39/1055* (2013.01); *A61M 2039/1094* (2013.01); *A61M 2205/0227* (2013.01); *A61M 2205/0272* (2013.01); *A61M 2205/0288* (2013.01); *A61M 2205/12* (2013.01); *A61M 2205/121* (2013.01); *A61M 2205/14* (2013.01); *A61M 2205/3306* (2013.01); *A61M 2205/3317* (2013.01); *A61M 2205/52* (2013.01); *A61M 2205/581* (2013.01); *A61M 2205/582* (2013.01); *A61M 2205/6027* (2013.01); *A61M 2205/6054* (2013.01); *A61M 2205/6063* (2013.01)

(58) Field of Classification Search
CPC .... A61M 2005/14573; A61M 2205/14; A61M 2205/60; A61M 2205/6009; A61M 2205/6018; A61M 2205/6054; A61M 2039/1005; A61M 2039/1044
See application file for complete search history.

(56) References Cited

U.S. PATENT DOCUMENTS

| | | | |
|---|---|---|---|
| 4,913,703 A * | 4/1990 | Pasqualucci | A61M 5/142 604/153 |
| 5,391,250 A | 2/1995 | Cheney, II et al. | |
| 5,485,408 A | 1/1996 | Blomquist | |
| 5,522,803 A | 6/1996 | Teissen-Simony | |
| 5,602,472 A | 2/1997 | Bergstedt et al. | |
| 5,644,225 A * | 7/1997 | Alfors | G01D 18/00 324/202 |
| 5,665,065 A | 9/1997 | Colman et al. | |
| 5,788,099 A | 8/1998 | Treu et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,171,276 B1 | 1/2001 | Lippe et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,585,695 B1 | 7/2003 | Adair et al. | |
| 6,591,876 B2 | 7/2003 | Safabash | |
| 6,641,533 B2 | 11/2003 | Causey, III et al. | |
| 6,656,157 B1 | 12/2003 | Duchon et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,725,168 B2 | 5/2010 | Neer et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,967,785 B2 | 6/2011 | Morgan et al. | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,135,250 B1 | 3/2012 | Wach et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,512,288 B2 | 8/2013 | Moberg et al. | |
| 8,771,233 B2 | 7/2014 | Watanabe et al. | |
| 9,452,255 B2 | 9/2016 | Tieck et al. | |
| 9,517,299 B2 | 12/2016 | Tieck et al. | |
| 9,744,290 B2 | 8/2017 | Tieck et al. | |

(56) References Cited

U.S. PATENT DOCUMENTS

| | | | |
|---|---|---|---|
| 2002/0173748 A1 | 11/2002 | McConnell et al. |
| 2003/0065287 A1 | 4/2003 | Spohn et al. |
| 2003/0120212 A1 | 6/2003 | Dedig et al. |
| 2004/0251896 A1 | 12/2004 | Mizutani et al. |
| 2005/0007104 A1 | 1/2005 | Lequesne et al. |
| 2005/0135151 A1 | 6/2005 | Hannah et al. |
| 2005/0244493 A1 | 11/2005 | Withiam et al. |
| 2007/0073235 A1 | 3/2007 | Estes et al. |
| 2007/0100281 A1 | 5/2007 | Morris et al. |
| 2007/0123819 A1 | 5/2007 | Mernoe et al. |
| 2007/0167912 A1 | 7/2007 | Causey et al. |
| 2008/0021438 A1 | 1/2008 | Dacquay et al. |
| 2009/0317002 A1 | 12/2009 | Dein |
| 2010/0010443 A1 | 1/2010 | Morgan et al. |
| 2010/0137790 A1 | 6/2010 | Yodfat |
| 2010/0160861 A1 | 6/2010 | Causey, III et al. |
| 2010/0164727 A1 | 7/2010 | Bazargan et al. |
| 2010/0168670 A1 | 7/2010 | Srisathapat et al. |
| 2010/0168711 A1 | 7/2010 | Bazargan et al. |
| 2011/0004165 A1 | 1/2011 | Iio et al. |
| 2011/0137162 A1 | 6/2011 | Bruce et al. |
| 2011/0160655 A1 | 6/2011 | Hanson et al. |
| 2011/0224649 A1 | 9/2011 | Duane et al. |
| 2011/0257578 A1 | 10/2011 | Zanotti et al. |
| 2012/0101470 A1 | 4/2012 | Rasmussen et al. |
| 2012/0215094 A1 | 8/2012 | Rahimian et al. |
| 2012/0259282 A1 | 10/2012 | Alderete et al. |
| 2012/0323208 A1 | 12/2012 | Bochenko et al. |
| 2012/0330228 A1 | 12/2012 | Day et al. |
| 2013/0018356 A1 | 1/2013 | Prince et al. |
| 2013/0181538 A1 | 7/2013 | Calasso |
| 2013/0204227 A1 | 8/2013 | Bochenko et al. |
| 2013/0267894 A1 | 10/2013 | Woolford et al. |
| 2013/0310807 A1 | 11/2013 | Adair et al. |
| 2014/0018735 A1 | 1/2014 | Causey et al. |
| 2014/0103911 A1 | 4/2014 | Honda et al. |
| 2014/0276213 A1 | 9/2014 | Bochenko |
| 2015/0374907 A1 | 12/2015 | Morton |
| 2016/0015885 A1 | 1/2016 | Pananen et al. |
| 2016/0051742 A1 | 2/2016 | Strohhofer et al. |
| 2016/0120751 A1 | 5/2016 | Mounce et al. |
| 2017/0028124 A1 | 2/2017 | Deak et al. |
| 2017/0333612 A1 | 11/2017 | Childers et al. |

FOREIGN PATENT DOCUMENTS

| | | |
|---|---|---|
| CN | 202605422 U | 12/2012 |
| CN | 103128719 A | 6/2013 |
| CN | 103228303 A | 7/2013 |
| CN | 103269732 A | 8/2013 |
| CN | 103328022 A | 9/2013 |
| CN | 203885937 U | 10/2014 |
| CN | 106061528 A | 10/2016 |
| EP | 2 155 288 A1 | 2/2010 |
| EP | 2 313 144 A1 | 4/2011 |
| EP | 2 409 720 A1 | 1/2012 |
| EP | 2 352 535 B1 | 9/2015 |
| JP | 2002-528234 A | 9/2002 |
| JP | 2010-532239 A | 10/2010 |
| JP | 2011-125470 A | 6/2011 |
| WO | WO-2008/114218 A2 | 9/2008 |
| WO | WO-2010/037753 A1 | 4/2010 |
| WO | WO-2010/070799 A1 | 6/2010 |
| WO | WO-2013/134486 A2 | 9/2013 |
| WO | WO-2017/123703 A2 | 7/2017 |

OTHER PUBLICATIONS

US Non-Final Office Action dated Jul. 1, 2022, from U.S. Appl. No. 16/514,495, 7 pages.
Australian Examination Report dated Aug. 13, 2019, from application No. 2018241148.
Australian Examination Report dated Feb. 1, 2021, from application No. 2020203469.
Brazilian Office Action dated Mar. 24, 2020, from application No. 112017001256-1.
Canadian Examiner's Report dated Dec. 9, 2019, from application No. 3030922.
Chinese Office Action dated Jan. 21, 2021, from application No. 201910117209.9.
Chinese Office Action dated Jan. 29, 2021, from application No. 201910117617.4.
European Office Action dated Jul. 9, 2019, from application No. 15745670.8.
European Office Action dated Nov. 29, 2019, from application No. 15745670.8.
Final Office Action dated Feb. 4, 2021, from U.S. Appl. No. 14/801,266.
Final Office Action dated Jul. 18, 2018, from U.S. Appl. No. 14/801,429.
Final Office Action dated Jul. 19, 2018 from U.S. Appl. No. 14/801,266.
Final Office Action dated Jul. 19, 2018, from U.S. Appl. No. 14/801,548.
Final Office Action dated Jun. 6, 2019, from U.S. Appl. No. 14/801,548.
Final Office Action dated Mar. 24, 2020, from U.S. Appl. No. 14/801,429.
Final Office Action dated Mar. 25, 2020, from U.S. Appl. No. 14/801,548.
Final Office Action dated Mar. 6, 2020, from U.S. Appl. No. 14/801,266.
Final Office Action dated May 16, 2019, from U.S. Appl. No. 14/801,266.
Final Office Action dated May 17, 2019, from U.S. Appl. No. 14/801,429.
Final Office Action dated Nov. 2, 2018, from U.S. Appl. No. 14/801,338.
Final Office Action dated Oct. 22, 2020, from U.S. Appl. No. 14/801,429.
Indian Examination Report dated Oct. 2, 2020, from application No. 201617042366.
International Preliminary Report on Patentability dated Feb. 2, 2017, from related international application No. PCT/US2015/040974.
International Search Report and Written Opinion dated Dec. 1, 2015, from application No. PCT/US2015/040974.
International Search Report and Written Opinion mailed Oct. 9, 2020 for PCT Application No. PCT/US2020/041869.
Israeli Office Action dated Apr. 5, 2020, from application No. 249567.
Japanese Office Action dated Mar. 31, 2019, for Japanese Application No. 2018-094445.
Japanese Office Action for Application No. 2019-141925 dated Sep. 1, 2020 with English translation (7 pages).
Korean Office Action dated Jan. 27, 2021, from application No. 10-2020-7037331.
Non-Final Office Action dated December 4, 208, from U.S. Appl. No. 14/801,548.
Non-Final Office Action dated Jul. 27, 2020, from U.S. Appl. No. 14/801,429.
Non-Final Office Action dated Jun. 19, 2020, from U.S. Appl. No. 14/801,266.
Non-Final Office Action dated May 22, 2019, from U.S. Appl. No. 14/801,338.
Non-Final Office Action dated Nov. 20, 2018, from U.S. Appl. No. 14/801,266.
Non-Final Office Action dated Nov. 20, 2018, from U.S. Appl. No. 14/801,429.
Non-Final Office Action dated Oct. 10, 2019, from U.S. Appl. No. 14/801,266.
Non-Final Office Action dated Oct. 10, 2019, from U.S. Appl. No. 14/801,429.
Non-Final Office Action dated Oct. 29, 2019, from U.S. Appl. No. 14/801,548.
Non-Final Office Action dated Sep. 9, 2020, from U.S. Appl. No. 14/801,266.

(56) References Cited

OTHER PUBLICATIONS

Notice of Allowance dated Apr. 30, 2021, from U.S. Appl. No. 14/801,429.
Notice of Allowance dated Aug. 16, 2018, from U.S. Appl. No. 15/896,954.
Notice of Allowance dated Aug. 16, 2018, from U.S. Appl. No. 15/897,048.
Notice of Allowance dated Aug. 30, 2019, from U.S. Appl. No. 14/801,338.
Notice of Allowance dated Aug. 8, 2018, from U.S. Appl. No. 15/896,904.
Notice of Allowance dated Jul. 26, 2021, from U.S. Appl. No. 14/801,266.
Notice of Allowance dated Mar. 20, 2019, from U.S. Appl. No. 16/184,839.
Notice of Allowance dated Mar. 29, 2019, from U.S. Appl. No. 16/184,854.
Notice of Allowance dated May 29, 2020, from U.S. Appl. No. 14/801,548.
Russian Office Action dated Nov. 6, 2019, from application No. 2019112138.
US Non-Final Office Action dated Jan. 22, 2019, from U.S. Appl. No. 16/184,839.
US Non-Final Office Action dated Jan. 22, 2019, from U.S. Appl. No. 16/184,854.
US Notice of Allowance dated Apr. 27, 2017, from related U.S. Appl. No. 15/344,442.
US Notice of Allowance dated Aug. 5, 2016, from U.S. Appl. No. 14/803,880.
US Notice of Allowance dated Aug. 5, 2016, from U.S. Appl. No. 14/803,944.
US Notice of Allowance dated Jul. 29, 2016, from U.S. Appl. No. 14/801,503.
US Notice of Allowance dated May 1, 2017, from related U.S. Appl. No. 15/344,453.
US Notice of Allowance dated May 3, 2017, from related U.S. Appl. No. 15/344,449.
US Notice of Allowance dated Nov. 6, 2017, from U.S. Appl. No. 15/655,815.
US Notice of Allowance dated Nov. 7, 2017, from U.S. Appl. No. 15/655,839.
US Notice of Allowance dated Nov. 8, 2017, from U.S. Appl. No. 15/655,826.
US Office Action dated Apr. 18, 2016, from U.S. Appl. No. 14/801,503.
US Office Action dated Apr. 19, 2016, from U.S. Appl. No. 14/803,944.
US Office Action dated Apr. 19, 2018, from U.S. Appl. No. 14/801,338.
US Office Action dated Apr. 20, 2016, from U.S. Appl. No. 14/803,880.
US Office Action dated Apr. 20, 2018, from U.S. Appl. No. 15/896,954.
US Office Action dated Apr. 20, 2018, from U.S. Appl. No. 15/897,048.
US Office Action dated Apr. 6, 2018, from U.S. Appl. No. 15/896,904.
US Office Action dated Aug. 25, 2017, from U.S. Appl. No. 15/655,826.
US Office Action dated Jan. 20, 2017, from related U.S. Appl. No. 15/344,442.
US Office Action dated Jan. 20, 2017, from related U.S. Appl. No. 15/344,449.
US Office Action dated Jan. 20, 2017, from related U.S. Appl. No. 15/344,453.
US Office Action dated Jan. 24, 2018, from U.S. Appl. No. 14/801,548.
US Office Action dated Jan. 25, 2018, from U.S. Appl. No. 14/801,429.
US Office Action dated Jan. 29, 2018, from U.S. Appl. No. 14/801,266.
US Office Action dated Sep. 11, 2017, from U.S. Appl. No. 15/655,839.
US Office Action dated Sep. 7, 2017, from U.S. Appl. No. 15/655,815.
First Office Action issued by the China National Intellectual Property Administration (CNIPA) for corresponding Chinese Patent Application No. 202080050351.7, mailed Oct. 28, 2023, 8 pages.
English translation of the First Office Action issued by the China National Intellectual Property Administration (CNIPA) for corresponding Chinese Patent Application No. 202080050351.7, mailed Oct. 28, 2023, 9 pages.
Second Office Action, issued by The State Intellectual Property Office of People's Republic of China, in corresponding CN Application 202080050351.7, dated Jul. 31, 2024, 4 pages.
English translation of the Second Office Action, issued by The State Intellectual Property Office of People's Republic of China, in corresponding CN Application 202080050351.7, dated Jul. 31, 2024, 6 pages.

* cited by examiner

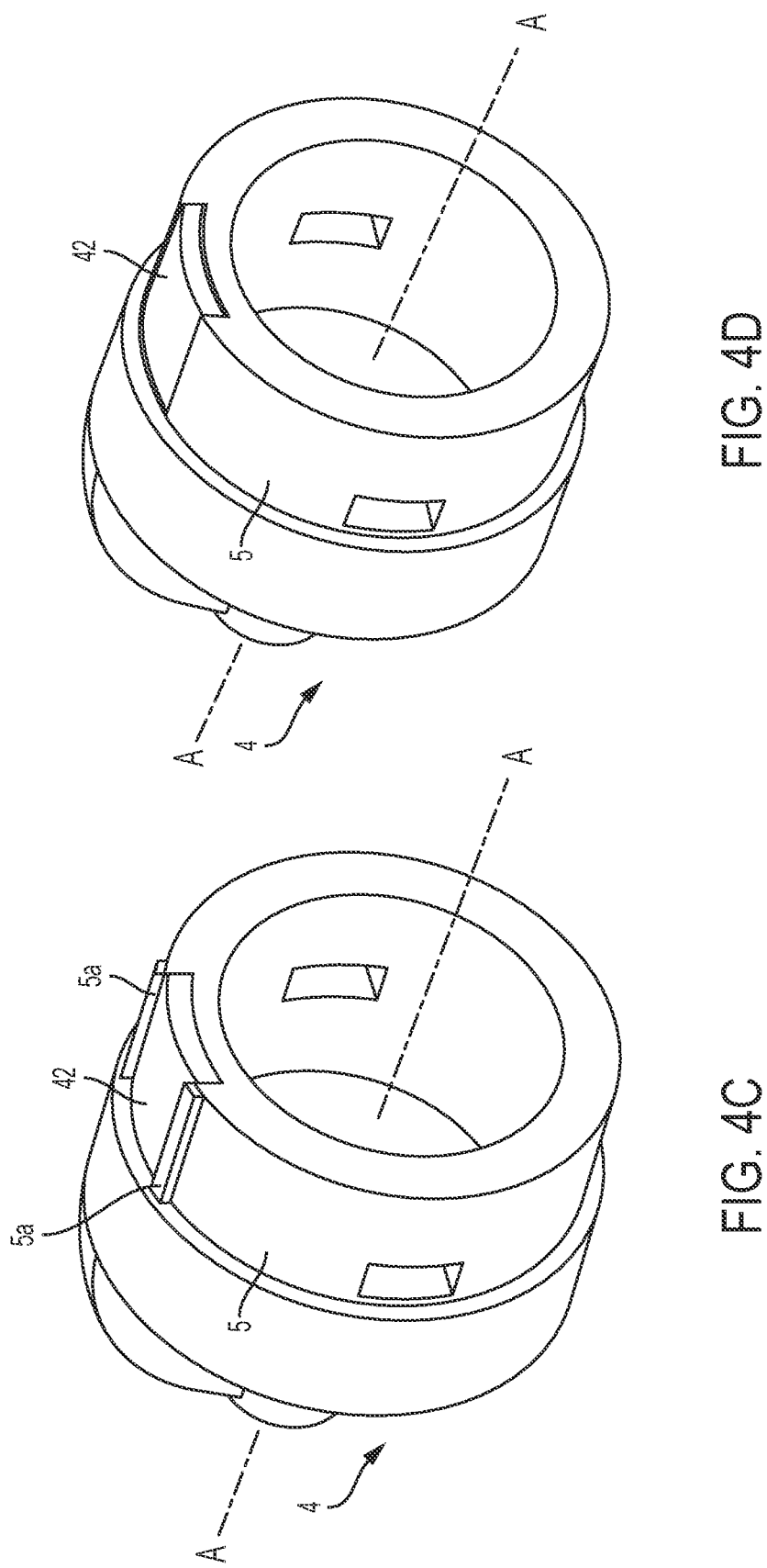

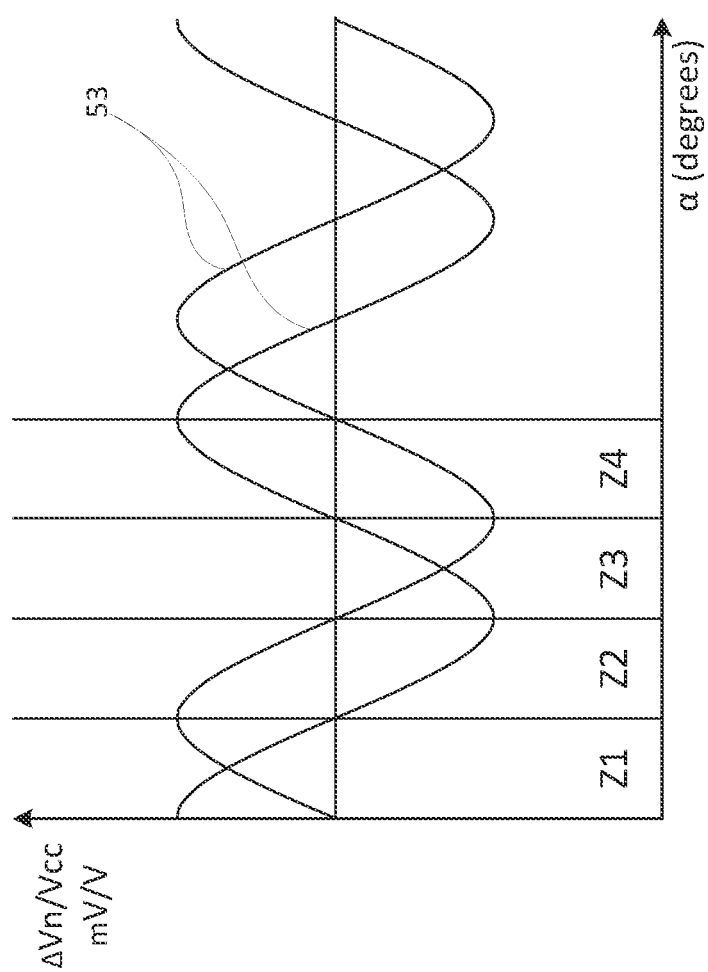

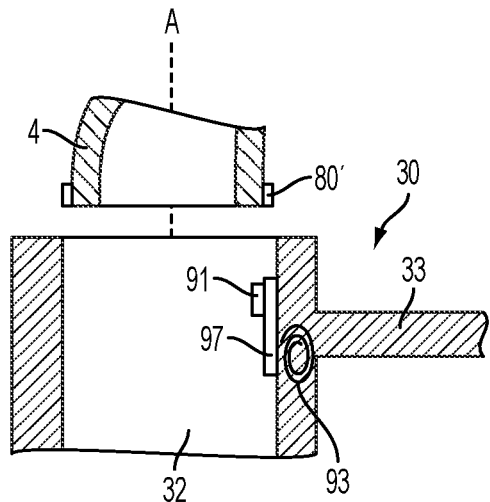 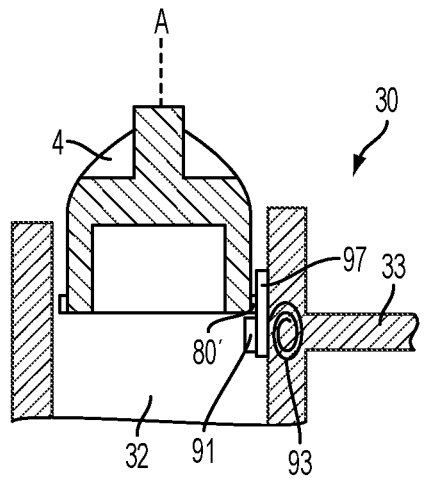
FIG. 12  FIG. 13
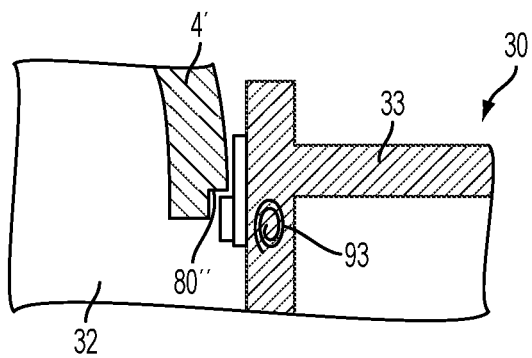
FIG. 14
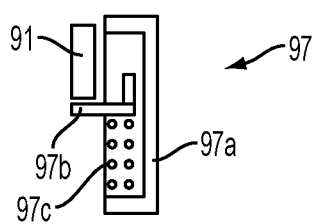
FIG. 15

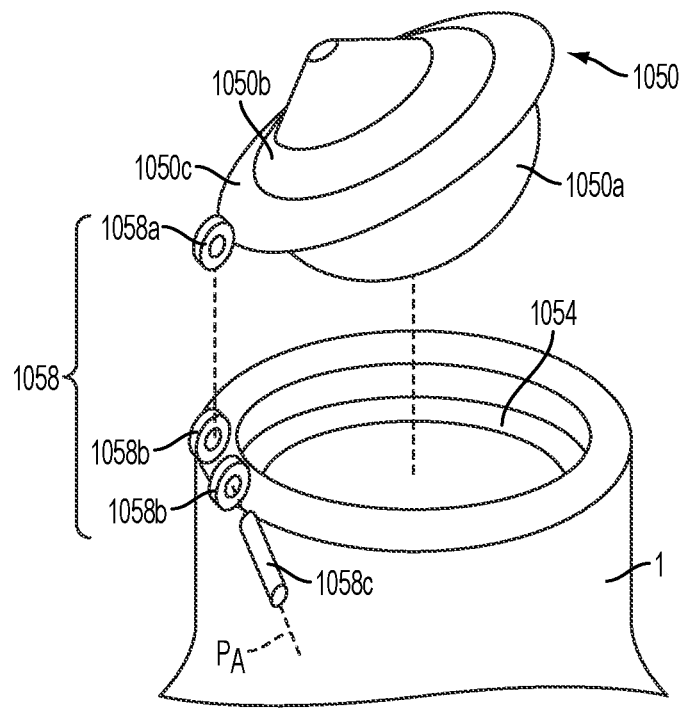
FIG. 84
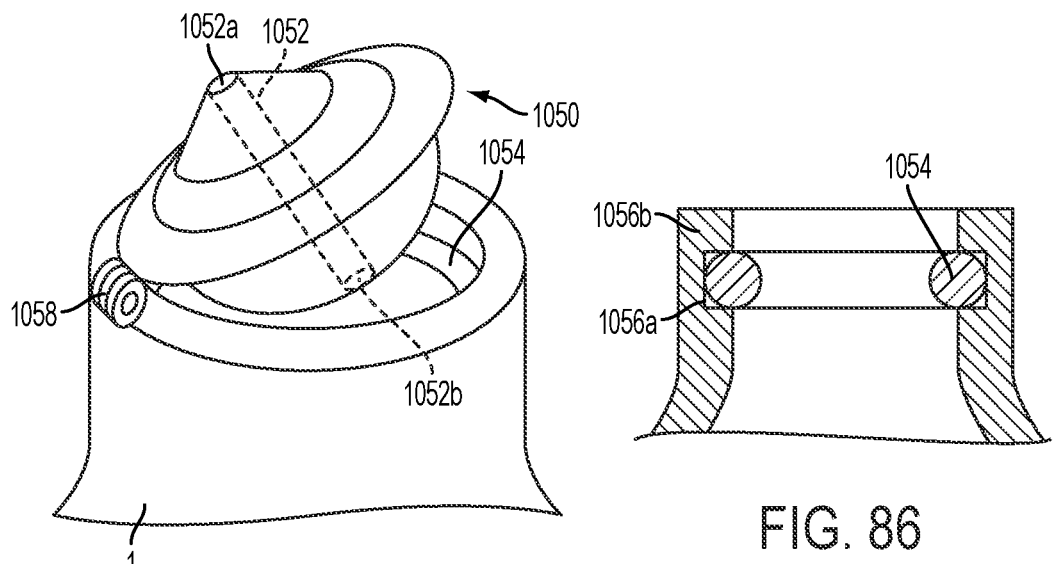
FIG. 85
FIG. 86

SMART CONNECTION INTERFACE

CROSS-REFERENCE TO RELATED PATENT APPLICATIONS

This application is a Continuation of U.S. patent application Ser. No. 14/801,266, filed Jul. 16, 2015, issued as U.S. Pat. No. 11,185,627 on Nov. 30, 2021, which claims the benefit of U.S. Provisional Patent Application Nos. 62/027,019, filed Jul. 21, 2014; 62/087,445, filed Dec. 4, 2014; 62/150,064, filed Apr. 20, 2015; 62/159,504, filed May 11, 2015, which are incorporated herein by reference in their entirety.

BACKGROUND OF THE INVENTION

1. Field of the Invention

The present disclosure relates to connection interfaces for syringes and reservoirs and, in particular embodiments, to connection interfaces for interfacing a syringe or reservoir to an infusion pump, infusion set tubing, or both. Further embodiments relate to infusion pump systems and infusion set systems that include such connection interfaces, and to methods that employ the same.

2. Description of the Related Art

Infusion pump devices and systems are used in medical contexts, to deliver or dispense infusion media to patients, where such infusion media may be, for example, a prescribed medication such as insulin, a cancer therapy drug, an HIV therapy drug or other media for treating a medical or biological condition. In one form, such infusion pump devices have a relatively compact pump housing adapted to receive a syringe or reservoir that contains a prescribed medication for administration to a patient.

Infusion pump devices typically include a small drive motor connected through a drive linkage to a piston in the syringe or reservoir. The drive motor operates to selectively move the piston within the syringe or reservoir, to drive fluidic media from the reservoir and to the user. Programmable controls are normally provided for operating the drive motor continuously or at periodic intervals to obtain a controlled delivery of the medication over a period of time. Such infusion pumps are utilized to administer insulin and other medications, with exemplary pump constructions being shown and described in U.S. Pat. Nos. 4,562,751; 4,678,408; 4,685,903; 5,080,653 and 5,097,122, each of which is incorporated by reference herein, in its entirety.

Infusion sets are tubing and connection apparatus that provide a fluid flow path for infusion media to flow from the reservoir or syringe in the pump to the user. Connectors for attaching the infusion set tubing to the reservoirs can take various forms. Some examples of such connectors are described in U.S. Pat. No. 6,585,695, which is incorporated by reference herein, in its entirety.

Nevertheless, it remains desirable to develop improved designs of connection methods to facilitate infusion procedures and to provide suitable interface connections that provide additional features for ease of use and manufacture, and other advantages.

SUMMARY OF THE PREFERRED EMBODIMENTS

Connection interfaces for syringes and reservoirs are configured for interfacing a syringe or reservoir to an infusion pump, infusion set tubing, or both. Infusion pump systems include infusion pump devices, infusion sets and connection interfaces that connect the infusion pump devices with the infusion sets. In particular embodiments, the connection interfaces include a cap configured to be secured to a reservoir to form a reservoir/cap unit (or base/reservoir/cap unit) that is configured to be installed within a reservoir receptacle of an infusion pump device. In particular embodiments, the cap includes a first releasable coupler and a second releasable coupler, where the first releasable coupler releasably attaches the cap to the reservoir (or to a base fixed to the reservoir) to form the reservoir/cap unit (or base/reservoir/cap unit), while the second releasable coupler releasably attaches the cap to the infusion pump device.

In particular embodiments, at least one detectable feature is arranged on the cap or the reservoir for detection by at least one sensor element when the reservoir of the reservoir/cap unit is received in the reservoir receptacle of the infusion pump device. The sensor element may be any one or more of a magnetic detection sensor, an inductive sensor, an RF sensor, a mechanical detection sensor, an optical sensor or an electronic contact sensor. Similarly, the detectable feature may be any one or more of a magnetically detectable feature, an inductively detectable feature, an RF detectable feature, a mechanically detectable feature, on optically detectable feature and an electronic contact detectable feature.

Also, particular embodiments relate to particular second releasable couplers configured to releasably attach the cap to the infusion pump device that, in further embodiments, are employed with any one or more of the embodiments that employ detectable features. Yet other embodiments relate to reservoir filling systems and processes including or employing transfer guards for filling reservoirs that, in further embodiments, are reservoirs to which a cap secures to form a reservoir/cap unit (or base/reservoir/cap unit).

An infusion pump system according to an embodiment of the present invention includes an infusion pump device to receive a reservoir containing infusion media and to selectively dispense the infusion media from the reservoir when the reservoir is inserted and secured in an infusion pump housing of the infusion pump device. The infusion pump system according to such embodiment also includes at least one sensor element held by the infusion pump device, and a connector interface to connect the reservoir with the infusion pump device, where the connector interface includes a cap to connect to the reservoir to form a reservoir/cap unit. The infusion pump system according to such embodiment also includes at least one detectable feature arranged on the reservoir/cap unit for detection by the at least one sensor element on the infusion pump device when the cap is aligned or coupled with the infusion pump housing.

An infusion pump system according to an embodiment of the present invention includes an infusion pump device to receive a reservoir containing infusion media and to selectively dispense the infusion media from the reservoir when the reservoir is inserted and secured in an infusion pump housing of the infusion pump device; at least one sensor element held by the infusion pump device; a connector interface to connect the reservoir with the infusion pump device, the connector interface including a cap to connect to the reservoir to form a reservoir/cap unit; and at least one detectable feature arranged on the reservoir/cap unit for detection by the at least one sensor element on the infusion pump device when the cap is aligned or coupled with the infusion pump housing.

In particular embodiments, the at least one detectable feature is a magnet or a magnetic strip. In particular embodiments, the at least one detectable feature is an inductively detectable member. In particular embodiments, the at least one detectable feature is a radio frequency (RF) detectable device. In particular embodiments, the at least one detectable feature is a mechanically detectable feature. In particular embodiments, the at least one detectable feature is an optically detectable feature.

In particular embodiments, the connector interface further includes a twist-lock with push button release feature. In particular embodiments, the connector interface further includes a rotatable ring lock and release feature. In particular embodiments, the connector interface further includes a pawl push-in lock with pinch release feature. In particular embodiments, the connector interface further includes a slot and tab connection feature. In particular embodiments, the connector interface further includes a spring connection feature.

In particular embodiments, the infusion pump system includes a side-loading reservoir receptacle.

In particular embodiments, the connector interface further includes a vent on the cap or on the infusion pump device.

In particular embodiments, the at least one sensor element and the at least one detectable feature are configured such that detection is by one or more of magnetic effects, inductive effects, RF or RFID interaction, mechanical interaction, optical effects, and electrical contact.

Magnetic Detection

An infusion pump system according to a further embodiment of the present invention includes an infusion pump device having a reservoir receptacle for receiving a reservoir containing an infusion media, and for selectively dispensing infusion media from the reservoir when the reservoir is received within the reservoir receptacle, where infusion pump device includes at least one magnetic detection sensor element. The infusion pump system embodiment further includes a connector interface system for connecting the reservoir with the infusion pump device. In particular embodiments, a connector interface system includes a cap configured to connect to the reservoir to form a reservoir/cap unit, and where at least one magnetic detectable feature is arranged on the cap or the reservoir for detection by the at least one sensor element when the reservoir of the reservoir/cap unit is received in the reservoir receptacle of the infusion pump device. In further embodiments, the connector interface system includes the reservoir to be received within the reservoir receptacle of the infusion pump device, where the reservoir contains or is to contain infusion media to be selectively dispensed from the reservoir when the reservoir is received within the reservoir receptacle. In further embodiments, the connector interface system includes an infusion set coupled to the cap via a tubing for conveying infusion media dispensed from the reservoir.

A connector interface system according to an embodiment of the present invention includes a cap to connect to a reservoir to form a reservoir/cap unit for installation into an infusion pump device. At least one magnetic detectable feature is arranged on the cap for detection by at least one sensor element on the infusion pump device when the reservoir of the reservoir/cap unit is received in a reservoir receptacle of the infusion pump device, where the at least one magnetic detectable feature includes a magnet that is attached to a housing of the cap.

A connector interface system according to further embodiments of the present invention includes a reservoir to be received within a reservoir receptacle of an infusion pump device, the reservoir to contain infusion media to be selectively dispensed from the reservoir when the reservoir is received within the reservoir receptacle. The connector interface systems according to such further embodiments also include a connector interface to connect the reservoir with the infusion pump device, the connector interface including a cap to connect to the reservoir to form a reservoir/cap unit. The connector interface systems according to such further embodiments also includes an infusion set coupled to the cap via a tubing for conveying infusion media dispensed from the reservoir, and at least one magnetic detectable feature arranged on the cap for detection by at least one sensor element on the infusion pump device when the reservoir of the reservoir/cap unit is received in the reservoir receptacle of the infusion pump device. The at least one magnetic detectable feature includes a magnet that is attached to a housing of the cap.

The use of a magnet in the cap helps with the automatic detection of whether the reservoir is fully secured in the pump. Once secured infusion can start. If the reservoir subsequently works loose, infusion can be interrupted and an alarm sounded. In a preferred embodiment an infusion pump for a medication fluid includes a receptor for a reservoir of the medication fluid; a first replaceable reservoir positionable within the reservoir receptor, said reservoir having: a cap which, when the replaceable reservoir is within the reservoir receptor, is rotatable with respect to the infusion pump from a first position where the reservoir is locked within the receptor, and a second position where the reservoir may be removed from the reservoir receptor; a magnet situated on the cap; a sensor in the infusion pump configured to produce the signal dependent on detected magnetic field; the magnet and the sensor being positioned so that the detected magnetic field when the cap is in the first position differs from the magnetic field when the cap is in the second position; circuitry connected to the sensor to determine from the signal whether the reservoir is in the first position (locked) or the second position (worked loose or undone for removal). The aspect of the magnetic field that is sensed may be any of magnetic field strength, magnet field polarity or magnet field direction or any combination thereof, such as magnetic field strength in a particular direction.

The magnet and sensor may be positioned to be adjacent when the cap is in the first position, and separated when the cap is in the second position; and said circuitry is configured such that the cap is indicated as being in the first position when the magnetic field strength at the sensor exceeds a first threshold value.

Various alternatives are possible including one in which the sensor includes two magnetic detectors and the circuitry detects the first position when the field strength detected by the first detector is equal to the field strength detected by the second detector indicating that the magnet is equidistant from the first and second magnetic detectors. This arrangement can even be combined with the first such that a first detector detects a first magnet by its field strength maximum to indicate its proximity and the other two detect a position of equal field strength. In such an arrangement the cap has two magnets disposed with an angular separation with respect to the axis of the cap and the infusion pump has three sensors, the first of which is positioned adjacent the magnet when the cap is in the first position and separated when the cap is in the second position and the second and third sensors being positioned to be angularly equidistant from the second magnet when the cap is in the first position, and the circuitry is arranged to detect the first position when the magnetic field strength exceeds a first threshold value as detected by the first sensor and when the magnetic field strength as detected by the second and third sensor are equal. In a further development the cap has three magnets spaced at an angle θ and the infusion pump has four sensors, a first being positioned adjacent a first sensor when the cap is in the first position; the sensors being spaced at an angle θ, the magnets being positioned with respect to the first magnet at angles of a half (2n+1) θ, where n represents consecutive integers 1, 2, 3, etc., and said magnets alternate in polarity for successive values of n; said circuitry being arranged to detect the first position when the magnetic field strength detected by the first sensor is a maximum, and the sum of the magnetic field strength for the other sensors equals zero.

In these arrangements the pump can be made to distinguish between one reservoir and a different reservoir, say with a different insulin, and requiring different dosing by including a second replaceable reservoir positionable within the reservoir receptor in place of the first replaceable reservoir, wherein the magnets of the first and second replaceable reservoirs all have respective opposite polarities, the sensor being arranged to be able to detect the opposite polarity when the second replaceable reservoir is in the first position, the circuitry being configured to indicate that the second replaceable reservoir is in the infusion pump rather than the first replaceable reservoir.

In particular embodiments, the at least one magnetic detectable feature has at least one detectable parameter that is associated with one or more characteristics of the cap, the reservoir, a cannula, or a tubing connected between the cap and the cannula. In particular embodiments, the association is provided in a table or other data arrangement.

In particular embodiments, the one or more characteristics includes one or more of: a type or identity of a manufacturer of the reservoir or the cap; a size of the reservoir or the cap; a type or concentration of infusion media in the reservoir; a volume amount of infusion media in the reservoir; a date corresponding to a manufacturing date, expiration date, or fill date related to infusion media in the reservoir; a date corresponding to a manufacturing date or expiration date of the reservoir or the cap; a location corresponding to a place where the reservoir or infusion media in the reservoir was made, filled, or otherwise processed; a location corresponding to a place where the cap was made, assembled, or otherwise processed; a location corresponding to a place where the reservoir, infusion media in the reservoir, or the cap is authorized to be used; a lot number or code associated with a batch in which the reservoir, the cap, or infusion media was made, cleaned, filled, or otherwise processed; a serial number; a unique ID; user identification information for authorized users; a type, length, or size of the cannula; or a type, length, or size of the tubing connected between the cap and the cannula.

In particular embodiments, the at least one detectable parameter of the magnetic detectable feature includes one or more of: proximity of the at least one magnetic detectable feature, polarity direction of the at least one magnetic detectable feature, field strength of the at least one magnetic detectable feature, location on the cap of the at least one magnetic detectable feature, or pattern of locations on the cap of a plurality of magnetic detectable features.

In particular embodiments, the at least one magnetic detectable feature has a first polarity direction arranged to saturate the at least one sensor element in a first saturation state when the reservoir of the reservoir/cap unit is fully received in the reservoir receptacle of the infusion pump device, or a second polarity direction arranged to saturate the at least one sensor element in a second saturation state when the reservoir of the reservoir/cap unit is fully received in the reservoir receptacle of the infusion pump device, the first saturation state being opposite to the second saturation state.

In particular embodiments, the at least one magnetic detectable feature includes a compass sensor detectable feature having a detectable resolution associated with one or more predefined characteristics of the cap, the reservoir, a cannula, or a tubing connected between the cap and the cannula.

In particular embodiments, the at least one magnetic detectable feature includes a plurality of magnets arranged at different respective locations on the cap.

In particular embodiments, the at least one magnetic detectable feature includes a plurality of magnetic detectable features in locations that allow the magnetic detectable features to magnetically interact with the at least one sensor element to provide detectable signals for detection of axial or rotational motion or position of the cap or the reservoir relative to the reservoir receptacle, when the reservoir/cap unit is received in the reservoir receptacle.

In particular embodiments, the cap includes at least one thread arranged to engage a corresponding thread or groove in the infusion pump device when the reservoir/cap unit is received in the reservoir receptacle in the infusion pump device, wherein the at least one magnetic detectable feature is located on the at least one thread.

In particular embodiments, the at least one magnetic detectable feature includes a magnetic field angle α associated with one or more predefined characteristics of the cap, the reservoir, a cannula, or a tubing connected between the cap and the cannula.

In particular embodiments, the at least one magnetic detectable feature includes a magnetic field that is inclined at an angle β relative to a side of the cap. This magnetic field can be independent of a shape of the magnet used to produce it.

In particular embodiments, the at least one magnetic detectable feature includes a magnetic field that is inclined at an angle β relative to a side of the cap, wherein the angle β is between 5° to 85°, 95° to 175°, 185° to 265°, or 275° to 355° relative to the side of the cap.

In particular embodiments, the at least one magnetic detectable feature includes a magnetic field that is inclined at an angle β relative to a side of the cap, wherein the angle β is between 2.5° to 87.5°, 92.5° to 177.5°, 182.5° to 267.5°, or 272.5° to 357.5° relative to the side of the cap.

In particular embodiments, the at least one magnetic detectable feature includes a magnetic field that is inclined at an angle β relative to a side of the cap, the angle β is between 10° to 80°, 100° to 170°, 180° to 260°, or 285° to 350° relative to the side of the cap.

In particular embodiments, the at least one magnetic detectable feature includes a magnetic field that is inclined at an angle β relative to a side of the cap, wherein angle β is set to provide a three-dimensional magnetic field angle α relative to the side of the cap.

In particular embodiments, the at least one magnetic detectable feature includes two or more magnets included in the cap, wherein each magnet has its own magnetic field set at an independently set angle β relative to a side of the cap.

In particular embodiments, the at least one magnetic detectable feature has at least one detectable parameter that is associated with one or more characteristics of the cap, the reservoir, a cannula, or a tubing connected between the cap and the cannula, wherein as the cap is rotated into the infusion pump device, the two or more magnets create a magnetic field sequence that uniquely identifies the one or more characteristics of the cap, the reservoir, a cannula, or a tubing connected between the cap and the cannula.

In particular embodiments, the infusion set further includes a cannula, and the at least one magnetic detectable feature has at least one detectable parameter that is associated with one or more characteristics of the cannula or the tubing of the infusion set.

In particular embodiments, the characteristic of the cannula or the tubing of the infusion set includes a size or length of the cannula, or a size or length of the tubing.

An infusion pump system according to embodiments of the present invention includes an infusion pump device having a reservoir receptacle to receive a reservoir containing infusion media and to selectively dispense the infusion media from the reservoir when the reservoir is received within the reservoir receptacle. The infusion pump system embodiments further include at least one sensor element held by the infusion pump device, and a connector interface to connect the reservoir with the infusion pump device, where the connector interface includes a cap to connect to the reservoir to form a reservoir/cap unit. The infusion pump system embodiments further include at least one magnetic detectable feature arranged on the cap for detection by the at least one sensor element on the infusion pump device when the reservoir of the reservoir/cap unit is received in the reservoir receptacle of the infusion pump device, where the at least one magnetic detectable feature includes a magnet that is attached to a housing of the cap.

In particular embodiments of the infusion pump system, the at least one magnetic detectable feature has at least one detectable parameter that is associated with one or more characteristics of a cannula or a tubing of an infusion set associated with the connector interface.

In particular embodiments of the infusion pump system, the characteristic of the cannula or the tubing of the infusion set includes a size or length of the cannula, or a size or length of the tubing.

In particular embodiments of the infusion pump system, the at least one magnetic detectable feature has at least one detectable parameter that is associated with one or more characteristics of the cap, the reservoir, or a tubing connected between the cap and a cannula.

In particular embodiments of the infusion pump system, the at least one detectable parameter includes one or more of: proximity of the at least one magnetic detectable feature, polarity direction of the at least one magnetic detectable feature, field strength of the at least one magnetic detectable feature, location on the cap of the at least one magnetic detectable feature, or pattern of locations on the cap of a plurality of magnetic detectable features.

In particular embodiments of the infusion pump system, the at least one sensor is configured to be saturated in a first saturation state when the reservoir of the reservoir/cap unit having a magnetic detectable feature of a first polarity direction is fully received in the reservoir receptacle of the infusion pump device, and wherein the at least one sensor is configured to be saturated in a second saturation state when the reservoir of the reservoir/cap unit having a magnetic detectable feature of a second polarity direction is fully received in the reservoir receptacle of the infusion pump device, the first saturation state being opposite to the second saturation state, and the first polarity direction being opposite to the second polarity direction.

In particular embodiments of the infusion pump system, in the one or more characteristics includes one or more of: a type or identity of a manufacturer of the reservoir or the cap; a size of the reservoir or the cap; a type or concentration of the infusion media in the reservoir; a volume amount of the infusion media in the reservoir; a date corresponding to a manufacturing date, expiration date, or fill date related to the infusion media in the reservoir; a date corresponding to a manufacturing date or expiration date of the reservoir or the cap; a location corresponding to a place where the reservoir or the infusion media in the reservoir was made, filled, or otherwise processed; a location corresponding to a place where the cap was made, assembled, or otherwise processed; a location corresponding to a place where the reservoir, the infusion media in the reservoir, or the cap is authorized to be used; a lot number or code associated with a batch in which the reservoir, the cap, or the infusion media was made, cleaned, filled, or otherwise processed; a serial number; a unique ID; user identification information for authorized users; a type, length, or size of the cannula; or a type, length, or size of the tubing connected between the cap and the cannula.

In particular embodiments of the infusion pump system, the at least one magnetic detectable feature includes a compass sensor detectable feature having a detectable resolution associated with one or more predefined characteristics of the cap, the reservoir, a cannula, or a tubing connected between the cap and the cannula.

In particular embodiments of the infusion pump system, the at least one magnetic detectable feature includes a plurality of magnets arranged at different respective locations on the cap.

In particular embodiments of the infusion pump system, the at least one magnetic detectable feature includes a plurality of magnetic detectable features in locations that allow the magnetic detectable features to magnetically interact with the at least one sensor element to provide detectable signals for detection of axial or rotational motion or position of the cap or the reservoir relative to the reservoir receptacle, when the reservoir/cap unit is received in the reservoir receptacle.

In particular embodiments of the infusion pump system, the at least one sensor is configured to detect a magnetic field angle of the at least one magnetic detectable feature, the magnetic field angle being associated with one or more predefined characteristics of the cap, the reservoir, a cannula, or a tubing connected between the cap and the cannula.

In particular embodiments of the infusion pump system, the at least one magnetic detectable feature includes a magnetic field that is inclined at an angle $\beta$ relative to a side of the cap and independent of a shape of the magnet to produce an angled magnetic field at the angle $\beta$.

In particular embodiments of the infusion pump system, the at least one magnetic detectable feature includes a magnetic field that is inclined at an angle $\beta$ relative to a side of the cap, wherein the angle $\beta$ is between 5° to 85°, 95° to 175°, 185° to 265°, or 275° to 355° relative to the side of the cap.

In particular embodiments of the infusion pump system, the at least one magnetic detectable feature includes a magnetic field that is inclined at an angle $\beta$ relative to a side of the cap, wherein the angle $\beta$ is between 2.5° to 87.5°, 92.5° to 177.5°, 182.5° to 267.5°, or 272.5° to 357.5° relative to the side of the cap.

In particular embodiments of the infusion pump system, the at least one magnetic detectable feature includes a magnetic field that is inclined at an angle $\beta$ relative to a side of the cap, the angle β is between 10° to 80°, 100° to 170°, 180° to 260°, or 285° to 350° relative to the side of the cap.

In particular embodiments of the infusion pump system, the at least one magnetic detectable feature includes a magnetic field that is inclined at an angle β relative to a side of the cap, wherein angle β is set to provide a three-dimensional magnetic field angle α relative to the side of the cap.

It is preferred to set the magnet in the side of the cap such that the North-South magnetic field direction lies in the wall of the cap, is at an angle with and intersects the plane containing the axis of the cap, i.e. skew and on the side of the cap. It is also possible however to orient the magnetic field so that it lies in the surface of a hypothetical cone coaxial with the cap i.e. tilt, with or without the skew. The sensor would then be arranged to detect the field direction and interpret it as the characteristics discussed above. In either case it is preferable not to orient the magnetic field directly parallel or transverse to the axis of the cap.

In particular embodiments of the infusion pump system, the at least one magnetic detectable feature includes two or more magnets included in the cap, wherein each magnet has its own magnetic field set at an independently set angle β relative to a side of the cap.

In particular embodiments of the infusion pump system, the at least one magnetic detectable feature has at least one detectable parameter that is associated with one or more characteristics of the cap, the reservoir, a cannula, or a tubing connected between the cap and the cannula, wherein as the cap is rotated into the infusion pump device, the two or more magnets create a magnetic field sequence that uniquely identifies the one or more characteristics of the cap, the reservoir, a cannula, or a tubing connected between the cap and the cannula.

A further option in these arrangements is to provide electronics coupled to the output of the sensor, which defines a first threshold of magnetic field detection indicating that the reservoir cap combination is in the vicinity of the infusion pump. This first threshold could simply be triggered by the detection of a given minimum magnetic field strength. A second threshold of magnetic field detection would indicate that the reservoir/cap unit is secured in place on the pump. This could either be determined by a maximum in magnetic field strength, either with a particular orientation or regardless of orientation. A third criterion could then be derived from the detected field angle when the cap is in place, with different measured angle representing different characteristics, as discussed above. These characteristics can be fed to the pump to determine operation, or to determine that the reservoir/cap combination is unauthorized or unsuitable for use with that pump, in which case the pump would shut down and/or an audible or visual warning be given.

An infusion pump system for a medication fluid according to further embodiments of the present invention includes a receptacle for a reservoir of the medication fluid and a first replaceable reservoir positionable within the reservoir receptacle. In such embodiments, the reservoir has a cap which, when the replaceable reservoir is within the reservoir receptacle, is rotatable with respect to the infusion pump from a first position where the reservoir is locked within the receptacle, and a second position where the reservoir may be removed from the reservoir receptacle. Such embodiments include a magnet situated on the cap and a sensor in the infusion pump configured to produce the signal dependent on detected magnetic field. The magnet and the sensor are positioned so that the detected magnetic field when the cap is in the first position differs from the magnetic field when the cap is in the second position. Such embodiments include circuitry connected to the sensor to determine from the signal whether the reservoir is in the first position or the second position.

In particular embodiments, the magnet and sensor are positioned to be adjacent when the cap is in the first position, and separated when the cap is in the second position, and the circuitry indicates that the cap is in the first position when the magnetic field strength exceeds a first threshold value.

In particular embodiments, the circuitry is configured to indicate that the reservoir is in the reservoir receptacle irrespective of whether the cap is in the first or second position when the magnetic field strength exceeds a second threshold value lower than the first threshold value.

In particular embodiments, the sensor includes two magnetic detectors and the circuitry detects the first position when the field strength detected by the first detector is equal to the field strength detected by the second detector indicating that the magnet is equidistant from the first and second magnetic detectors In particular embodiments, the cap has two magnets disposed with an angular separation with respect to the axis of the cap and the infusion pump has three sensors, the first of which is positioned adjacent the magnet when the cap is in the first position and separated when the cap is in the second position and the second and third sensors being positioned to be angularly equidistant from the second magnet when the cap is in the first position, and the circuitry is arranged to detect the first position when the magnetic field strength exceeds a first threshold value as detected by the first sensor and when the magnetic field strength as detected by the second and third sensor are equal.

In particular embodiments, the cap has three magnets spaced at an angle θ and the infusion pump has four sensors, a first being positioned adjacent a first sensor when the cap is in the first position. In such embodiments, the sensors are spaced at an angle θ, the magnets are positioned with respect to the first magnet at angles of a half (2n+1) θ, where n represents consecutive integers 1, 2, 3, etc., and said magnets alternate in polarity for successive values of n. In such embodiments, the circuitry is arranged to detect the first position when the magnetic field strength detected by the first sensor is a maximum, and the sum of the magnetic field strength for the other sensors equal zero.

Particular embodiments further include a second replaceable reservoir positionable within the reservoir receptacle in place of the first replaceable reservoir, wherein the magnetic fields of the magnets of the first and second replaceable reservoirs have different orientations, the sensor is arranged to be able to detect the different orientation when the second replaceable reservoir is in the first position, and the circuitry is configured to indicate that the second replaceable reservoir is in the infusion pump rather than the first replaceable reservoir.

In particular embodiments, the different orientation is a reversal of the polarity of the magnetic field. In particular embodiments, the different orientation is a change in the plane of magnetization of the magnetic field.

In particular embodiments, the sensor includes a Hall effect device. In particular embodiments, the sensor includes an AMR angle sensor.

Inductive Detection

An infusion pump system according to an embodiment of the present invention includes an infusion pump device having a reservoir receptacle for receiving a reservoir containing an infusion media, and for selectively dispensing infusion media from the reservoir when the reservoir is received within the reservoir receptacle, where infusion pump device includes at least one inductive sensor element. The infusion pump system embodiment further includes a connector interface system for connecting the reservoir with the infusion pump device. In particular embodiments, a connector interface system includes a cap to connect to the reservoir to form a reservoir/cap unit for installation into an infusion pump device, and where at least one inductively detectable feature is provided on the cap or the reservoir for detection by the at least one inductive sensor element on the infusion pump when the reservoir of the reservoir/cap unit is received in the reservoir receptacle of the infusion pump device. The at least one inductively detectable feature includes at least one electrically conductive material. In further embodiments, the connector interface system includes the reservoir to be received within the reservoir receptacle of the infusion pump device, where the reservoir contains or is to contain infusion media to be selectively dispensed from the reservoir when the reservoir is received within the reservoir receptacle. In further embodiments, the connector interface system includes an infusion set coupled to the cap via a tubing for conveying infusion media dispensed from the reservoir.

In further embodiments, the at least one inductively detectable feature has at least one detectable parameter including one or more of: the existence of one or more inductively detectable features, proximity of the at least one inductively detectable feature relative to the at least one sensor element, a size of the at least one inductively detectable feature, a shape of the at least one inductively detectable feature, a material of the at least one inductively detectable feature, a pattern of locations of one or more inductively detectable features, or the number of inductively detectable features.

In further embodiments, the at least one inductively detectable feature includes a plurality of inductively detectable features arranged at different respective locations on the cap.

In particular embodiments, the at least one inductively detectable feature includes a plurality of inductively detectable features in locations that allow the inductively detectable features to inductively interact with the at least one sensor element to provide detectable signals for detection of axial or rotational motion or position of the cap or the reservoir relative to the reservoir receptacle, when the reservoir/cap unit is received in the reservoir receptacle.

In further embodiments, the cap includes a housing having an opening for receiving a portion of the reservoir, the opening defining a central axis, and wherein the at least one inductively detectable feature includes at least one electrically conductive body having a ring shape or partial ring shape arranged around the central axis.

In further embodiments, the at least one inductively detectable feature includes at least one electrically conductive body having a first end and a second end, the first end of the electrically conductive body having a smaller dimension than the second end of the electrically conductive body.

In further embodiments, the at least one electrically conductive body is arranged on or in the cap in a position such that a predefined one of the first and second ends of the electrically conductive body moves in a predefined direction relative to the at least one sensor, followed by the other of the first and second ends of the electrically conductive body, as the reservoir of the reservoir/cap unit is received in the reservoir receptacle of the infusion pump device.

In further embodiments, the at least one electrically conductive body has a triangular shape or an arrow-head shape.

In further embodiments, the at least one sensor element includes at least one electrically conductive coil provided on or in the infusion pump device, at a location at which the at least one electrically conductive body induces a detectable change in a current flow in the at least one electrically conductive coil, as the reservoir of the reservoir/cap unit is received in the reservoir receptacle of the infusion pump device.

In further embodiments, the at least one sensor element includes at least one electrically conductive coil provided around an axis of the reservoir receptacle of the infusion pump device.

In further embodiments, the at least one sensor element includes at least one electrically conductive coil provided in a ring-shaped member coupled to one end of the reservoir receptacle of the infusion pump device.

In further embodiments, the infusion pump device includes electronics for controlling the selective dispensing of infusion media from the reservoir when the reservoir is received within the reservoir receptacle, the electronics configured to inhibit dispensing of infusion media from the reservoir unless the at least one inductively detectable feature is detected by the at least one sensor element.

A connector interface for connecting a reservoir containing an infusion media with an infusion pump device according to a further embodiment includes a cap configured to connect to the reservoir to form a reservoir/cap unit, and at least one inductively detectable feature arranged on the cap or the reservoir for detection by at least one inductive sensor element on the infusion pump device when the reservoir of the reservoir/cap unit is received in the reservoir receptacle of the infusion pump device.

In further embodiments of such connector interface, the at least one inductively detectable feature has at least one detectable parameter that is associated in a table or other data arrangement with one or more characteristics of the cap, reservoir or infusion pump device.

In further embodiments of such connector interface, the at least one detectable parameter includes one or more of: a proximity or distance between the one or more electrically conductive targets and the one or more coils, or the size, shape, material location or pattern of locations of the one or more electrically conductive targets.

In further embodiments of such connector interface, the at least one detectable parameter of the inductively detectable feature provides a detectable signature that indicates the presence of a reservoir/cap unit in a fully installed position within reservoir receptacle, or information associated with the cap, the reservoir or the reservoir/cap unit.

In further embodiments of such connector interface, the detectable parameter of the of at least one inductively detectable feature is associated with one or more characteristics that include one or more of: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users.

In further embodiments of such connector interface, the at least one inductively detectable feature includes: (a) one or more electrically conductive targets in one or more locations for inductive interaction with the one or more coils when the reservoir/cap unit is received in the reservoir receptacle; or (b) a plurality of electrically conductive targets in locations that allow the one or more electrically conductive targets to inductively interact with the one or more coils to provide detectable signals for detection of axial or rotational motion or position of the cap or the reservoir relative to the reservoir receptacle, when the reservoir/cap unit is received in the reservoir receptacle.

In further embodiments of such connector interface, the at least one inductively detectable feature includes: (a) one or more electrically conductive targets on the cap or the reservoir; (b) one or more electrically conductive targets supported by one or more moveable support structures on the infusion pump device for engagement with an engagement portion on the cap or the reservoir and for linear movement with the cap or the reservoir upon the cap or the reservoir being received in the reservoir receptacle of the infusion pump device, where the engagement portion is provided at a predefined location on the cap or the reservoir to provide a predefined amount of movement of an electrically conductive target relative to a predefined coil, where the engagement portion includes one or more protrusions, bumps, extensions, ramps or depressions; (c) one or more electrically conductive targets supported on one or more moveable members supported in one or more channels in the infusion pump device, where each moveable member has one end arranged in a location to be contacted by an engagement portion of the cap or the reservoir upon the cap or the reservoir being received in the reservoir receptacle, to move the moveable member and electrically conductive target supported thereon from a first position to a second position in a direction of a longitudinal dimension of the channel as the cap or the reservoir is received in the reservoir receptacle, where each moveable member is biased by a bias spring toward the first position, and where each moveable member includes one or more seals for sealing with an inner surface of a channel; or (d) a structure mounted on a piston inside the reservoir.

In further embodiments of such connector interface, the one or more or plurality of electrically conductive targets include: (a) at least one metallic ring or band on the cap or the reservoir that extends circumferentially around an axis of the cap or the reservoir; (b) at least one electrically conductive target having a predefined shape, size or conductive characteristic that provides a predetermined induction signature; (c) at least one electrically conductive target having a triangular shape, tapered shape or arrow-head shape with one end that is wider than an opposite end to provide a time varying induction signature when the at least one electrically conductive target is moved relative to the at least one inductive sensor; (d) a plurality of electrically conductive targets having the same shape relative to each other; (e) a plurality of electrically conductive targets having different shapes relative to each other; or (f) a plurality of electrically conductive targets arranged in a pattern to provide a predetermined induction signature.

In further embodiments of such connector interface, the one or more or plurality of electrically conductive targets are: (a) attached to an outer surface of the cap or the reservoir, (b) attached to an inner surface of the cap or the reservoir, or (c) embedded within a wall of the cap or the reservoir.

An infusion pump system according to further embodiments includes a connector interface as described in any of the preceding paragraphs and an infusion pump device having a reservoir receptacle for receiving the reservoir, and for selectively dispensing the infusion media from the reservoir when the reservoir is received within the reservoir receptacle, wherein the infusion pump device includes at least one inductive sensor element for detecting the inductively detectable feature.

In further embodiments of such infusion pump system, the infusion pump device includes electronics for controlling the selective dispensing of infusion media from the reservoir when the reservoir is received within the reservoir receptacle, the electronics configured to inhibit dispensing of infusion media from the reservoir unless the at least one inductively detectable feature is detected by the at least one inductive sensor element.

In further embodiments of such infusion pump system, the electronics are connected with a memory that stores the table or other data arrangement, and the electronics are configured to control the selective dispensing of infusion media from the reservoir when the reservoir is received within the reservoir receptacle, the selective dispensing being based, at least in part on the one or more characteristics associated in the table or other data arrangement with the at least one detectable parameter of the inductively detectable feature.

In further embodiments of such infusion pump system, the electronics are configured to record information in the memory, the information corresponding to: (a) at least one detectable parameter detected by the at least one inductive sensor, or (b) at least one characteristic associated in the table or other data arrangement with at least one detectable parameter detected by the at least one inductive sensor.

In further embodiments of such infusion pump system, the electronics are further configured to record location information corresponding to a geographic location of the infusion pump device when the at least one detectable parameter of the inductively detectable feature is detected.

In further embodiments of such infusion pump system, the electronics are further configured to record time information corresponding to a time or date when the at least one detectable parameter is detected.

In further embodiments of such infusion pump system, the at least one inductive sensor includes one or more electrically conductive coils on the infusion pump device, the one or more electrically conductive coils being electrically connected with an electrical circuit that is coupled to processing electronics configured to detect electrical induction effects in the electrical circuit caused by movement or proximity of the at least one inductively detectable feature relative to the one or more electrically conductive coils.

In further embodiments of such infusion pump system, (a) the at least one inductively detectable feature is arranged on the cap, the reservoir or the infusion pump device, at a location to be detected by the at least one inductive sensor element when the reservoir/cap unit is fully received in the reservoir receptacle of the infusion pump device, but not detected by the at least one inductive sensor element when the reservoir/cap unit is not fully received in the reservoir receptacle of the infusion pump device; or (b) the cap includes at least one thread arranged to engage a corresponding thread or groove in the infusion pump device when the reservoir/cap unit is received in the reservoir receptacle of the infusion pump device, wherein the at least one inductively detectable feature is located on the at least one thread.

An infusion pump system according to a further embodiment includes an infusion pump device having a reservoir receptacle for receiving a reservoir containing an infusion media, and for selectively dispensing infusion media from the reservoir when the reservoir is received within the reservoir receptacle, wherein the infusion pump device includes at least one inductive sensor. The infusion pump system further includes a connector interface for connecting the reservoir with the infusion pump device, wherein the connector interface has a cap configured to connect to the reservoir to form a reservoir/cap unit, said reservoir/cap unit having an identifying pattern of engagement members. The infusion pump system further includes inductively detectable target members inside the reservoir receptacle and disposed to be engaged by respective one of the engagement members to move the target members into detectable proximity to the inductive sensor, thereby detecting the identifying pattern of engagement members when the reservoir of the reservoir/cap unit is received in the reservoir receptacle of the infusion pump device.

In further embodiments of the above-described infusion pump system, the identifying pattern of engagement members represents one or more of the following characteristics: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users; and the infusion pump system contains electronics including a memory that stores a table associating said characteristics with identifying patterns of engagement members, and the electronics are configured to control the selective dispensing of infusion media from the reservoir when the reservoir is received within the reservoir receptacle, the selective dispensing being based, at least in part on the one or more characteristics associated in the table with the detected identifying pattern.

An infusion pump device according to a further embodiment includes a reservoir receptacle for receiving the reservoir, and for selectively dispensing infusion media from the reservoir when the reservoir is received within the reservoir receptacle. The infusion pump device further includes at least one inductive sensor element for detecting the inductively detectable feature on the reservoir, representing its contents or characteristics of any tubing or infusion set connected thereto. The infusion pump device further includes electronics connected to the at least one sensor element and configured to control said selective dispensing at least partially in accordance with said detected feature.

Further embodiments include a method of configuring an infusion pump device having a reservoir receptacle for receiving a reservoir containing an infusion media, and for selectively dispensing infusion media from the reservoir when the reservoir is received within the reservoir receptacle, there being provided a connector interface for connecting the reservoir with the infusion pump device, wherein the connector interface has a cap configured to connect to the reservoir to form a reservoir/cap unit. The method includes providing the reservoir/cap unit with an inductively detectable feature containing data required to configure the pump for that particular reservoir/cap unit when the reservoir of the reservoir/cap unit is received in the reservoir receptacle of the infusion pump device; detecting the inductively detectable feature using an inductive sensor on the pump; and configuring the pump in accordance with the detected data.

RF Detection

An infusion pump system according to an embodiment of the present invention includes an infusion pump device having a reservoir receptacle for receiving a reservoir containing an infusion media, and for selectively dispensing infusion media from the reservoir when the reservoir is received within the reservoir receptacle, where infusion pump device includes at least one Radio Frequency (RF) sensor (e.g., a transmitter/receiver) element. The infusion pump system embodiment further includes a connector interface system for connecting the reservoir with the infusion pump device. A connector interface system according to an embodiment of the present invention has a cap configured to connect to the reservoir to form a reservoir/cap unit for installation into an infusion pump device, and where at least one RF detectable feature is provided on the cap or the reservoir for detection by the at least one RF sensor element on the infusion pump device when the reservoir of the reservoir/cap unit is received in the reservoir receptacle of the infusion pump device. In further embodiments, the connector interface system includes the reservoir to be received within the reservoir receptacle of the infusion pump device, where the reservoir contains or is to contain infusion media to be selectively dispensed from the reservoir when the reservoir is received within the reservoir receptacle. In further embodiments, the connector interface system includes an infusion set coupled to the cap via a tubing for conveying infusion media dispensed from the reservoir.

In particular embodiments, the at least one RF detectable feature has at least one detectable parameter that is associated with one or more characteristics of the cap, the reservoir, a cannula, or a tubing connected between the cap and the cannula.

In particular embodiments, the at least one detectable parameter includes one or more of: the existence of one or more RF detectable features on the cap or the reservoir; the location or pattern of locations of one or more RF detectable features on the cap or the reservoir; the type of RF detectable feature on the cap or the reservoir; the type or content of data stored by the RF detectable feature; the polarity, direction or orientation, RSSI or other RF signal strength, or amplitude or phase of an RF signal from the RF detectable feature.

In particular embodiments, the detectable parameter of the of at least one RF detectable feature is associated with one or more characteristics that include one or more of: a type or identity of a manufacturer of the reservoir or the cap; a size of the reservoir or the cap; a type or concentration of infusion media in the reservoir; a volume amount of infusion media in the reservoir; a date corresponding to a manufacturing date, expiration date, or fill date related to infusion media in the reservoir; a date corresponding to a manufacturing date or expiration date of the reservoir or the cap; a location corresponding to a place where the reservoir or infusion media in the reservoir was made, filled, or otherwise processed; a location corresponding to a place where the cap was made, assembled, or otherwise processed; a location corresponding to a place where the reservoir, infusion media in the reservoir, or the cap is authorized to be used; a lot number or code associated with a batch in which the reservoir, the cap, or infusion media was made, cleaned, filled, or otherwise processed; a serial number; a unique ID; user identification information for authorized users; a type, length, or size of the cannula; or a type, length, or size of the tubing connected between the cap and the cannula.

In further embodiments, the at least one RF detectable feature includes a plurality of RF detectable features arranged at different respective locations on the cap.

In further embodiments, the at least one RF detectable feature includes a plurality of RF detectable features in locations that allow the RF detectable features to interact with the at least one RF sensor element to provide detectable signals for detection of axial or rotational motion or position of the cap or the reservoir relative to the reservoir receptacle, when the reservoir/cap unit is received in the reservoir receptacle.

In further embodiments, the at least one RF detectable feature includes a radio frequency identification (RFID) tag that is attached to the cap.

In further embodiments, the at least one RF detectable feature includes a passive RF device that receives power through inductive coupling with the at least one RF sensor element.

In further embodiments, the at least one RF detectable feature includes an RF detectable device having a directional antenna or an antenna with at least one RF shield or wave guide configured to direct RF signals to or from the antenna.

In further embodiments, the at least one RF detectable feature has a memory that stores information, and an antenna for communicating information stored in the memory, the memory includes a first section that stores permanent information and a second section that is writeable for storing information written to the RF detectable feature.

In further embodiments, the information stored in the memory includes information identifying one or more of: a type or identity of a manufacturer of the reservoir; a size of the reservoir; a type or concentration of infusion media in the reservoir; a volume amount of infusion media in the reservoir; a volume amount of infusion media that has been dispensed from the reservoir; a date corresponding to an expiration date or fill date related to infusion media in the reservoir; a location corresponding to a place where the reservoir or infusion media in the reservoir was made, filled, or otherwise processed; a lot number or code associated with a batch in which the reservoir or infusion media was made, cleaned, filled or otherwise processed.

In further embodiments, the information stored in the memory includes information identifying one or more characteristics relating to an infusion set connected to the cap, the one or more characteristics including at least one of: a type or identity of a manufacturer of the infusion set; a length of tubing in the infusion set; a diameter of the tubing in the infusion set; a length of a needle or cannula in the infusion set; a diameter of the needle or cannula in the infusion set; a date corresponding to an expiration date, manufacturing date or assembly date of the infusion set; a location corresponding to a place where the infusion set was made or assembled; a lot number or other code associated with a batch in which the infusion set was made, cleaned or otherwise processed.

In further embodiments, the information stored in the memory includes information identifying one or more characteristics of the connector interface, the one or more characteristics including at least one of a type or manufacturer of the connection interface; a size dimension of the cap; a date corresponding to an expiration date, manufacturing date or assembly date of the connector interface; a location corresponding to the place where the connector interface was made or assembled; a lot number or other code associated with a batch in which the connector interface was made, cleaned or otherwise processed.

In further embodiments, the infusion set further includes a cannula, and wherein the at least one RF detectable feature has at least one detectable parameter that is associated with one or more characteristics of the cannula or the tubing of the infusion set.

In further embodiments, the characteristic of the cannula or the tubing of the infusion set includes a size or length of the cannula, or a size or length of the tubing.

In further embodiments, the infusion pump device includes electronics connected with an electronic memory, the electronics and electronic memory are configured to control the selective dispensing of infusion media from the reservoir when the reservoir is received within the reservoir receptacle, the selective dispensing being based, at least in part on the one or more characteristics associated with the at least one detectable parameter in a table or other data arrangement stored in the electronic memory.

In further embodiments, the infusion pump device includes electronics configured to record information in a memory, the information corresponding to one or more of: (a) at least one detectable parameter detected by the at least one RF sensor, (b) at least one characteristic associated with at least one detectable parameter detected by the at least one RF sensor, (c) location information corresponding to a geographic location of the infusion pump device when the at least one detectable parameter is detected, or (d) time information corresponding to a time or date when the at least one detectable parameter is detected.

In further embodiments, the infusion pump device includes electronics for controlling the selective dispensing of infusion media from the reservoir when the reservoir is received within the reservoir receptacle, the electronics configured to inhibit dispensing of infusion media from the reservoir unless the at least one RF detectable feature is detected by the RF sensor element.

A connector interface for connecting a reservoir containing an infusion media with an infusion pump device according to a further embodiment includes a cap configured to connect to the reservoir to form a reservoir/cap unit. At least one RF detectable feature is arranged on the cap or the reservoir for detection by at least one RF sensor element when the reservoir of the reservoir/cap unit is received in the reservoir receptacle of the infusion pump device.

In further embodiments: (a) the at least one RF detectable feature includes a radio frequency identification (RFID) tag that is attached to a housing of the cap to the reservoir or on a plunger within the reservoir, (b) the at least one RF detectable feature includes a passive RF device that receives power through inductive coupling with the RF sensor, (c) the at least one RF detectable feature includes an RF detectable device having a directional antenna or an antenna with at least one RF shield or wave guide configured to direct RF signals to or from the antenna, (d) the at least one RF detectable feature includes an RF detectable device having an antenna, the antenna being arranged adjacent or in a vent opening on the cap, and (e) the at least one RF detectable feature includes an antenna printed with conductive ink on the cap, the reservoir, or a label applied to the reservoir or cap; or (f) the at least one RF detectable feature has a memory that stores information, and an antenna for communicating information stored in the memory, the memory includes a first section that stores permanent information and a second section that is writeable for storing information written to the RF detectable feature, where: (i) the information stored in the memory includes information identifying one or more of: a type or identity of a manufacturer of the reservoir; a size of the reservoir; a type or concentration of infusion media in the reservoir; a volume amount of infusion media in the reservoir; a volume amount of infusion media that has been dispensed from the reservoir; a date corresponding to an expiration date or fill date related to infusion media in the reservoir; a location corresponding to a place where the reservoir or infusion media in the reservoir was made, filled, or otherwise processed; a lot number or code associated with a batch in which the reservoir or infusion media was made, cleaned, filled or otherwise processed; (ii) the information stored in the memory includes information identifying one or more characteristics relating to an infusion set connected to the cap, the one or more characteristics including at least one of: a type or identity of a manufacturer of the infusion set; a length of tubing in the infusion set; a diameter of the tubing in the infusion set; a length of a needle or cannula in the infusion set; a diameter of the needle or cannula in the infusion set; a date corresponding to an expiration date, manufacturing date or assembly date of the infusion set; a location corresponding to a place where the infusion set was made or assembled; a lot number or other code associated with a batch in which the infusion set was made, cleaned or otherwise processed; or (iii) the information stored in the memory includes information identifying one or more characteristics of the connector interface, the one or more characteristics including at least one of a type or manufacturer of the connection interface; a size dimension of the cap; a date corresponding to an expiration date, manufacturing date or assembly date of the connector interface; a location corresponding to the place where the connector interface was made or assembled; a lot number or other code associated with a batch in which the connector interface was made, cleaned or otherwise processed.

In further embodiments, the at least one RF detectable feature has at least one detectable parameter that is associated with one or more characteristics of the cap, reservoir, downstream structure, or infusion pump device.

In further embodiments, the at least one RF detectable feature has at least one detectable parameter including one or more of: the existence of one or more RF detectable feature(s) on the cap or the reservoir; the location or pattern of locations of one or more RF detectable features on the cap or the reservoir; the type of RF detectable feature on the cap or the reservoir; the type or content of data stored by the RF detectable feature; the polarity, direction or orientation, RSSI or other RF signal strength, amplitude or phase of an RF signal from the RF detectable feature.

In further embodiments, the at least one RF detectable feature has at least one detectable parameter that is associated with one or more characteristics that include one or more of: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users.

In further embodiments, an infusion pump system includes a connector interface as described in any of the preceding paragraphs and an infusion pump device having a reservoir receptacle for receiving the reservoir, and for selectively dispensing infusion media from the reservoir when the reservoir is received within the reservoir receptacle, wherein the infusion pump device includes at least one Radio Frequency (RF) sensor (e.g., a transmitter/receiver) element to detect the reservoir in the reservoir receptacle.

In further embodiments, the infusion pump device includes electronics for controlling the selective dispensing of infusion media from the reservoir when the reservoir is received within the reservoir receptacle, the electronics being configured to inhibit dispensing of infusion media from the reservoir unless the at least one RF detectable feature is detected by the RF sensor element.

In further embodiments, electronics are provided connected with a memory that stores a table or other data arrangement, and the electronics are configured to control the selective dispensing of infusion media from the reservoir when the reservoir is received within the reservoir receptacle, the selective dispensing being based, at least in part on the one or more characteristics associated in the table or other data arrangement with the at least one detectable parameter of the RF detectable feature.

In further embodiments, the electronics are configured to record information in the memory, the information corresponding to: (a) at least one detectable parameter detected by the at least one RF sensor, or (b) at least one characteristic associated in the table or other data arrangement with at least one detectable parameter detected by the at least one RF sensor.

In further embodiments, the electronics are further configured to record location information corresponding to a geographic location of the infusion pump device when the at least one detectable parameter of the RF detectable feature is detected.

In further embodiments, the at least one RF detectable feature includes: (a) one or more RF detectable features in one or more locations for RF interaction with the at least one RF sensor when the reservoir/cap unit is received in the reservoir receptacle; or (b) a plurality of RF detectable features in locations that allow the one or more of the RF detectable features to interact with the at least one RF sensor to provide detectable signals for detection of axial or rotational motion or position of the cap or the reservoir relative to the reservoir receptacle, when the reservoir/cap unit is received in the reservoir receptacle.

An infusion pump system according to a further embodiment includes an infusion pump device having a reservoir receptacle for receiving a reservoir containing an infusion media, and for selectively dispensing infusion media from the reservoir when the reservoir is received within the reservoir receptacle. The infusion pump system further includes a connector interface for connecting the reservoir with the infusion pump device wherein the connector interface has a cap configured to connect to the reservoir to form a reservoir/cap unit, said reservoir/cap unit containing an RFID chip. The RFID chip contains data representing one or more of the following characteristics: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users. The infusion pump system further includes a structure on the infusion pump device for detecting reception of the reservoir in the reservoir receptacle. The infusion pump system contains electronics connected to the reception detecting structure and having circuitry to interrogate the RFID chip to read characteristics therefrom to control the selective dispensing of infusion media from the reservoir (1) when the reservoir is detected as received within the reservoir receptacle, the selective dispensing being based, at least in part on the characteristics read from the RFID chip.

In further embodiments, an infusion pump device has a reservoir receptacle for receiving a reservoir containing an infusion media, and for selectively dispensing infusion media from the reservoir when the reservoir is received within the reservoir receptacle; an RFID chip reader configured to read data from an RFID chip on the reservoir, the data representing the contents of the reservoir or characteristics of any tubing or infusion set connected thereto; and electronics connected to the RFID reader and configured to control said selective dispensing at least partially in accordance with said read data.

Further embodiments include a method of configuring an infusion pump device having a reservoir receptacle for receiving a reservoir containing an infusion media, and for selectively dispensing infusion media from the reservoir when the reservoir is received within the reservoir receptacle, there being provided a connector interface for connecting the reservoir with the infusion pump device, wherein the connector interface has a cap configured to connect to the reservoir to form a reservoir/cap unit. In such embodiments, the method includes providing the reservoir/cap unit with an RFID chip containing data required to configure the pump for that particular reservoir/cap unit when the reservoir (1) of the reservoir/cap unit is received in the reservoir receptacle (32) of the infusion pump device (30); interrogating the RFID chip to obtain the data; and configuring the pump in accordance with the detected data.

Mechanical Detection

An infusion pump system according to an embodiment of the present invention includes an infusion pump device having a reservoir receptacle for receiving a reservoir containing an infusion media, and for selectively dispensing infusion media from the reservoir when the reservoir is received within the reservoir receptacle, where infusion pump device includes at least one mechanical detection sensor element. The infusion pump system embodiment further includes a connector interface system for connecting the reservoir with the infusion pump device. A connector interface system according to an embodiment has a cap configured to connect to the reservoir to form a reservoir/cap unit, and where at least one mechanically detectable feature is arranged on the cap or the reservoir for detection by the at least one sensor element when the reservoir of the reservoir/cap unit is received in the reservoir receptacle of the infusion pump device. In further embodiments, the connector interface system includes the reservoir to be received within the reservoir receptacle of the infusion pump device, where the reservoir contains or is to contain infusion media to be selectively dispensed from the reservoir when the reservoir is received within the reservoir receptacle. In further embodiments, the connector interface system includes an infusion set coupled to the cap via a tubing for conveying infusion media dispensed from the reservoir.

In further embodiments, the at least one mechanically detectable feature includes a plurality of mechanically detectable features arranged at different respective locations on the cap.

In further embodiments, the at least one mechanically detectable feature includes a plurality of mechanically detectable features in locations that allow the mechanically detectable features to mechanically interact with the at least one sensor element to provide detectable signals for detection of axial or rotational motion or position of the cap or the reservoir relative to the reservoir receptacle, when the reservoir/cap unit is received in the reservoir receptacle.

In further embodiments, the at least one mechanically detectable feature is arranged on the cap or on the reservoir, at a location to be detected by the at least one sensor element when the reservoir/cap unit is fully received in the reservoir receptacle of the infusion pump device, but not detected by the at least one sensor element when the reservoir/cap unit is not fully received in the reservoir receptacle of the infusion pump device.

In further embodiments, the at least one mechanically detectable feature includes at least one protrusion on an outer surface of the cap or the reservoir.

In further embodiments, the at least one mechanically detectable feature includes a plurality of protrusions at mutually different locations on the cap or the reservoir.

In further embodiments, the at least one mechanically detectable feature includes first and second protrusions located about 180 degrees from each other with respect to a central axis through the reservoir/cap unit.

In further embodiments, the infusion pump device includes electronics for controlling the selective dispensing of infusion media from the reservoir when the reservoir is received within the reservoir receptacle, the electronics configured to inhibit dispensing of infusion media from the reservoir unless the at least one mechanically detectable feature is detected by the at least one sensor element.

In further embodiments, the at least one sensor element includes at least one moveable actuator arranged on the infusion pump device, and wherein the at least one mechanically detectable feature is provided on at least one predefined location of the cap or the reservoir, for engagement with at least one moveable actuator on the infusion pump device when the reservoir/cap unit is fully received in the reservoir receptacle of the infusion pump device.

In further embodiments, the infusion pump device has a housing portion in which a channel is located. The channel has a longitudinal dimension and is open to the reservoir receptacle on one end of its longitudinal dimension. In such embodiments, the at least one moveable actuator includes a moveable member arranged within the channel. The moveable member has a first end arranged within the housing portion of the infusion pump device, and a second end arranged to extend through the open end of the channel and into the reservoir receptacle for engaging the cap or the reservoir when the reservoir/cap unit is received in the reservoir receptacle of the infusion pump device.

In particular embodiments, the moveable member is made of a compressible material that compresses in at least one dimension and expands in at least one other dimension when the second end of the moveable member is engaged by the cap or the reservoir as the reservoir/cap unit is received in the reservoir receptacle of the infusion pump device.

In further embodiments, the at least one sensor element includes an electrical switch located in the infusion pump device housing, wherein the first end of the moveable member is arranged adjacent the electrical switch, and wherein the moveable member is arranged to activate the electrical switch when the moveable member expands in said other dimension In further embodiments, the moveable member includes at least one seal for sealing the channel to inhibit the passage of fluid through the channel, where the at least one seal includes at least one seal structure on the moveable member and that engages an inner surface of the channel.

A connector interface for connecting a reservoir containing an infusion media with an infusion pump device according to a further embodiment includes a cap configured to connect to the reservoir to form a reservoir/cap unit, and wherein at least one mechanically detectable feature is arranged on the cap or the reservoir for detection by at least one sensor element on the pump device when the reservoir of the reservoir/cap unit is received in the reservoir receptacle of the infusion pump device.

In further embodiments, the at least one mechanically detectable feature includes at least one protrusion on an outer surface of the cap or the reservoir, a plurality of protrusions at mutually different locations on the cap or the reservoir, or first and second protrusions located about 180 degrees from each other with respect to a central axis through the cap or the reservoir.

In further embodiments, (a) the at least one mechanically detectable feature includes a plurality of mechanically detectable features arranged at different respective locations on the cap or the reservoir; (b) the at least one mechanically detectable feature is arranged on the cap or on the reservoir, at a location to be detected by the at least one sensor element when the reservoir/cap unit is fully received in the reservoir receptacle of the infusion pump device, but not detected by the at least one sensor element when the reservoir/cap unit is not fully received in the reservoir receptacle of the infusion pump device; (c) the at least one mechanically detectable feature includes a plurality of mechanically detectable features in locations that allow the mechanically detectable features to mechanically interact with the at least one sensor element to provide detectable signals for detection of axial or rotational motion or position of the cap or the reservoir relative to the reservoir receptacle, when the reservoir/cap unit is received in the reservoir receptacle; or (d) the cap includes at least one thread arranged to engage a corresponding thread or groove in the infusion pump device when the reservoir/cap unit is received in the reservoir receptacle of the infusion pump device, wherein the at least one mechanically detectable feature is located on the at least one thread.

In further embodiments, the at least one mechanically detectable feature has at least one detectable parameter that is associated with one or more characteristics of the cap, reservoir or infusion pump device.

In further embodiments, the at least one detectable parameter includes one or more of: the existence of one or more mechanically detectable feature on the cap or the reservoir; the location or pattern of locations of one or more mechanically detectable features on the cap or the reservoir; or the size or shape of the mechanically detectable feature on the cap or the reservoir.

In further embodiments, the detectable parameter of the of at least one mechanically detectable feature is associated with one or more characteristics that include one or more of: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users.

An infusion pump system according to a further embodiment includes a connector interface as described in any of the above embodiments, and an infusion pump device having a reservoir receptacle for receiving the reservoir, and for selectively dispensing infusion media from the reservoir when the reservoir is received within the reservoir receptacle, wherein the infusion pump device includes at least one mechanical detection sensor element to detect the mechanically detectable feature.

In further embodiments of such an infusion pump system, the infusion pump device includes electronics for controlling the selective dispensing of infusion media from the reservoir when the reservoir is received within the reservoir receptacle, the electronics configured to inhibit dispensing of infusion media from the reservoir unless the at least one mechanically detectable feature is detected by the at least one sensor element.

In further embodiments of such an infusion pump system, the electronics are connected with a memory that stores a table or other data arrangement, and the electronics are configured to control the selective dispensing of infusion media from the reservoir when the reservoir is received within the reservoir receptacle, the selective dispensing being based, at least in part on the one or more characteristics associated in the table or other data arrangement with the at least one detectable parameter of the mechanically detectable feature.

In further embodiments of such an infusion pump system, the electronics are configured to record information in the memory, where the information corresponds to: (a) at least one detectable parameter of the mechanically detectable feature detected by the at least one sensor, or (b) at least one characteristic associated in the table or other data arrangement with at least one detectable parameter of the mechanically detectable feature detected by the at least one sensor.

In further embodiments of such an infusion pump system, the electronics are further configured to record location information corresponding to a geographic location of the infusion pump device when the at least one detectable parameter of the mechanically detectable feature is detected.

In further embodiments of such an infusion pump system, the electronics are further configured to record time information corresponding to a time or date when the at least one detectable parameter of the mechanically detectable feature is detected.

In further embodiments of such an infusion pump system, the at least one sensor element includes at least one moveable actuator arranged on the infusion pump device.

In further embodiments of such an infusion pump system, the detectable feature includes at least one mechanically detectable feature provided on at least one predefined location of the cap or the reservoir, for engagement with at least one moveable actuator on the infusion pump device when the reservoir/cap unit is fully received in the reservoir receptacle of the infusion pump device.

In further embodiments of such an infusion pump system, the infusion pump device has a housing portion in which a channel is located, the channel having a longitudinal dimension, the channel being open to the reservoir receptacle on one end of its longitudinal dimension.

In further embodiments of such an infusion pump system, the at least one moveable actuator includes a moveable member arranged within the channel, the moveable member having a first end arranged within the housing portion of the infusion pump device, the moveable member having a second end arranged to extend through the open end of the channel and into the reservoir receptacle for engaging the cap or the reservoir when the reservoir/cap unit is received in the reservoir receptacle of the infusion pump device.

In further embodiments of such an infusion pump system, the moveable member is made of a compressible material that compresses in at least one dimension and expands in at least one other dimension when the second end of the moveable member is engaged by the cap or the reservoir as the reservoir/cap unit is received in the reservoir receptacle of the infusion pump device.

In further embodiments of such an infusion pump system, the at least one sensor element further includes an electrical switch located in the infusion pump device housing, wherein the first end of the moveable member is arranged adjacent the electrical switch, and wherein the moveable member is arranged to activate the electrical switch when the moveable member expands in said other dimension.

In further embodiments of such an infusion pump system, the moveable member includes at least one seal for sealing the channel to inhibit the passage of fluid through the channel, the at least one seal including at least one seal structure on the moveable member and that engages an inner surface of the channel.

An infusion pump system according to a further embodiment includes an infusion pump device having a reservoir receptacle for receiving a reservoir containing an infusion media, and for selectively dispensing infusion media from the reservoir when the reservoir is received within the reservoir receptacle; and a connector interface for connecting the reservoir with the infusion pump device wherein the connector interface has a cap configured to connect to the reservoir to form a reservoir/cap unit, said reservoir/cap unit having an identifying pattern of engagement members. The infusion pump device has movable members movable between a first position in which the movable members project into the reservoir receptacle and a second retracted position, each movable member further having an associated electrical switch which is actuated when the movable member is in the retracted position. Each of the engagement members of the pattern of engagement members on the reservoir/cap unit is positioned to engage a respective one of the movable members and move it from the first position to the second position when the reservoir of the reservoir/cap unit is received in the reservoir receptacle of the infusion pump device thereby detecting the identifying pattern of engagement members.

In further embodiments of such an infusion pump system, the identifying pattern of engagement members represents one or more of the following characteristics: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users. In addition, the infusion pump system contains electronics connected to the electrical switches including a memory that stores a table associating said characteristics with identifying patterns of engagement members. The electronics are configured to control the selective dispensing of infusion media from the reservoir when the reservoir is received within the reservoir receptacle, the selective dispensing being based, at least in part on the one or more characteristics associated in the table with the detected identifying pattern.

An infusion pump device according to a further embodiment has a reservoir receptacle for receiving a reservoir containing an infusion media, and for selectively dispensing infusion media from the reservoir when the reservoir is received within the reservoir receptacle. The infusion pump device according to such embodiments further includes at least one mechanical detection sensor element to detect a mechanically detectable feature on the reservoir, representing its contents or characteristics of any tubing or infusion set connected thereto. The infusion pump device further includes electronics connected to the at least one sensor element and configured to control said selective dispensing at least partially in accordance with said detected feature.

Further embodiments include a method of configuring an infusion pump device having a reservoir receptacle for receiving a reservoir containing an infusion media, and for selectively dispensing infusion media from the reservoir when the reservoir is received within the reservoir receptacle, there being provided a connector interface for connecting the reservoir with the infusion pump device, wherein the connector interface has a cap configured to connect to the reservoir to form a reservoir/cap unit. The method according to such embodiments includes providing the reservoir/cap unit with an identifying pattern of engagement members containing data required to configure the pump for that particular reservoir/cap unit when the reservoir of the reservoir/cap unit is received in the reservoir receptacle of the infusion pump device. The method further includes detecting the pattern of engagement member using feelers extending into the reservoir receptacle, each operating an electrical switch on detection of respective engagement member to produce electric signals corresponding to the data; and configuring the pump in accordance with the detected data.

Optical Detection

An infusion pump system according to an embodiment of the present invention includes an infusion pump device having a reservoir receptacle for receiving a reservoir containing an infusion media, and for selectively dispensing infusion media from the reservoir when the reservoir is received within the reservoir receptacle, where infusion pump device includes at least one optical sensor element. The infusion pump system embodiment further includes a connector interface system for connecting the reservoir with the infusion pump device. In particular embodiments, the connector interface system has a cap configured to connect to the reservoir to form a reservoir/cap unit, and where at least one optically detectable feature is arranged on the cap or the reservoir for detection by the at least one optical sensor element when the reservoir of the reservoir/cap unit is received in the reservoir receptacle of the infusion pump device. In further embodiments, the connector interface system includes the reservoir to be received within the reservoir receptacle of the infusion pump device, where the reservoir contains or is to contain infusion media to be selectively dispensed from the reservoir when the reservoir is received within the reservoir receptacle. In further embodiments, the connector interface system includes an infusion set coupled to the cap via a tubing for conveying infusion media dispensed from the reservoir.

In further embodiments, the at least one optically detectable feature has at least one detectable parameter that is associated in a table or other data arrangement with one or more characteristics of the cap, reservoir or infusion pump device.

In particular embodiments, the at least one detectable parameter includes one or more of: the existence of one or more optically detectable features on the cap; the location or pattern of locations of one or more optically detectable features on the cap; the type of optically detectable feature on the cap; the type or content of data stored by the optically detectable feature; or the polarity, wavelength, phase, intensity, direction or orientation of an optical signal emitted or reflected by the optically detectable feature.

In particular embodiments, the detectable parameter of the of at least one optically detectable feature is associated with one or more characteristics that include one or more of: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users.

In further embodiments, the infusion pump device includes electronics for controlling the selective dispensing of infusion media from the reservoir when the reservoir is received within the reservoir receptacle, the electronics configured to inhibit dispensing of infusion media from the reservoir unless the at least one optically detectable feature is detected by the at least one optical sensor element.

In further embodiments, the electronics are connected with a memory that stores the table or other data arrangement, and the electronics are configured to control the selective dispensing of infusion media from the reservoir when the reservoir is received within the reservoir receptacle, the selective dispensing being based, at least in part on the one or more characteristics associated in the table or other data arrangement with the at least one detectable parameter of the optically detectable feature.

In further embodiments, the electronics are configured to record information in the memory, the information corresponding to: (a) at least one detectable parameter detected by the at least one optical sensor, or (b) at least one characteristic associated in the table or other data arrangement with at least one detectable parameter detected by the at least one optical sensor.

In further embodiments, the electronics are further configured to record location information corresponding to a geographic location of the infusion pump device when the at least one detectable parameter of the optically detectable feature is detected.

In further embodiments, the electronics are further configured to record time information corresponding to a time or date when the at least one detectable parameter of the optically detectable feature is detected.

In further embodiments, the at least one optically detectable feature is configured to alter an optical signal in an optically detectable manner by altering one or more of the wavelength, direction, phase or other characteristic of the optical signal.

In further embodiments, the at least one optically detectable feature includes: (a) at least one surface of the cap or the reservoir that has at least one of a material, coating, surface contour or pattern, ribs, grooves, undulations, roughness, abrasions, apertures, detents or an attached article, that inhibits or changes optical reflective characteristics of the at least one surface of the cap; (b) a bar code, matrix code or other optically detectable pattern that represents encoded information; or (c) an adhesive-backed tag that adheres to the cap and that has an outer surface configured to alter an optical signal in an optically detectable manner.

In further embodiments, the at least one optical sensor includes an optical emitter device configured to emit an optical signal, and an optical detector device configured to detect an optical signal emitted from the optical emitter device and reflected from optically detectable feature when the reservoir/cap unit is fully received in the reservoir receptacle of the infusion pump device.

In further embodiments, the infusion pump device has a housing portion in which at least one channel is located, each channel having a longitudinal dimension and arranged in optical alignment with the reservoir receptacle on one end of its longitudinal dimension.

In further embodiments, the optical emitter device and the optical detector device of the optical sensor are arranged in optical alignment with the at least one channel.

In further embodiments, at least one seal seals the at least one channel to inhibit the passage of fluid through the at least one channel.

In further embodiments, the at least one seal includes (a) an optically transparent or partially transparent material that at least partially fills the at least one channel along at least part of the longitudinal dimension of the at least one channel, or (b) an optically transparent or partially transparent window material at one end of the at least one channel.

In further embodiments, (a) the at least one optically detectable feature includes at least one optically detectable feature provided on at least one predefined location of the cap or the reservoir, for optical alignment with the optical sensor on the infusion pump device when the reservoir/cap unit is fully received in the reservoir receptacle of the infusion pump device; (b) the at least one optically detectable feature includes a plurality of optically detectable features arranged at different respective locations on the cap or on the reservoir; (c) the at least one optically detectable feature is arranged on the cap or on the reservoir, at a location to be detected by the at least one optical sensor element when the reservoir/cap unit is fully received in the reservoir receptacle of the infusion pump device, but not detected by the at least one optical sensor element when the reservoir/cap unit is not fully received in the reservoir receptacle of the infusion pump device; (d) the at least one optically detectable feature includes a plurality of optically detectable features in locations that allow the optically detectable features to optically interact with the at least one sensor element to provide detectable signals for detection of axial or rotational motion or position of the cap or the reservoir relative to the reservoir receptacle, when the reservoir/cap unit is received in the reservoir receptacle; or (e) the cap includes at least one thread arranged to engage a corresponding thread or groove in the infusion pump device when the reservoir/cap unit is received in the reservoir receptacle of the infusion pump device, wherein the at least one optically detectable feature is located on the at least one thread.

A connector interface for connecting a reservoir with an infusion pump device according to an embodiment of the present invention includes a cap configured to connect to the reservoir to form a reservoir/cap unit, and wherein at least one optically detectable feature is arranged on the cap or the reservoir for detection by at least one optical sensor element in the infusion pump device when the reservoir of the reservoir/cap unit is received in the reservoir receptacle of the infusion pump device.

In particular embodiments of such a connector interface, the at least one detectable parameter includes one or more of: the existence of one or more optically detectable features on the cap; the location or pattern of locations of one or more optically detectable features on the cap; the type of optically detectable feature on the cap; the type or content of data stored by the optically detectable feature; or the polarity, wavelength, phase, intensity, direction or orientation of an optical signal emitted or reflected by the optically detectable feature.

In particular embodiments of such a connector interface, the at least one optically detectable feature includes: (a) at least one surface of the cap or the reservoir that has at least one of a material, coating, surface contour or pattern, ribs, grooves, undulations, roughness, abrasions, apertures, detents or an attached article, that inhibits or changes optical reflective characteristics of the at least one surface of the cap; (b) a bar code, matrix code or other optically detectable pattern that represents encoded information; or (c) an adhesive-backed tag that adheres to the cap and that has an outer surface configured to alter an optical signal in an optically detectable manner.

In particular embodiments of such a connector interface, the at least one optically detectable feature has at least one detectable parameter that is associated with one or more characteristics of the cap, reservoir or infusion pump device.

In particular embodiments of such a connector interface, the at least one optically detectable feature has at least one detectable parameter associated with one or more characteristics that include one or more of: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users.

An infusion pump system according to an embodiment of the present invention includes a connector interface according to any of the above-described embodiments; an infusion pump device having a reservoir receptacle for receiving the reservoir containing infusion media, and for selectively dispensing infusion media from the reservoir when the reservoir is received within the reservoir receptacle, wherein the infusion pump device includes at least one optical sensor element.

In particular embodiments, the infusion pump device includes electronics for controlling the selective dispensing of infusion media from the reservoir when the reservoir is received within the reservoir receptacle, the electronics being configured to inhibit dispensing of infusion media from the reservoir unless the at least one optically detectable feature is detected by the at least one optical sensor element.

In particular embodiments of the infusion pump system, electronics are connected with a memory that stores a table or other data arrangement, and the electronics are configured to control the selective dispensing of infusion media from the reservoir when the reservoir is received within the reservoir receptacle, the selective dispensing being based, at least in part on one or more characteristics associated in the table or other data arrangement with the at least one detectable parameter of the optically detectable feature.

In particular embodiments of the infusion pump system, electronics are configured to record information in the memory, the information corresponding to: (a) at least one detectable parameter detected by the at least one optical sensor, or (b) at least one characteristic associated in the table or other data arrangement with at least one detectable parameter detected by the at least one optical sensor.

In particular embodiments of the infusion pump system, the electronics are further configured to record location information corresponding to a geographic location of the infusion pump device when the at least one detectable parameter of the optically detectable feature is detected.

In particular embodiments of the infusion pump system, the electronics are further configured to record time information corresponding to a time or date when the at least one detectable parameter of the optically detectable feature is detected.

In particular embodiments of the infusion pump system, the at least one optically detectable feature is configured to alter an optical signal incident on the detectable features in an optically detectable manner by altering one or more of the wavelength, direction, phase or other characteristic of the optical signal.

In particular embodiments of the infusion pump system, the at least one optical sensor includes an optical emitter device configured to emit an optical signal, and an optical detector device configured to detect an optical signal emitted from the optical emitter device and reflected from optically detectable feature when the reservoir/cap unit is fully received in the reservoir receptacle of the infusion pump device.

In particular embodiments of the infusion pump system, the infusion pump device has a housing portion mounting the optical emitter device and the optical detection device, said housing defining respective channels for the optical emitter device and the optical detector device.

In particular embodiments of the infusion pump system, at least one seal seals the channels to inhibit the passage of fluid therethrough.

In particular embodiments of the infusion pump system, the at least one seal includes: (a) an optically transparent or partially transparent material in each channel, or (b) an optically transparent or partially transparent window material at one end of the channels, or (c) both (a) and (b).

In particular embodiments of the infusion pump system: (a) the at least one optically detectable feature includes at least one optically detectable feature provided on at least one predefined location of the cap or the reservoir, for optical alignment with the optical sensor on the infusion pump device when the reservoir/cap unit is fully received in the reservoir receptacle of the infusion pump device; (b) the at least one optically detectable feature includes a plurality of optically detectable features arranged at different respective locations on the cap or on the reservoir; (c) the at least one optically detectable feature is arranged on the cap or on the reservoir, at a location to be detected by the at least one optical sensor element when the reservoir/cap unit is fully received in the reservoir receptacle of the infusion pump device, but not detected by the at least one optical sensor element when the reservoir/cap unit is not fully received in the reservoir receptacle of the infusion pump device; (d) the at least one optically detectable feature includes a plurality of optically detectable features in locations that allow the optically detectable features to optically interact with the at least one sensor element to provide detectable signals for detection of axial or rotational motion or position of the cap or the reservoir relative to the reservoir receptacle, when the reservoir/cap unit is received in the reservoir receptacle; or (e) the cap includes at least one thread arranged to engage a corresponding thread or groove in the infusion pump device when the reservoir/cap unit is received in the reservoir receptacle of the infusion pump device, wherein the at least one optically detectable feature is located on the at least one thread.

An infusion pump system according to an embodiment of the present invention includes an infusion pump device having a reservoir receptacle for receiving a reservoir containing an infusion media, and for selectively dispensing infusion media from the reservoir when the reservoir is received within the reservoir receptacle, wherein the infusion pump device includes an optical emitter device and an optical detection device. The infusion pump system further includes a connector interface for connecting the reservoir with the infusion pump device wherein the connector interface has a cap configured to connect to the reservoir to form a reservoir/cap unit, said reservoir/cap unit being movable from a first position in which the reservoir is not received in the reservoir receptacle to a second position in which it is received within the reservoir receptacle, the reservoir/cap unit further having an identifying pattern of areas of different reflectivity or refractivity, disposed on the reservoir/cap unit such that when the reservoir/cap unit is moved from the first position to the second position said areas identifying pattern passes between the optical emitter device and the optical detection device, thereby detecting the identifying pattern as the reservoir of the reservoir/cap unit is received in the reservoir receptacle of the infusion pump device.

In particular embodiments of the infusion pump system, the identifying pattern of engagement members represents one or more of the following characteristics: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users; and the infusion pump system contains electronics including a memory that stores a table associating said characteristics with identifying patterns of engagement members, and the electronics are configured to control the selective dispensing of infusion media from the reservoir when the reservoir is received within the reservoir receptacle, the selective dispensing being based, at least in part on the one or more characteristics associated in the table with the detected identifying pattern.

An infusion pump device according to an embodiment of the present invention has a reservoir receptacle for receiving the reservoir containing infusion media, the pump device being for selectively dispensing infusion media from the reservoir when the reservoir is received within the reservoir receptacle, wherein the infusion pump device includes: at least one optical sensor element, for detecting an optically detectable feature on the reservoir, representing its contents or characteristics of any tubing or infusion set connected thereto; and electronics connected to the at least one sensor element and configured to control said selective dispensing at least partially in accordance with said detected feature.

Further embodiments include a method of configuring an infusion pump device having a reservoir receptacle for receiving a reservoir containing an infusion media, and for selectively dispensing infusion media from the reservoir when the reservoir is received within the reservoir receptacle, there being provided a connector interface for connecting the reservoir with the infusion pump device, wherein the connector interface has a cap configured to connect to the reservoir to form a reservoir/cap unit and an identifying pattern of areas of different reflectivity or refractivity, where the method includes providing the reservoir/cap unit with representing data required to configure the pump for that particular reservoir/cap unit when the reservoir of the reservoir/cap unit is received in the reservoir receptacle of the infusion pump device, detecting the pattern using an optical emitter device and an optical detection device on the pump; and configuring the pump in accordance with the detected data.

Electrical Contact Detection

An infusion pump system according to an embodiment of the present invention includes an infusion pump device having a reservoir receptacle for receiving a reservoir containing an infusion media, and for selectively dispensing infusion media from the reservoir when the reservoir is received within the reservoir receptacle, where infusion pump device includes at least one electrical detection sensor element. The infusion pump system embodiment further includes a connector interface system for connecting the reservoir with the infusion pump device. In particular embodiments, the connector interface system has a cap configured to connect to the reservoir to form a reservoir/cap unit, and where at least one electrically detectable feature is arranged on the cap or the reservoir for detection by the at least one sensor element when the reservoir of the reservoir/cap unit is received in the reservoir receptacle of the infusion pump device. In further embodiments, the connector interface system includes the reservoir to be received within the reservoir receptacle of the infusion pump device, where the reservoir contains or is to contain infusion media to be selectively dispensed from the reservoir when the reservoir is received within the reservoir receptacle. In further embodiments, the connector interface system includes an infusion set coupled to the cap via a tubing for conveying infusion media dispensed from the reservoir.

In further embodiments, the at least one electrically detectable feature has at least one detectable parameter that is associated with one or more characteristics of the cap, the reservoir, a cannula, or a tubing connected between the cap and the cannula.

In particular embodiments, the at least one detectable parameter includes one or more of: the existence of one or more electrically detectable features on the cap; the location or pattern of locations of one or more electrically detectable features on the cap; the type of electrically detectable feature on the cap, the electrical resistance of the electrically detectable feature, or the electrical impedance of the electrically detectable feature.

In particular embodiments, the detectable parameter of the of at least one electrically detectable feature is associated with one or more characteristics that include one or more of: a type or identity of a manufacturer of the reservoir or the cap; a size of the reservoir or the cap; a type or concentration of infusion media in the reservoir; a volume amount of infusion media in the reservoir; a date corresponding to a manufacturing date, expiration date, or fill date related to infusion media in the reservoir; a date corresponding to a manufacturing date or expiration date of the reservoir or the cap; a location corresponding to a place where the reservoir or infusion media in the reservoir was made, filled, or otherwise processed; a location corresponding to a place where the cap was made, assembled, or otherwise processed; a location corresponding to a place where the reservoir, infusion media in the reservoir, or the cap is authorized to be used; a lot number or code associated with a batch in which the reservoir, the cap, or infusion media was made, cleaned, filled, or otherwise processed; a serial number; a unique ID; user identification information for authorized users; a type, length, or size of the cannula; or a type, length, or size of the tubing connected between the cap and the cannula.

In further embodiments, the at least one first electrically conductive contact member includes a plurality of first electrically conductive contact members arranged at different respective locations on the cap.

In further embodiments, the at least one first electrically conductive contact member includes a plurality of first electrically conductive contact members in locations on the cap that allow one or more of the first electrically conductive contact members to come into electrical contact with the at least one second electrically conductive contact member to provide detectable signals for detection of axial or rotational motion or position of the cap or the reservoir relative to the reservoir receptacle, when the reservoir/cap unit is received in the reservoir receptacle.

In further embodiments, the at least one first electrically conductive contact member is arranged on the cap, at a location to come into electrical contact with the at least second electrically conductive contact member when the reservoir/cap unit is fully received in the reservoir receptacle of the infusion pump device, but not in electrical contact with the at least one second electrically conductive contact member when the reservoir/cap unit is not fully received in the reservoir receptacle of the infusion pump device.

In further embodiments, each first electrically conductive contact member of each electrically detectable feature includes one or more of: (a) an electrically conductive metal member, (b) an electrically conductive plating, (c) an electrically conductive coating, (d) an electrically conductive ink, or (e) a smooth strip or pad of electrically conductive material.

In further embodiments, one or more of the first electrically conductive contact members includes a biased conductive portion that is biased radially outward relative to a housing of the cap.

In further embodiments, the infusion set further includes a cannula, and wherein the at least one electrically detectable feature has at least one detectable parameter that is associated with one or more characteristics of the cannula or the tubing of the infusion set.

In further embodiments, the characteristic of the cannula or the tubing of the infusion set includes a size or length of the cannula, or a size or length of the tubing.

In further embodiments, the infusion pump device includes electronics connected with an electronic memory, the electronics and electronic memory are configured to control the selective dispensing of infusion media from the reservoir when the reservoir is received within the reservoir receptacle, the selective dispensing being based, at least in part on the one or more characteristics associated with the at least one detectable parameter in a table or other data arrangement stored in the electronic memory.

In further embodiments, the infusion pump device includes electronics configured to record information in a memory, the information corresponding to one or more of: (a) at least one detectable parameter detected by the at least one sensor, (b) at least one characteristic associated with at least one detectable parameter detected by the at least one sensor, (c) location information corresponding to a geographic location of the infusion pump device when the at least one detectable parameter is detected, or (d) time information corresponding to a time or date when the at least one detectable parameter is detected.

In further embodiments, the infusion pump device includes electronics for controlling the selective dispensing of infusion media from the reservoir when the reservoir is received within the reservoir receptacle, the electronics configured to inhibit dispensing of infusion media from the reservoir unless the at least one electrically detectable feature is detected by the sensor element.

In particular embodiments, the at least one second electrically conductive contact member is embedded in or affixed to a wall portion of the infusion pump device, within the reservoir receptacle.

In particular embodiments, the second electrically conductive contact member includes a biased portion that is biased radially inward relative to an axis of the reservoir receptacle, the axis of the reservoir receptacle being along the axis of the cap or of the reservoir when the reservoir/cap unit is received in the reservoir receptacle.

In particular embodiments, the second electrically conductive contact member includes a sheet or strip of electrically conductive metal material having two or more extension portions that are bent or folded partially to extend outward from the rest of the sheet or strip, the sheet or strip having sufficient flexibility to allow the extension portions to bend or fold further inward toward the rest of the sheet or strip when a pressing force is applied to the extension portions, and a natural spring force sufficient to bias the extension portions toward a non-pressed state.

A connector interface for connecting a reservoir containing an infusion media with an infusion pump device according to a further embodiment includes a cap configured to connect to the reservoir to form a reservoir/cap unit, where an electrically detectable feature having at least one first electrical contact is arranged on the cap or the reservoir, for selective connection with a sensor element in the infusion pump device when the reservoir of the reservoir/cap unit is received in a reservoir receptacle of the infusion pump device, wherein the selective connection conveys data.

In particular embodiments of such a connector interface, the data includes one or more of: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users.

An infusion pump system according to an embodiment of the present invention includes a connector interface as described above, and an infusion pump device having the reservoir receptacle for receiving the reservoir containing the infusion media, and for selectively dispensing the infusion media from the reservoir when the reservoir is received within the reservoir receptacle, wherein the infusion pump device includes a plurality of second electrical contacts forming the sensor element.

A further embodiment of such an infusion pump system includes electronics coupled to the plurality of electrical contacts of the sensor element to detect when said selective connection has been made indicating that the reservoir/cap unit is correctly received in the reservoir receptacle.

In a further embodiment of such an infusion pump system, the reservoir/cap unit is movable within the reservoir receptacle from a first position in which it is correctly received for operation with the infusion pump device and on partially received position, wherein the sensor element and the detectable feature are configured such that in the partially received position either none or different ones of said plurality of contacts connect with the at least one electrical contact and the electronics is configured to indicate that the reservoir/cap unit is not correctly received in the reservoir receptacle.

In a further embodiment of any of the above infusion pump systems, at least one electrical contact is configured in a given pattern such that when the reservoir/cap unit is received in the reservoir receptacle the selective connection indicates data about the cap, the reservoir, or infusion pump device.

In a further embodiment of any of the above infusion pump systems, the at least one electrical contact is connected to a chip inside the cap having an internal memory contouring data about the cap or the reservoir, and the sensor element and electronics are configured to receive the data for communication to the pump.

In a further embodiment of any of the above infusion pump systems, the electronically detectable feature includes an electrical resistance or an electrical impedance, wherein the sensor element is configured to detect the impedance and determine therefrom data about the cap (4), the reservoir (1), downstream connected structure, or the infusion pump device.

In a further embodiment of any of the above infusion pump systems, the infusion pump device includes electronics for controlling the selective dispensing of infusion media from the reservoir when the reservoir is received within the reservoir receptacle, the electronics configured to inhibit dispensing of infusion media from the reservoir unless the at least one electrically detectable feature is detected by the at least one sensor element.

In a further embodiment of any of the above infusion pump systems, the electronics are connected with a memory that stores a table or other data arrangement, and the electronics are configured to control the selective dispensing of infusion media from the reservoir when the reservoir is received within the reservoir receptacle, the selective dispensing being based, at least in part on the one or more characteristics associated in the table or other data arrangement with the at least one detectable parameter of the electrically detectable feature.

In a further embodiment of any of the above infusion pump systems, the electronics are configured to record information in the memory, where the information corresponds to: (a) at least one detectable parameter detected by the at least one sensor, or (b) at least one characteristic associated in the table or other data arrangement with at least one detectable parameter detected by the at least one sensor.

In a further embodiment of any of the above infusion pump systems, the electronics are further configured to record location information corresponding to a geographic location of the infusion pump device when the at least one detectable parameter of the electrically detectable feature is detected.

In a further embodiment of any of the above infusion pump systems, the electronics are further configured to record time information corresponding to a time or date when the at least one detectable parameter of the electrically detectable feature is detected.

In a further embodiment of any of the above infusion pump systems, the at least one first electrical contact arranged on the cap includes one or more of: (a) an electrically conductive metal member, (b) an electrically conductive plating, (c) an electrically conductive coating, (d) an electrically conductive ink, (e) a biased conductive portion that is biased radially outward relative to an axis of the cap or the reservoir, or (f) a smooth, strip or pad configuration.

In a further embodiment of any of the above infusion pump systems, the second electrical contacts are attached to, embedded in, molded in, applied onto or affixed to a wall portion of the infusion pump device, within the reservoir receptacle.

In a further embodiment of any of the above infusion pump systems, the second electrical contacts: (a) have a smooth, strip or pad configuration; (b) include a biased portion that is biased radially inward relative to an axis of the reservoir receptacle, the axis of the reservoir receptacle being along the axis of the cap or of the reservoir when the reservoir/cap unit is received in the reservoir receptacle; or (c) include a sheet or strip of electrically conductive metal material having two or more extension portions that are bent or folded partially to extend outward from the rest of the sheet or strip, the sheet or strip having sufficient flexibility to allow the extension portions to bend or fold further inward toward the rest of the sheet or strip when a pressing force is applied to the extension portions, and a natural spring force sufficient to bias the extension portions toward a non-pressed state.

In a further embodiment of any of the above infusion pump systems: (a) each first electrically conductive contact member of the at least one electrically detectable feature is attached to a housing of the cap or to the reservoir; (b) the at least one electrically detectable feature includes a plurality of first electrically conductive contact members arranged at different respective locations on the cap or on the reservoir; (c) the at least one electrically detectable feature is arranged on the cap or on the reservoir, at a location to be detected by the at least one sensor element when the reservoir/cap unit is fully received in the reservoir receptacle of the infusion pump device, but not detected by the at least one sensor element when the reservoir/cap unit is not fully received in the reservoir receptacle of the infusion pump device; (d) the at least one electrically detectable feature includes a plurality of electrically detectable features in locations that allow the electrically detectable features to electrically interact with the at least one sensor element to provide detectable signals for detection of axial or rotational motion or position of the cap or the reservoir relative to the reservoir receptacle, when the reservoir/cap unit is received in the reservoir receptacle; or (e) the cap includes at least one thread arranged to engage a corresponding thread or groove in the infusion pump device when the reservoir/cap unit is received in the reservoir receptacle in the infusion pump device, wherein the at least one electrically detectable feature is located on the at least one thread.

A further embodiment of any of the above infusion pump systems includes electronics configured to detect electrical leakage between the plurality of second electrical contact, for example due to moisture or a saline environment, and to ignore said data in the presence of such leakage.

An infusion pump device according to a further embodiment includes a reservoir receptacle for receiving a reservoir containing an infusion media, and for selectively dispensing the infusion media from the reservoir when the reservoir is received within the reservoir receptacle, where the infusion pump device includes a plurality of second electrical contacts forming a sensor element to detect an electrical contact feature on the reservoir, representing its contents or characteristics of any tubing or infusion set connected thereto. The infusion pump device further includes electronics connected to the sensor element and configured to control said selective dispensing at least partially in accordance with said detected feature.

Further embodiments include a method of configuring an infusion pump device having a reservoir receptacle for receiving a reservoir containing an infusion media, and for selectively dispensing infusion media from the reservoir when the reservoir is received within the reservoir receptacle, there being provided a connector interface for connecting the reservoir with the infusion pump device, wherein the connector interface has a cap configured to connect to the reservoir to form a reservoir/cap unit. The method includes providing the reservoir/cap unit with a first contact arranged in the pattern representing the data required to configure the pump for that particular reservoir/cap unit when the reservoir of the reservoir/cap unit is received in the reservoir receptacle of the infusion pump device; detecting the said pattern using a matrix of resiliently loaded contacts on the reservoir receptacle, when the reservoir/cap unit is received in the reservoir receptacle and deriving the data therefrom; and configuring the pump in accordance with the derived data.

Further embodiments include a method of configuring an infusion pump device having a reservoir receptacle for receiving a reservoir containing an infusion media, and for selectively dispensing infusion media from the reservoir when the reservoir is received within the reservoir receptacle, there being provided a connector interface for connecting the reservoir with the infusion pump device, wherein the connector interface has a cap configured to connect to the reservoir to form a reservoir/cap unit, where the method includes providing the reservoir/cap unit with a chip and contacts connected to the chip on a surface facing the infusion pump device. In such embodiments, the chip contains data required to configure the pump for that particular reservoir/cap unit when the reservoir of the reservoir/cap unit is received in the reservoir receptacle of the infusion pump device. The method in such embodiments includes connecting the contacts to corresponding contacts on the infusion pump device as the reservoir/cap unit is received in the reservoir receptacle; reading said data from the chip into the infusion pump device; and configuring the pump device in accordance with the read data.

Reservoir/Cap/Infusion Set Units (Twist And Lock)

A reservoir unit system for an infusion pump device according to an embodiment of the present invention includes a reservoir container having a neck portion and an interior volume for containing an infusion medium, where the neck portion has a port opening through which infusion media may be received into the interior volume of the reservoir, and where the neck portion has a flow channel with a first opening to the interior volume of the reservoir container and a second opening for connection in flow communication with a tubing. This reservoir unit system embodiment also includes a cap having a cap body supported in the neck portion of the reservoir for rotation about an axis between a first rotary position and a second rotary position, where the cap body has a first channel opening to the interior volume of the reservoir, and a second channel having first and second ends, the first end in fluid flow communication with the first channel in the cap body, and the second end.

This reservoir unit system embodiment may further include a transfer guard that is removably connected to the reservoir neck portion for selective rotation about the axis relative to the reservoir neck portion between a first transfer guard rotary position and a second transfer guard rotary position. The transfer guard is operatively engaged with the cap body for rotating the cap body from the first rotary position to the second rotary position as the transfer guard is selectively rotated from the first transfer guard rotary position to the second transfer guard rotary position. The second end of the second channel in the cap body is in fluid flow communication with the first opening of the flow channel in the neck portion when the cap body is in the first rotary position, and wherein the second end of the second channel in the cap body is out of fluid flow communication with the first opening of the flow channel in the neck portion when the cap body is in the second rotary position.

In particular embodiments: (a) the cap body has at least one extension configured to receive a manual force to rotate the cap body about the axis relative to the reservoir container, and the transfer guard is operatively engaged with the at least one extension of the cap body for rotating the cap body from the first rotary position to the second rotary position as the transfer guard is selectively rotated from the first transfer guard rotary position to the second transfer guard rotary position, where the transfer guard includes a transfer guard body having a first end for receiving the neck portion of the reservoir container, the transfer guard body having an opening through which the at least one extension of the cap body is received and an engagement surface for engaging the at least one extension of the cap body when the reservoir container is received in the first end of the transfer guard body, where the transfer guard body has a second end for receiving a portion of a supply container, the transfer guard configured to connect the supply container in fluid flow communication with the reservoir container when the reservoir container is received in the first end of the transfer guard body and the supply container is received in the second end of the transfer guard body; (b) the cap body has at least one extension configured to receive a manual force to rotate the cap body about the axis relative to the reservoir container, and the reservoir neck portion has at least one extension arranged in a position to align with the at least one extension of the cap body when the cap body is in the first rotary position, and arranged in a position out of alignment with the at least one extension of the cap body when the cap body is in the second rotary position; or (c) the cap body has an extension that has a longitudinal dimension extending outward relative to the axis, the reservoir neck portion has an extension that has a longitudinal dimension extending outward relative to the axis, where the longitudinal dimension of the extension of the cap body is directed in the same direction as the longitudinal dimension of the extension of the reservoir neck portion when the cap body is in the first rotary position, and where the longitudinal dimension of the extension of the cap body is directed in a different direction than the longitudinal dimension of the extension of the reservoir neck portion when the cap body is in the second rotary position.

In further embodiments, the cap includes a pierceable septum in the first channel of the cap body.

In further embodiments, the cap includes at least one detectable element that can be detected by a sensor on an infusion pump device, where the at least one detectable element is located on the extension.

In particular embodiments, the at least one detectable element includes at least one of a magnetically detectable element, an inductively detectable element, an optically detectable element, a mechanically detectable element, an electrically detectable electrical contact element, a radio frequency (RF) detectable element; or a radio frequency (RF) detectable element that includes an RFID tag. The detail and function of the detectable element and associated sensors is as described above.

Reservoir/Cap/Infusion Set Units (Spring Loaded Plunger)

A reservoir unit system for an infusion pump device according to another embodiment of the present invention includes a reservoir container having a neck portion and an interior volume for containing an infusion medium, where the neck portion has a port opening through which infusion media may be received into the interior volume of the reservoir container, and where the neck portion has a flow channel with a first opening to the interior volume of the reservoir container and a second opening for connection in flow communication with a tubing. This reservoir unit system embodiment further includes a cap structure having a moveable plunger body supported in the neck portion of the reservoir for linear motion along an axial direction of the reservoir container, between a first position and a second position. The plunger body has at least one passage for fluid flow communication through the plunger body between the port opening and the interior volume of the reservoir container. The cap structure has a bias member providing a bias force that biases the moveable plunger body toward the first position.

This reservoir unit system embodiment further includes a transfer guard having a first end that is removably connectable to the neck portion of the reservoir container, where the transfer guard includes an engagement portion arranged to engage the moveable plunger body and hold the plunger body in the second position against the bias force of the bias member when the transfer guard is connected to the neck portion of the reservoir container. The engagement portion is arranged to disengage the moveable plunger body to allow the moveable plunger body to move from the second position to the first position under the bias force of the bias member when the transfer guard is removed from the neck portion of the reservoir container.

The moveable plunger body has an outer surface arranged relative to the first opening of the flow channel in the neck portion of the reservoir container such that: (a) when the moveable plunger body is in the first position, the outer surface of the plunger body is aligned with the first opening of the flow channel to block fluid flow communication between the flow channel and the interior volume of the reservoir container, and (b) when the moveable plunger body is in the second position, the outer surface of the plunger body is sufficiently separated from the first opening of the flow channel to allow fluid flow communication between the flow channel and the interior volume of the reservoir container.

In particular embodiments, the engagement portion includes a hollow needle that provides a fluid flow communication path between first and second ends of the hollow needle.

In particular embodiments, the transfer guard includes a second end configured to interface with a supply container, the second end of the hollow needle being arranged in fluid flow communication with an interior volume of the supply container when the second end of the transfer guard interfaces with the supply container.

In particular embodiments, a portion of the hollow needle extends through the port opening with the first end of the hollow needle arranged in fluid flow communication with the interior volume of the reservoir container when the first end of the transfer guard is connected with the neck portion of the reservoir container.

In further embodiments, the neck portion of the reservoir container includes one or more first stop surfaces and one or more second stop surfaces arranged to hold the moveable plunger within the interior volume of the neck portion, yet allow movement of the moveable plunger between the first and second positions.

In particular embodiments, the one or more first stop surfaces include a ring-shaped projection arranged at or adjacent a section of the neck portion where an interior volume of the neck portion opens into the rest of the interior volume of the reservoir container, and the one or more second stop surfaces include a ring-shaped projection arranged at or adjacent the port opening of the reservoir container.

In particular embodiments, one or more of the first and second stop surfaces are (a) formed integral with the neck portion of the reservoir container as a unitary molded structure, or (b) formed as separate elements that are fixed to the neck portion of the reservoir container.

In further embodiments, a pierceable septum is provided within the neck portion of the reservoir container, adjacent the port opening of the reservoir container, the pierceable septum arranged to be pierced by the second end of the hollow needle when the second end of the transfer guard is interfaced with the neck portion, the pierceable septum arranged to seal the port opening of the reservoir container when the second end of the transfer guard is not interfaced with the neck portion of the reservoir container.

In further embodiments, the cap structure includes at least one detectable element that can be detected by a sensor on an infusion pump device, where the at least one detectable element is located on the moveable plunger or the bias member.

In particular embodiments, the at least one detectable element includes at least one of a magnetically detectable element, an inductively detectable element, an optically detectable element, a mechanically detectable element, an electrically detectable electrical contact element, a radio frequency (RF) detectable element; or a radio frequency (RF) detectable element that includes an RFID tag. The detail and function of the detectable element and associated sensor is the same as set out in respect of the earlier described embodiments.

BRIEF DESCRIPTION OF THE DRAWINGS

FIGS. 4C and 4D are perspective views of caps according to embodiments of the present invention.

FIGS. 4U-4V are graphs, representing sensor outputs and magnetic field angles according to embodiments of the present invention.

FIG. 12 is an enlarged, side, cross-section view of a portion of an embodiment of a cap located outside another example of an infusion pump device of an infusion pump system of FIGS. 7 and 8.

FIG. 13 is an enlarged, side, cross-section view of a portion of an embodiment of a cap located in an infusion pump device of FIG. 12.

FIG. 14 is an enlarged, side, cross-section view of a portion of another embodiment of a cap located in an infusion pump device of FIG. 12.

FIG. 15 is an enlarged, side, cross-section view of an embodiment of a linkage structure in an infusion pump device of FIGS. 12-14.

FIG. 84 is an enlarged, partial exploded, partial perspective view of a portion of a reservoir and a cap having a cap-to-reservoir connection interface according to another embodiment of the present invention.

FIG. 85 is an enlarged, partial perspective view of a cap connected to a portion of a reservoir of FIG. 84.

FIG. 86 is an enlarged, partial, side, cross-section view of a portion of a reservoir of FIGS. 84 and 85.

DETAILED DESCRIPTION

In the following description, reference is made to the accompanying drawings which form a part of this application and which illustrate several embodiments of the present invention. It is understood that other embodiments may be utilized and structural and operational changes may be made without departing from the scope of the present invention.

In various drawings, like numerals are used to represent the same elements or similar elements that may perform or operate in a similar manner. The use of the term "and/or" herein is intended to represent an "inclusive OR." In addition, the user of the term "or" herein is intended to represent an "inclusive OR" except where such a meaning would not make sense.

Embodiments of the present invention relate to connection interfaces for syringes and reservoirs. Particular embodiments relate to connection interfaces for interfacing a syringe or reservoir (such as reservoir 1 described below) to an infusion pump device (such as infusion pump device 30 described below), an infusion set tubing (such as tubing 52 described below), or both. Further embodiments relate to infusion pump systems and infusion set systems that include such connection interfaces, and to methods of making and using such connection interfaces and systems.

Figure 1:
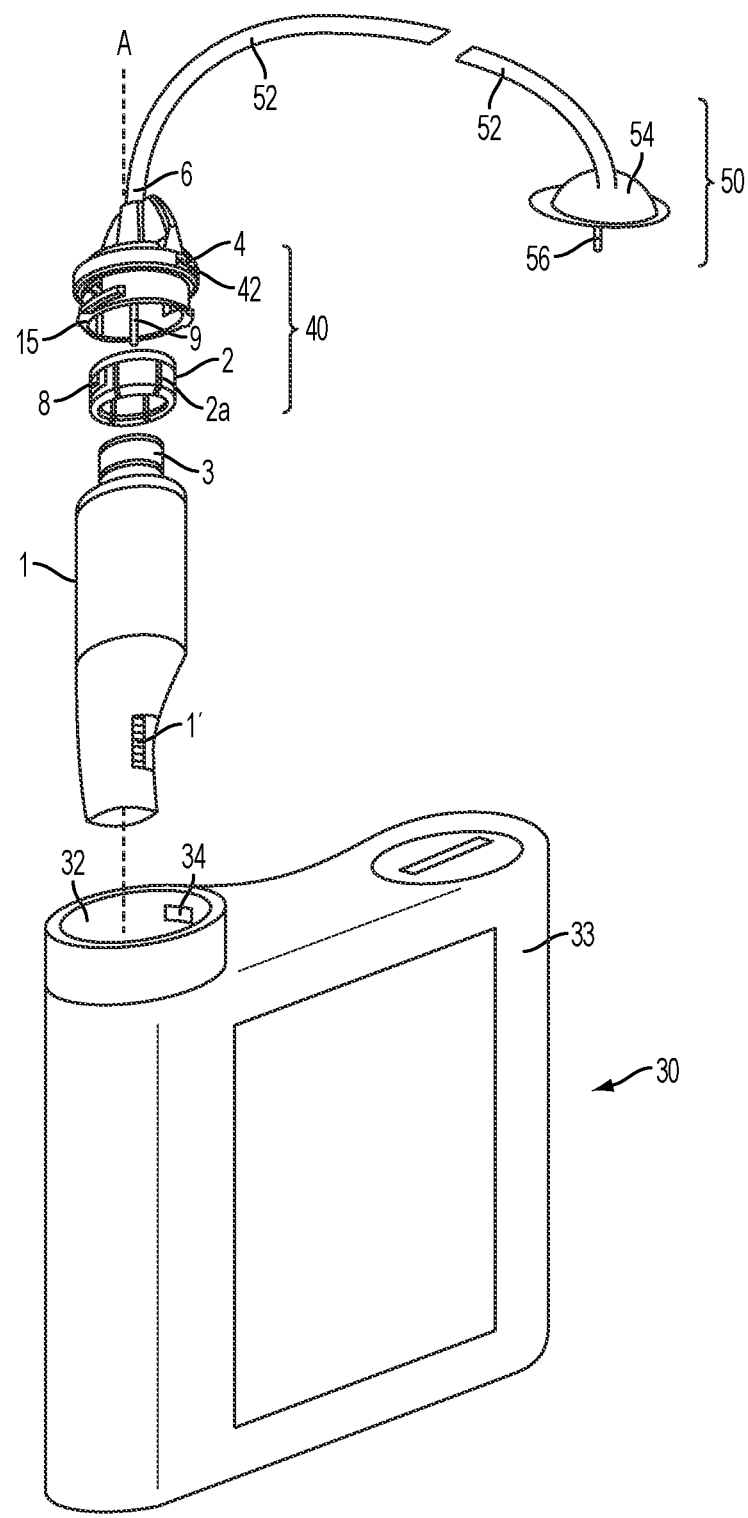
FIG. 1 is a partially exploded, perspective view of an infusion pump system including an infusion pump device, reservoir, infusion set and connection interface apparatus according to an embodiment of the present invention.

An infusion pump system according to an embodiment of the present invention is shown, in a partially exploded, perspective view, in FIG. 1. The infusion pump system in FIG. 1 includes a reservoir 1, an infusion pump device 30, a connection interface 40, and an infusion set 50. The infusion set system in FIG. 1 includes the infusion set 50 and the connection interface 40. Further system embodiments may include one or more, but not all of the above-noted components, and/or additional components not shown in FIG. 1.

As described below, the reservoir 1 is configured to be received within a receptacle 32 of the infusion pump device 30 and to interface with a drive device (not shown) located within the infusion pump device, for selectively driving infusion media from the reservoir in a controlled manner. The reservoir 1 is also configured to be connected in fluid flow communication with the infusion set 50, for providing a flow path for infusion media from the reservoir to a user. In particular embodiments described herein, the connection interface 40 is configured to connect and interface the reservoir 1 with the infusion set 50 and with the infusion pump device 30, using releasable couplers.

The infusion set 50 includes a tubing 52 and a needle or cannula housing 54. In particular embodiments, the tubing 52 may be generally flexible and bendable, but may also include or be encased in a protective sheath made of a suitably rigid material or is otherwise configured to inhibit kinking of the tubing 52. The needle or cannula housing 54 is configured to be secured to a user, such as, but not limited to, adhering the housing 54 to a user's skin, at a desired infusion location on the user. The housing 54 may include adhesive material on its base, or other suitable material or structure, for securing the housing 54 to the user's skin. The housing 54 contains and supports a hollow needle or cannula 56 that is in fluid flow communication with the tubing 52 and that is configured to extend (or to be extended) out from the base and into the user's skin, when the housing 54 is secured to the user's skin. When extended into a user's skin, the hollow needle or cannula 56 can convey infusion media from the tubing 52, into the user. Examples of infusion sets that may be employed as an infusion set 50 include, but are not limited to a Quick-Set® infusion set, a Silhouette® infusion set, a Sure-T® infusion set, a Mio® infusion set, or the like. However, other embodiments of the present invention may include or operate with other suitable infusion set configurations.

Examples of infusion pump devices that may be employed as an infusion pump device 30 include, but are not limited to a Paradigm® infusion pump, a Revel™ infusion pump, a MiniMed® 530G infusion pump, MiniMed 640G, or the like. Other examples include those described in U.S. Pat. Nos. 4,562,751; 4,678,408; 4,685,903; 5,080,653 and 5,097,122, each of which is incorporated by reference herein, in its entirety. However, other embodiments of the present invention may include or operate with other suitable infusion pump devices. The infusion pump device 30 includes a drive motor or other drive device with drive linkage (not shown) arranged to engage corresponding drive linkage 1' on a piston in the reservoir 1, when the reservoir 1 is properly received within the reservoir receptacle 32. In particular embodiments, the drive linkage 1' corresponds to an "engagement side 128" described in U.S. Pat. No. 8,167,846 titled "Reservoir Filling Systems And Methods", which is incorporated herein by reference, in its entirety. In other embodiments, other suitable drive linkage structure is employed as the drive linkage 1' for operatively coupling the piston in the reservoir 1 to the drive device in the infusion pump device 30, when the reservoir 1 is received in the reservoir receptacle of the infusion pump device 30.

The drive device operates to selectively move the piston within the syringe or reservoir, to drive fluidic media from the reservoir and to the user. The infusion pump device 30 includes control electronics connected to the drive device for controlling the drive device to selectively drive the piston and dispense fluid from the reservoir and into the tubing 52 of the infusion set 50. In particular embodiments, the control electronics are programmable to deliver fluid from the reservoir continuously or at one or more predefined intervals over time, in accordance with one or more programmed delivery routines. The control electronics may be further configured to operate one or more display devices and user input devices on or associated with the infusion pump device. The control electronics may include or be connected with the electronics 60 described below with reference to FIG. 5.

1. Connection Interface Structure and Operation

In the embodiment of FIG. 1, the connection interface 40 includes a base 2 and a connection cap 4. In other embodiments, the base 2 is omitted or is formed as part of (unitary with or fixed to) the reservoir 1 or the cap 4. In the embodiment of FIG. 1, the base 2 is a separate element that is fixedly attached to the reservoir 1 by securing it around a swage 3 of the reservoir 1, during (or after) manufacturing of the reservoir 1. For example, the base 2 may include one or more slots 2a and may be made of a rigid, but sufficiently malleable material that can be crimped over the swage 3 to secure the base to the reservoir 1. In particular embodiments, the base 2 is fixedly connected to the reservoir 1 in a manner that inhibits rotation or motion of the base 2 relative to the reservoir 1. Other embodiments may include other suitable structure or materials for securing the base 2 to the swage 3. In other embodiments of the present invention, the base 2 is configured to be attachable to (and removable from) the reservoir, so that the connector interface could be used with reservoirs, cartridges or syringes that were not initially manufactured with the base attached.

The base 2, swage 3 and the cap 4 may be made of any one or more suitable materials having sufficient rigidity and strength to operate as described herein, including, but not limited to plastic, metal, ceramic, composite or other suitable material. In one example, the base 2 is made of a metal material that can be crimped over the crimp seal swage 3, the base is made of a metal foil material that can be formed over a port of the reservoir 1, and the base 2 is made of a plastic material (such as, but not limited to a plastic material that is molded into a single unitary structure having the shape of the cap 4). In particular embodiments, the cap 4 is made of a molded plastic material.

Figure 2:
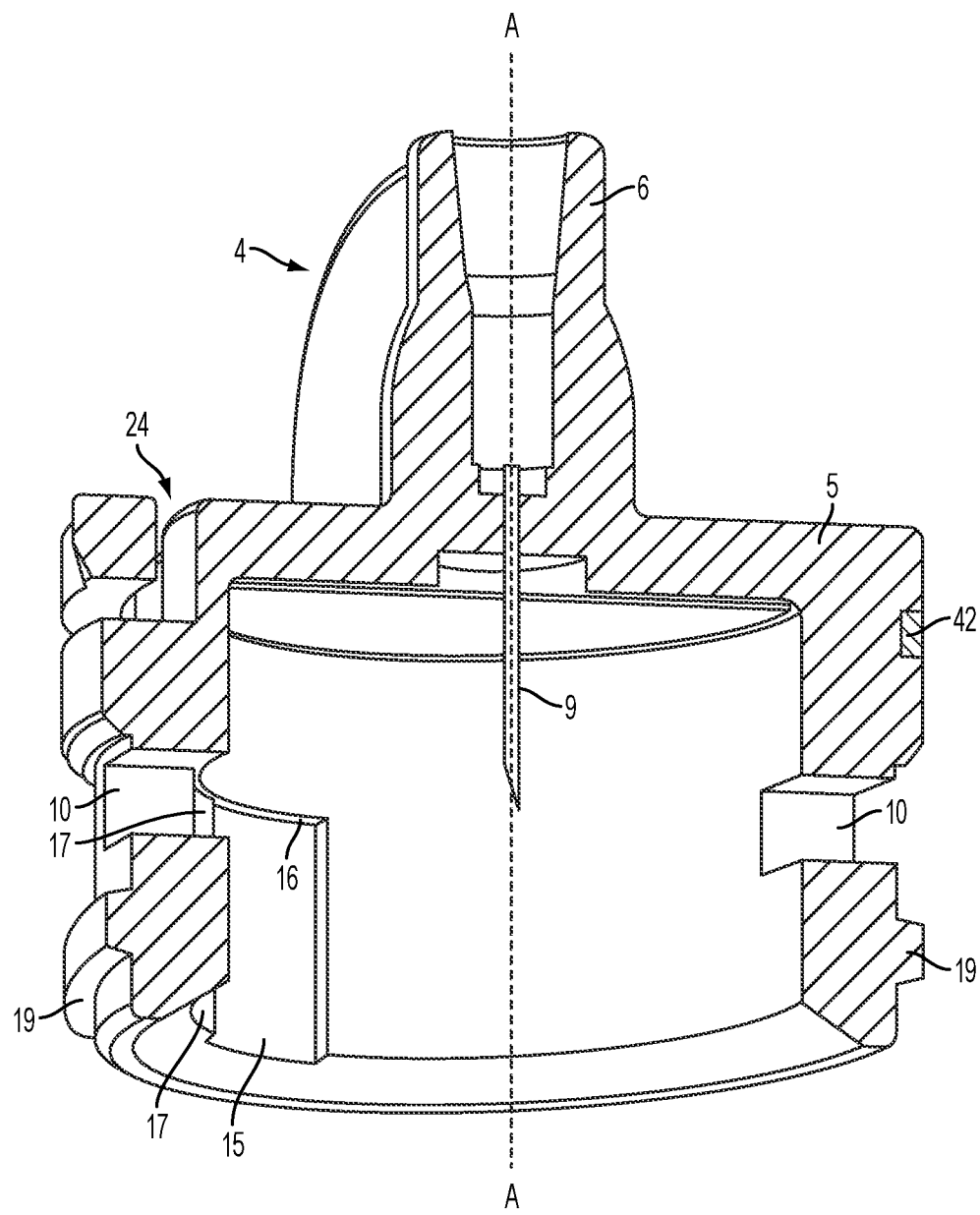
FIG. 2 is an enlarged, side, cross-section view of a cap of a reservoir connection interface apparatus according to an embodiment of the present invention.
Figure 3:
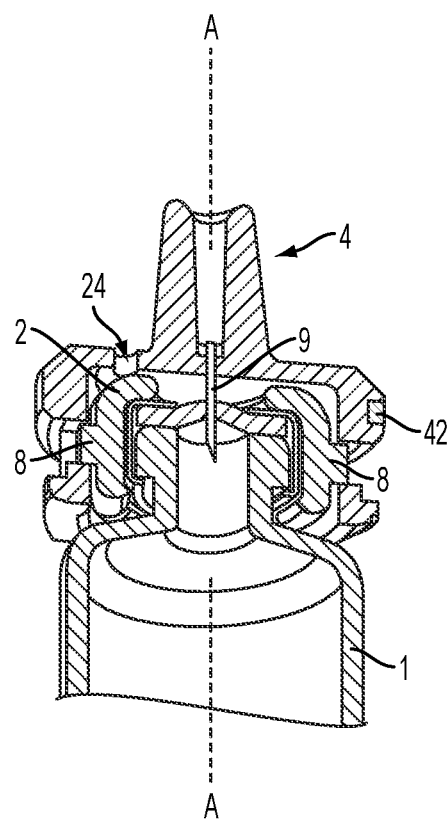
FIG. 3 is a partial side, cross-section view of the cap of the embodiment in FIG. 2, connected with a reservoir.

The cap 4 of the connector interface 40 connects, in fluid flow communication, with the tubing 52 of the infusion set 50. An example embodiment of the cap 4 is shown in FIGS. 2 and 3. A cross-section view of the cap 4 is shown in FIG. 2, with the cap separated from a reservoir. A cross-section view of the cap 4 is shown in FIG. 3, with the cap attached to a neck portion of a reservoir 1. In the embodiment of FIGS. 2 and 3, the cap 4 includes a housing 5 having an open end that opens into an interior volume of the cap housing 5. The housing 5 also includes a tubing port 6 that connects with the tubing 52 of the infusion set 50 in any suitable manner, including, but not limited to a friction fit, clamp, adhesive, combinations thereof, or the like. In particular embodiments, the cap 4 is connected with the tubing 52 during manufacture or assembly of the cap 4, before the cap 4 is made available to the user. In other embodiments, the cap 4 has a port configured to be connected to the tubing 52 after manufacture of the cap, for example, by the user, medical technician or other authorized person. The cap 4 also includes a needle 9 located internal to the cap housing and provided in fluid flow communication with the tubing port 6. In particular embodiments, the cap 4 includes one or more vent openings 24 that provide an air passage from the environment outside of the cap 4, to the interior volume of the cap body 5. As described herein, the one or more vent openings 24 allow pressure equalization between the exterior environment and the interior environment of the cap body 5.

The cap 4 portion of the connector interface 40 removably attaches to the base 2 (and, thus, to the reservoir 1) with a first releasable coupler. In embodiments in which the base 2 is omitted, the first releasable coupler removably attaches the cap 4 directly to the reservoir 1. In addition, the cap 4 removably attaches to the infusion pump device 30 with a second releasable coupler. In particular embodiments, the first releasable coupler includes any suitable structure that allows selective coupling and decoupling of the cap with the base 2, while the second releasable coupler includes a similar or different structure that allows selective coupling and decoupling of the cap with the infusion pump device 30. Example embodiments of first releasable couplers for coupling a cap to a base of a connection interface, and second releasable coupler for coupling a cap to an infusion device are described in U.S. Pat. No. 6,585,695, which is incorporated herein, in its entirety.

In one embodiment, the first releasable coupler includes one or more protrusions or detents provided on one of the base 2 or the cap 4, and corresponding openings in the other of the base 2 or the cap 4, for receiving the protrusions or detents. An example embodiment of a first releasable coupler is described with reference to the cap 4, base 2 and reservoir 1 shown in FIGS. 2 and 3. In other embodiments, other suitable coupler structures for releasably coupling or permanently coupling the cap 4, base 2 and reservoir 1 (or for releasably coupling or permanently coupling the cap 4 directly to the reservoir 1) are employed.

In the embodiment of FIGS. 2 and 3, the cap 4 portion of the connector interface 40 is removably attachable to the base 2 with a first releasable coupler that includes detents on the base 2 and detent openings disposed in a housing portion of the cap 4. Two detents 8 are provided on an outer surface of the base 2 and are spaced 180 degrees apart, but only one detent 8 is in view in FIG. 1. The detents 8 are sized to fit in two detent openings 10 in the cap 4. As with the pair of detents 8, the detent openings 10 are radially spaced apart by 180 degrees.

The base 2 is connected to the reservoir 1, to form an integrated unit with the reservoir 1. The integrated unit of the reservoir 1 and the base 2 is, in turn, connected to the cap 4. For example, in the embodiment of FIG. 1, the integrated base/reservoir unit is connected to the cap 4 by inserting the base 2 into an open, lower end of the cap 4. The detents 8 slide into and mate with correspondingly shaped and longitudinally open entry slots 15 within the interior housing walls of the cap 4. When the base 2 is fully inserted in the cap housing 5, the leading edges of the detents 8 abut an annular stop shoulder 16 formed within the cap 4. After the detents 8 are in this position, the base 2 is rotated within the cap 4 toward a locked position. Referring to FIG. 2, this rotation displaces the detents 8 in a rotational direction for engagement with cam surfaces 17 within the cap 4. The rotational force on the detents 8 over the cam surfaces 17 provides a compression force on the detents 8. Continued rotation of the base 2 displaces the detents 8 past the cam surfaces 17 and into alignment with the detent openings 10. The detents 8 enter the detent openings 10 with a snap-action. Thus, the detents 8 are effectively locked within the detent openings 10 to inhibit longitudinal separation of the base 2 from the cap 4. Accordingly, the base/reservoir unit is connected with the cap 4 to form an integrated base/reservoir/cap unit. (In embodiments in which the base 2 is omitted or incorporated in the reservoir or cap, the references made herein to a base/reservoir/cap unit shall be read to mean reservoir/cap unit)

In particular embodiments, the internal needle 9 of the cap 4 is disposed so that when the base/reservoir unit is fully inserted in the cap 4, the needle pierces the septum (not shown) of the reservoir 1. In such embodiments, the insertion motion and force of the base/reservoir unit into the open end of the cap 4, to the point where the detents 8 abut the annular stop shoulder 16, causes the needle 9 to pierce the reservoir septum, permitting fluid in the reservoir to flow into the needle 9 and the tubing 52 of the infusion set 50.

To disconnect the base 2 from the cap 4, the base 2 is manually rotated relative to the cap 4 in a reverse direction relative to the direction for connection. This causes the detents 8 to move along the cam surfaces 17 into re-alignment with the entry slots 15. When the detents 8 are moved to re-aligned with the entry slots 15, the cap 4 and base 2 can be separated with minimal longitudinal force.

As shown in FIG. 1, the cap 4 is connects to the base 2 and the reservoir 1 along a common axis A, to form a unit (a base/reservoir/cap unit). When connected together, the base/reservoir/cap unit is received within a reservoir receptacle 32 of an infusion pump device 30, along the axis A. The axis A in FIG. 1 corresponds to the longitudinal axis of the reservoir 1 and of the reservoir receptacle 32, as the base/reservoir/cap unit is inserted (or aligned to be inserted) into the reservoir receptacle 32. The axis A also corresponds to the central axis of the cap 4 and base 2 in FIG. 1.

When properly installed within the reservoir receptacle 32, the cap 4 (or base/reservoir/cap unit) is releasably secured in the housing of a infusion pump device 30, for example, with the second releasable coupler. In the embodiment of FIGS. 1 and 2, the second releasable coupler includes external threads 19 on the housing 5 of the cap 4. The threads 19 are arranged to engage corresponding threads (not shown) in a reservoir receptacle 32 of the infusion pump device 30 in order to secure the base/reservoir/cap unit to the infusion pump device 30. In other embodiments, the second releasable coupler includes other suitable coupling structures for coupling the cap 4 to the infusion pump device 30 in a selectively releasable manner, including but not limited to structures as described herein with reference to FIGS. 35-75.

Various embodiments described herein employ a reservoir connection apparatus that includes a cap (such as cap 4 or other cap embodiments) that attaches to a reservoir (such as reservoir 1 or other reservoir embodiments). While the same or different reference numbers are used herein to designate various cap embodiments (including reference numbers 4, 204, 404, 504, 704, 804, 904*a-e*, 964, 974, 984, 994, 1004, 1014, 1024 and 1050), it will be understood that a cap of any one of the disclosed embodiments may be employed and operate in a manner the same or similar to the cap described with respect to another embodiments herein, where such employment or operation is not inconsistent with the configuration of the cap. In addition, it will be understood that features of a cap of any one of the disclosed embodiments may be included or incorporated with or in a cap of any of the other disclosed embodiments and that, where applicable, caps of various embodiments may be interchanged or modified in accordance with other embodiments. Also, while the same or different reference numbers are used herein to designate various reservoir embodiments (including reference numbers 1, 201 and 301), it will be understood that a reservoir of any one of the disclosed embodiments may be employed and operate in a manner the same or similar to the reservoir described with respect to another embodiments herein, where such employment or operation is not inconsistent with the configuration of the reservoir.

2. Detection of Reservoir

According to embodiments of the present invention, when the cap 4 (or the corresponding reservoir/base/cap unit) is received in the infusion pump device 30, the system is configured to detect a proper (or improper) coupling of the cap 4 (or of the reservoir/base/cap unit) with the infusion pump device 30. In further embodiments, the sensor and detectable feature interact in a manner to communicate certain information relating to a characteristic of one or more of the reservoir 1, reservoir contents, cap 4, infusion set 50 or infusion pump device 30.

In other words the detectable feature/sensor combination has one or both of two primary functions, these being:
- (a) to detect the state of closure/seating of the reservoir within the pump; and
- (b) to convey details of the reservoir/cap/infusion set combination to the pump.

These two functions can be performed by a single detectable feature/sensor combination or by respective detectable feature/sensor combinations performing the individual functions. In the latter case any of the arrangement hereinafter described for detecting closure may be combined with any of the arrangements for deriving data and the reservoir/cap infusion set combination. For example an RFID arrangement for conveying data about the reservoir/cap/infusion set combination can be combined with a magnetic or optical technique to detect closure.

The type of details/data falling within category (b) can either be of an information nature, such as the reservoir serial number or a unique ID or can be information to be used by the pump in determining the user's authority or the patient dosage, for example, the identity and concentration of the drug, e.g. insulin or the length, type or size of tubing, which may be relevant for the pump to determine allowable back pressure before an occlusion alarm sounds.

In particular embodiments, one of the cap 4 and the infusion pump device 30 is provided with at least one sensor, and the other of the cap 4 and the infusion pump device 30 is provided with at least one detectable feature that is detected by the sensor when the cap 4 is properly and operably coupled with the infusion pump device 30. In further embodiments, the cap 4 and the infusion pump device 30 are each provided with at least one sensor and at least one detectable feature, arranged to interact with at least one corresponding detectable feature and sensor on the other of the cap 4 and infusion pump device 30. For example, the sensor and detectable feature may interact in a manner such that the sensor detects the presence or position (or both) of the detectable feature or other parameters of the detectable feature, when the cap 4 is properly received or operatively coupled (or both) with the infusion pump device 30. As referenced herein, proper receipt or operative coupling corresponds to a position of the cap 4 (or base/reservoir/cap unit) at which the drive linkage 1' of the reservoir 1 is operatively engaged with the drive device in the infusion pump device 30. In other embodiments, proper receipt or operative coupling corresponds to another suitable, pre-defined position of the cap 4 (or base/reservoir/cap unit).

In the embodiment of FIG. 1, element 34 represents at least one sensor or detectable feature on the infusion pump device 30, and element 42 represents the other of at least one sensor or detectable feature on the cap 4 of the connection interface 40. When the connection interface 40 is coupled to the reservoir 1 and the base/reservoir/cap unit is fully and properly received in the reservoir receptacle 32 of the infusion pump device 30 (as shown in FIG. 3), the element 42 on the cap 4 is in sufficient alignment or proximity (or both) with the element 34 to allow the at least one sensor to detect the at least one detectable feature. However, when the connection interface 40 is not coupled to the reservoir 1, or when the base/reservoir/cap unit is not fully or properly received in the reservoir receptacle 32 of the infusion pump device 30 (as shown in FIG. 1), the element 42 on the cap 4 is not in sufficient alignment or proximity (or both) with the element 34, such that the at least one sensor does not detect the at least one detectable feature.

As discussed above, in various embodiments, element 34 on the infusion pump device 30 is at least one sensor or detectable feature (or both), and element 42 on the cap is at least one of the other of the sensor or detectable feature (or both). For purposes of clarity in the disclosure, further description of various embodiments refers to the element 34 on the infusion pump device 30 as at least one sensor, while element 42 on the cap 4 is referred to as at least one detectable feature. However, it will be understood that in other embodiments, the element 34 on the infusion pump device 30 can be at least one detectable feature (or a combination of at least one sensor and at least one detectable feature), while element 42 on the cap 4 can be at least one sensor (or a combination of at least one detectable feature and at least one sensor).

a. Magnetic Detection

As described above, either one of the element 34 or element 42 may include at least one sensor element, while the other of the element 34 or element 42 includes at least detectable feature. In particular embodiments, each detectable feature includes one or more magnets, while the sensor element is configured to detect the presence or other characteristic of a magnet, when in a sufficient proximity or location relative to the magnet. Such sensor(s) include, but are not limited to, magnetoresistance (MR), Hall effect, magnetic reed, or other sensor device that provides a detectable response to the presence or alignment (or both) of a magnet. Magnets include any suitable permanent magnet material. In further embodiments, the magnets include, but are not limited to, magnetically conductive materials connected with permanent or electromagnets magnets, electromagnets, or other suitable magnetized material or device.

In particular embodiments, the element 42 on the cap 4 includes at least one magnet, while the element 34 on the infusion pump device 30 includes at least one sensor. In that embodiment, the cap 4 need not include sensor electronics and, thus, may be made to be more readily disposable after one use (or a predefined number of uses, a predefined time period of use, or a combination thereof).

For example, element 42 represents one or more magnets carried by the cap 4 at a predefined location on or in the cap housing, while element 34 represents one or more sensors at a predefined location in or adjacent the reservoir receptacle 32 of the infusion pump device 30. In particular embodiments, the one or more magnets (element 42) are embedded within the structure of the cap housing, so as to be out of view and out of contact with users during normal operation of the system. In other embodiments, the one or more magnets may be attached to a surface of the cap housing or otherwise secured to the housing of the cap 4.

In particular embodiments, element 34 is a single sensor device, while element 42 is a single magnet, where the elements 34 and 42 are arranged such that they come into alignment or proximity (or both) when the base/reservoir/cap unit is fully or properly received in the reservoir receptacle 32 of the infusion pump device 30. In other embodiments, element 34 and element 42 comprises a plurality of sensor devices and a plurality of magnets, respectively.

Figure 4A:
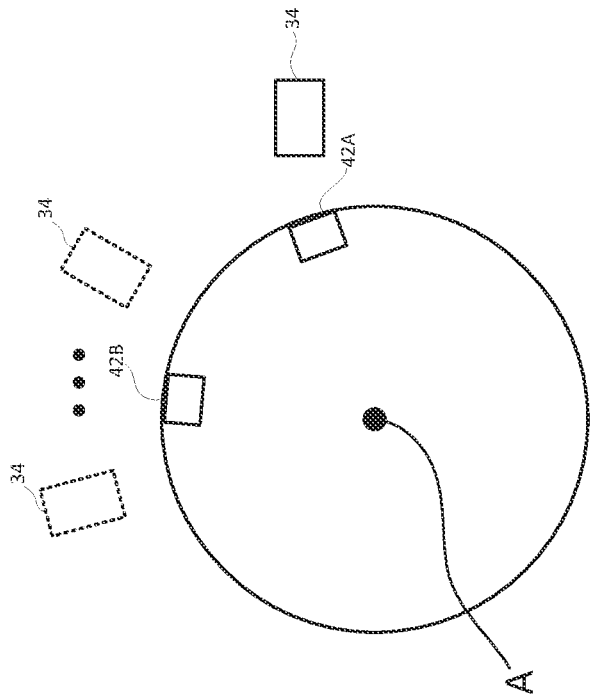
FIGS. 4A and 4B are schematic diagrams, each showing a top-down representation of cap, sensors and detectable elements employed by a connection interface apparatus according to embodiments of the present invention.
Figure 4B:
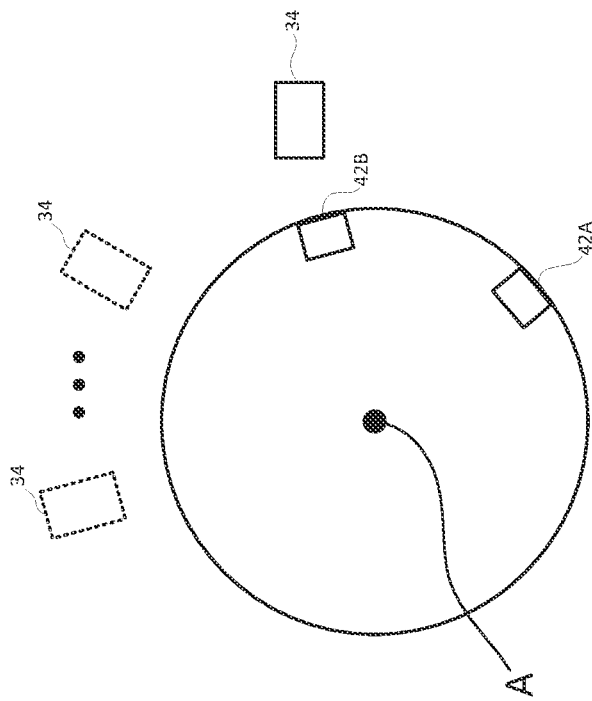

For example, FIGS. 4A and 4B represent an embodiment in which a plurality of elements 42 are arranged on the cap 4, at a corresponding plurality of locations, such that each respective element 42 is at a different location on the cap 4 relative to each other respective element 42. The drawings in FIGS. 4A and 4B represent a top-down view of the cap 4, to show example locations of elements 42, relative to the axis A of the cap 4. In the embodiment in FIGS. 4A and 4B, a plurality of elements 42 (labeled 42A and 42B) are so arranged at different locations, spaced circumferentially around or linearly along (or both) the axis A through the center of the cap 4. While FIGS. 4A and 4B show two elements 42 (42A and 42B), other embodiments include more than two elements 42.

In the embodiment of FIGS. 4A and 4B, the element 42A is arranged to be in sufficient alignment or proximity (or both) with the element 34 on the infusion pump device 30 to allow detection as described above, when the base/reservoir/cap unit is fully and properly received in the reservoir receptacle 32, as shown in FIG. 4B. However, another element 42B is arranged to be in alignment or proximity (or both) with the element 34 on the infusion pump device 30 to allow detection as described above, when the base/reservoir/cap unit are not fully or properly received in the reservoir receptacle 32, as shown in FIG. 4A (for example, but not limited to, when the base/reservoir/cap unit is not fully rotated or fully inserted (or both) in the reservoir receptacle 32 to complete the connection of the second releasable coupler described above). In the embodiment of FIGS. 4A and 4B, when element 42A is in detectable alignment or proximity (or both) with element 34, element 42B is out of detectable alignment or proximity (or both) with element 34. Similarly, when element 42B is in detectable alignment or proximity (or both) with element 34, element 42A is out of detectable alignment or proximity (or both) with element 34.

In the embodiment in FIGS. 4A and 4B, a single element 34 is arranged to be in alignment or proximity (or both) with each of the plurality of elements 42 (e.g., 42A and 42B), depending upon the relative position of the base/reservoir/cap unit within the reservoir receptacle 32. In other embodiments, a plurality of elements 34 are arranged (for example, at a corresponding plurality of locations spaced circumferentially or linearly (or both) around and along the axis A, as represented by the broken line representations of additional elements 34), to come into alignment or proximity (or both) with one or more elements 42 at predefined positions of the base/reservoir/cap unit relative to the reservoir receptacle 32. In those embodiments, the sensor and magnet elements may be arranged to allow detection of various positions of the base/reservoir/cap unit, as that unit is being received within the reservoir receptacle 32 of the infusion pump device 30.

In particular embodiments in which multiple sensor or multiple magnet elements (or both) are employed on one or both of the cap 4 and infusion pump device 30, the multiple elements may be arranged to allow detection of various predefined states of the cap 4. Thus, in example embodiments, the multiple elements are arranged spaced apart around the circumference of the axis A to allow detection of the rotational position (or movement) of the cap 4 around the axis A, relative to the infusion pump device 30. Alternatively or in addition, the multiple elements are arranged spaced apart in the axial dimension A of the cap 4 to allow detection of the linear position (or movement) of the cap 4 along the axis A, relative to the infusion pump device 30. In other embodiments, one or more elements are arranged to detect angular differences (or movement) between the axial dimension A of the cap and the axial dimension of the reservoir receptacle 32. Accordingly, in different embodiments, the sensor element(s) provide one or more sensor signals representing a rotational position of the cap 4, a linear position of the cap 4, an angular position of the cap 4, or any combination thereof.

In further embodiments in which multiple magnet elements are employed, at least two of the magnet elements have mutually different detectable parameters, such as, but not limited to, different magnetic polarity directions, field strengths, locations or patterns of magnets on the cap, or any combination thereof. In those embodiments, the sensor element(s) is configured to detect and discern one magnet element from the other, based on the detected parameter. In those embodiments, the different magnets (with different detectable parameters) are arranged at a plurality of predefined locations on the cap 4 (or the infusion pump device 30) to be detected by the sensor element(s), as described above, when the cap 4 is in different respective positions within the reservoir receptacle 32 of the infusion pump device 30.

In particular embodiments, the cap 4 includes one or more magnets that are integrated into the cap. Example embodiments of a cap 4 are shown in FIGS. 4C and 4D, where the element 42 includes a magnet that is integrated into the housing 5 of the cap 4. In the embodiments of FIGS. 4C and 4D, the magnet (element 42) is secured to and embedded in an outer peripheral surface of the cap housing 5, such that an outer surface of the magnet (element 42) is exposed and faces outward from the cap housing 5. In particular embodiments, the outer surface of the magnet (element 42) has a shape or contour that is similar to the shape and contour of the outer surface of the cap housing 5 around the magnet (element 42), such that the outer surface of the magnet (element 42) is or appears flush with the outer surface of the cap housing 5. In other embodiments, one or more magnets (element 42) may be recessed, embedded, molded or otherwise formed inside a wall of the cap housing 5, recessed from and not flush with the outer surface of the cap housing 5.

The magnet (element 42) may be secured to the housing 5 of the cap 4 in any suitable manner, including, but not limited to a swaging, mechanical fitting, adhering with an adhesive material or mechanical connector, soldering, welding, heat staking, molding, co-molding or the like. For example, a magnet (element 42) may be molded onto or into the cap housing 5, as part of a process of forming (by molding) the cap housing 5, or as a process carried out after forming (by molding or otherwise) the cap housing 5. Such molding processes can include, but are not limited to, injection molding, molding with an insert mold, molding in a multi-shot (e.g., a two-shot) mold, or other suitable molding processes.

In the embodiment of FIG. 4C, the magnet (element 42) is secured to the housing 5 by swaging, wherein the magnet (element 42) has been pressed or forced into the surface of the cap housing 5. In the embodiment of FIG. 4C, a lip 5a may be formed adjacent one or more sides of the magnet (element 42) due to displacement of some of the material of the cap housing 5 during a swaging process. In a particular embodiment, a hot swaging procedure is employed, in which a magnet (element 42) is sintered or hot-pressed into the cap housing 5. In other embodiments, a cold swaging procedure is employed, or a combination of hot and cold swaging is employed to secure the magnet (element 42) to the cap housing 5.

In the embodiment of FIG. 4D, the magnet (element 42) is secured to the housing 5 by a mechanically fitting the magnet (element 42) in a depression formed in the cap housing 5. In FIG. 4D, the magnet (element 42) has a size and shape that matches or corresponds to the size and shape of the depression in the cap housing 5. In particular embodiments, as shown in FIG. 4D, the magnet (element 42) has a shape that flares outward or widens in the direction toward the axis A, and the depression in the cap housing 5 is correspondingly shaped to flare or widen in the direction toward the axis A. In such embodiments, the width of the magnet (element 42) in the circumferential direction of the cap housing 5 is smaller at the outer or exposed surface of the magnet (element 42) than at the inner surface (the surface of the magnet (element 42) that faces toward the axis A). Also, in such embodiments, the width of the inner surface (the surface of the magnet (element 42) that faces toward the axis A) may be selected to be greater than the width of the outward-facing end of the depression in the cap housing 5, so as to help retain the magnet (element 42) within the depression. In further embodiments, one or more additional mechanisms as described above may be employed in combination with a mechanical fit, to further help retain the magnet (element 42) within the depression, including but not limited to swaging, adhering with an adhesive material or mechanical connector, soldering, welding, heat staking, molding, co-molding or the like.

In further embodiments, the magnet (element 42) may be secured to the cap 4 in any other suitable manner. In embodiments as described herein, when the cap 4 (or base/reservoir/cap unit) is installed within the reservoir receptacle 32 of the infusion pump device 30, the magnet (element 42) is located in a position for magnetic detection by or other interaction with the sensor element (element 34) located on the infusion pump device 30. In particular embodiments, the sensor element (element 34) and associated electronics 60 (FIG. 5) are configured to detect one or more of the presence, position (axially rotational, angular and/or linear) of the cap 4 (or base/reservoir/cap unit) within the reservoir receptacle 32 of the infusion pump device 30.

To illustrate how multiple sensors and multiple magnetic elements can lead to a more accurate detection of the angular position of a cap in an infusion pump device reference is again made to FIGS. 4A and 4B. For the purpose of this example multiple sensors 34 are positioned around the inside of a reservoir receptacle 32 of a pump device as shown in FIG. 1. The angular spacing of the sensors 34 is referred to as an angle theta. For the purpose of this discussion the sensors 34 will be counted in an anticlockwise direction starting from the sensor shown with the unbroken line. On the cap, magnets 42 are shown arranged at angular positions such that when one magnet, for example, 42a is aligned with the sensor the next magnet in an anticlockwise direction lies exactly at a midway position between the two subsequent sensors. The angular spacing of the second magnet from the first magnet to achieve this would be one and a half theta.

Considering now the operation, FIG. 4A shows the situation in which the cap is open i. e. unlocked. In this situation the second magnet 42B is aligned with the first sensor 34 and the first magnet 42A is out of range of any of the three sensors illustrated in FIG. 4A. The cap is then manually closed by rotating about the axis A in an anticlockwise direction until it reaches the condition shown in FIG. 4B in which the first magnet 42A is aligned with the first sensor 34. Such alignment would be detected by the first sensor 34 as a maximum in the magnetic field strength. As the rotation of the cap approaches the position shown in 42B so the second magnet 42B passes the second sensor 34 (counting anticlockwise from the sensor shown as a solid line) and progresses towards the third sensor. As the second magnet 42B passes the second sensor the magnetic field strength detected at the second sensor increases and then decreases. As it approaches the third sensor 34 the magnetic field strength detected by that third sensor increases. When the second magnet 42B is exactly midway between the second and third sensors they will each detect an equal magnetic field. The position of the equal magnetic field corresponds exactly to the alignment position of the first magnet 42A with the first sensor (shown as a solid line) which is the closed/locked position.

Accordingly, the more accurate closed position can be detected by an exact match between the outputs of the second and third sensors. The situation shown in FIGS. 4A and 4B is with two magnets. Adding a third magnet at a spacing of theta from the second magnet and a fourth sensor also at a spacing of theta from the third sensor would improve the sensitivity further.

A yet further refinement of this system would be to arrange the first magnet 42A on the cap to have an opposite polarity to the second magnet 42B. In the simplest case this would enable the first sensor 34 (where only one sensor is provided) to distinguish immediately between the open position shown in FIG. 4A where one pole is presented to the sensor 34 from the position in FIG. 4B where the opposite pole is presented.

In a situation with multiple sensors and magnets in which the sensors are equally spaced with an angle theta and the magnets are spaced from the first magnet 42A by an angle of one half (2n+1) theta and with alternating pole polarities in the magnets starting from the first magnet 42A and progressing in an anticlockwise direction the closed position would be detected when the first magnet 42A aligns with the first sensor 34 and the second magnet 42B is equidistant between the second and the third sensors 34 and the third magnet (not shown) is equidistant between the third and the fourth sensors. In this situation the magnetic fields from the second and third magnets would cancel at the third sensor and the magnetic fields detected by the second and fourth sensors would be of equal and opposite polarity. The exact mid-position, hence closed position of FIG. 4B, can then be detected as the position in which the sum of the magnetic fields detected by the second, third and fourth sensors is zero. This manner of detection is also immune to external magnetic fields.

Figure 4E:
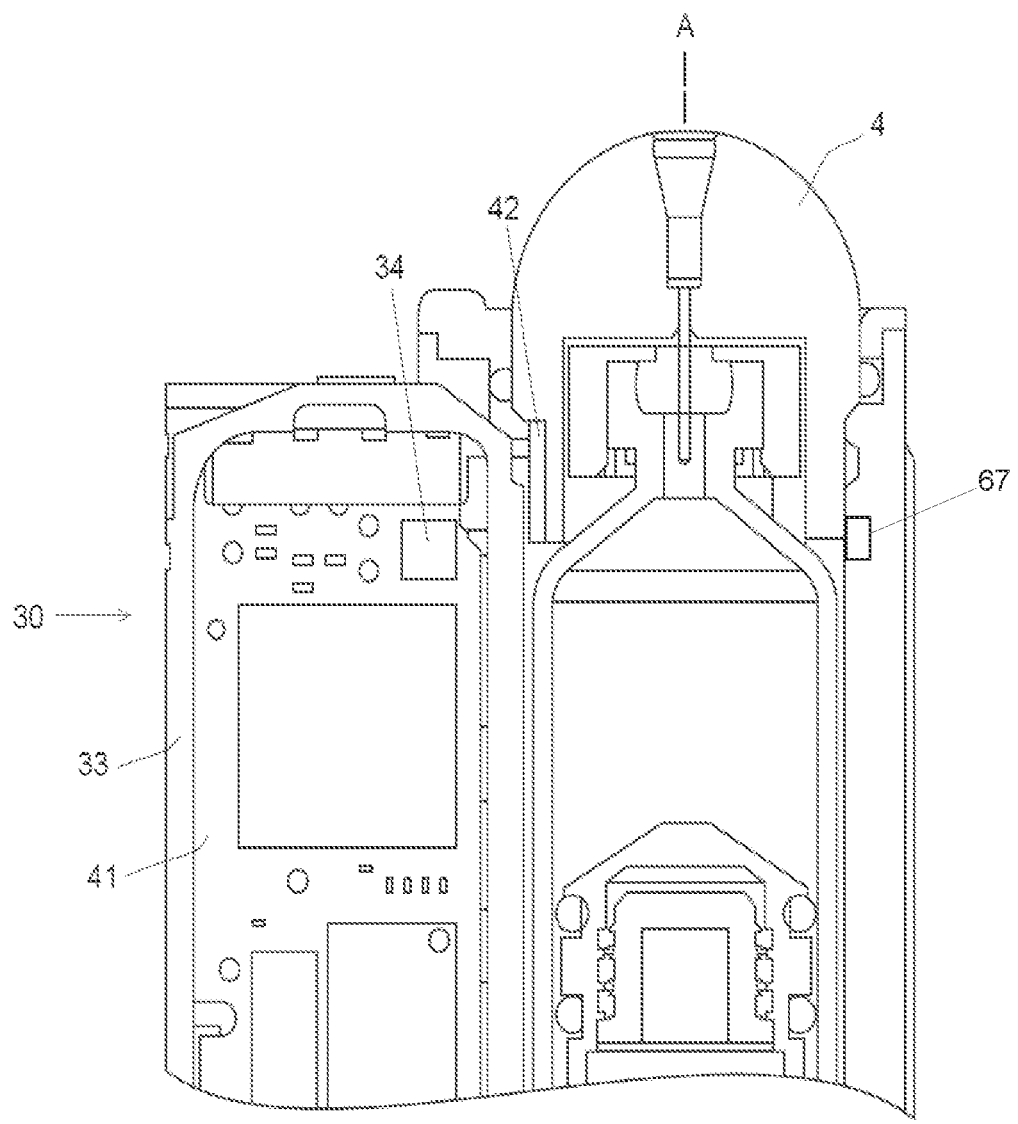
FIG. 4E is a schematic cross-sectional diagram of a portion of an infusion pump device on which a cap of FIG. 4C or 4D is installed.

FIG. 4E shows cross-section view of an example of a cap 4 (and base/reservoir/cap unit) with an integrated magnet (element 42), installed within the reservoir receptacle 32 of an infusion pump device 30. In the embodiment of FIG. 4E, the sensor element (element 34) is located on an electronic circuit board (PCB) 41, and/or within a stack of electronic components or electronic circuit boards, within the housing 33 of the infusion pump device 30. Associated electronics (e.g., electronics 60 in FIG. 5) may be located on the same electronic circuit board or stack, or on a different electronic circuit board or stack within the housing 33 of the infusion pump device 30. The sensor element (element 34) and associated PCB 41 (or electronic component stack) are located within the infusion pump device 30, in sufficient proximity to the reservoir receptacle 32 for detection or other interaction with the magnet (element 42), when the cap 4 (or base/reservoir/cap unit) is installed within the reservoir receptacle 32.

In the embodiment in FIG. 4E, the magnet (element 42) may be affixed to or otherwise integrated into the housing of the cap 4, as described herein. The magnet (element 42) is selected to have sufficient strength and magnetization, such that a magnetic field created by the magnet (element 42) can be detected and, in particular embodiments, measured by the sensor element (element 34). The sensor element (element 34) may be contained within the housing 33 of the infusion pump device, at a location sufficiently proximal to the cap 4, to detect or otherwise interact with the magnet (element 42). In particular embodiments, the sensor (element 34) and associated electronics (e.g., electronics 60 in FIG. 5) are activated during an installation or setup process in which a new cap 4 (or base/reservoir/cap unit) is installed in the infusion pump device 30.

In such embodiments, the sensor (element 34) or a separate dedicated sensor (not shown) may be configured to detect installation activities (such as, but not limited to, an insertion of a cap 4 (or base/reservoir/cap unit) into the reservoir receptacle) or an activation of a designated manual operator (e.g., manually activated by the user during setup). Upon detection of an installation activity, the sensor (element 34) and associated electronics are activated to poll or read continuously or intermittently, to seek a magnetic field or signature from a magnet (element 42). Upon detection (or other interaction) with a magnet (element 42), the sensor element (element 34) and associated electronics may be configured to read magnetic field information to determine one or more of a presence, connection state, position, or other detectable parameter associated with the cap 4 (or base/reservoir/cap unit).

Thus, in particular embodiments, the infusion pump device 30 may be configured to have a useful life that is significantly greater than the useful like of the cap 4 (or base/reservoir/cap unit). In such embodiments, a cap 4 (or base/reservoir/cap unit) may be installed, replaced with a new or different cap (or base/reservoir/cap unit), or re-installed in the infusion pump device 30, as appropriate. Particular embodiments are configured such that electronics (e.g., electronics 60 in FIG. 5) can determine and differentiate between different caps (or base/reservoir/cap units), including different models or different types of caps (or base/reservoir/cap units), and/or can authenticate a cap (or base/reservoir/cap unit) as an authorized component (e.g., authorized for use with the infusion pump device 30, and/or user). Particular embodiments are configured such that information read by the sensor element (element 34) may be processed by electronics (e.g., electronics 60 in FIG. 5) to detect a connected state of the cap 4 (or base/reservoir/cap unit) with the infusion pump device 30. Such information may also be used to detect a dislodgment or other undesired movement of the cap 4 (or base/reservoir/cap unit) relative to the reservoir receptacle 32 of the infusion pump device 30, for example, caused by rigorous exercise or other rigorous motion of the user. A graph showing an example of a plot of magnetic flux density as a function of engagement angle of a cap 4 relative to the axis A is shown in FIG. 4F.

Figure 4F:
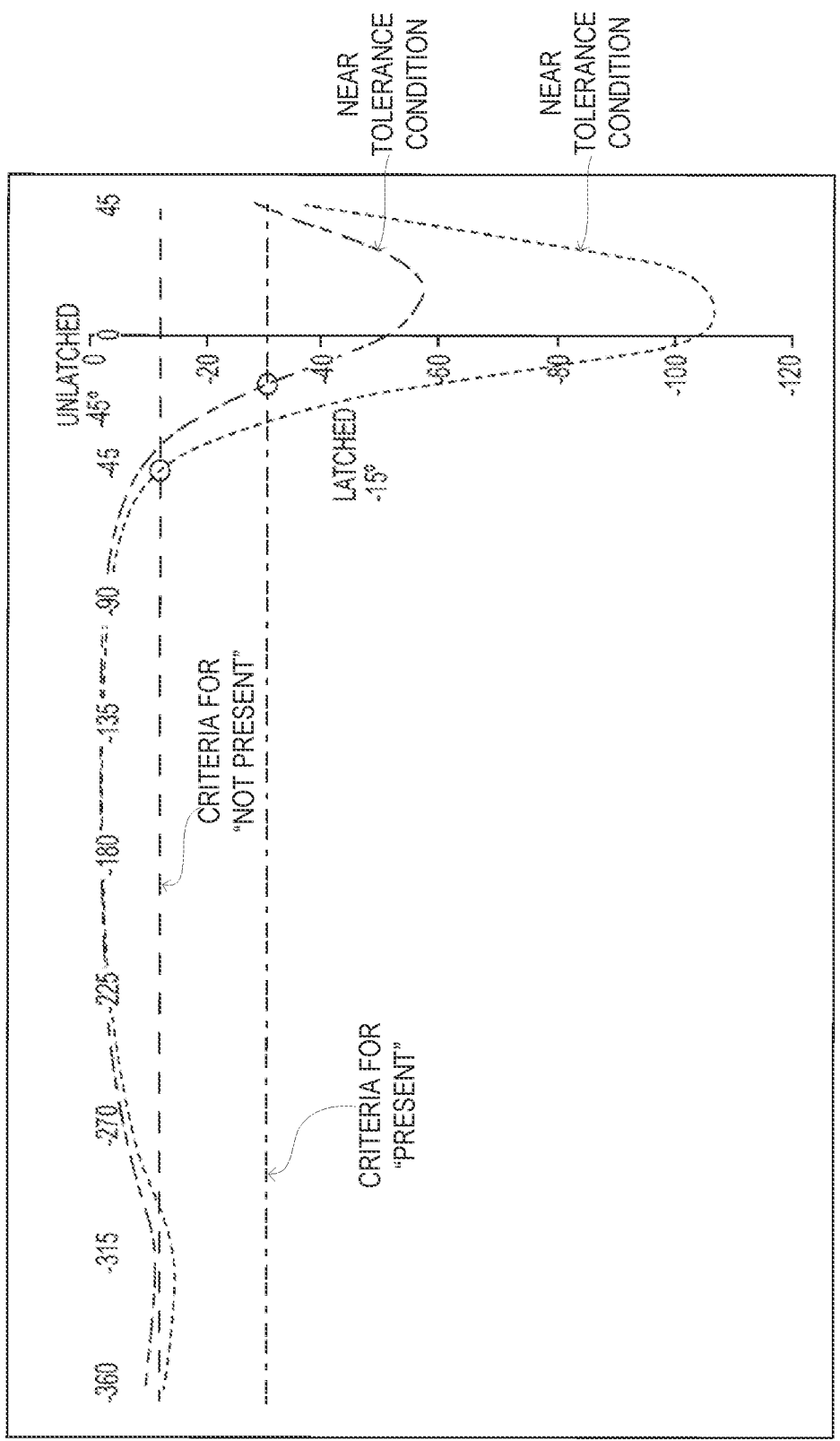
FIG. 4F is a chart plotting an example of a magnetic flux density as a function of an engagement angle of a cap in an infusion pump device of FIG. 4E.

FIG. 4F is a graph showing how a magnet in the cap is detected as latched and unlatched through an angular rotation of 360 degrees. It uses a simple arrangement with one detector 34 and one magnet 42 essentially as shown in FIGS. 1 to 3. The correct angular position of the cap is detected based on the measured magnetic field strength at the detector. The upper horizontal broken line represents the field strength to indicate no latching (e.g., the cap is not in the right position or is loose). The lower broken horizontal line indicates the field strength where latching is present (e.g., the cap is in the right position). The two curves represent the magnet strength based on design tolerances that locate the magnet closer or further from the sensor. The upper curve represents what would be expected if tolerances stack up to keep the magnet far from the sensor. The lower curve represents when the tolerances stack up to bring it closest to the sensor. Both curves show that even with tolerances, detection of the correct position and latching can be determined, since both curves exceed the "present" or reservoir IN criteria close to 0 degrees.

In particular embodiments, one or more detectable parameters of the magnetic field of a magnet (element 42) may be associated with one or more characteristics of the cap 4 (or other component of the base/reservoir/cap unit), infusion set, infusion pump device 30, user. For example, the shapes, sizes, grades, materials, direction of magnetization, and other properties of magnets (elements 42) can influence detectable parameters of the magnetic fields provided by such magnets (elements 42). Accordingly, embodiments are configured such that the output of the sensor (element 34) is dependent on one or more detectable parameters of the magnetic field of the magnet (element 42). In particular embodiments, the one or more detectable parameters of the magnet (element 42) on a given cap 4 (or base/reservoir/cap unit) provides a signature that is distinguishable from one or more other magnets (elements 42) on one or more other caps (or base/reservoir/cap unit). Thus, each different cap 4 (or base/reservoir/cap unit) can have a different detectable signature relative to each other cap 4 (or base/reservoir/cap unit). Alternatively, groups or classes of multiple caps 4 (or base/reservoir cap units) can have the same or similar signature as other caps 4 (or base/reservoir/cap units) in the same group or class, but have different detectable signature from one or more (or all) caps (or base/reservoir/cap units) in one or more (or all) other groups or classes.

In one embodiment, a property of the magnet (element 42) that is selected or configured for detection is the magnet grade. In such embodiments, different caps 4 (or base/reservoir cap units), or different groups of caps 4 (or base/reservoir cap units) can have a different grade of magnet than other caps 4 (or base/reservoir/cap units) or other groups of caps 4 (or other groups of base/reservoir/cap units). For example, caps 4 (or base/reservoir/cap units) having respectively different grades of magnets (elements 42) can provide signatures that are the same shape, but respectively different in amplitudes. Thus, in particular embodiments, one or more characteristics of the cap 4 (or base/reservoir/cap unit), infusion set, infusion pump device, or user is associated with a grade of magnet (element 42) or its associated amplitude signature.

In another embodiment, a property of the magnet (element 42) that is selected or configured for detection is the magnet shape and/or the magnet size. In such embodiments, different caps 4 (or base/reservoir cap units), or different groups of caps 4 (or base/reservoir cap units) can have a different magnet shapes or sizes than other caps 4 (or base/reservoir/cap units) or other groups of caps 4 (or other groups of base/reservoir/cap units). For example, caps 4 (or base/reservoir/cap units) having respectively different sizes or shapes of magnets (elements 42) can provide signatures that are different directions, shapes and/or amplitudes. Thus, in particular embodiments, one or more characteristics of the cap 4 (or base/reservoir/cap unit), infusion set, infusion pump device, or user is associated with a shape or size of magnet (element 42) or its associated amplitude signature.

Figure 4G:
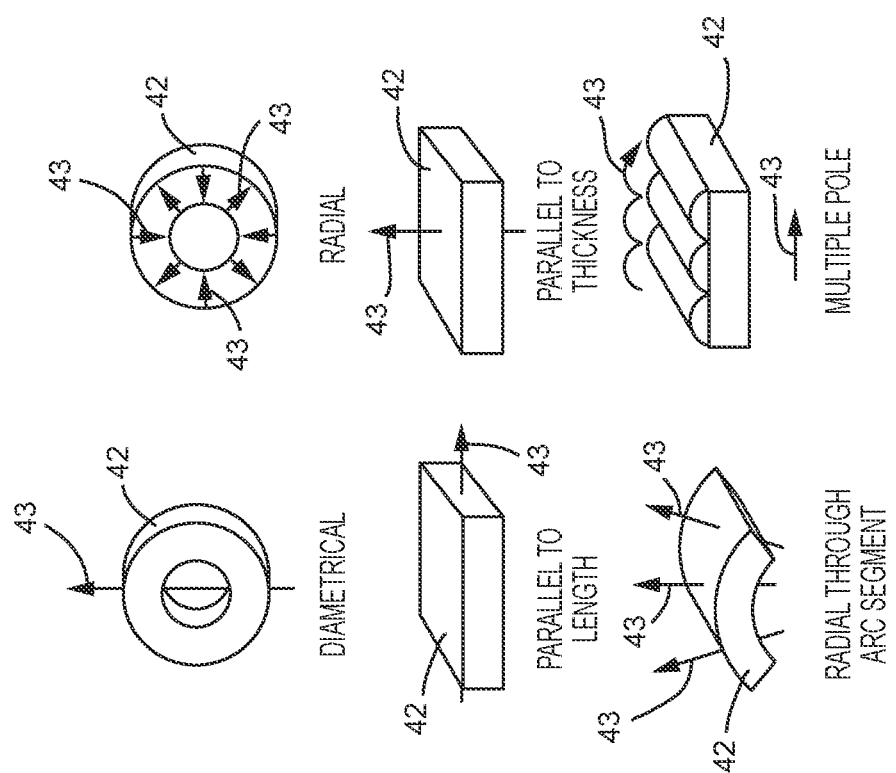
FIG. 4G are schematic diagrams of magnet shapes and magnetic field directions.

Examples of different magnet shapes that provide different magnet field directions or shapes are shown in FIG. 4G. Particular embodiments employ one or more magnets (elements 42) having one or more shapes as shown in FIG. 4G. In other embodiments, a magnet (element 42) may have a different shape, with respect to those shown in FIG. 4G. The shape and configuration of the magnet can determine the polarity or field direction or shape, as represented by the arrows 43 in FIG. 4G, where, for example, the arrow head is on a side of the magnet (element 42) that represents a north magnetic pole. Thus, for example, the magnet configurations in FIG. 4G can provide a detectable field direction or shape that is diametrical, radial, parallel to the length of the magnet (element 42), parallel to the thickness of the magnet (element 42), radial through an arc segment, or a combination of multiple poles. In particular embodiments, the sensor (element 34) and associated electronics (e.g., electronics 60 in FIG. 5) are configured to detect and differentiate one magnet (element 42) from another, based, at least in part, on the direction or shape of the magnetic field signature. Thus, in particular embodiments, one or more characteristics of the cap 4 (or base/reservoir/cap unit), infusion set, infusion pump device, or user is associated with a shape of magnet (element 42) and its associated magnetic field direction or shape.

In another embodiment, a property of the magnet (element 42) that is selected or configured for detection is the polarity or magnetic field direction. In particular embodiments, the sensor (element 34) is configured to provide a first output when in detectable presence of a magnet (element 42) having a first field direction, and a second output when in detectable presence of a magnet (element 42) having a second field direction that is opposite to the first field direction. For example, the sensor (element 34) may be configured to detect and differentiate between a magnet having a south facing (seeking) pole and a magnet having a north facing (seeking) pole.

In such embodiments, different caps 4 (or base/reservoir cap units), or different groups of caps 4 (or base/reservoir cap units) can have a different magnet pole directions than other caps 4 (or base/reservoir/cap units) or other groups of caps 4 (or other groups of base/reservoir/cap units). For example, one or more caps 4 (or base/reservoir/cap units) having magnets (elements 42) with north poles directed in a first direction can provide signatures that are detectably different from one or more (or all) other caps 4 (or base/reservoir/cap units) having magnets (elements 42) with south poles directed in the first direction. In such embodiments, different caps 4 (or different base/reservoir/cap units or associated infusion sets) can employ the same magnet shape and size, but arranged in different pole directions. Thus, in particular embodiments, one or more characteristics of the cap 4 (or base/reservoir/cap unit), infusion set, infusion pump device, or user is associated with a pole direction of the magnet (element 42).

Figure 4H:
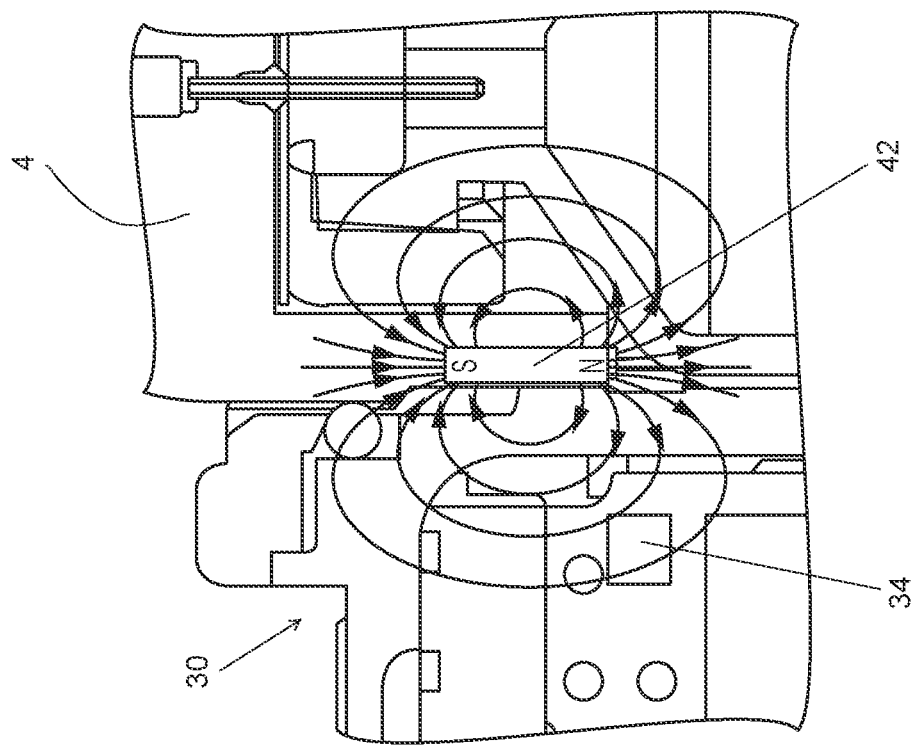
FIGS. 4H and 4I are schematic cross-sectional diagrams of a portion of an infusion pump device on which a cap of FIG. 4C or 4D is installed, with respectively different directed magnetic fields.
Figure 4I:
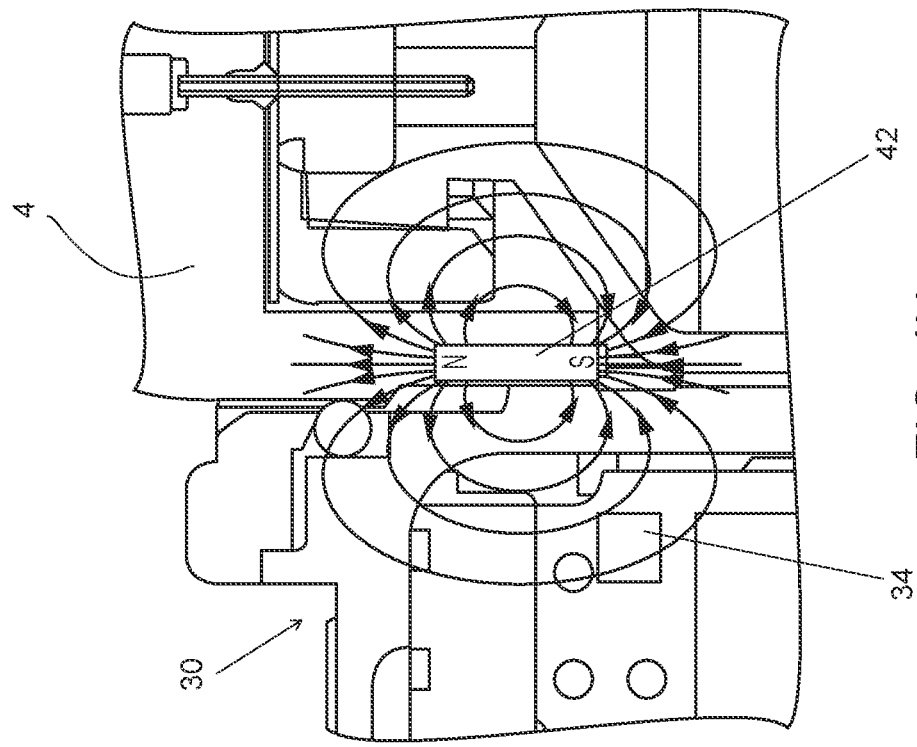

Thus, for example, with reference to the partial cross-section view of the cap 4 (or base/reservoir/cap unit) and the infusion pump device 30 in FIG. 4H, the cap 4 has a magnet (element 42) that is arranged with its north pole facing upward in the drawing. In contrast, the partial cross-section view of the cap 4 (or base/reservoir/cap unit) and the infusion pump device 30 in FIG. 4I shows the cap 4 (or base/reservoir/cap unit) with a magnet (element 42) that is arranged about 180 degrees opposite to the magnet (element 42) in FIG. 4H, such that its south pole is facing upward in the drawing. In other embodiments, the cap 4 (or base/reservoir/cap unit) may include a magnet (element 42) that is arranged with its north pole facing in a selected detectable direction that is less than or more than 180 degrees opposite to the magnet (element 42) in FIG. 4H. As shown by the direction of arrows in FIGS. 4H and 4I, the different orientations of the north pole side of the magnet (element 42) in those drawings provides different magnetic field directions relative to each other. In such embodiments, the sensor element (element 34) is configured to detect and differentiate the direction of the magnetic field.

Accordingly, in particular embodiments, one or more of the shapes, sizes, grades, materials and other properties of magnets (elements 42) provides detectable parameters or a signature that is associated with one or more predefined characteristics of the cap 4 (or other component of the base/reservoir/cap unit), infusion set, infusion pump device 30, user. In particular embodiments a combination of such magnet properties are selected or associated with one more characteristics of the cap 4 (or other component of the base/reservoir/cap unit), infusion set, infusion pump device 30, or user.

Certain embodiments in FIGS. 4C-I include magnets (elements 42) having a particular three-dimensional shape. In other embodiments, one or more magnets (as element 42) is configured in the form of a magnetic strip, a strip of magnetic material, or a strip of material having one or more discrete or continuous magnets along a length dimension of the strip. In particular embodiments, the magnet (element 42) includes a readable strip, similar to magnetic strips employed on credit cards, but embedded with information or codes associated with one more characteristics of the cap 4 (or other component of the base/reservoir/cap unit), infusion set, infusion pump device 30, or user.

Particular embodiments are configured to allow detection of different characteristics of a the cap 4 (or other components of the base/reservoir/cap unit or connected infusion set), based on one or more detected parameters of the magnet (element 42). In certain embodiments, such characteristics may include, but are not limited to, the type or features of the infusion set that is connected to the cap 4. For example, a cap (or base/reservoir/cap unit) may be configured to connect with a variety of different infusion set products (such as, but not limited to the following infusion set products: Quick-Set® infusion set, Silhouette® infusion set, Sure-T® infusion set, Mio® infusion set, or the like). In addition, different infusion sets may be configured with a variety of different feature options for meeting user needs or preferences, such as, but not limited to, tubing length, cannula length and cannula type. In particular embodiments, different infusion sets, features and options may be associated with different respected detectable parameters of the magnet (element 42) and, thus, differentiated based on detected parameters of the magnet (element 42).

The sensor (element 34) in particular embodiments described herein may include one or more Hall effect sensors or other suitable devices, that varies an output voltage in response to changes in a magnetic field. Such sensors can be contained in a suitably sealed package that inhibits passage of dust, dirt, mud or water from the external environment to the sensor electronics. Such sensors can be configured in a surface mount package, in a single in-line package, or other suitable arrangement, for example, mounted on a circuit board within the infusion pump device 30, at a location that is sufficiently adjacent and oriented relative to the magnet (element 42) for proper detection when the cap (or base/reservoir/cap unit) is installed on the infusion pump device 30.

For maximizing sensitivity of a Hall effect sensor, it can be desirable to arrange the magnet (element 42) such that, during detection operations, flux lines of the magnet (element 42) are perpendicular (or generally perpendicular) to a sensing area of the Hall effect sensor, e.g., a defined surface area (or plane) of a semi-conductor material in the sensor. In addition, the size of the magnet (element 42) and its proximity to the sensor (element 34) may be selected for improved detection sensitivity.

In particular embodiments, the magnet (element 42) may be configured in the shape of a segment of an arc, but is magnetized and oriented in a manner to provide higher flux density in a selected direction to accommodate a desired position of the sensor (element 34), or a desired position of a circuit board on which the sensor (element 34) is mounted.

Figure 4J:
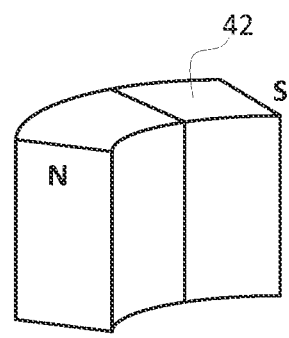
FIGS. 4J and 4K are schematic perspective views of a circumferentially magnetized magnet and arrangement, according to an embodiment of the present invention.
Figure 4K:
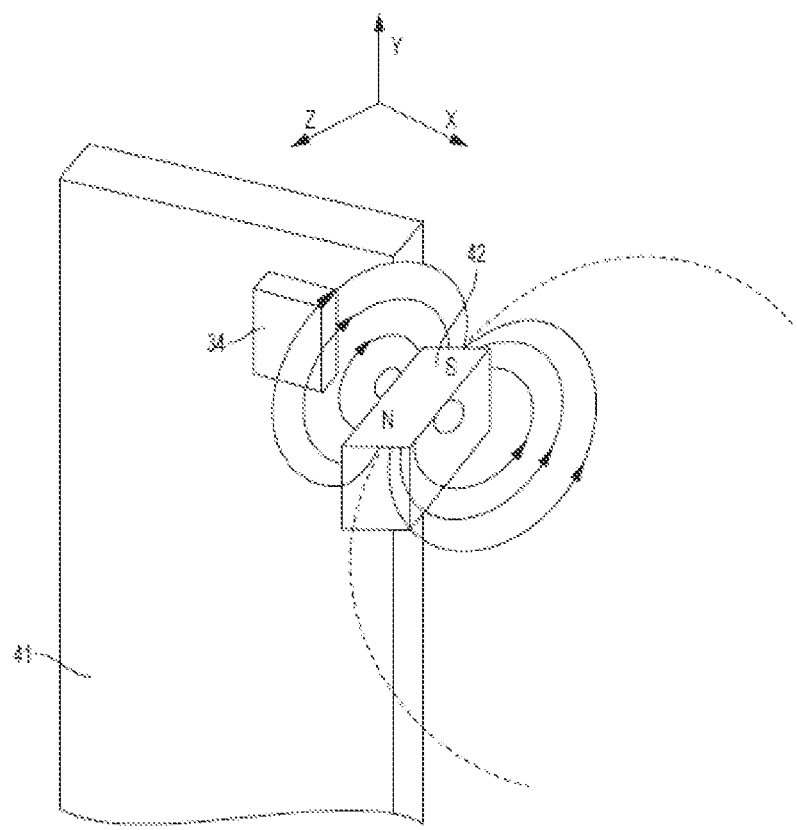

For example, an arc-shaped magnet (element 42) that is magnetized through its circumference is shown in FIG. 4J. The drawing in FIG. 4K shows an arrangement of the magnet (element 42) of FIG. 4J relative to a circuit board (e.g., PCB 41) in an infusion pump device (not shown in FIG. 4K). As shown in FIG. 4K, a Hall effect sensor (element 34) may be arranged with its sensor plane arranged perpendicular (or generally perpendicular) to the magnetic field flux lines produced by the magnet (element 42) of FIG. 4J for maximized sensor output when the cap 4 (or base/reservoir/cap unit) (not shown in FIG. 4K) is in an installed position within the infusion pump device 30. The circumferentially magnetized magnet (element 42) in FIG. 4K provides a relatively high density of flux in the Z-axis direction of the drawing. Accordingly, in the embodiment in FIG. 4K, the sensor plane of the Hall effect sensor (element 34) is arranged parallel to the plane of the surface of the circuit board (e.g., PCB 41) on which the sensor (element 34) is mounted, such that the sensor plane is perpendicular to the Z axis in the drawing.

Figure 4L:
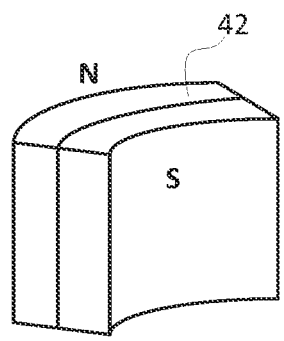
FIGS. 4L and 4M are a schematic perspective view of a radially magnetized magnet and a schematic cross section view of an arrangement of that magnet within a portion of an infusion pump device, according to an embodiment of the present invention.

Another example of an arc-shaped magnet (element 42) is shown in FIG. 4L, where the magnet (element 42) is radially magnetized such that the North pole of the magnet (element 42) faces radially outward, while the South pole of the magnet (element 42) faces radially inward. In further embodiments, a leaded package is used in conjunction with a radially magnetized magnet (element 42), for improved flux direction control.

Figure 4M:
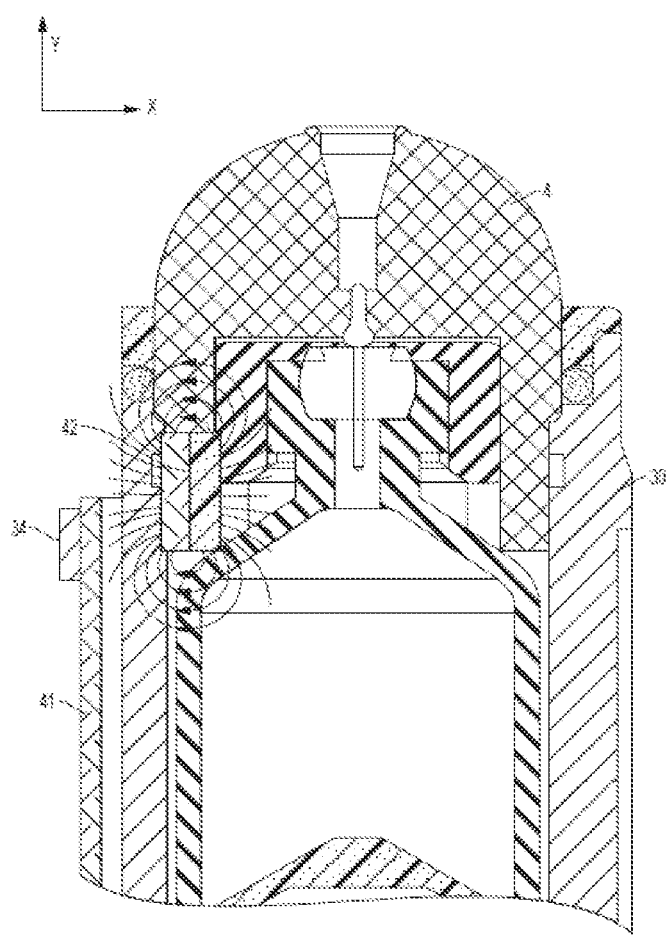

The drawing in FIG. 4M shows an arrangement of the magnet (element 42) of FIG. 4L relative to a circuit board (e.g., PCB 41) in an infusion pump device 30. As shown in FIG. 4M, a Hall effect sensor (element 34) may be arranged with its sensor plane perpendicular (or generally perpendicular) to the magnetic field flux lines produced by the magnet (element 42) of FIG. 4L for maximized sensor output when the cap 4 (or base/reservoir/cap unit) is in an installed position within the infusion pump device 30. The radially magnetized magnet (element 42) in FIG. 4M provides a relatively high density of flux in the X-axis direction of the drawing. Accordingly, in the embodiment in FIG. 4M, the sensor plane of the Hall effect sensor (element 34) is arranged parallel to the plane of the surface of the circuit board (e.g., PCB 41) on which the sensor (element 34) is mounted, such that the sensor plane is perpendicular to the X axis in the drawing.

Figure 4N:
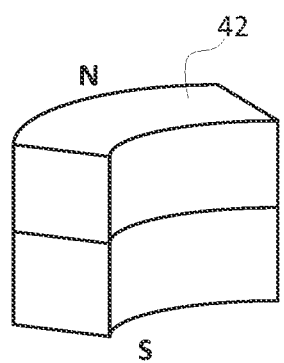
FIGS. 4N and 4O are a schematic perspective view of an axially magnetized magnet and a schematic cross section view of an arrangement of that magnet within a portion of an infusion pump device, according to an embodiment of the present invention.

Another example of an arc-shaped magnet (element 42) is shown in FIG. 4N, where the magnet (element 42) is axially magnetized such that the North pole of the magnet (element 42) faces axially upward in the drawing, while the South pole of the magnet (element 42) faces axially downward in the drawing. In further embodiments, a leaded package is used in conjunction with a radially axially magnet (element 42), for improved flux direction control.

Figure 4O:
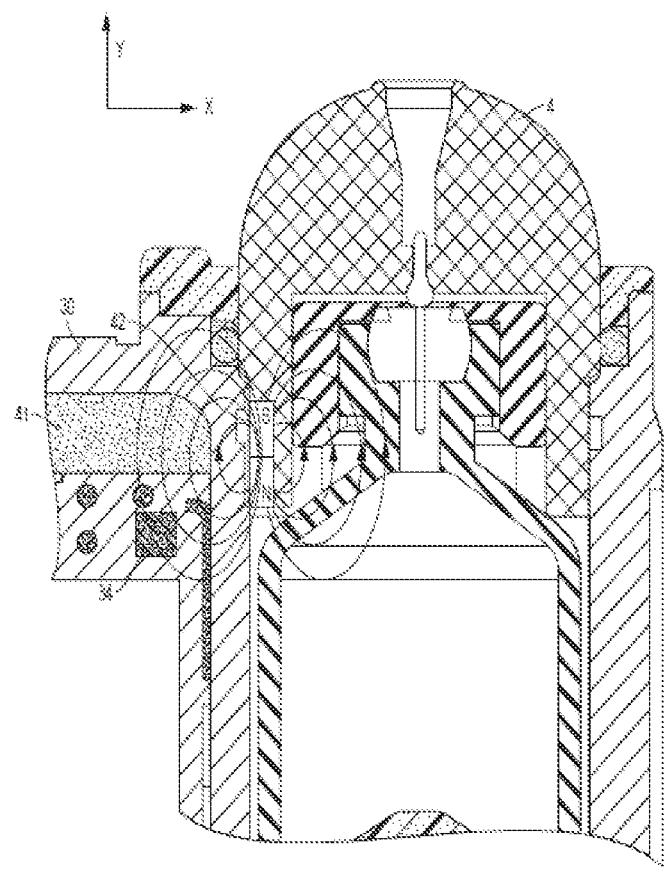

The drawing in FIG. 4O shows an arrangement of the magnet (element 42) of FIG. 4N relative to a circuit board (e.g., PCB 41) in an infusion pump device 30. As shown in FIG. 4O, a Hall effect sensor (element 34) may be arranged with its sensor plane perpendicular (or generally perpendicular) to the magnetic field flux lines produced by the magnet (element 42) of FIG. 4N for maximized sensor output when the cap 4 (or base/reservoir/cap unit) is in an installed position within the infusion pump device 30. The axially magnetized magnet (element 42) in FIG. 4N provides a relatively high density of flux in the Y-axis direction of the drawing. Accordingly, in the embodiment in FIG. 4O, the sensor plane of the Hall effect sensor (element 34) is arranged parallel to the plane of the surface of the circuit board (e.g., PCB 41) on which the sensor (element 34) is mounted, such that the sensor plane is perpendicular to the Y axis in the drawing.

In any of the embodiments of FIGS. 4J-4O, a leaded package may be used in conjunction with the magnet (element 42), for improved flux direction control. Furthermore, in any of the embodiments in FIGS. 4J-4O, the Hall effect sensor (or the circuit board on which the sensor is mounted) may be rotated or otherwise adjusted relative to the orientations shown in FIGS. 4K, 4M and 4O, for improved performance or space considerations within the infusion pump device (or both). In particular embodiments, the Hall effect sensor (element 34) may be mounted on a second board or subassembly (relative to other electronics), for improved flexibility in positioning or orientating the sensor.

Accordingly, in particular embodiments, the magnetization orientation of the magnet (element 42) may be selected (e.g., from among circumferential, radial, axial or other suitable orientations), to accommodate a desired position or orientation of the sensor (element 34) in the infusion pump device 30 (or a desired position or orientation of the circuit board on which the sensor (element 34) is mounted).

In further embodiments, the sensor (element 34) is configured to detect and differentiate between different magnetization orientations (e.g., from among circumferential, radial, axial or other suitable orientations) of magnets (elements 42) on different caps 4 (or base/reservoir/cap units). Thus, in particular embodiments, the orientation or direction of magnetization of the magnet (element 42) relative to a particular orientation and direction of the sensor plane of the sensor (element 34), or of the plane of the circuit board on which the sensor (element 34) is mounted, is a detectable parameter that can be associated with one or more characteristics of the cap 4 (or the base/reservoir/cap unit or the infusion set connected to the cap 4).

Figure 4P:
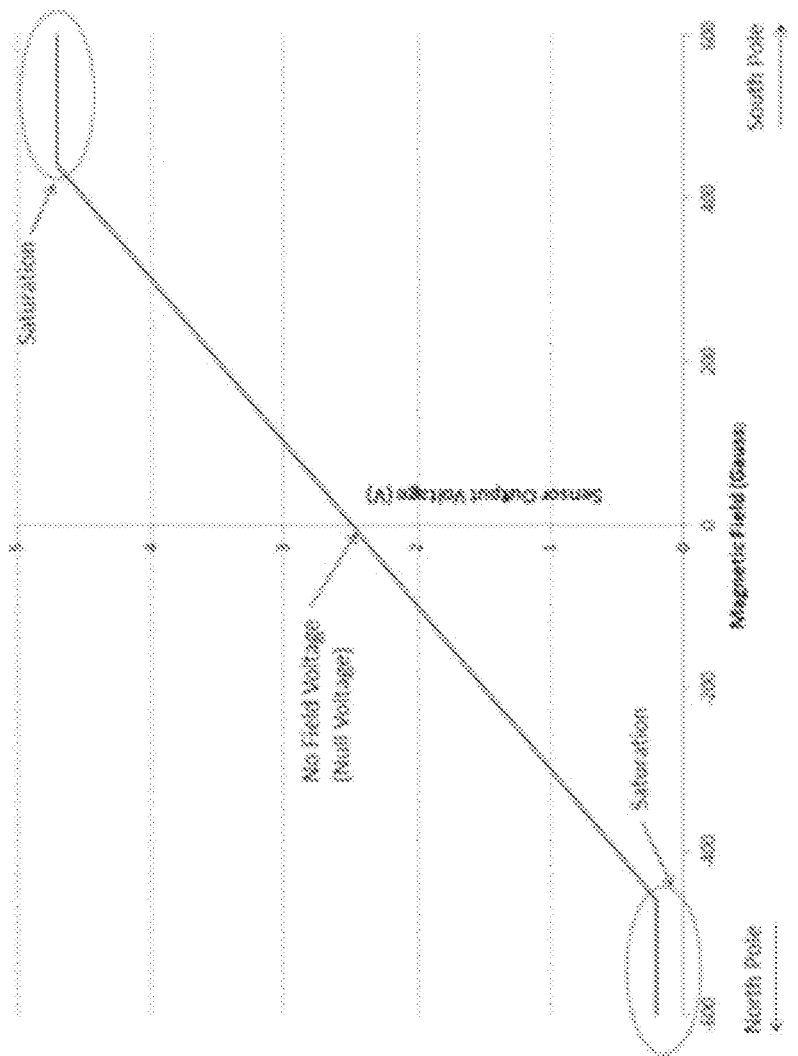
FIG. 4P is a graph representing an example of a linear response output of a linear Hall effect sensor.

A Hall effect sensor can operate as an analog transducer, directly returning a voltage that is proportional to the applied magnetic field, and can be sensitive to both positive and negative fields. A linear Hall effect sensor can provide a linear response as shown in the graph of FIG. 4P, by applying a fixed offset (null voltage) to the output of the sensor when no magnetic field is present. When a positive field is present, the voltage output increases above the null voltage until the output of the sensor is saturated. Similarly, when a negative field is present, the voltage output is decreased below the null voltage until the output of the sensor is saturated. Thus, according to particular embodiments, the null voltage and sensor (element 34) output may be used to differentiate between a South pole and a North pole of a magnet (element 42) and, thus, to differentiate a radially magnetized magnet (element 42) having a North pole facing radially outward (as shown in FIG. 4L), from a radially magnetized magnet (element) having a South pole facing radially outward (not shown). Accordingly, a cap 4 (or base/reservoir/cap unit) having a magnet (element 42) with a North pole facing radially outward may be detectably differentiated from another cap 4 (or base/reservoir/cap unit) having a magnet (element 42) with a South pole facing radially outward. Thus, in particular embodiments, the orientation or direction of magnetization is a detectable parameter that can be associated with one or more characteristics of the cap 4 (or the base/reservoir/cap unit or the infusion set connected to the cap 4). For example, characteristics associated here may be a 7-day infusion set vs. a 3-day infusion set, or a DUO® set (combination infusion and sensor set) vs. a non-DUO® set. Moreover, due to the linear response detected by a Hall effect sensor, whether a cap 4 (or base/reservoir/cap unit) is properly rotated and seated/secured into the infusion pump device also may be determined as a user installs a cap 4 by detecting the linear response from the null voltage state (e.g., beginning of installation) to a saturation voltage state (properly seated/secured). The progress of installation (e.g., the cap 4 is 10%, 28%, 65%, 90%, etc. inserted/rotated away from full/complete installation) or just an incomplete installation status/loose cap may be detected along the linear response between the null voltage and the saturation voltage.

Figure 4Q:
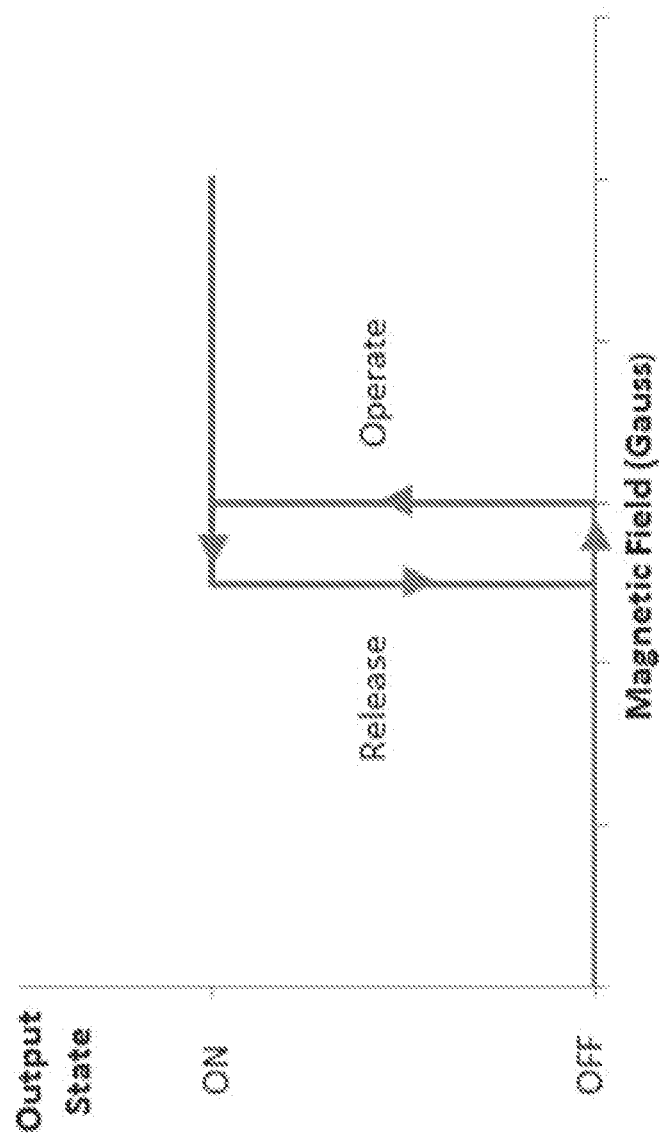
FIG. 4Q is a graph representing an example of an output of a digital Hall effect switch sensor with hysteresis.

In further embodiments, a Hall effect sensor (element 34) includes or is coupled with electronic circuitry that allows the sensor to operate with digital (on/off) switch modes as a digital Hall effect sensor. Such electronic circuitry may be in or associated with an electronic circuit connected with the sensor (element 34) as described with reference to FIG. 5, and may include a Schmitt trigger circuit connected to the output of the sensor (element 34). As shown in FIG. 4Q, a hysteresis may be provided in the switching operation, to avoid bouncing between on and off states. In such embodiments, the magnetic field on the sensor (element 34) increases as a magnet (element 42) on a cap 4 or base/reservoir/cap unit is moved into proximity of the sensor (element 34) during or upon installation of the cap 4 (or base/reservoir/cap unit) in the infusion pump device 30. However, the output does not change until the operating point is exceed and the sensor is switched to an on state. Further increases in the magnetic field beyond the operate point does not affect the sensor output. If the magnet field is decreased below the operate point (e.g., as the magnet (element 42) is moved away from the sensor (element 34)), the sensor output will not be affected until a release point is reached, at which the sensor is switched to an off state.

A digital Hall effect sensor (element 34) according to particular embodiments may include a unipolar sensor that employs a single polarity to both operate and release, as the magnetic field moves in or out of range (e.g., as the magnet (element 42) is moved toward or away from the sensor (element 34)). Such unipolar can be configured to be sensitive to one of either a North magnetic pole or a South magnetic pole.

A digital Hall effect sensor (element 34) according to further embodiments may include an omnipolar sensor that operates with either a North magnetic pole or a South magnetic pole. Such omnipolar sensors can be turned On when in a magnetic field of sufficient strength and remains on until the magnetic field is removed. With an omnipolar sensor, the magnet (element 34) may be mounted with either the North pole or the South pole facing outward, which can simplify manufacturing processes.

Yet further embodiments employ a bipolar digital Hall effect sensor (element 34) that operates to turn On (from an Off state) when in the presence of a sufficiently strong magnetic field of a first polarity (such as, but not limited to South), and then to turn Off (from an On state) when in the presence of a sufficiently strong magnetic field of a second polarity (such as, but not limited to North). In other embodiments, a bipolar digital Hall effect sensor (element 34) is employed to discriminate between North and South poles based on a detected magnetic field, to determine the polarity direction of a magnet (element 42) in the range of the sensor (element 34). Thus, in particular embodiments, bipolar digital Hall effect sensors (elements 34) are employed to provide the capability to differentiate between different infusion sets or other characteristics of the cap 4 (or of the base/reservoir/cap unit or the infusion set connected to the cap 4). For example, a cap 4 (or base/reservoir/cap unit) having a magnet (element 42) that has a first polarity direction (such as, but not limited to North facing upward or outward) may include one or more first predefined characteristics (such as, but not limited to, a first type of infusion set), while a cap 4 (or base/reservoir/cap unit) having a magnet (element 42) that has a second polarity direction (such as, but not limited to South facing upward or outward) may include one or more second predefined characteristics different from the first predefined characteristic (such as, but not limited to, a second type of infusion set that is different from the first type).

In further embodiments, the sensor (element 34) described herein may include one or more Magneto-Resistive (MR) or Anisotropic Magneto-Resistive (AMR) sensors or other suitable devices that employ a paramagnetic material. Embodiments of such MR or AMR sensors may be arranged in a Wheatstone Bridge (or series of Wheatstone Bridges), to sense changes in the resistance of the paramagnetic material resulting from an incident magnetic field. In particular embodiments, such sensor arrangements may provide a maximum resistance value when the direction of the current is parallel to an applied magnetic field, providing a null or zero output voltage. In further embodiments, such devices may provide an output voltage that varies with the direction of the incident magnetic field, such that an incident angle of the magnetic field can be detected and differentiated. In such embodiments, the magnetic field incident angle can be a detectable parameter that is associated with one or more predefined characteristics of the cap 4 (or the base/reservoir/cap unit or the infusion set connected to the cap 4) that carries the magnet (element 42) producing the incident field.

Alternatively, or in addition, an MR or AMR sensor (element 34) can detect and differentiate between different magnitudes of incident magnetic fields. In such embodiments, the magnetic field magnitude can be a detectable parameter that is associated with one or more predefined characteristics of the cap 4 (or the base/reservoir/cap unit or the infusion set connected to the cap 4) that carries the magnet (element 42) producing the incident field.

In particular embodiments, an MR or AMR sensor (element 34) is connected to operate with digital (on/off) switch modes, similar to the digital Hall effect sensor embodiments described above. However, for maximizing sensitivity of a MR or AMR sensor, it can be desirable to arrange the magnet (element 42) such that, during detection operations, flux lines of the magnet (element 42) are in or parallel to (or generally parallel to) a sensing area of the sensor, e.g., a defined surface area (or plane) of a paramagnetic material in the MR or AMR sensor. For example, an AMR sensor (element 34) may be arranged on a planar surface of a circuit board that faces similar to the direction of the circuit board 41 in FIG. 4O.

Figure 4R:
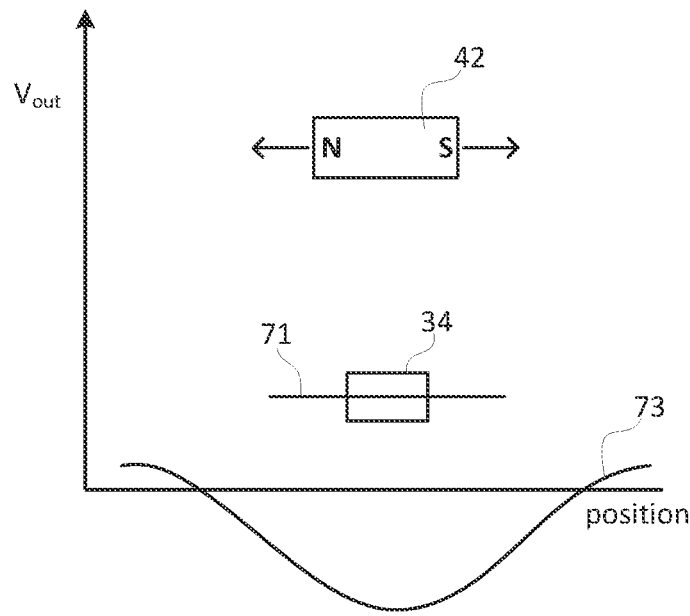
FIGS. 4R and 4S are graphs, each representing an example of an output of an AMR sensor upon relative movement of an adjacent magnet.
Figure 4S:
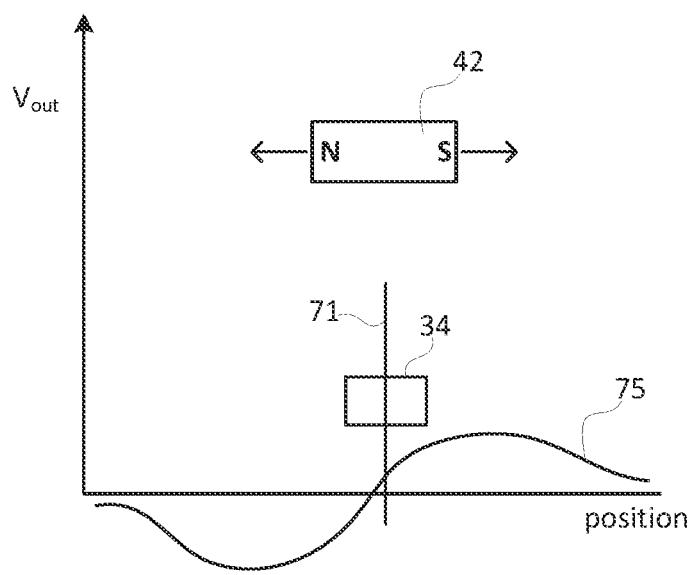

FIGS. 4R and 4S are graphs representing examples of outputs of an AMR sensor (element 34) upon movement of the magnet (element 42) relative to the sensor (element 34). With reference to FIGS. 4R and 4S, the sensitive axis 71 of the MR or AMR sensor (element 34) can be arranged, relative to the position and orientation of the magnet (element 42) when the cap 4 (or base/reservoir/cap unit) (not shown in FIGS. 4R and 4S) is in an installed position within the infusion pump device 30, to accommodate desired sensitivity and operation. For example, by orienting the MR or AMR sensor (element 34) with its sensitive axis 71 parallel to the direction of magnetization of the magnet (element 42), as shown in FIG. 4R, the magnetic field is nearly perpendicular to the sensitive axis 71 when the relative position of the magnet (element 42) and the sensor (element 34) is such that a pole of the magnet (element 42) is near the sensor (element 34).

As relative motion of the magnet (element 42) and the sensor (element 34) occurs in the direction of the sensitive axis 71, the output of the sensor (element 34) changes toward a maximum output level, where the maximum output is provided when the magnet (element 42) is positioned such that the sensor (element 34) is at the midpoint between the North and South poles of the magnet (element 42). The U-shaped curve 73 in FIG. 4R represents an output voltage level of the MR or AMR sensor (element 34) having a sensitive axis 71 that is parallel to the direction of magnetization of the magnet (element 42), as the relative position of the magnet (element 42) and the sensor (element 34) changes in the direction of the sensitive axis 71 of the sensor. Such an output response can be employed, for example, to provide a presence detection operation, in which the detection of a voltage output as shown in FIG. 4R is associated with a determination that a cap 4 (or base/reservoir/cap unit) is in an installed position within the infusion pump device 30.

Alternatively, by orienting the MR or AMR sensor (element 34) with its sensitive axis 71 perpendicular to the direction of magnetization of the magnet (element 42), as shown in FIG. 4S, the sensor output differentiates between the North and South poles of the magnet (element 42). Accordingly, an embodiment as shown in FIG. 4S can be employed for detection of the presence of the magnet (element 42), as well as the particular polar orientation of the magnet (element 42), when the cap 4 (or base/reservoir/cap unit) is in an installed position within the infusion pump device 30.

For example, with reference to the arrangement in FIG. 4S, as the relative position of the magnet (element 42) and the sensor (element 34) is such that the North pole of the magnet (element 42) is located near the sensor (element 34), the magnetic field is nearly aligned with or parallel to the sensitive axis 71 of the sensor (element 34), such that the sensor output is maximized. As the relative position of the magnet (element 42) and the sensor (element 34) change such that the sensor (element 34) is located at the midpoint between the two poles of the magnet (element 42), the magnetic field is nearly perpendicular to the sensitive axis 71 of the sensor (element 34), resulting in a null voltage output. As the relative position of the magnet (element 42) and the sensor (element 34) change such that the sensor (element 34) is located near the South pole of the magnet (element 42), the magnetic field of the magnet (element 42) is again aligned with the sensitive axis 71 of the sensor (element 34), but in the opposite direction of the sensitive axis, such that the sensor output becomes minimum. The S-shaped curve 75 in FIG. 4S represents an output voltage level of the MR or AMR sensor (element 34) having a sensitive axis 71 that is perpendicular to the direction of magnetization of the magnet (element 42), as the relative position of the magnet (element 42) and the sensor (element 34) changes in the direction of the sensitive axis 71 of the sensor. Accordingly, the sensor output can be employed for detection of the presence of the magnet (element 42), as well as the particular polar orientation of the magnet (element 42), when the cap 4 (or base/reservoir/cap unit) is in an installed position within the infusion pump device 30.

Similar arrangements and outputs can be described for Hall effect sensors (as element 34), as described above. However, an S-shaped curve similar to curve 75 in FIG. 4S would be produced with a Hall effect sensor having a sensitive axis arranged parallel to the direction of magnetization of the magnet (element 42), while a U-shaped curve similar to curve 73 in FIG. 4R would be produced with a Hall effect sensor having a sensitive axis arranged perpendicular to the direction of magnetization of the magnet (element 42).

According to further embodiments of the present invention, a compass-type sensor element (such as a magnetometer) may be utilized in place of, or in addition to, the sensor element (element 34) in the infusion pump device 30. The compass-type sensor element may be one used popularly in mobile phones that provide compass functionality to the mobile phone via a Compass App, such as in the APPLE® IPHONE®. The compass-type sensor element may be configured to interact with a compass sensor detectable feature element, such as, but not limited to a magnet (element 42), a concave or circular (magnetic/metallic) disk, or any suitable component or shape or combination thereof that produces a magnetic field that acts as an "Earth" to the compass-type sensor element, such that depending on the orientation of the compass sensor detectable feature element that is arranged on the cap 4 (and/or base, reservoir, tubing, etc.), a resolution of 360 degrees, finer or coarser, may be possible. Such embodiments can provide further ways to differentiate between various caps 4 (and/or base, reservoir, tubing, etc.) that may be available to the user and automatically detectable by the infusion pump device 30.

In particular embodiments, detectable resolutions (degrees or ranges of degrees) can be parameters that are associated with different characteristics of the cap 4 (or other components of the base/reservoir cap unit or connected infusion set), where such associations can be stored in electronic memory and employed by processing electronics (such as, but not limited to memory 66 and processing electronics 62 of electronic circuit 60) as described below with respect to FIGS. 5 and 6. For example, associations of different resolution degrees with different tubing length (for tubing 52 of the infusion set 50) can be stored such that detecting a cap 4 with a 360-degree reading may indicate that the cap has a 7-inch tubing attached thereto, and detecting a cap 4 with a 90-degree reading may indicate that the cap 4 has a 12-inch tubing attached thereto, while detecting a cap 4 with a 180-degree reading may indicate that the cap 4 has an 18-inch tubing attached thereto. Other embodiments may employ other suitable predefined relationships between resolution degrees and tubing length (or other characteristic of the cap 4 or other components of the base/reservoir cap unit or connected infusion set).

Once the infusion pump device 30 detects the tubing length, the infusion pump device 30, for example, may automatically set the priming sequence for the detected tubing length (and/or perform one or more other predefined tasks that depend or relate, at least in part, to the detected tubing length). Such embodiments can further automate infusion media delivery (such as, but not limited to insulin delivery), thus making therapy easier for the user.

In particular embodiments, the sensor (element 34) includes an AMR angle sensor that is configured to detect one or more magnetic field angles. For example, the sensor (element 34) may include an AMR angle sensor having dual Wheatstone bridges that are offset from each other by 45°. Such embodiments may be configured to detect the angle of orientation of the magnet (element 42) in the cap 4 (or base/reservoir/cap unit) relative to the sensing plane of the sensor (element 34).

Referring briefly back to FIGS. 4H and 4I a magnet 42 is shown with its North/South direction aligned vertically as shown in those Figures, i. e. parallel to the axis of the cap 4. Only one item of information can be carried by the positioning of the magnet as there are only two possible orientations. The first orientation has the north seeking pole uppermost i. e. facing outwardly with respect to the reservoir and up as shown in FIG. 4H, and the second is where the north seeking pole faces downwardly as shown in FIG. 4I i. e. towards the reservoir. A convenient implementation of this "upright" alignment of the magnet i. e. the alignment with the magnet parallel to the cap axis is that shown in FIGS. 4C and 4D.

If more information is to be conveyed it is proposed to mount the magnet within the cylindrical outer wall of the cap such that its field (North-South direction) is at an angle with respect to the axis of the cap. In other words at an angle with respect to the direction of the cylindrical wall itself such as to lie on a notional helix running around the wall. As there are a large number of possible angular orientations, a greater amount of information can be conveyed by the selection of the angle. This can be implemented in two possible ways. Either a bar magnet can actually be mounted at an angle within the cylindrical surface of the cap or a piece of magnetizable material can be mounted vertically aligned within the cylindrical wall of the cap such as shown in FIGS. 4C and 4D, and then magnetized at the desired angle.

Figure 4T:
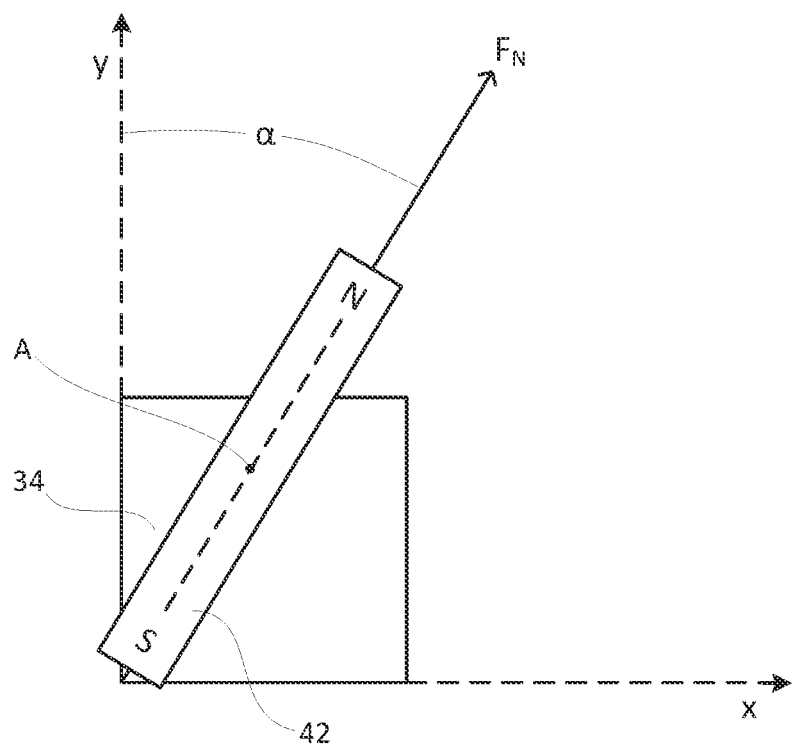
FIGS. 4Ta-4Td are graphs, each representing a magnet angle relative to an AMR sensor.
Figure 4T:
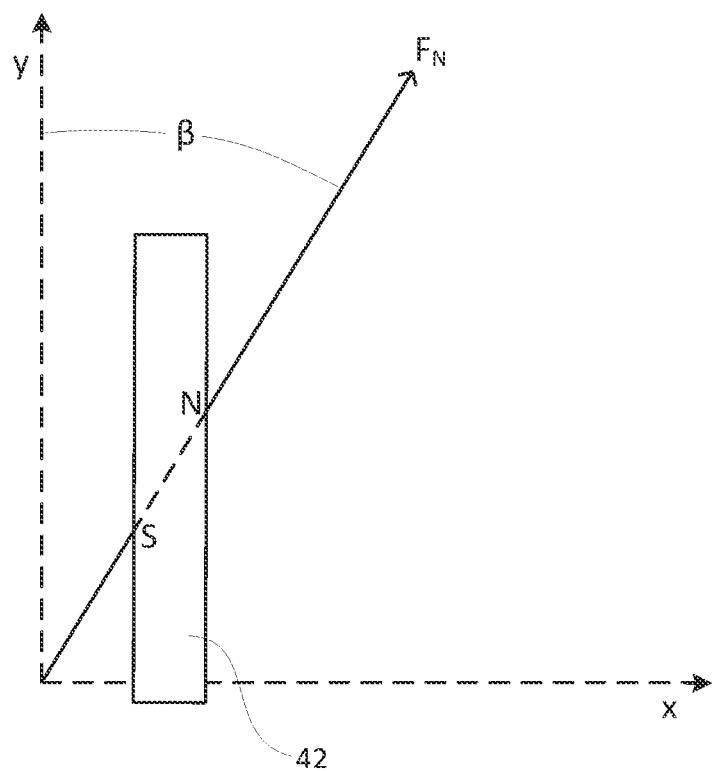
Figure 4T:
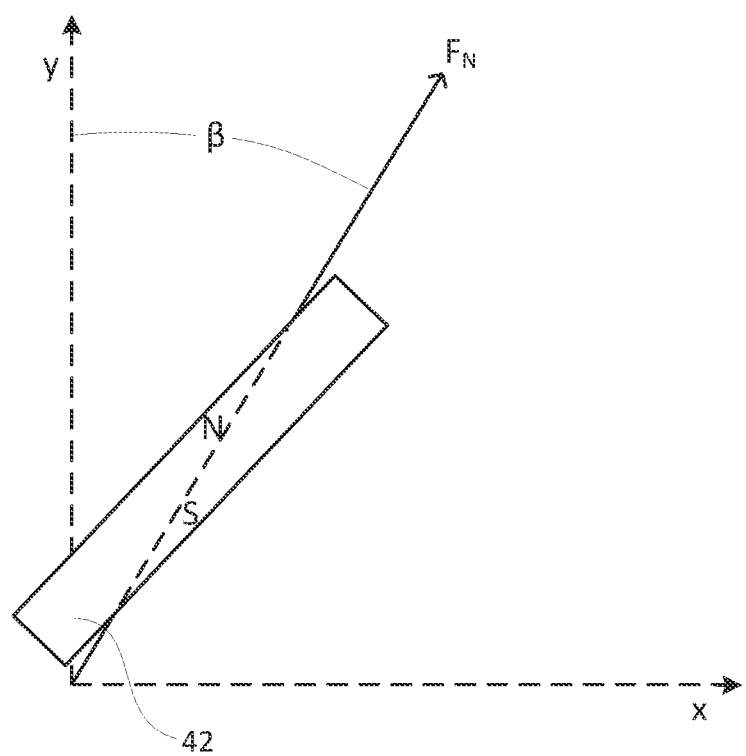
Figure 4T:
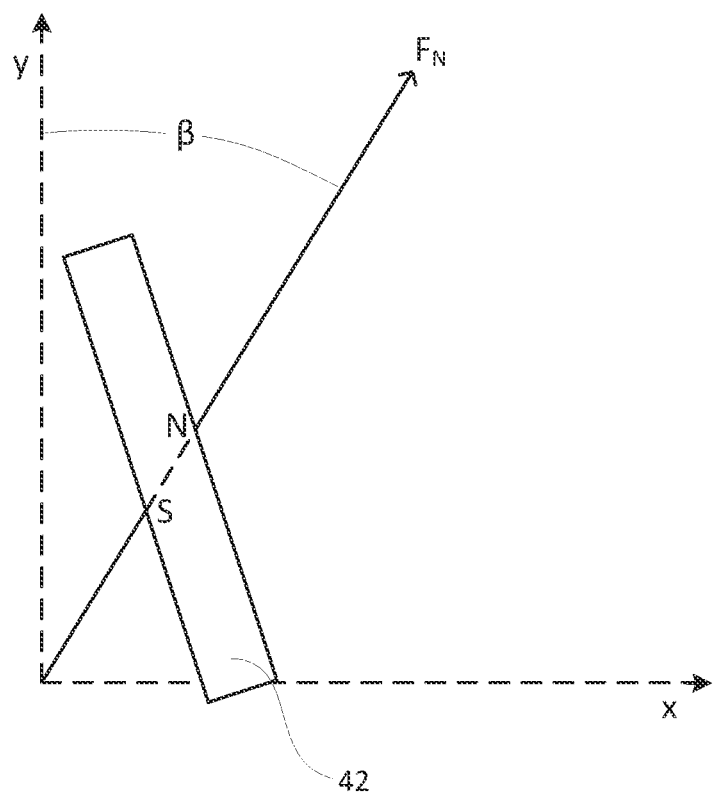

In the embodiment illustrated in FIGS. 4Ta to 4Td the angle of the magnetic field is sensed by an AMR angle sensor 34 placed in the pump immediately beside the reservoir receptacle. The amount of information that can be conveyed is only dependent on the resolution of the AMR angle sensor.

An example of a commercially available AMR angle sensor is the ADA 4571 manufactured by Analog Devices of 1 Technology Way, P.O. Box 9106, Norwood, Massachusetts 02062-9106, United States of America. This device is an integrated AMR angle sensor and signal conditioner.

An AMR angle sensor typically contains dual Wheatstone bridges that are offset by 45° and generate a quadrature output (sine and cosine) signals. When a simple dipole bar magnet is rotated about a mid-point between its north and south poles in a plane parallel to the surface of the chip, the chip will deliver two sinusoidal signals, one following a cos $(2\alpha)$ and the second following a sin $(2\alpha)$ function, $\alpha$ being the angle between the sensor axis and the direction of the field created by the bar magnet. The active area of a single sensor gives an available angle of 180 degrees (to increase that requires an increase in the number of sensors). Thus using an AMR angle sensor the direction of a magnetic field can be measured electrically by taking the bridge outputs and solving for angle $\alpha$. If the sine output is $V_{SIN}$, and the cosine output is $V_{COS}$, the angle $\alpha$ is given by the expression arctan $(V_{SIN}/V_{COS})/2$. By deriving the magnetization angle of the magnet, we can establish whether a specific magnet has been installed into the cap 4 (or base/reservoir/cap unit).

The drawings in FIGS. 4Ta-4V are provided to help explain certain examples of how such angle detection can be carried out with an AMR angle sensor. However, other embodiments may employ other suitable angle sensors or AMR angle sensor configurations. For example, other sensor and magnet arrangements may be employed, where the magnetic field strength is sufficient to saturate the sensor. For example, a working field strength of H>25 kA/m (resp. 40-50 mT) over temperature, ie a high temperature Hall Effect sensor may be employed. However, other suitable field strengths may be employed in other embodiments.

With reference to FIG. 4Ta, an angle α of a magnet (element 42) is shown schematically. With the sensor plane of the sensor (element 34) in the plane of the sheet of FIG. 4Ta and the magnet (element 42) arranged within detectable proximity to the sensor plane, the output of the sensor (element 34) will be defined by the angle α of the magnet (element 42). An output of the sensor (element 34), relative to the angle α of a magnet (element 42) is graphically represented in FIG. 4U, where the sensor (element 34) has dual, saturated-mode Wheatstone bridges that generate quadrature (sine and cosine) signals. By selecting the angle of the magnet (element 42) in FIG. 4Ta about the axis A, the output of the sensor (element 34) would lie on the sinusoid, as represented by the graph in FIG. 4U.

Therefore, the graph in FIG. 4U represents an example output voltage (ΔVn/Vcc) 53 of an AMR angle sensor (as element 34), based on the angle α. Accordingly, by associating the output of the AMR angle sensor (as element 34) with the corresponding angle α, the angle β (the angle between an axis Y (generally parallel to the external side ("ESC") of the cap 4 and/or to the centerline A of the cap 4 shown in FIGS. 1-3) and the north direction ($F_N$) of the magnetic field) of a magnetic field from a magnet (element 42) on a cap 4 (or base/reservoir/cap unit) can be determined. Furthermore, by associating each angle β with a predefined characteristic of the cap 4 (or other component of the base/reservoir/cap unit or infusion set connected thereto), the output of the AMR angle sensor (element 34) can be associated with such predefined characteristic. In this manner, the output of the AMR angle sensor (element 34) can be used to detect a particular characteristic of the cap 4 (or other component of the base/reservoir/cap unit or infusion set connected thereto).

In particular embodiments, such angle sensors can be employed to provide presence detection, magnet angle detection (e.g., associated with predefined characteristics), or both. For example, using an AMR angle sensor or other suitable angle sensor (as element 34), the presence of a cap 4 (or base/reservoir/cap unit) can be detected by providing a magnet of sufficient strength and direction to drive the bridge circuit output of the sensor (element 34) to within a predefined zone, when the cap 4 (or base/reservoir/cap unit) is in a proper or fully installed position within the reservoir receptacle 32 of the infusion pump device. Insufficient field strength in this arrangement would be interpreted as the cap not fully installed. It is also understood that although FIG. 4Ta shows the magnetic field angle α in an x-y plane, the magnetic field angle α is not limited to the x-y plane and can also be set at magnetic field angle α relative to a z axis to provide a three-dimensional magnetic field angle α.

Although a particular embodiment is shown in FIG. 4Ta showing the effect of an angle α, the use of an angled magnetic field at an angle α relative to the sensor 34 is not limited to a bar magnet 42 physically skewed at an angle α. Rather as shown in FIGS. 4Tb-4Td, various configurations and orientations of a magnet (element 42) can be used to provide the angled magnetic field at an angle β relative to an external side ("ESC") of the cap 4 (β is the angle between an axis Y and the north direction ($F_N$) of the magnetic field, where the axis Y is generally parallel to the external side ESC of the cap 4 and/or to the centerline A of the cap 4 shown in FIGS. 1-3). In particular embodiments, the magnetic field is inclined at the angle β relative to the housing (or an external side ESC) of the cap 4, regardless of the shape of the actual magnet 42 to produce an angled magnetic field at the desired angle β.

For instance, in non-limiting embodiments in which the magnet 42 is a bar shaped magnet, the magnetic field would be inclined at an angle relative to the sides and/or ends of the bar shape to produce the desired magnetic field angle β relative to the external side ESC of the cap 4, regardless of the actual physical angle of the bar shaped magnet 42 relative to the cap 4. Traditionally, bar magnets have a field directed outward of the ends of the magnet with no angular deviation. Accordingly, in particular embodiments, the magnet can be of any shape, size and/or orientation, as discussed above and below, as long as it produces a magnetic field at the desired angle β. This can also facilitate manufacturing in embodiments where the material is placed in the cap 4 and then magnetized (after placing the material in the cap) to produce the desired magnetic field at angle β. It is noted that the magnetic field may be non-uniform or distorted, if inclined at an angle β that does not align with the ends of said bar magnet 42 (or if an asymmetrical shaped magnet is used). However, these non-uniformities or distortions need not be severe enough to prevent the sensor 34 from detecting (or correctly determining) the angle β of the magnetic field of the magnet 42 in the cap 4.

In particular embodiments, an angle β between 5° to 85°, 95° to 175°, 185° to 265° or 275° to 355° can provide sufficient ability to detect an angled magnetic field for the magnet 42 in cap 4. If a sufficiently accurate sensor can be used, then the angle β can be between 2.5° to 87.5°, 92.5° to 177.5°, 182.5° to 267.5° or 272.5° to 357.5° to provide sufficient ability to detect an angled magnetic field for the magnet 42 in cap 4. If less accurate sensors are used, the angle β can be between 10° to 80°, 100° to 170°, 180° to 260° or 285° to 350° to provide sufficient ability to detect an angled magnetic field for the magnet 42 in cap 4. The magnetic field may be at any angle within these ranges to provide a sufficient angular alignment and detection of the magnetic field by the sensor 34. Use of the angled magnetic field helps avoid interference from magnetic fields produced by magnet sources having the fields oriented in a planar direction relative to the cap 4 or that are randomly and temporarily near the infusion pump device. It is also understood that although FIGS. 4Tb-4Td show the magnetic field angle β in an x-y plane, the magnetic field angle β is not limited to the x-y plane and can also be set at magnetic field angle β relative to a z axis to provide a three-dimensional magnetic field angle β.

Although the angle β is shown in FIGS. 4Tb-4Td as it relates to the external side ESC of the cap 4, which is generally parallel to the an axis Y (and/or to the centerline A of the cap 4 shown in FIGS. 1-3), it is understood that the external side ESC of the cap 4 is not limited to being generally parallel to axis Y (and/or to the centerline A of the cap 4 shown in FIGS. 1-3). For instance, if the external side ESC of the cap 4 is inclined in one direction (such as, but not limited to, a slight taper towards the top center of the cap or a taper inward toward the base), the angle β can be adjusted to account for this incline to form a new angle β' or still utilized as angle β with reference to the Y axis (and/or to the centerline A of the cap 4 shown in FIGS. 1-3).

In particular embodiments, a single magnet 42 in cap 4 is used. Further differentiation of the cap 4 may be done by selecting and using different magnets each with magnetic fields at different angles β to allow detection of different characteristics as further described below. However, in other embodiments, additional magnets (e.g., 2, 3, 4, 5 or more magnets) may be included in the cap 4, each with their own magnetic field set at a selected angle β. The magnets would then be detected, sequentially, as the cap 4 is rotated into the housing of the infusion pump device to provide a magnetic field sequence that uniquely identifies a characteristic, infusion set or other characteristic of the cap 4 (or base/reservoir/cap unit or associated infusion set).

Figure 4V:
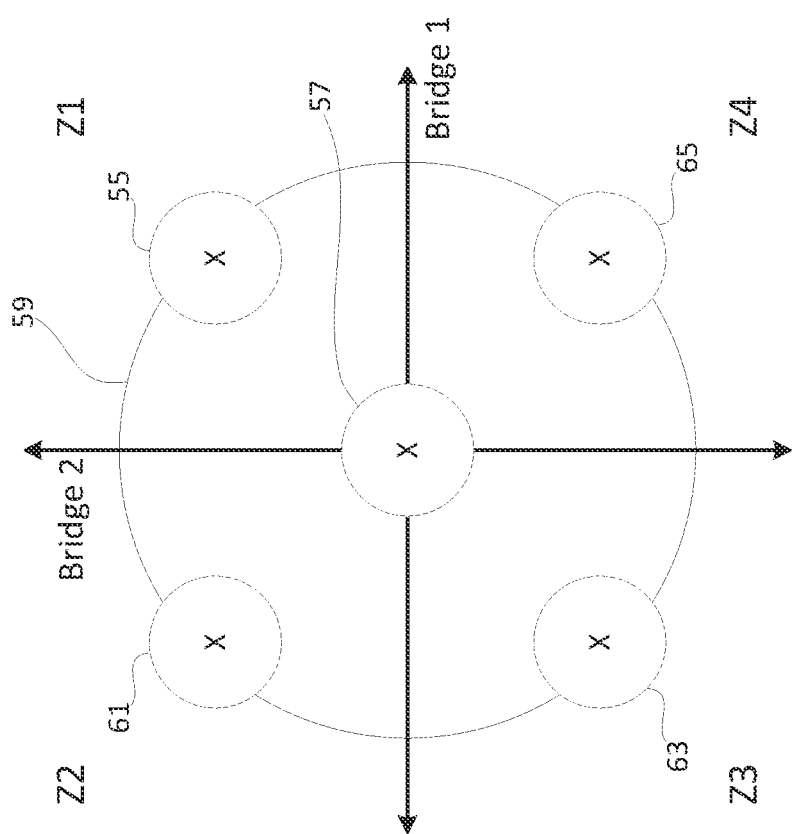

While any suitable number of predefined zones may be employed, depending upon the sensitivity and resolution capabilities of the sensor (element 34) and associated electronics, the graph in FIG. 4U shows four zones, labeled Z1, Z2, Z3 and Z4, respectively. The four zones Z1-Z4 are also shown in FIG. 4V, for example, by filtering the bridge outputs of the sensor (element 34) through a comparator and digitizing the output. In zone Z1 of FIGS. 4U and 4V, V sin>0 and V cos>0 (which can be associated with a digital value [1,1]). In zone Z2 of FIGS. 4U and 4V, V sin>0 and V cos<0 (which can be associated with a digital value [1,0]). In zone Z3 of FIGS. 4U and 4V, V sin<0 and V cos<0 (which can be associated with a digital value [0,0]). In zone Z4 of FIGS. 4U and 4V, V sin<0 and V cos<0 (which can be associated with a digital value [0,1]).

While resolution of 4 states is shown in FIGS. 4U and 4V, other embodiments may be configured to detect IN position or OUT position (with the reservoir not fully installed in the infusion pump) states as described above, 3 states, 4 states or more than 4 states, by compartmentalizing the analog output into larger (or smaller) zones. For example, four different IN position states (in addition to the OUT position state 57) can be associated with the four zones Z1, Z2, Z3 and Z4, to detect in positions at 55, 61, 63 and 65, respectively, depending upon the angle of the magnet (element 42). Thus, a magnet (element 42) having a first magnetic field angle α1 may provide a detectable signal associated with the IN position 55, when the cap 4 (or base/reservoir/cap unit) carrying that magnet (element 42) is in a proper or fully installed position within the reservoir receptacle 32 of the infusion pump device. Similarly, another magnet (element 42) having a second magnetic field angle α2 may provide a detectable signal associated with the IN position 61, when the cap 4 (or base/reservoir/cap unit) carrying that magnet (element 42) is in a proper or fully installed position within the reservoir receptacle 32 of the infusion pump device. Similarly, another magnet (element 42) having a third magnetic field angle α3 may provide a detectable signal associated with the IN position 63, when the cap 4 (or base/reservoir/cap unit) carrying that magnet (element 42) is in a proper or fully installed position within the reservoir receptacle 32 of the infusion pump device. Similarly, another magnet (element 42) having a fourth magnetic field angle α4 may provide a detectable signal associated with the IN position 65, when the cap 4 (or base/reservoir/cap unit) carrying that magnet (element 42) is in a proper or fully installed position within the reservoir receptacle 32 of the infusion pump device.

By associating one of the zones with the position and angle of the magnet, when the cap 4 (or base/reservoir/cap unit) is in a proper or fully installed position within the reservoir receptacle 32 of the infusion pump device, a detection of a sensor output in that zone can be associated with a detection of the cap 4 (or base/reservoir/cap unit) in a proper or fully installed position within the reservoir receptacle 32. Thus, for example, where zone Z1 is associated with an IN position (e.g., a fully installed position), if the output of the sensor (element 34) falls within that zone Z1, then the electronics connected or associated with the sensor 34 determines that the cap 4 (or base/reservoir/cap unit) is in an IN position (e.g., a fully installed position). However, if the output of the sensor (element 34) falls within an OUT position (e.g., in the zone labeled 57), then the electronics connected or associated with the sensor 34 determines that the cap 4 (or base/reservoir/cap unit) is in an OUT position (e.g., not fully installed position). In addition, the sensor (element 34) and electronics connected or associated therewith can be configured to resolve external magnetic field interference, by determining the external magnetic field 59, if the output of the sensor (element 34) does not fall within one of the previously-discussed zones 55 and 57.

In an example embodiment, four different caps 4 (or base/reservoir/cap units) may be provided with four distinct magnetic field orientations, respectively. Thus, a single type of magnet may be used in all four different caps 4 (or base/reservoir/cap units), but with the magnetic field angle α arranged in each cap at a different one of four distinct orientations to relative to each other cap (e.g., by defining which magnet pole faces toward the top of the set connector). This can simplify manufacturing and reduce manufacturing costs by allowing the use of the same type of magnet (but arranged in different respective orientations) in multiple different types of caps 4 (or base/reservoir/cap units). Alternatively, the magnet may be magnetized with a desired field orientation, after the magnet is installed in the cap 4 (or base/reservoir/cap unit).

Accordingly, AMR angle sensors (or other angle sensors) can be employed as sensor element 34 to provide presence detection, to detect the presence of a cap 4 (or base/reservoir/cap unit), e.g., by detecting a sensor output corresponding to a predefined in position (e.g., position 55). Alternatively or in addition, the AMR angle sensors (or other angle sensors) can be employed as sensor element 34 to differentiate between different types of caps 4 (or base/reservoir/cap units or infusion sets connected thereto) by detecting and differentiating between states (e.g., positions 55, 61, 63 and 65). While the example in FIG. 4V shows four different detectable states, other embodiments may be configured to differentiate between less than four or more than four states.

For instance, an infusion pump system may be configured to provide a different sensor output for each of three potential magnetization angles (20°, 65°, and 145° with respective ranges of +/−5°), for differentiation of three different caps 4 (or three different base/reservoir/cap units or infusion sets connected thereto). It is possible to have magnets magnetized at other angles, but it may be preferable to overlap between the respective outputs for better differentiation of different infusion sets.

In particular embodiments, anisotropic materials are used for the magnet (element 42). In other embodiments, isotropic materials may be utilized, or a combination of anisotropic and isotropic materials are used for the magnet (element 42). In particular embodiments, a magnetization process can be the last step in the processing and fabrication of magnets. Magnetization can be accomplished in any suitable manner, such as, but not limited to exposing the magnet to a large external magnetic field, for example by discharging a bank of capacitors, where a pulse of high energy realigns the magnetic domains and creates a remnant magnetization (Br) in the magnet. The remnant magnetization of an isotropic material will have the same direction as the external field used to magnetize the magnet, while an anisotropic material can be magnetized only in its preferred direction. This preferred direction allows anisotropic magnets, such as sintered NdFeB, to have higher magnetic properties than isotropic materials, such as bonded NdFeB.

In further embodiments, a magnetic strip is arranged on the cap housing 5, to extend in a direction around the axis A of the cap 4, such that different locations on the magnetic strip are aligned with (or pass) the sensor (element 34) on the infusion pump device, as the cap 4 (or base/reservoir/cap unit) is inserted into the reservoir receptacle 32 at different rotational positions relative to the axis A. In such embodiments, the rotational position of the cap 4 (or base/reservoir/cap unit) can be detected, based on the particular location on the magnetic strip that is aligned with (or passes) the sensor (element 34).

In such embodiments, the sensor (element 34) or a separate dedicated sensor (not shown) may be configured to detect installation activities (such as, but not limited to, detection of a first portion of the magnetic strip, or an activation of a designated manual operator as described above). Upon detection of an installation activity, the sensor (element 34) and associated electronics are activated to poll or read continuously or intermittently, to seek a magnetic field or signature from the magnetic strip. Upon detection (or other interaction) with the magnetic strip, the sensor element (element 34) and associated electronics may be configured to read information from the magnetic strip. Such information can be employed by the electronics (e.g., electronics 60 in FIG. 5) to control or set initial or ongoing operations of the infusion pump device 30 and/or perform other actions as described herein. During usage of the infusion pump device 30, the sensor element (element 34) and associated electronics may monitor the position of the cap 4 (or base/reservoir/cap unit), for example, to determine whether the cap 4 (or base/reservoir/cap unit) dislodges or otherwise moves relative to the infusion pump device 30, during administration of therapy to the user. If dislodgement or an improper movement of the cap 4 (or base/reservoir/cap unit) relative to the infusion pump device 30 occurs during therapy, the electronics (e.g., electronics 60 in FIG. 5) may control or stop operation of the infusion pump device 30, as appropriate. If a proper installation of the cap 4 (or base/reservoir/cap unit) is subsequently detected, then the electronics (e.g., electronics 60 in FIG. 5) may be configured to resume treatment (e.g., resume delivery of infusion media) in accordance with a pre-programmed treatment profile (e.g., infusion media delivery profile) associated with the user, or in accordance with a pre-defined default treatment (delivery) program.

In particular embodiments, the housing of the infusion pump device includes an auxiliary magnet (for example auxiliary magnet 67 in FIG. 4E) positioned to interface with the magnet of the cap 4 (or base/reservoir/cap unit) when it is initially inserted into the reservoir receptacle 32 of the infusion pump device 30, for example, prior to rotating the cap 4 into a locked position. The auxiliary magnet is positioned with its poles arranged relative to poles of the magnet in the cap 4 (or base/reservoir/cap unit), to repulse the magnet in the cap 4 (or base/reservoir/cap unit). In such embodiments, the auxiliary magnet interacts with the magnet in the cap 4 (or base/reservoir/cap unit) to apply a sufficiently repulsive force on the magnet in the cap 4 that it can be felt, but also manually overcome by the user applying a manual twisting force on the cap 4, to affirmatively allow insertion and twisting (rotation relative to the axis A) of the cap 4 (or base/reservoir/cap unit) in the reservoir receptacle 32 of the infusion pump device 30. In addition, a repulsive force from the auxiliary magnet can be provided to force a loose cap 4 (or base/reservoir/cap unit) outward (linearly relative to the axis A), so that it is apparent to the user that the loose cap 4 (or base/reservoir/cap unit) is not properly installed within the reservoir receptacle 32 of the infusion pump device 30.

In some embodiments, the auxiliary magnet is located on the infusion pump device 30, beneath the cap 4 (or base/reservoir/cap unit), in sufficient alignment and proximity to with the magnet on the cap 4 (or base/reservoir/cap unit) when the cap 4 (or base/reservoir/cap unit) is first inserted into the reservoir receptacle 32 to provide the repulsive action. In this case, the field of the auxiliary magnet is aligned to cause repulsion and may be angled to match with the field of the magnet in the cap 4 (or base/reservoir/cap unit). In other embodiments, the auxiliary magnet is mounted in the side of the housing 33 of the infusion pump device 30, in the region of the receptacle 32, with the field of the auxiliary magnet aligned to provide a repulsive force in a direction that tends to push the cap 4 (or base/reservoir/cap unit) outward from the reservoir receptacle 32 (linearly relative to the axis A).

In still other embodiments, the auxiliary magnet is placed adjacent or along the rotational path that the magnet in the cap 4 (or base/reservoir/cap unit) will follow as it is rotated during an installation process for installing the cap 4 (or base/reservoir/cap unit) in the reservoir receptacle 32. In further examples of such embodiments, a catch or stop surface formed by a lip and/or slot cut into the threads is provided such that the repulsion between the magnets must be overcome to move the cap 4 away from the catch or stop surface, such as out of the slot beneath the lip. In such embodiments, the magnets may be used to help avoid unthreading of the cap 4 from the housing 33 of the infusion pump device 30, unless sufficient user intervention (manual force) is applied to overcome the repulsive force.

In particular embodiments, the auxiliary magnet is magnetized after being placed in the housing to orient the field to provide the appropriate, desired repulsive force. In some embodiments, the pole is aligned at an angle to reduce the repulsive effect or to align it with the magnetic field of the magnet in the cap 4 (or base/reservoir/cap unit) to maximize the repulsive force.

In further embodiments, the auxiliary magnet is configured to attract the magnet in the cap 4 (or base/reservoir/cap unit) and help hold the magnet in the cap 4 (or base/reservoir/cap unit) in place, when the cap 4 (or base/reservoir/cap unit) is arranged in a desired position relative to the reservoir receptacle 32. In further embodiments in which magnetic attraction is employed, a non-magnetized component made from ferric material that will interact magnetically with the magnet in the cap may be employed instead of or in addition to the auxiliary magnet. For example, one or more non-magnetized, magnetically interactive element can be placed at one or more strategic locations along the rotational path of the cap 4, to help move the cap 4 to or retain the cap 4 (or base/reservoir/cap unit) in one or more predefined positions.

In some embodiments, the auxiliary magnet is formed or provided as a flat piece of material, and may come in a variety of shapes, such as but not limited to, round, square, triangular or the like. In particular embodiments, the auxiliary magnet is in the shape of a sphere that allows the material of the auxiliary magnet to be placed in any orientation desired during manufacturing. In such embodiments, the magnetic field may be induced, after assembly. In other embodiments, the auxiliary magnet is magnetized prior to being mounted to the infusion pump device 30. In particular embodiments, the auxiliary magnet has a curved shape that matches or fits the curved shape of the cap (or base/ reservoir/cap unit). In particular embodiments, the auxiliary magnet is formed in a suitable size and shape to be accommodated in the housing 33 of the infusion pump device 30, and provide a magnetic field of desired size and strength.

In particular embodiments, the auxiliary magnet is placed in positions that minimize interference with a sensor 34 provided to detect the presence of the magnet 42 in the cap 4 (or base/reservoir/cap unit). For instance, the sensor may be on the opposite side of the reservoir receptacle 32 (diametrically opposite side, relative to the axis A), with respect to the location of the auxiliary magnet. In other embodiments, the sensor 34 may be arranged at any other suitable location in the housing 33 of the infusion pump device 30, where the field of the auxiliary magnet does not provide a detectable reading on the sensor 34. In other embodiments, the auxiliary magnet is placed at any suitable location, even if it is detectable by the sensor 34, and the sensor 34 is calibrated to account for the presence of the auxiliary magnet. In such embodiments, the sensor 34 may be configured to measure a difference in the magnetic field as the magnet 42 in the cap 4 (or base/reservoir/cap unit) moves into a properly installed position (or other predefined position) relative to the sensor 34.

In particular embodiments, electronics 60 associated with the sensor element(s) are configured to determine the position of the cap 4, based on the particular parameters detected by the sensor element(s). A generalized diagram of example electronics 60 associated with a sensor element 34 is shown in FIG. 5. The electronics 60 in FIG. 5 include processing electronics 62 connected to receive electronic signals from the sensor, through a communication link 64. In one embodiment, the communication link 64 comprises one or more electrically conductive wires or traces or other electrically conductive material, wireless connection (such as, but not limited to radio frequency RF, Bluetooth, WiFi, inductive coupling, or other wireless communication link), or a combination thereof.

In particular embodiments, the processing electronics 62 includes one or more electronic processors configured to process information received from the sensor element 34. Such electronic processors may include, but are not limited to, a programmable general purpose processor, microprocessor, programmed or hardware configured special purpose processor, or the like, that is programmed with software, hardware, firmware, combinations thereof or otherwise configured to perform operations described herein. The electronics 60 includes one or more electronic memory devices 66 that stores data, programs or other software employed by the processing electronics 62 to perform operations described herein. In particular embodiments, the electronics 60 also includes a receiver, transmitter or transceiver 68, configured to receive, transmit, or both receive and transmit information from or to a further electronic device (not shown), such as, but not limited to, a user's computer, a health care entity's computer, or the like. The electronics 60 also includes or is connected with one or more power sources (not shown) for providing electrical power to the processing electronics 62 and, as needed, to the memory 66 and transceiver 68. In particular embodiments in which the sensor element 34 requires electrical power, the above-noted power source(s) or a separate power source associated with the sensor element provides electrical power to the sensor element, for example, through the link 64 or through a separate electrical connection (not shown).

The processing electronics 62 is programmed or otherwise configured to process information received from the sensor element 34 and determine the presence or position of the cap 4 relative to the reservoir receptacle 32 of the infusion pump device 30 or other parameter of the cap 4 (or base/reservoir cap unit), based on the particular parameters detected by the sensor element(s). In one example embodiment, the processing electronics 62 is configured to detect the presence or absence of a signal from the sensor element 34, to determine the presence or absence of the cap 4 in a predefined position relative to the reservoir receptacle 32. In other embodiments, the processing electronics 62 is configured to process a signal from the sensor element 34 to determine one or more parameters associated with the position of the cap 4, such as, but not limited to, the amount of rotation or linear displacement of the cap 4 relative to the reservoir receptacle 32, a rotational position of the cap 4 around the axis A, a linear position of the cap 4 along the dimension of the axis A, an angular position of the axis A of the cap 4 relative to the axis A of the reservoir receptacle 32, or any combination thereof. In yet other embodiments, the processing electronics 62 is configured to process a signal from the sensor element 34 to determine one or more other parameters associated with a characteristic of the cap 4 (or base/reservoir/cap unit).

In particular embodiments, the electronics 60 are attached to or contained within a housing 33 of the infusion pump device 30. In other embodiments (such as embodiments in which the element 42 includes a sensor device), the electronics 60 are attached to or contained within the cap 4. In yet other embodiments, some of the components of the electronics 60 are attached to or contained within the housing 33 of the infusion pump device 30, while other components of the electronics 60 are attached to or contained within the cap 4. For example, in one embodiment, one or both of the processing electronics 62 and transceiver 68 are on or in the infusion pump device 30, while some or all of the memory 66 is on or in the cap 4.

In embodiments described above, magnet elements and sensor elements are arranged on the cap 4 and the infusion pump device 30, for detecting the position of the cap 4 relative to the infusion pump device 30 (e.g., for detecting a proper connection of the cap 4 or the base/reservoir/cap unit with the infusion pump device 30). In other embodiments, one or more magnet and sensor elements as described above are employed to detect one or more other characteristics associated with the cap 4 or the base/reservoir/cap unit, infusions set 50 (or combinations or components thereof), in addition to or as an alternative to detecting presence in or proper connection with the infusion pump device 30. In various embodiments, such other characteristics include but are not limited to characteristics of the cap 4, reservoir 1 (or its contents), infusion set 50, connection interface 40, or any combination thereof.

In those embodiments, a particular characteristic may be associated with one or more detectable parameters, where the detectable parameters include, but are not limited to one or more of: the existence of one or more magnet or sensor elements on the cap 4, the pattern or location of one or more magnet or sensor elements on the cap 4 (circumferential or linearly location relative to the dimension of the axis A), the type of magnet or sensor element on the cap 4, the polarity, magnetic field angle $\beta$ or field strength of the magnet, or the like. In particular embodiments, the detectable parameters provide a detectable signature associated with the cap 4 (or the infusion pump device 30), where such signature can be unique to the cap 4 with respect to other caps, or may be non-unique with respect to signatures of other caps.

Accordingly, in particular embodiments, each different characteristic of the reservoir 1, infusion set 50 or connection interface 40, is associated with a respectively different detectable parameter (for example, location or type) of the magnet or sensor element. By reading the signature of the cap (or infusion pump device 30), the parameters that define the signature are detected. In those embodiments, the processing electronics 62 is configured to detect one or more detectable parameters of the magnet or sensor element; then determine one or more characteristics of the cap, base/reservoir/cap unit, reservoir, or infusion set based on the detectable parameter(s); and conduct one or more further predefined actions based on or using the determined characteristic(s).

Figure 5:
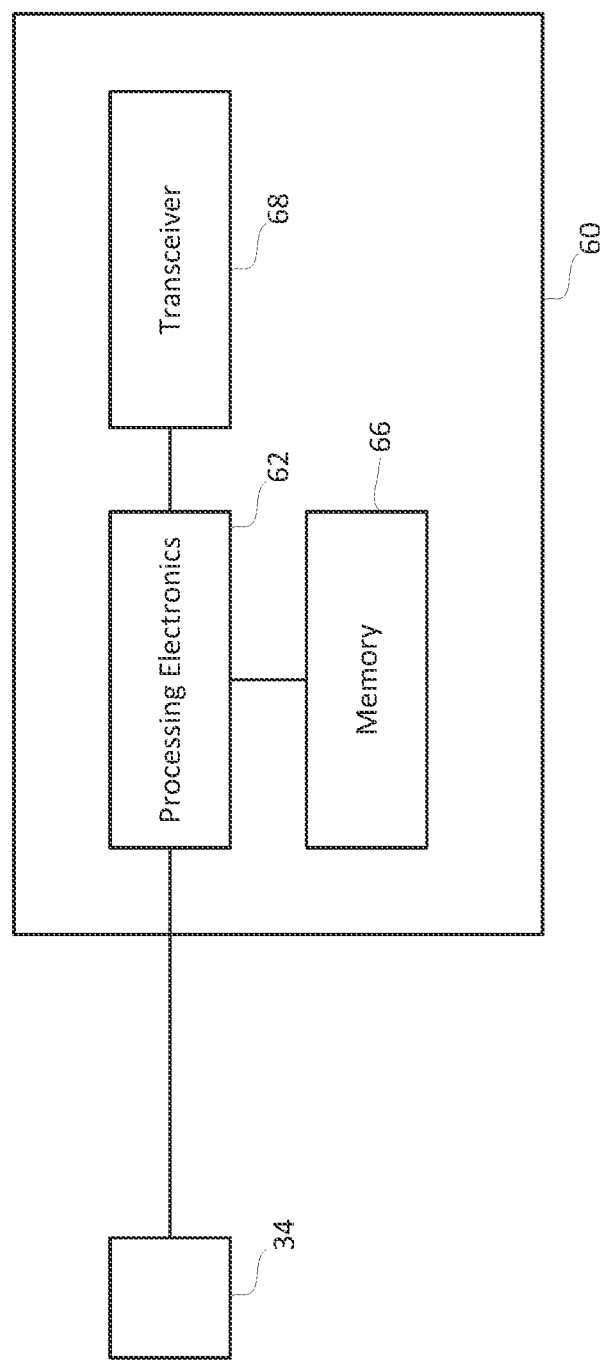
FIG. 5 is a schematic diagram showing a generalized representation of an electronic circuit employed by a connection interface apparatus according to embodiments of the present invention.

In particular embodiments, the electronic circuit 60 and processing electronics 62 in FIG. 5 is configured to perform a process 150, such as explained with reference to the flowchart in FIG. 6. For example, in the process 150, a plurality of predefined parameters (parameters that could potentially be detected) are associated on a one-to-one basis (or other predefined association) with a corresponding plurality of characteristics of the cap 4, base/reservoir/cap unit, reservoir 1 or its contents, infusion set 50, connection interface 40, or any components or combination thereof. At 152, the associations of detectable parameters and the plurality of characteristics is stored in a memory, such as memory 66.

At 154 in the process 150, one or more parameters of one or more detectable elements 42 are detected by one or more sensor elements 34, for example, during or upon installation (or attempted installation) of a cap 4 or base/reservoir/cap unit in the infusion pump device 30. At 156, the processing electronics 62 compares information received from the sensor element(s) 34 with one or more pre-defined stored threshold values, or with information stored in a table (or stored in another data arrangement that associates a plurality of different detectable magnet locations or other magnet parameters with a corresponding plurality of characteristics, for example, but not limited to, a one-to-one correspondence of each different magnet location with a different characteristic, respectively). Alternatively or in addition, the processing electronics 62 may be configured to compare information received from the sensor element 34 with one or more thresholds or with information stored in a table or in another data arrangement that associates a plurality of different types of magnets (such as, but not limited to, magnets having different polarities, magnetic field angle, field strength, or a combination of the preceding) with a corresponding plurality of characteristics (for example, but not limited to, a one-to-one correspondence of each different magnet type with a different characteristic, respectively). In those embodiments, the processing electronics 62 is configured to determine the magnet location, the magnet type or both, based on one or more comparisons of information received from the sensor element 34 with the stored information. In particular embodiments, the stored table or other data arrangement is stored in the electronic memory 66.

Examples characteristics of the reservoir 1 (or its contents) include, but are not limited to, one or more of: the type or identity of the manufacturer of the reservoir 1 or components or contents thereof, the size of the reservoir 1, the type of infusion media in the reservoir 1 (such as, but not limited to the type of insulin, other drug or other media), the concentration of the infusion media in the reservoir 1, the volume amount of infusion media in the reservoir 1, a date (such as, but not limited to a date corresponding to an expiration date, fill date or other date related to the infusion media in the reservoir 1 or the reservoir 1 itself), a location (such as, but not limited to a location corresponding to the place where the reservoir 1, the cap 4, or infusion media in the reservoir 1 (or all) was made, filled, or otherwise processed, or a location for authorized use of the reservoir 1), a lot number (or other code associated with the batch in which the reservoir 1 or infusion media was made, cleaned, filled or otherwise processed), a serial number, a unique ID, a manufacture date, user identification information (for authorized users of the reservoir 1), or other predefined characteristic.

Example characteristics relating to the infusion set 50 connected to the cap 4 include, but are not limited to one or more of: the type or manufacturer of the infusion set 50 or components thereof, the length of the tubing 52, the diameter of the tubing 52, the length of the needle or cannula 56, the diameter of the needle or cannula 56, a date (such as, but not limited to a date corresponding to an expiration date, manufacturing date or assembly date of the needle or cannula 56), a location (such as, but not limited to a location corresponding to the place where the needle or cannula 56 was made or assembled with the housing 54, or a location for authorized use of the infusion set or components thereof), a lot number (or other code associated with the batch in which the infusion set 50 or components thereof was made, cleaned or otherwise processed), a cannula type, a needle type, a lot number, a serial number, a unique ID, user identification information (for authorized users of the infusion set 50), or other predefined characteristic.

Example characteristics relating to the connection interface 40 include, but are not limited to one or more of the type or manufacturer of the connection interface 40, cap 4, base 2 or components thereof, the length, diameter or other size dimension of the cap 4, a date (such as, but not limited to a date corresponding to an expiration date, manufacturing date or assembly date of the cap 4 or base 2), a location (such as, but not limited to a location corresponding to the place where the cap 4 or base 2 was made or assembled, or a location for authorized use of the cap 4 or base 2), a lot number (or other code associated with the batch in which the cap 4 or base 2 was made, cleaned or otherwise processed), a serial number, a unique ID, user identification information (for authorized users of the infusion set 50), or other predefined characteristic.

In particular embodiments, the processing electronics 62 is further configured to conduct one or more predefined actions at 160 in the process 150, based on or using the characteristics determined at 158 in the process 150. One or more predefined actions may include, but is not limited to determining one or more operational settings for the infusion pump device 30, based on one or more of the characteristics determined from detected parameters of the signals from the sensor element 34. In further examples of such embodiments, the processing electronics 62 also provides signals to the drive device or other components of the infusion pump device 30, to control operations of the drive device (or other components) based on one or more characteristics determined from the detected parameters. In one example, based at least in part on the detected parameter, the processing electronics 62 determines and sets operational settings for one or more of: pumping rate (amount of fluid pumped per unit time), pumping time period (amount of time of pumping), pumping power (amount of fluid pressure), priming (filling) the infusion set tubing 52, priming (filling) the infusion set needle or cannula 56, detecting an occlusion in the fluid path from the reservoir 1 to the infusion set needle or cannula 56, handling an occlusion (pumping time, pressure, or program for dislodging, compensating for, or otherwise handling an occlusion).

Thus, in one example, the locations or types (or both) of the magnets correspond to one or more characteristics relating to the particular type or size of infusion set 50 connected to the cap 4, where the detected characteristics are employed by the processing electronics 62 to determine a pumping rate or pumping time period (or both) that is sufficient to prime (fill) the infusion set tubing 52, or the needle or cannula 56 (or both). In another example, the locations or types (or both) of the magnets correspond to one or more characteristics relating to the pumping time, pumping pressure or pumping program that is sufficient to dislodge or compensate for an occlusion in that particular type or size of infusion set 50.

In further embodiments, the processing electronics 62 is configured to perform (at 160 in the process 150) one or more other predefined actions based on or using the characteristic(s) determined at 158. Such other predefined actions may include, but are not limited to providing a control signal to deactivate or inhibit activation of a pump drive device in the infusion pump device 30, when the signal received from the sensor member 34 represents that the cap 4 or the base/reservoir/cap unit is not fully or properly received within the reservoir receptacle 32 of the infusion pump device 30. Alternatively or in addition, the processing electronics 62 is configured to provide a control signal to activate or allow activation of a pump drive device in the infusion pump device 30, when the signal received from the sensor member 34 represents that the cap 4 or the base/reservoir/cap unit is fully or properly received within the reservoir receptacle 32 of the infusion pump device 30.

Alternatively or in addition, the processing electronics 62 is configured to perform (at 160 in the process 150) yet one or more other predefined actions, such as, but not limited to providing an alarm signal, to activate an alarm indicator, when the signal received from the sensor member 34 represents that the cap 4 or the base/reservoir/cap unit is not fully or properly received within the reservoir receptacle 32 of the infusion pump device 30. In particular embodiments, the processing electronics 62 is configured to provide such an alarm or control signal (or both), only when the processing electronics 62 detects that the cap 4 or base/reservoir/cap unit is not fully and properly received within the reservoir receptacle 32, after having previously detected that the cap 4 or base/reservoir/cap unit is fully and properly received within the reservoir receptacle 32 (for example, indicating that a previously properly received cap 4 has since been moved or otherwise dislodged out of that position within the reservoir receptacle 32). In such embodiments, the processing electronics 62 may include (or be connected for communication with) a display device for displaying an alarm condition.

The alarm display device may include any suitable indicator such as, but is not limited to one or more of: a light emitting device, LED, LCD or other visual display device; a sound emitting device, speaker, buzzer or other audio display device; a vibrator, heater, or other tactile display device, or the like. In particular embodiments, the alarm display device is attached to or contained in the infusion pump device 30. In other embodiments, the alarm display device is attached to or contained in the cap 4. In yet other embodiments, the alarm display device is in an external device (such as, but not limited to a computer, smart phone, pager, or other electronic communication device) connected for communication with the electronics 60, for example, through a wired or wireless communication link.

In further embodiments, the processing electronics 62 is configured to perform (at 160 in process 150) other actions, such as, but not limited to recording data representing detected states or conditions (or characteristics) of one or more of the cap 4, base/reservoir/cap unit, and infusion pump device 30. In particular embodiments, the processing electronics 62 records such data in the electronic memory 66, in a form that can be retrieved by the processing electronics 62 or other processing electronics (not shown) at a time or date after recording. In such embodiments, the processing electronics 62 or other processing electronics may employ such data to generate reports, tables or other data structures for assisting with the evaluation of the recorded data. In yet further embodiments, the processing electronics 62 is configured to send such recorded data, reports, tables or other data structures to a predefined entity, for example, but not limited to, by transmitting the information through the transceiver 68. For example, in particular embodiments, the electronics 60 is configured to transmit recorded information to a remote facility at predefined or periodic intervals or upon receipt of such information from a sensor element.

In yet further embodiments, at 160 in process 150, the processing electronics 62 is further configured to determine operational settings for the infusion pump device 30, record data or perform other predefined tasks, based on one or more signals obtained from one or more additional sensors (not shown), from receiver or transceiver 68, from user input (through a user interface, not shown, connected to the electronics 60), or a combination thereof. In particular embodiments, the receiver or transceiver 68 includes a geographic positioning system receiver (such as, but not limited to a GPS or other satellite positioning system receiver) that receives or determines the geographic location of the infusion pump device 30, cap 4, or base/reservoir/cap unit. Alternatively or in addition, the processing electronics 62 is further configured to determine operational settings for the infusion pump device 30, record data or perform other predefined tasks as described below, based on one or more signals obtained from one or more electronic clocks or other timing devices (not shown) connected with the electronics 60.

In examples of such embodiments, the processing electronics 62 is configured to detect, record (or both) the geographic location of the infusion pump device 30, cap 4, or base/reservoir/cap unit, or the time or date (or any combination of location, time and date), when a particular parameter or event is detected. In one example, the particular parameter or event is one or more of: the receipt of a signal from the sensor element 34 indicating that the cap 4 or base/reservoir/cap unit has been properly and fully received within the reservoir receptacle 32; the receipt of a signal from the sensor element 34 indicating that the cap 4 or base/reservoir/cap unit has not been properly and fully received or has been moved or dislodged from its proper position within the reservoir receptacle 32; the receipt of a signal from the sensor element 34 indicating that the cap 4 or base/reservoir/cap unit has been (or not been) at one or more predefined positions within the reservoir receptacle 32, the receipt of a signal from the sensor element 34 indicating that a particular type of cap 4, infusion set 50 or reservoir 1 has been received in the reservoir receptacle 32; the movement or presence of the infusion pump device 30, cap 4, or base/reservoir/cap unit in a predefined geographic location or region; and the like. In such embodiments, the processing electronics 62 may record data representing the location or time (or both) at which any one or more predefined events occurs, such as, but not limited to the events described above. Alternatively or in addition, the processing electronics 62 may record data representing one or more detected parameters (or associated characteristics) as described above and locations or times (or both) at which any one or more of such parameters (or associated characteristics) are detected.

In further embodiments, the electronics 60 includes one or more further sensors (not shown) for detecting external or environmental magnetic fields. In such embodiments, the processing electronics 62 is configured to analyze information from the one or more sensors and provide a warning/alarm or provide control signals for adjusting operation of the infusion pump device 30 (or both), based on the detected external or environmental magnetic field. For example, the processing electronics 62 may adjust detection or processing parameters to compensate for the external or environmental magnetic fields, to minimize any effect of the external or environmental magnetic field on the detection of the magnet element(s) 34. Alternatively or in addition, the cap 4 is configured to minimize influence by external or environmental magnetic fields, where such cap configurations may include, but are not limited to, magnetic field shielding material.

In particular embodiments described above, the processing electronics 62 is configured to determine operational settings for the infusion pump device 30, provide alarm or control signals, record data or perform other predefined tasks base, at least in part, on detection of one or more detectable element(s) 12 (or information provided by a detectable parameter of the detectable elements(s) 42). In certain embodiments, the processing electronics 62 is configured to authenticate a base/reservoir/cap unit, cap 4 or reservoir 1, based on one or more of the parameters detected from the signals received from the sensor element 34. For example, the processing electronics 62 determines whether or not the detected parameters correspond to predefined characteristics associated with an authentic base/reservoir/cap unit, cap 4 or reservoir 1. In such embodiments, an authentic base/reservoir/cap unit, cap 4 or reservoir 1 may be for example, one that is authorized for use with the infusion pump device 30 by the manufacturer of at least one of the infusion pump device the base/reservoir/cap unit, cap 4, or reservoir 1. Alternatively or in addition, an authentic base/reservoir/cap unit, cap 4 or reservoir 1 may be one that is authorized by another predefined entity, such as, but not limited to, a government or industry standards or regulatory entity, or other predefined entity.

In certain embodiments, the processing electronics 62 coupled to the transceiver 68 may access, e.g., via a wired or wireless connection, directly or via another device(s), a database (e.g., on the Internet) to verify the authenticity of one or more of the base, reservoir, and/or cap using the serial number (unique ID, etc.) obtained from the base, reservoir, and/or cap, respectively, to confirm that such unit is authentic and genuine. Medical devices are stringently tested and heavily regulated, and use of unauthorized components may jeopardize proper treatment of the patient. Many of the components, such as the base/reservoir/cap, infusion set, etc., are single-use components, and the processing electronics 62 on the infusion pump device 30, e.g., may keep track of the serial numbers such that the patient is prohibited from re-using, purposefully or accidentally, a component where its safe useful life has already been depleted. Moreover, along with verifying authenticity, lot numbers, e.g., for the respective base, reservoir, and/or cap also may be checked against the database to ensure that no recalls are outstanding, and the user is alerted by (or even prohibited by) the infusion pump device 30 (or any other suitable device) to not use a particular base, reservoir, and/or cap and return it to the manufacturer if there is a recall underway, further enhancing the safety of the patient by using the most currently available information.

In particular embodiments, a detected geographic location, time or date (or any combination thereof) is included in the determination of authenticity. For example, the processing electronics 62 may be configured to determine that a base/reservoir/cap unit, cap 4 or reservoir 1 installed in the infusion pump device 30 is authentic, when the parameters detected from the signals received from the sensor element 34 correspond to characteristics that have been predefined (for example, pre-stored in memory 66) as an authentic base/reservoir/cap unit, cap or reservoir for use at a particular time, date or geographic location (or a combination thereof). In such embodiments, the memory 66 may store a table or other suitable data configuration that associates combinations of detectable magnet parameters and one or more dates, times and geographic locations (or any combination thereof) with an authentication determination.

Table 1 shows an example of an association of detectable parameters (labeled Parameters 1-N in Table 1) with different geographic locations (labeled Regions A-C).

TABLE 1

| Parameters 1 | Region A |
| Parameters 2 | Region A and Region B |
| Parameters 3 | Region C |
| . | |
| . | |
| . | |
| Parameters N | Region A, Region B and Region C |

In Table 1, a base/reservoir/cap unit, cap 4 or reservoir 1 that has a detectable magnet parameter corresponding to Parameter 1 is authentic, when the electronics 60 determines that the infusion pump device 30 is in Region A (but not when the electronics 60 determines that the infusion pump device 30 is in any other region). Also in Table 1, a detectable magnet parameter corresponding to Parameter 2 would indicate authenticity, when the electronics 60 determines that the infusion pump device 30 is in Region A or in Region B (but not when the electronics 60 determines that the infusion pump device 30 is in any other region). Similarly, in Table 1, a detectable magnet parameter corresponding to Parameter 3 would indicate authenticity, when the electronics 60 determines that the infusion pump device 30 is in Region C (but not when the electronics 60 determines that the infusion pump device 30 is in any other region). Further in Table 1, a detectable magnet parameter corresponding to Parameter N would indicate authenticity, when the electronics 60 determines that the infusion pump device 30 is in any of Regions A, B or C.

Table 2 shows a similar example, but of an association of detectable magnet parameters (labeled Parameters 1-N in Table 1) with different geographic locations (labeled Regions A-C) and dates (shown in years).

TABLE 2

| Parameter 1 | Region A | 2010-2020 |
| Parameter 2 | Region A and Region B | 2010-2015 |
| Parameter 3 | Region C | 2012-2020 |
| . | | |
| . | | |
| . | | |
| Parameter N | Region A, Region B and Region C | X |

In Table 2, a base/reservoir/cap unit, cap 4 or reservoir 1 that has a detectable magnet parameter corresponding to Parameter 1 is authentic, when the electronics 60 determines that the infusion pump device 30 is in Region A and also determines that the current date is within the years 2010 and 2020 (but not when the electronics 60 determines that the infusion pump device 30 is in any other region or that the date is outside of that date range). Also in Table 2, a detectable magnet parameter corresponding to Parameter 2 would indicate authenticity, when the electronics 60 determines that the infusion pump device 30 is in Region A or in Region B and also determines that the current date is within the years 2010 and 2015 (but not when the electronics 60 determines that the infusion pump device 30 is in any other region or that the date is outside of that date range). Similarly, in Table 2, a detectable magnet parameter corresponding to Parameter 3 would indicate authenticity, when the electronics 60 determines that the infusion pump device 30 is in Region C and also determines that the current date is within the years 2012 and 2020 (but not when the electronics 60 determines that the infusion pump device 30 is in any other region or that the date is outside of that date range). Further in Table 2, a detectable magnet parameter corresponding to Parameter N has no date restriction (as indicated by the X in Table 2) and would indicate authenticity, when the electronics 60 determines that the infusion pump device 30 is in any of Regions A, B or C.

While Tables 1 and 2 refer to Parameters 1-N (where N may be any suitable integer), other embodiments may employ a single detectable parameter or set of detectable parameters (e.g., Characteristic 1). Also, while Table's 1 and 2 refer to Regions 1, 2, 3 and N, other embodiments may employ any suitable number of predefined regions, including a single region. While the dates in Table 2 are represented in years, other embodiments may employ dates corresponding to days, weeks, months, or other suitable segments. In yet further embodiments, instead of or in addition to dates, a table (or other data configuration employed by the processing electronics 62) includes time data corresponding to separate ranges of time (similar to the separate date ranges shown in Table 2).

In particular embodiments, the electronics 60 is configured to allow operation of the infusion pump device 30 when the processing electronics 62 determines that the base/reservoir/cap unit, cap 4 or reservoir 1 is authentic, and to not allow infusion operation of the infusion pump device 30 when the processing electronics 62 does not determine that the base/reservoir/cap unit, cap 4 or reservoir 1 is authentic. For example, the processing electronics 62 may be configured to provide a control signal to the drive device to stop operation of the drive device, or inhibit sending a drive or power signal to the drive device, or perform another predefined action to not allow dispensing of infusion media from the infusion pump device 30. In other embodiments, the electronics 60 is configured to allow an infusion operation (or a limited or other predefined infusion operation) of the infusion pump device 30, but to also performs one or more further predefined actions when the processing electronics 62 does not determine that the base/reservoir/cap unit, cap 4 or reservoir 1 is authentic. Such other predefined actions include, but are not limited to, one or more of providing a readable message on a display device of the infusion pump device 30, providing an alarm signal for operating an alarm indicator on the infusion pump device 30, and recording data associated with one or more of the infusion operation, the detected characteristic(s), time, date, and geographic location, or any combination thereof.

In further embodiments, instead of associating one or more detectable parameters (e.g., Parameters 1-N in Tables 1 and 2) with geographic region, date, time or other predefined parameter, the processing electronics 62 is configured to employ magnetic detection by the sensor(s) 34 to determine presence or proper alignment, installation and connection of the base/reservoir/cap unit, cap 4 or reservoir 1 in the infusion pump device 30. Then, once proper alignment, installation or connection of the base/reservoir/cap unit, cap 4 or reservoir 1 in the infusion pump device 30 is detected, the processing electronics controls operation of the infusion pump device 30 based on whether or not the infusion pump device 30 is determined to be within a predefined (pre-authorized) region, or is being operated within a predefined (pre-authorized) time or date. In such embodiments, a table, list or other data configuration of predefined (pre-authorized) regions, times, dates or combinations thereof is stored in memory associated with the electronics 60, such as electronic memory 66. The processing electronics 62 may be configured, in further embodiments, to determine the geographic location, time, date (or any combination thereof) at predefined times, periodically, randomly or the like, once the infusion pump device 30 has started operation.

In any of the above or further embodiments, the processing electronics 62 may be configured to record information regarding the infusion pump device 30, base/reservoir/cap unit, cap 4 or reservoir 1, or the usage and operation thereof. In particular embodiments, the processing electronics 62 is configured to record, for example, in the memory 66 data corresponding to one or more of identification information associated with the base/reservoir/cap unit, cap 4 or reservoir 1, dates or times of connection, operation or disconnection of the base/reservoir/cap unit, cap 4 or reservoir 1 to the infusion pump device 30, dates or times of alarm conditions, dates or times of operation of the infusion pump device 30, detected parameters or conditions associated with detected parameters. In further embodiments, the geographic location of the infusion pump device at the time of any of the above recording events is recorded as an alternative to or in addition to recording of date or time information. In such embodiments, recordings of usage of an infusion pump device 30, base/reservoir/cap unit, cap 4 or reservoir 1 outside of a predefined geographic region, date or time (for example, beyond a predefined expiration date) may be made. In further embodiments, as an alternative to or in addition to recording the event, the processing electronics 62 is configured to provide one or more of an alarm indication and a display of a warning message on a display device in the infusion pump device, upon the detection of usage of an infusion pump device 30, base/reservoir/cap unit, cap 4 or reservoir 1 outside of a predefined geographic region, date or time.

In further embodiments, one or more wireless or wired communication devices is provided on the infusion pump device 30 (or other delivery device) and is configured and controlled to transmit volume information relating to the volume of infusion fluid remaining in or dispensed from the reservoir 1 (or other information corresponding to detected parameters or associated characteristics) for display on another electronic device separate from or located remote from the infusion pump device 30. In particular embodiments, the wireless communication device(s) are configured to connect for communication on a communication network (such as, but not limited to the Internet), with one or more pre-defined network connected devices. Such one or more pre-defined network connected devices may be located at remote geographic locations relative to the infusion pump device 30 (or other delivery device). In particular embodiments, such network connected devices include a server configured to receive information from the infusion pump device 30 (or other delivery device) or from another network connected device (such as a cradle, user computer, or the like) that communicates with the infusion pump device 30 (or other delivery device). Such information may include, but is not limited to information corresponding to one or more detected parameters or one or more associated characteristics, or other information regarding the reservoir 1, cap 4, base/reservoir/cap unit or infusion set as described above.

In such embodiments, the network connected server may be associated with an entity that records information, supplies associated products such as refills or replacement parts, provides medical treatment or medical insurance to the user or the like. In one example, the network connected server is associated with the Carelink™ system of Medtronic Inc. In other embodiments, the network connected server is one or more other servers and associated entities. Accordingly, such information may be employed by the server (or associated entity) to determine whether or not (or when) to send refills, new or replacement reservoirs, caps, infusion set needle housings, infusion set tubing, or other components of the cap 4, base/reservoir/cap unit, or infusion set. In further embodiments, such information may be provided to the user's doctor or other medical treatment entity associated with the user (for tracking, diagnosing, adjusting treatment plans or other suitable uses). Thus, in such embodiments, refills or replacement components may be sent to users, automatically (without requiring the user to place an order), and usage information can be provided to the user's healthcare provider, insurance provider or other suitable entities, automatically.

In further embodiments, the network connected server is configured to provide (and the infusion pump device 30 or other delivery device is configured to receive) information through the above-noted network communication connection or other network connection. Such information may include, but is not limited to, instructions or recommendations for replacing or refilling a reservoir 1, cap 4, base/reservoir/cap unit or infusion set, messages or notices from healthcare providers, insurance carriers or manufacturers, recall notices or the like. In particular embodiments, electronics (such as electronics 60) in the infusion pump device 30 (or other delivery device) is configured to perform one or more predefined actions (as discussed above) in response to receipt of a predefined instruction, notice or message.

In embodiments described above, one of the elements 34 and 42 includes at least one magnet, while the other of the elements 34 and 42 includes at least one sensor. In other embodiments, one of the elements 34 and 42 includes both a magnet and a sensor arranged so that they do not directly interact, while the other of the elements 34 and 42 includes a metal or other material that is magnetizable or conducts magnetic flux when in alignment or proximity (or both) with the magnet (when the base/reservoir/cap unit is fully and properly received in the reservoir receptacle 32 of the infusion pump device 30), but does not become magnetized by the magnet or conduct magnetic flux when out of alignment or proximity with the magnet. In those embodiments, the sensor is configured and arranged in sufficient alignment and proximity to the metal or other material to detect the state of the metal or other material being magnetized when the base/reservoir/cap unit is fully or properly received in the reservoir receptacle 32 of the infusion pump device 30.

b. Inductive Detection

In particular embodiments as described above, one (or all) of the cap 4, reservoir 1, and the infusion pump device 30 is provided with at least one sensor, and the other (or all) of the cap 4, reservoir 1, and the infusion pump device 30 is provided with at least one detectable feature that is detected by the sensor when the cap 4 is properly coupled with the infusion pump device 30. Embodiments as described above include one or more magnetic detectable features and magnet detection sensors. Other embodiments described herein include one or more detectable features that are detected by other sensing configurations (including RF, optical, mechanical or electrical contact sensing configurations). In other embodiments, the one or more detectable features 42 includes an inductively detectable member (or target) that can be detected by an inductive sensor, and the one or more sensor elements 34 includes an inductive sensor.

Thus, in one example, element 42 represents one or more inductively detectable members (or targets) carried by the cap 4, while element 34 represents one or more inductive sensor elements located on the infusion pump device, in or adjacent the reservoir receptacle 32. In further embodiments, the relative locations of the inductive sensor element(s) and inductively detectable member(s) (target(s)) is reversed such that the inductively detectable member(s) 42 (or target(s)) are located in and carried by the infusion pump device 30, while the inductive sensor(s) 34 are carried by the cap 4. In yet further embodiments, the inductively detectable member(s) (or target(s)) and the inductive sensor element(s) are each located in and carried by the infusion pump device 30.

Arrangements and configurations of magnetic sensors and magnetic detectable features (as the sensors and detectable features 34 and 42) described above and shown in FIGS. 1-6 are incorporated herein by reference to apply to embodiments employing inductively detectable features and inductive sensors, as the sensors and detectable features 34 and 42. Thus, in particular embodiments, inductively detectable targets and inductive sensors are employed in place of magnetic detectable features and magnetic sensors in the above-described embodiments. In addition and where applicable, further arrangements and configurations described with respect to RF, optical, and mechanical sensors and detectable features (as the sensors and detectable features 34 and 42) may be employed and are incorporated herein by reference to apply to embodiments having inductively detectable features and inductive sensors, as the sensors and detectable features 34 and 42.

Inductive sensors may be configured as non-contact proximity sensors used to detect the presence of metallic or other electrically conductive objects. Thus, in particular embodiments, one or more inductively detectable members (or targets) includes one or more electrically conductive materials attached to, embedded in or otherwise provided on the cap 4. Such electrically conductive members (or targets) may be made of any suitable electrically conductive material such as, but not limited to, copper, gold, silver, nickel, a ferrous metal, other conductive metals or other electrically conductive materials. In particular embodiments, the electrically conductive members (or targets) include electrically conductive ink or other electrically conductive material that is printed or otherwise applied to the cap 4. In further embodiments, the electrically conductive members (or targets) include electrically conductive polymer materials molded and/or formed as desired. The inductively detectable members (or targets) may be passive (not powered by a separate power source).

In addition, one or more sensors are provided on the infusion pump device 30, where each sensor includes (or is connected with) one or more electrically conducive coil. Each coil is attached to, embedded in or otherwise provided on the infusion pump device 30, in the region of the reservoir receptacle 32. Each electrically conductive coil may be configured with any suitable electrically conductive material such as, but not limited to, copper, gold, silver, nickel, a ferrous metal, conductive inks or other conductive metals or electrically conductive materials, formed in a coil configuration suitable for inductive interaction with a target.

In particular embodiments, a single electrically conductive coil is provided on the infusion pump device 30 and a single electrically conductive member (or target) for inductive interaction with the coil is provided on the cap 4 (or base/reservoir/cap unit). In other embodiments, a plurality of electrically conductive coils are provided on the infusion pump device 30 (and/or a plurality of electrically conductive members or targets are provided on the cap 4) in locations that allow the electrically conductive member(s) (target(s)) to inductively interact with the coil(s) to provide detectable signals for detection of axial or rotational (angular) motion or position (or both) of the cap 4 relative to the reservoir receptacle 32. The detectable signals provided by the interaction of the electrically conductive member(s) (or target(s)) and the coil(s) are dependent, in part, on various parameters such as the distance between the electrically conductive member and the coil, and the size, shape and material of the electrically conductive member (or target). Accordingly, those parameters can be selected to provide a detectable signature that can indicate the presence of a cap 4 (or base/reservoir/cap unit) in a fully installed position within reservoir receptacle, as well as other information associated with the cap 4 (or the base/reservoir/cap unit) or the infusion set connected to the cap 4.

Figure 7:
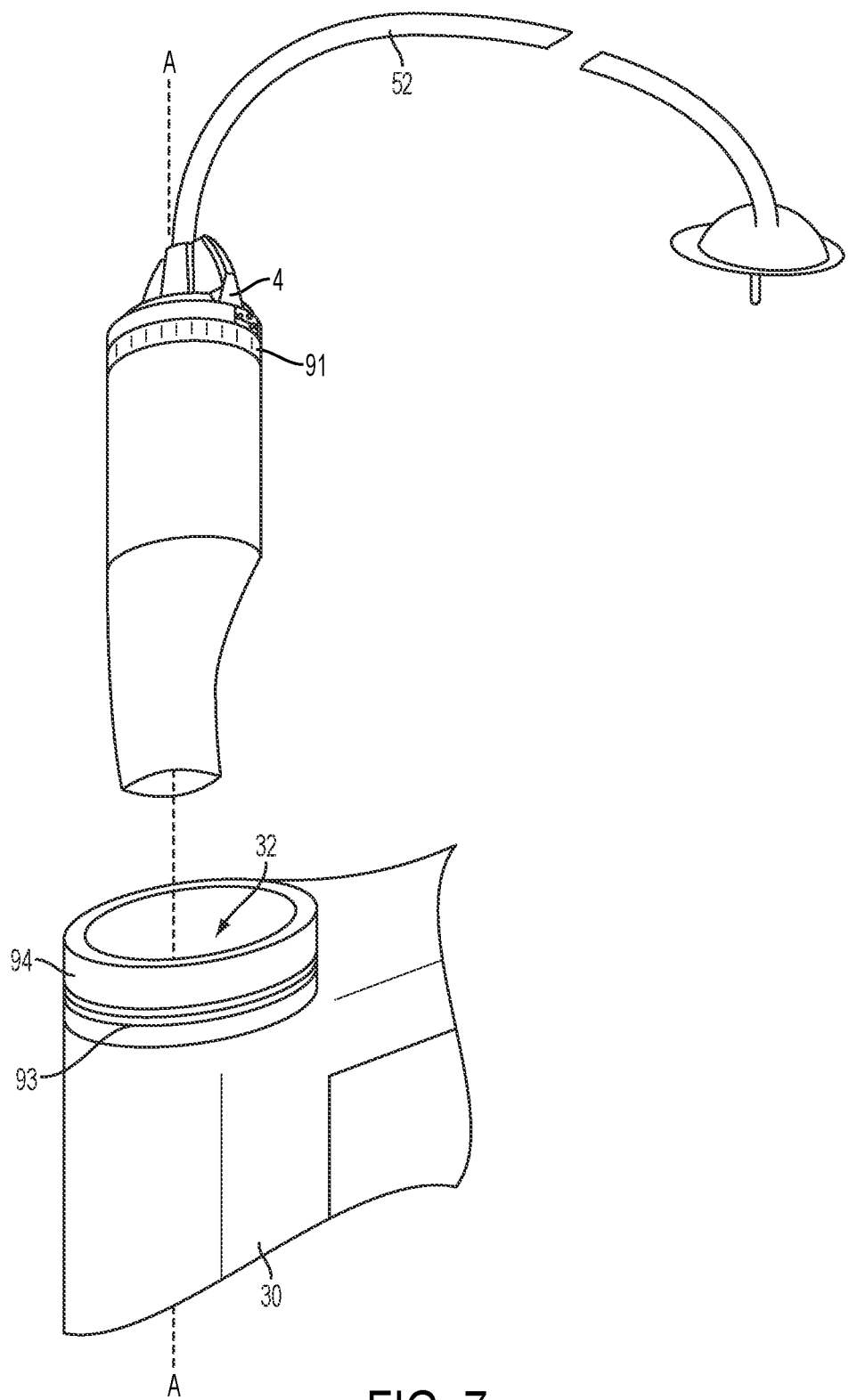
FIG. 7 is a perspective view of an infusion pump system including a base/reservoir/cap unit outside of an infusion pump device, according to an embodiment of the present invention.
Figure 8:
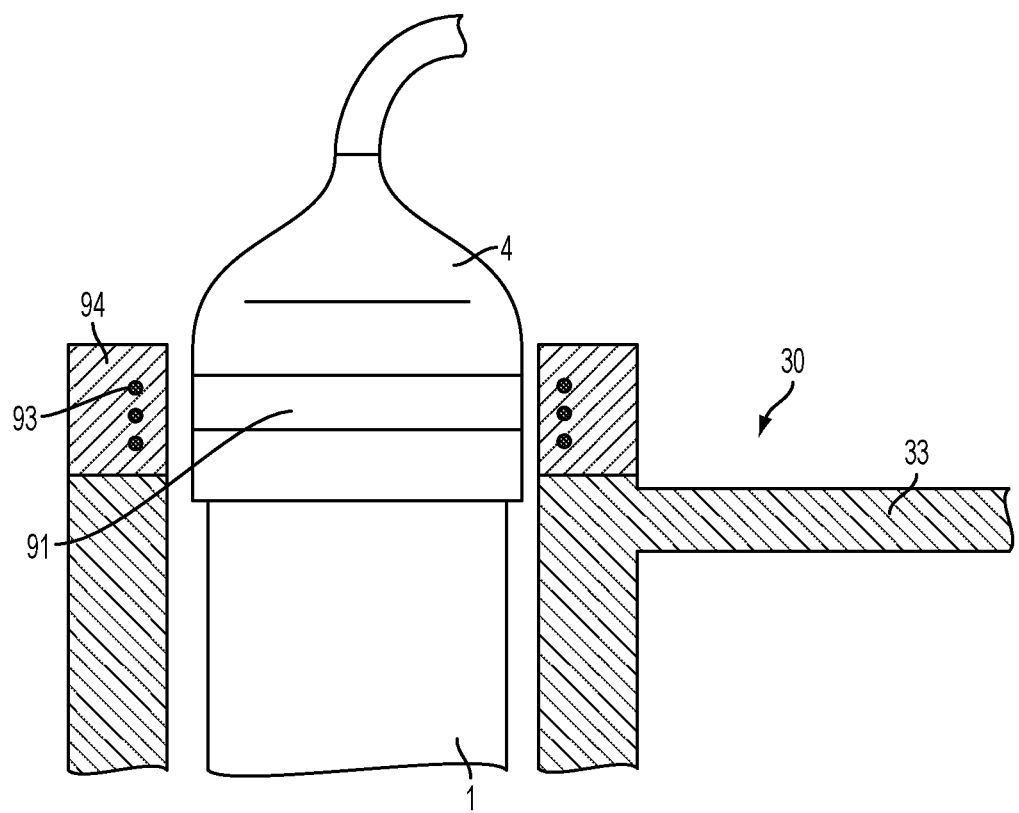
FIG. 8 is an enlarged, side, cross-section view of a portion of an infusion pump system of the embodiment of FIG. 7, with the base/reservoir/cap unit located inside the infusion pump device.

For example, in the embodiment of FIGS. 7 and 8, an electrically conductive member or target 91 in the form of a metallic ring or band is provided on the cap 4. FIG. 7 shows a perspective view of a portion of an infusion pump device 30, with a base/reservoir/cap unit outside of the reservoir receptacle 32 of the infusion pump device 30. FIG. 8 shows an enlarged partial side, cross-section view of a portion of the infusion pump device 30, with a base/reservoir/cap unit (only a portion shown in view) located within the reservoir receptacle 32.

Figure 9:
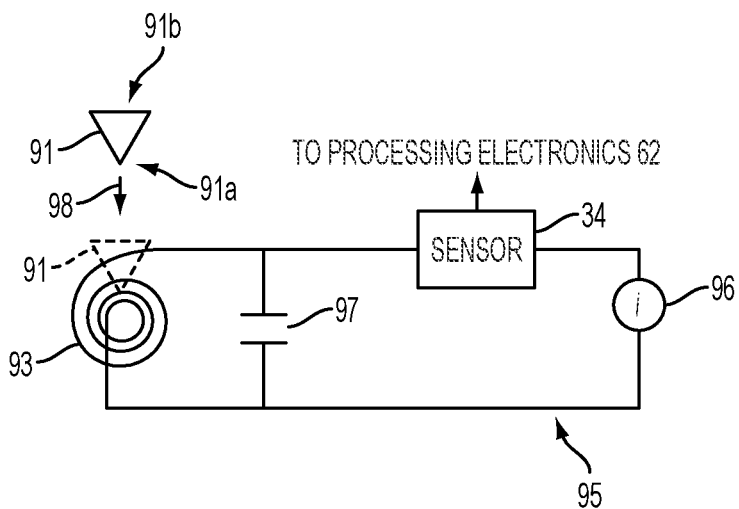
FIG. 9 is a schematic diagram showing a generalized representation of an electronic circuit for embodiments of an infusion pump system of FIGS. 7 and 8.

In the embodiment in FIGS. 7 and 8, the target 91 is in the form of a ring or band that is attached to an outer surface of the cap 4 and extends circumferentially around the axis A of the cap 4 (and reservoir 1 of the base/reservoir/cap unit). In other embodiments, the ring or band of the target 91 is attached to an inner surface of the cap 4, or is embedded within a wall of the cap 4, for example, to minimize or avoid contact by the user or other objects (e.g., to minimize damage to the target 91). In other embodiments, the target 91 has a shape different from a ring or band (such as, but not limited to a triangular or arrow-head shape as shown in the embodiment of FIG. 9). In further embodiments, the target 91 is composed of a plurality of electrically conductive members of the same shape or different shapes. For example, a plurality of electrically conductive members forming a target 91 may be arranged in a predetermined pattern to provide an induction signature associated with the target 91, where the induction signature is dependent at least in part on the number or pattern (or both) of the electrically conductive members of the target 91.

Also in the embodiment in FIGS. 7 and 8, an electrically conductive coil 93 of an inductive sensor (or separate but connected with an inductive sensor) is provided on the infusion pump device 30. The coil 93 is part of (or connected to) an inductive sensing circuit, such as, but not limited to the circuit 95 in FIG. 9. In the embodiment in FIGS. 7 and 8, the coil 93 extends around the circumference of the reservoir receptacle 32 of the infusion pump device 30, and around the axis A of the reservoir receptacle 32. In particular embodiments, the coil 93 includes a metallic wire or other electrically conductive material that is wound around the axis A and attached to, embedded within or otherwise provided on a wall forming the reservoir receptacle 32 of the infusion pump device 30. In other embodiments, the coil is attached to, embedded within or otherwise provided on the wall forming the reservoir receptacle 32 of the infusion pump device 30, but not circumferentially around the axis A of the reservoir receptacle 32.

In further embodiments, the upper end (reservoir-receiving end) of the reservoir receptacle 32 includes an upper ring member 94 that is attached to the lower portion of the reservoir receptacle 32, where the coil 93 is attached to, embedded within or otherwise provided on the ring member 94. This allows the coil 93 and ring member 94 to be made separately from the rest of the infusion pump device 30 and then assembled with the infusion pump device 30 during or after manufacture of the infusion pump device 30. In such embodiments, the ring member 94 may be made of any suitably rigid material, such as but not limited to plastic, metal, ceramic, composite material or combinations thereof. The ring member 94 is attached to the rest of the reservoir receptacle 32 by any suitable attachment mechanism including, but not limited to, welding, glue, resin or other adhesive material, screw threads, friction fit, or the like.

The ring member 94 is arranged at a location on the reservoir receptacle 32 to allow the coil 93 to inductively interact with the target 91 on the cap 4, when (or as) the cap is received within the reservoir receptacle. For example, the coil 93 may be disposed on the ring member 94 in a location where the coil 93 will be adjacent and in sufficient proximity to the target 91, when (or as) the cap is received within the reservoir receptacle 32 such that the target 91 is in sufficient proximity to the coil 93 to causes (by induction) a detectable change in a current flowing in the coil 93 (and in the circuit 95 in FIG. 9).

In one example embodiment, a sensor 34 is connected in an electronic detection circuit with the coil 93 (for example, in the circuit 95 in FIG. 9). FIG. 9 shows a generalized diagram of an electronic detection circuit. In the circuit 95, a current source 96 is connected across the coil 93, and the sensor 34 is connected between the current source 96 and the coil 93. The circuit 95 includes a tank circuit formed with a capacitor 97 connected across the coil 93. With current from the current source 96, the coil 93 in the circuit 95 provides a time-varying magnetic field. Changes in the position and motion of the target 91 within that magnetic field produces detectable changes in the inductance of the coil 93 and the equivalent resistance of the circuit 95. In particular embodiments, the sensor 34 provides an output signal to processing electronics (such as processing electronics 62 in FIG. 5), where the sensor output signal is dependent upon the inductance of the coil and resistance or impedance of the circuit (and, thus, dependent upon motion and position of the target 91 relative to the coil 93). In further embodiments, the sensor 34 may be composed of an electrical link to processing electronics (such as processing electronics 62) that processes the signal in the circuit 95 to determine the presence of the target 91 or other information from that signal.

The target 91 is attached to the cap 4 at a location and position such that the target 91 moves in the direction of arrow 98 relative to the coil 93, when the cap 4 (or base/reservoir/cap unit) moves into the reservoir receptacle 32 of the infusion pump device 30. As a result, the target 91 moves to a position adjacent the coil 93 (or to a different position adjacent the coil 93 relative to a starting position), when the cap 4 (or base/reservoir/cap unit) moves into the reservoir receptacle 32 of the infusion pump device 30. In the drawing of FIG. 9, the target 91 is shown in solid line and again in broken line, to represent two different positions of the target 91 and a movement from the solid line position to the broken line position, in the direction of arrow 96.

The movement and change of position of the target 91 adjacent and relative to the coil 93 produces a detectable effect on the current signal in the circuit 95, at least partially depend upon (a function of) the distance between the target 91 and the coil 93, and the size, shape and composition of the target 91. The position of the target 91 relative to the coil 93 after the target 91 has been moved in the direction of arrow 96 produces a detectably different signal in the circuit 95 relative to the signal when the target 91 is not adjacent to the coil 93 (e.g., prior to installation of the cap 4 or after removal of the cap 4 from the reservoir receptacle 32).

In particular embodiments, the sensor 34 (or processing electronics 62) is configured to detect the inductance (or other parameter) associated with the tank circuit in circuit 95 without the target 91 present (e.g., before installation of a cap 4 or base/reservoir/cap unit). This provides the sensor 34 (or processing electronics 62) with a base or calibration value associated with the target 91 not being present. Then, after the cap 4 (or base/reservoir/cap unit) is installed in the reservoir receptacle, the sensor 34 (and processing electronics 62) are configured to detect the changed inductance (or other parameter) associated with the tank circuit in circuit 95 when the target 91 is present (relative to the base or calibration value). When the change in the inductance (or other parameter) is detected, the processing electronics 62 determines (in response to that detection) that a cap 4 (or base/reservoir/cap unit) has been installed.

In an embodiment described above, the target 91 is provided in the form of a ring or band around the cap 4. In other embodiments, the target 91 can be formed as a partial ring or band, or may have another shape. For example, in the embodiment in FIG. 9, the target 91 has a triangular shape (or tapered, arrow-head shape) having first and second opposite ends, where the first end 91a has a smaller width dimension (e.g., the horizontal dimension in FIG. 9) than the second end 91b. In that embodiment, as the cap 4 is moved into the reservoir receptacle 32, the first end 91a (smaller dimension end) of the target 91 moves toward the center (or across) the coil 93 followed by the second end 91b (larger dimension end) of the target 91. As such, the first end 91a (smaller dimension end) of the target 91 will effect eddy currents, followed by an effect on eddy currents by the second end 91b (larger dimension end) of the target 91, resulting in a time varying signal that is at least partially dependent on the shape and direction of motion of the target 91.

Similarly, when the cap 4 (or base/reservoir/cap unit) is moved in a direction out of the reservoir receptacle 32 (opposite to the direction of arrow 96), the second end 91b (larger dimension end) of the target 91 will be in front of the first end 91a (smaller dimension end) of the target 91 in the direction of motion, causing a detectable effect on eddy currents different from the effect of moving in the direction of arrow 96. Accordingly, the movement of the cap 4 (or base/reservoir/cap unit) results in a time varying signal (or detectable signature) in the circuit 95 that is partially dependent on the direction of motion of (into or out of the reservoir receptacle) and the size and shape of the target 91.

In particular embodiments, the infusion pump device 30 is operable with any of a plurality of different caps 4 (or base/reservoir/cap units), where each cap (or each base/reservoir/cap unit) has one or more targets 91 that produce a different detectable signal in the circuit 95 (and, thus, has a detectably different signature) relative to each other cap 4 of the plurality of different caps 4. For example, caps 4 (or base/reservoir/cap units or associated infusion sets) from different manufacturers, for different reservoirs, for different reservoir contents, or having other differing features (relative to other caps 4 or base/reservoir cap units or associated infusion sets) can have a correspondingly different target 91 (e.g., a different shape, size, material or combination thereof), to produce a different detectable signal (or target signature) relative to such other caps 4 or base/reservoir cap units or associated infusion sets. In particular embodiments, processing electronics (such as processing electronics 62) are configured to determine information about a cap 4 (or base/reservoir/cap unit), based on the detectable signal (or signature) produced when the cap 4 (or base/reservoir/cap unit) is moved in the direction of arrow 96 (or opposite direction) as the cap 4 is installed or removed from the reservoir receptacle, or when the cap 4 is in an installed position.

For example, processing electronics (such as processing electronics 62 in FIG. 5) may be configured to perform a process 150 as described above with respect to FIG. 6, but where the detectable parameters are signal parameters effected by features of the target 91, such as, but not limited to the size, shape, material, or number of electrically conductive members in the target 91, or the number of targets 91 and position of the target(s) 91 on the cap (or base/reservoir/cap unit), or any combination thereof. In such embodiments, a memory associated with the processing electronics (such as memory 66 associated with processing electronics 62) stores data in association with possible detectable signal parameters (or target signatures). The processing electronics 62 are configured to compare parameters of a detected signal (or a detected target signature) with stored parameters and obtain from the stored data, certain selected data that is associated with parameters of the detected signal (or target signature).

The stored data may include, but is not limited to, data corresponding to a plurality of different models, sizes, types or styles of caps 4 (or base/reservoir/cap units, reservoirs or associated infusion sets), manufacturers of the caps 4 (or base/reservoir/cap units, reservoirs or associated infusion sets), the type of infusion media in the reservoir 1 (such as, but not limited to the type of insulin, other drug or other media), the concentration of the infusion media in the reservoir 1, the volume amount of infusion media in the reservoir 1, a date (such as, but not limited to a date corresponding to an expiration date, fill date or other date related to the infusion media in the reservoir 1 or the reservoir 1 itself), a location (such as, but not limited to a location corresponding to the place where the reservoir 1, the cap 4, or infusion media in the reservoir 1 (or all) was made, filled, or otherwise processed, or a location for authorized use of the reservoir 1), a lot number (or other code associated with the batch in which the reservoir 1 or infusion media was made, cleaned, filled or otherwise processed), a serial number, a unique ID, a manufacture date, user identification information (for authorized users of the reservoir 1), or other predefined data or characteristic associated with the caps (or base/reservoir/cap units, reservoirs or associated infusion sets). In this manner, the processing electronics can determine various characteristics of or information about the cap 4 (or base/reservoir/cap unit, reservoir 1 or associated infusion set) from the detected signal (or signature) produced as the cap 4 (or base/reservoir/cap unit) is installed or removed from the infusion pump device 30, or when the cap 4 (or base/reservoir/cap unit) is in an installed position.

While the embodiment in FIG. 9 has a target 91 in the shape of a triangle, other embodiments employ targets 91 having other suitable shapes or combinations of shapes. For example, the target 91 in the embodiment in FIGS. 7 and 8 has a ring or band shape. In particular embodiments, the shape of the target 91 or the pattern of plural targets 91 (or the shape and pattern) is selected to provide a detectably different signal when the target 91 is moved in the direction of arrow 96 (e.g., into the reservoir receptacle 32) relative to the signal produced when the target 91 is moved in the direction opposite to the direction of arrow 96 (e.g., out from the reservoir receptacle 32). In this manner, the processing electronics 62 may be configured to detect such different signals, to determine whether the cap 4 (or base/reservoir/cap unit) is being installed or being removed from the reservoir receptacle.

The shape, size and material of the target 91 and the number and pattern of plural targets 91 can affect the eddy currents and, thus, the detectable signal (or signature) produced when the target 91 is moved or located adjacent the coil 93. Accordingly, one or more of the shape, size and material of the target 91 and the number and pattern of plural targets 91 can be selected to provide a particular unique or non-unique detectable signal (or signature), as described above.

In particular embodiments, the cap 4 (or base/reservoir/cap unit) may include a plurality of targets 91, or the infusion pump device 30 may include a plurality of coils 93 (or both), arranged in different positions along the axis A or around the axis A (or both). In such embodiments, the position of the cap 4 (or base/reservoir/cap unit) relative to the length dimension of the axis A or relative to a circumference around the axis A (or both) can be detected, to detect the linear position or the rotational position (or both), of the cap 4 (or base/reservoir/cap unit) relative to the axis A (and, thus, relative to the reservoir receptacle 32 of the infusion pump device 30). For example, rotational position can be detected with a plurality of targets 91 and/or a plurality of coils 93, in a manner similar to the plurality of sensors and plurality of detectable members 34 and 42 in FIGS. 4A and 4B.

In certain embodiments described above, the target(s) 91 are provided on the cap 4 (or base/reservoir/cap unit), while the coil(s) 93 are provided on the infusion pump device 30. In other embodiments, the target(s) 91 and the coil(s) 93 are, both, provided on the infusion pump device 30. In example embodiments, one or more targets 91 are supported on the infusion pump device 30 with a corresponding one or more coils 93, where each target 91 is held by a support structure that moves the target 91 in a predefined direction upon and in response to the installation of the cap 4 (or base/reservoir/cap unit) in the reservoir receptacle 32 of the infusion pump device 30.

Figure 10:
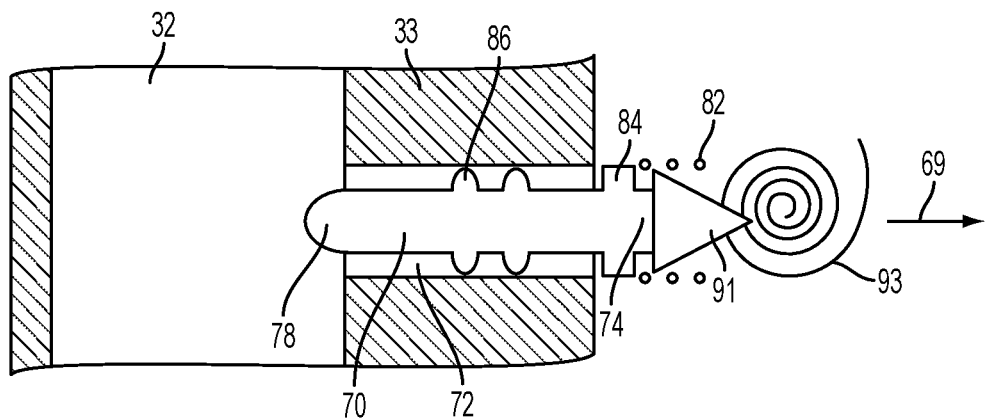
FIG. 10 is an enlarged, side, cross-section view of a portion of an embodiment of an infusion pump device of an infusion pump system of FIGS. 7 and 8.
Figure 11:
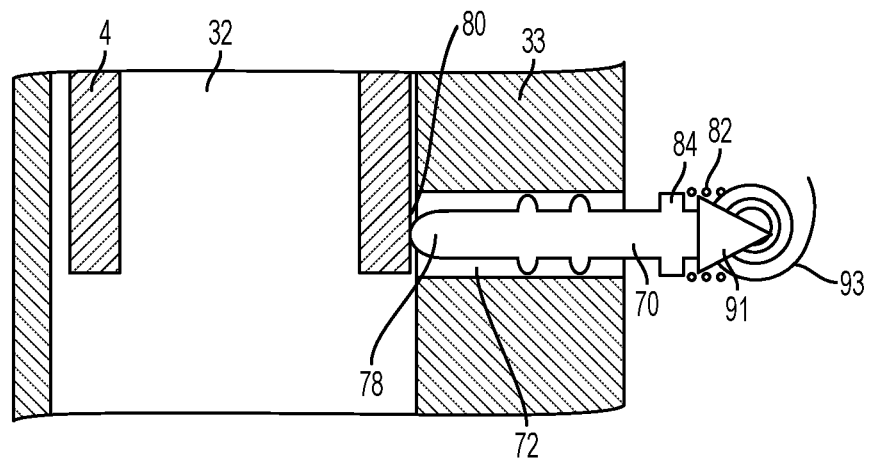
FIG. 11 is an enlarged, side, cross-section view of a portion of an embodiment of a cap located in an infusion pump device of an infusion pump system of FIGS. 7 and 8.

Representative examples of mechanically moveable support structures for moving a target 91 in response to the installation of a cap 4 (or base/reservoir/cap unit) in a reservoir receptacle 32 are described with reference to FIGS. 10-15. The drawings in FIGS. 10 and 11 show enlarged partial cross-section views of a portion of the infusion pump device 30. In FIG. 10, the reservoir receptacle 32 of the infusion pump device 30 is free of the cap 4 (base/reservoir/cap unit). In FIG. 11, the cap 4 (base/reservoir/cap unit) is installed in the reservoir receptacle 32 of the infusion pump device 30.

In FIGS. 10 and 11, the infusion pump device 30 holds a mechanically moveable member or actuator. The mechanically moveable member (actuator) is arranged to engage an engagement portion of the cap 4 (or other component of the base/reservoir/cap unit) and to be moved from the first position to the second position, as a result of a manual movement of the cap 4 (or base/reservoir/cap unit) into the reservoir receptacle 32 and to a proper and fully received position within the reservoir receptacle 32.

The mechanically moveable member carries one or more targets 91 (one shown in FIGS. 10 and 11), and moves the target(s) 91 relative to one or more respective coils 93 (one shown in FIGS. 9 and 10), when the mechanically moveable member is moved to the second position. Accordingly, a manual movement of the cap 4 (or base/reservoir/cap unit) into the reservoir receptacle 32 and to a proper and fully received position within the reservoir receptacle 32 causes the mechanically moveable member to move in a predefined direction to the second position and, thus, move one or more targets 91 adjacent and relative to one or more coils 93. Each coil 93 is connected in a circuit (such as discussed above with respect to circuit 95) for detecting whether or not a target 91 has moved to the second position. Accordingly, by detecting the state or position of the target 91, the electronics determines whether or not the cap 4 (or base/reservoir/cap unit) is properly and fully received within the reservoir receptacle 32.

In the embodiment of FIGS. 10 and 11, a mechanically moveable member 70 is supported for movement within a channel 72 located in the infusion pump device 30. The moveable member 70 in FIGS. 10 and 11 has a generally elongated shaft or cylinder shape and is made of a suitably rigid material that holds its shape during normal operation such as, but not limited to plastic, metal, ceramic, wood, composite material, or any combination thereof. In other embodiments, the moveable member 70 may have any other suitable shape or form.

The channel 72 may be formed within the structure of the housing 33 of the infusion pump device 30 or within a further structure located within the housing 33. A first end of the channel 72 is open into the reservoir receptacle 32. A second end of the channel 2 is open into another portion of the interior of the housing 33 of the infusion pump device 30. In the illustrated embodiment, the channel 72 is linear along a longitudinal dimension (horizontal dimension in FIGS. 10 and 11), and the moveable member 70 has a corresponding longitudinal shape that extends along the longitudinal dimension of the channel 72. In other embodiments, the channel 72 (and the moveable member 70) may have correspondingly curved shapes or other suitable shapes that allow the moveable member 70 to move between first and second positions within the channel 72.

The moveable member 70 has a first end 74 (the end on the right side of the moveable member 70 in FIGS. 10 and 11) that holds a target 91. The target 91 may be attached to the moveable member 70 in any suitable manner including, but not limited to adhesives, screws, bolts, clamps or other mechanical connectors, or by embedding or molding the target 91 into the moveable member 70. The moveable member 70 has a second end 78 (the end on the left side of the moveable member 70 in FIGS. 10 and 11) that is arranged to be engaged by an engagement portion 80 of the cap 4 (or other component of the base/reservoir/cap unit) when the cap 4 (or base/reservoir/cap unit) is properly and fully received within the reservoir receptacle 32.

More specifically, the engagement portion 80 of the cap 4 (or other component of the base/reservoir/cap unit) has a contact surface that comes into contact with and engages a surface of the second end 78 of the moveable member 70, as the cap 4 (or the base/reservoir/cap unit) is manually inserted and moved into a proper and fully inserted position within the reservoir receptacle 32 of the infusion pump device 30. As the cap 4 (or the base/reservoir/cap unit) is manually moved toward the proper and fully inserted position within the reservoir receptacle 32, the engagement portion 80 engages the second end 78 of the moveable member 70. Then, further movement of the cap 4 (or the base/reservoir/cap unit) toward the a proper and fully inserted position causes the engagement portion 80 to push the second end 78 of the moveable member 70 and move the moveable member 70 in the direction of arrow 69 from a first position (shown in FIG. 9) to a second position (shown in FIG. 10).

The movement of the moveable member 70 from the first position (FIG. 10) to the second position (FIG. 11) causes the first end 74 of the moveable member 70 to move the target 91 adjacent and relative to the coil 93. The coil 93 is supported on the infusion pump device 30 (for example, within the housing 33) in a position adjacent and along the path of motion of the target 91, in sufficient proximity to the target 91 for inductive detection as described above. Accordingly, the target 91 is moved relative to the coil 93 by movement of the moveable member 70 (and detectable as described above), when the cap 4 (or the base/reservoir/cap unit) is moved to the proper and fully inserted position within the reservoir receptacle 32.

In particular embodiments, the engagement portion 80 on the cap 4 (or the base/reservoir/cap unit) has a feature (a protrusion, bump, extension, depression or the like) having the contact surface that engages the second end 78 of the moveable member 70, when the cap 4 (or the base/reservoir/cap unit) is in a fully and properly inserted position within the reservoir receptacle 32. In such embodiments, the protrusion (or other feature) may be shaped and located at a particular position on the cap 4 (or the base/reservoir/cap unit) to engage (or fully engage) the second end 78 of the moveable member 70 sufficient to move the moveable member 70 to the second position, only when the cap 4 (or the base/reservoir/cap unit) is fully and properly inserted within the reservoir receptacle 32. In such embodiments, the target 91, circuit 95 (including coil 93) and processing electronics 62 are configured to detect movement of the moveable member 70 to the second position, or to detect the presence of the moveable member 70 at the second position (or both), for example, to determine that the cap 4 (or the base/reservoir/cap unit) is fully and properly installed. In further embodiments, the target 91, circuit 95 (including coil 93) and processing electronics 62 are configured to detect movement of the moveable member 70 to one or more positions other than the second position, or to detect the presence of the moveable member 70 at such one or more other positions (or both), for example, to determine that the cap 4 (or the base/reservoir/cap unit) is not fully or properly installed in the reservoir receptacle 32.

In further embodiments, the protrusion (or other feature) of the engagement portion 80 has a predetermined size that results in a movement of the moveable member 70 in the direction of arrow 69 by a predetermined amount (corresponding to the predetermined size), when the cap (or the base/reservoir/cap unit) is fully and properly installed in the reservoir receptacle 32. Thus, engagement portion features of different sizes will result in different amounts of movement of the moveable member 70 (and of the target 91), when the cap (or the base/reservoir/cap unit) is installed in the reservoir receptacle 32. In particular embodiments, the size of the engagement portion feature is selected to provide a particular unique or non-unique detectable signal (or target signature), where parameters of that target signature are employed by processing electronics 62 (of FIG. 5) as detected parameters in a process 150 as described with respect to FIG. 6.

In such further embodiments, multiple different predetermined sizes of the engagement portion features (such as multiple different lengths of the protrusion) may be associated (on a one-to-one basis or other pre-defined association) with predefined data (e.g., stored in memory 66) corresponding different predefined characteristics of the cap 4 (or the base/reservoir/cap unit or associated infusion set), as described above with respect to FIG. 6. The predefined data may include, but is not limited to, data corresponding to a plurality of different models, sizes, types or styles of caps 4 (or base/reservoir/cap units, reservoirs or associated infusion sets), manufacturers of the caps 4 (or base/reservoir/cap units, reservoirs or associated infusion sets), the type of infusion media in the reservoir 1 (such as, but not limited to the type of insulin, other drug or other media), the concentration of the infusion media in the reservoir 1, the volume amount of infusion media in the reservoir 1, a date (such as, but not limited to a date corresponding to an expiration date, fill date or other date related to the infusion media in the reservoir 1 or the reservoir 1 itself), a location (such as, but not limited to a location corresponding to the place where the reservoir 1, the cap 4, or infusion media in the reservoir 1 (or all) was made, filled, or otherwise processed, or a location for authorized use of the reservoir 1), a lot number (or other code associated with the batch in which the reservoir 1 or infusion media was made, cleaned, filled or otherwise processed), a serial number, a unique ID, a manufacture date, user identification information (for authorized users of the reservoir 1), or other predefined data or characteristic associated with the caps (or base/reservoir/cap units, reservoirs or associated infusion sets). The associations of feature sizes and data can be stored in a memory (such as memory 66), as described with respect to 152 in process 150 of FIG. 5.

The stored associations are used by processing electronics (such as processing electronics 62) to determine one or more characteristics of a cap (or base/reservoir/cap unit), reservoir 1 (or its contents), infusion set 50, connection interface 40, or any combination thereof, as described with respect to 156 and 158 in process 150 of FIG. 5. In addition, such processing electronics may be configured to provide a predefined action based on or using the determined characteristic(s), as described with respect to 160 in process 150 of FIG. 5. In this manner, the processing electronics 62 may be configured to detect information (e.g., the associated predefined characteristics) about the cap 4 (or the base/reservoir/cap unit or associated infusion set), by detecting the amount of movement of the moveable member 70 in the direction of arrow 69 (or the position of the target 91) when the cap 4 (or the base/reservoir/cap unit) is installed in the reservoir receptacle 32, and by retrieving information associated with the detected amount of movement.

In particular embodiments, the second end 78 of the moveable member 70 extends a small distance into the reservoir receptacle 32, when the moveable member 70 is in the first position (FIG. 10). In that position, the second end 78 of the moveable member 70 is arranged in a location to be contacted by the engagement portion 80 of the cap 4 (or the base/reservoir/cap unit) as the cap 4 (or the base/reservoir/cap unit) is moved toward a proper and fully inserted position within the reservoir receptacle 32. In particular embodiments, the second end 78 of the moveable member 70 is rounded, tapered or provided with another suitable shape that helps to transfer the linear motion of the cap 4 or the base/reservoir/cap unit (e.g., downward motion in the direction of the reservoir receptacle 32 in FIGS. 10 and 11) to linear motion of the moveable member 70 along the longitudinal dimension of the channel 72, as the cap 4 (or the base/reservoir/cap unit) is moved toward a proper and fully inserted position within the reservoir receptacle 32.

In particular embodiments, the second end 78 of the moveable member 70 extends into the channel of the reservoir receptacle 32 by a distance sufficient to contact an outer surface of the cap 4 (or the base/reservoir/cap unit) and ride along that outer surface (allow that outer surface to slide over the second end 78 of the moveable member 70) without moving to the second position and, thus, without moving the target 91 relative to the coil 93, as the cap 4 (or the base/reservoir/cap unit) is manually inserted into the reservoir receptacle 32 and rotated toward a proper position. When the cap 4 (or base/reservoir/cap unit) is properly and fully received (inserted and rotated into proper position) in the reservoir receptacle 32, the engagement portion 80 on the cap 4 (or the base/reservoir/cap unit) comes into engagement with the second end 78 of the moveable member 70 and imparts a sufficient force onto the moveable member 70 to move the target 91 in the direction of arrow 69 to the second position.

In particular embodiments, the second end 78 of the moveable member 70 (or the entire moveable member 70) is made of a material that is sufficiently compliant, flexible and resilient to be compressed at least at the second end 78 by the engagement portion 80, when the second end 78 of the moveable member 70 is contacted by the engagement portion 80. For example, the material may be sufficiently compliant and flexible to accommodate for different cap 4 sizes or for manufacturing tolerances (or both). Thus, the second end 78 of the moveable member 70 may extend into the reservoir receptacle 32 by a distance sufficient to contact a cap 4 having any size outer diameter (within a predefined range), by compressing sufficiently to accommodate larger diameters within that range.

In particular embodiments in which the moveable member 70 shifts toward the switch when moving from the first position to the second position, the moveable member 70 includes or is engaged by a bias member 82 that imparts a bias force on the moveable member 70 to bias the moveable member 70 toward the first position (FIG. 9 position). The bias member 82 may be any suitable structure or device that imparts a force on the moveable member 70 in the direction of the first position, such as, but not limited to a coil spring, a leaf spring, other spring configuration, a magnet, a balloon or other pressurized expandable container, or the like. In the drawings of FIGS. 10 and 11, a coil spring is shown as one example of a bias member 82.

In such embodiments, the moveable member 70 includes a protrusion, extension or other structure that provides a stop surface for stopping further motion of the moveable member 70 in the direction of the first position, when the moveable member 70 reaches the first position. In the embodiment of FIGS. 10 and 11, the moveable member 70 includes a protruding shoulder 84 that provides the stop surface. In the illustrated embodiment, the protruding shoulder 84 is arranged outside of the channel 72 and adjacent the second end of the channel 72. The protruding shoulder 84 is configured to be larger (wider) than a dimension (e.g., the width dimension) of the channel 72, so that the protruding shoulder is not able to pass through the channel. Accordingly, the protruding shoulder 84 provides a stop surface (e.g., a surface of the shoulder 84) that engages a surface of the structure in which the channel 72 is located, when the moveable member 70 is in the first position (FIG. 10). However, the protruding shoulder 84 is spaced apart from that surface of the structure in which the channel 72 is located, when the moveable member 70 is in the second position (FIG. 11), or is between the first and second positions.

In particular embodiments, one or more seals or other features are provided for inhibiting the passage of moisture, liquid or other fluid through the channel 72, for example, in the event that moisture, liquid or other fluid enters the reservoir receptacle 32. Thus, the passage of moisture, liquid or other fluid from the reservoir receptacle 32 to other areas within the infusion pump housing 33 can be inhibited, for example, in the event that the infusion pump device 30 is exposed to moisture, liquid or other fluid (such as, for example, rain, pool water, shower water, or the like).

In the embodiment of FIGS. 10 and 11, the moveable member 70 is provided with one or more (two shown in the drawings) seal structures 86, for sealing against the interior surface of the channel 72. In the illustrated embodiment, two seal structures 86 are provided on the moveable member 70. In other embodiments, a single one or more than two seal structures 86 may be employed. In particular embodiments, each seal structure 86 includes a protruding extension or ring of material around the movable member 70 (e.g., around the circumference of the shaft or cylindrical structure of the moveable member 70). In certain embodiments, one or more seal structures 86 are formed of the same material as the moveable member 70 and is either formed as part of the moveable member 70 (e.g., molded or machined, or the like, with the moveable member 70) or formed separately and attached to the moveable member 70. In certain embodiments, one or more seal structures 86 are composed of an O-ring made of the same material as the moveable member. In other embodiments, one or more seal structures 86 are composed of an O-ring made of a different material as the moveable member, such as a flexible, resilient material suitable for sealing functions, including, but not limited to a rubber, plastic or silicone material.

The drawings in FIGS. 12-14 show further embodiments in which a target 91 is held by a support structure that allows the target 91 to move in a predefined direction upon and in response to the installation of the cap 4 (or base/reservoir/cap unit) in the reservoir receptacle 32 of the infusion pump device 30. Each of FIGS. 12 and 13 show enlarged, cross-section views of a portion of an infusion pump device 30 and a portion of a cap 4. In FIG. 12, the reservoir receptacle 32 of the infusion pump device 30 is free of the cap 4 (and base/reservoir/cap unit). In FIG. 13, the cap 4 (and base/reservoir/cap unit) is installed in the reservoir receptacle 32 of the infusion pump device 30. FIG. 14 shows an enlarged, cross-section view of a portion of an infusion pump device 30 and a portion of a cap 4 according to another embodiment.

In FIGS. 12 and 13, the coil 93 is contained in and held by the infusion pump device 30. In particular embodiments, the coil 93 is attached to or embedded in a housing wall of the infusion pump device (such as a wall defining a portion of the reservoir receptacle). The target 91 in FIGS. 12 and 13 is also contained in and held by the infusion pump device 30. In particular, the target 91 is attached to the housing 33 of the infusion pump device 30, through a mechanical linkage 97 that supports the target 91 for linear movement along the direction of the axis A of the reservoir receptacle 32.

The mechanical linkage 97 supports the target 91 for movement from a first position (as shown in FIG. 12) before the cap 4 (or base/reservoir/cap unit) is fully received within the reservoir receptacle 32, to a second position (as shown in FIG. 13) after the cap 4 (or base/reservoir/cap unit) is fully received or installed within the reservoir receptacle 32. In particular embodiments, the mechanical linkage 97 biases the target 91 toward the first position (shown in FIG. 12), to cause the target 91 to remain in or move to the first position when the cap 4 (or base/reservoir/cap unit) is not fully received within the reservoir receptacle 32 (and out of engagement with the target 91).

However, as the cap 4 (or base/reservoir/cap unit) is received in the reservoir receptacle 32 and moved toward a fully installed position, an engagement portion 80' on the cap 4 (or base/reservoir/cap unit) engages and contacts the target 91 and moves the target 91 toward the second position. When the cap 4 (or base/reservoir/cap unit) is fully installed, the engagement portion 80' remains engaged with the target 91 and holds the target 91 in the second position (as shown in FIG. 13). When the cap 4 (or base/reservoir/cap unit) is removed from the reservoir receptacle, the target 91 is released and allowed to move back to the first position (as shown in FIG. 12), for example, under the bias force of the mechanical linkage 97.

In particular embodiments, the engagement portion 80' is a surface of a rib or bottom edge of a portion of the cap 4 and extends fully around the circumference of the cap 4 (around the axis A, when the cap 4 is arranged within the reservoir receptacle 32). In other embodiments, the engagement portion 80' includes one or more bumps, ramps or other projecting portions of the cap 4, arranged at one or more selected locations, spaced around the circumference of the cap 4, to align with the target 91 when (or only when) the cap 4 is received within the reservoir receptacle 32 in a proper rotational position (rotational position about the circumference of the axis A) relative to the reservoir receptacle 32. Alternatively or in addition, the engagement portion 80' may be arranged at any one of a plurality of locations along the linear dimension of the axis A to move the target 91 by an amount (along the linear dimension of axis A) dependent upon the location (in the linear dimension) of the engagement portion 80'. Thus, a cap 4 with an engagement portion 80' as shown in FIGS. 12 and 13 will engage a target 91 and move the target 91 a greater distance that a cap 4 with an engagement portion 80" as shown in FIG. 14 (where the engagement portion 80" is located a greater distance away from the bottom edge of the cap 4 relative to the distance of the engagement portion 80' from the bottom edge of the cap 4).

The coil 93 is supported within the infusion pump device 30, at a location to interact in a detectable manner with the target 91 as described above, when the target 91 moves to or is located at the second position (FIG. 13 or FIG. 14). More specifically, the movement or position of the target 91 produces a detectable signal in coil 93 (and circuit 95). However, because the target 91 is moved to a second position in FIG. 13 that is different from the second position in FIG. 14, the detectable signal (or target signature) produced in the coil 93 (and circuit 95) is different for the target position in FIG. 13 relative to that of FIG. 14. In particular embodiments, processing electronics (such as processing electronics 62) is configured to discern between a detectable signal (or target signature) provided when the target 91 is moved to a second position of FIG. 13 relative to a different detectable signal (or different target signature provided when the target is moved to a second position of FIG. 14. While the embodiments in FIGS. 13 and 14 show two different caps 4 with respectively different engagement portion locations in the linear dimension of axis A, in other embodiments, more than two different caps 4 are provided with respectively different engagement portion locations (different locations along the linear dimension of the axis A, the circumference of the axis A or a combination thereof) to engage different targets 91 or to move an engaged target 91 by different amounts relative to each other cap 4. In this manner, different caps (or different types of caps or base/reservoir/cap units) may be configured to provide different target signatures, by virtue of having different engagement portion locations.

In the embodiments in FIGS. 12-14, a single coil 93 is arranged to detect the movement or location of the target 91, where a movement of the target by the distance shown in FIG. 13 provides a detectably different signal (target signature) than the movement of the target by the distance shown in FIG. 14. In other embodiments, multiple coils 93 are arranged such that at least one coil is in a position to detect the movement or position of the target 91 when the target is moved to a second position shown in FIG. 13, and at least one other coil is in a position to detect the movement or position of the target 91 when the target 91 is moved to a second position shown in FIG. 14. Thus, in particular embodiments, multiple coils 93 are arranged to correspond to multiple different second positions of the target 91 for different caps 4.

In certain embodiments, the coil 93 is attached to a surface of a wall defining a portion of the reservoir receptacle 32, for example, on an inside surface facing the interior of the reservoir receptacle, on an opposite facing surface of the wall or embedded within the wall. In embodiments in which the coil 93 is on the opposite-facing surface or embedded within a wall of the reservoir receptacle 32, the wall is made of a plastic or other suitable material that allows inductive coupling of the target 91 and the coil 93, through the wall, at least when the target 91 is at the second position (FIG. 12).

The linkage structure 97 may be any suitable structure that supports the target 91 for linear movement along the direction of the axis A. Such linkage structures may include, but are not limited to, rails, guide surfaces, bias springs, or combinations thereof. One example of a linkage structure 97 is shown in FIG. 15 and includes a rail 97a that has a linear dimension, a platform 97b that is supported by the rail 97a for movement in the linear dimension of the rail 97a and that provides a surface for holding the target 91, and a spring 97c that is supported by the rail 97a and biases the platform toward one end of the linear dimension of the rail 97a. The rail 97a is configured to couple to (or is formed in) the inside surface of a wall of the reservoir receptacle 32. In other embodiments, other suitable linkage structures 97 are employed to support the target 91.

In the embodiments of FIGS. 10-14, a single mechanically movable member 70 (FIGS. 10 and 11) or a single linkage-supported, moveable target 91 (FIGS. 12-14) are shown. In other embodiments, two or more (a plurality of) mechanically movable members (for example, similar to mechanically movable member 70 in FIGS. 10 and 11) or two or more (a plurality of) linkage-supported, moveable targets 91 (for example, similar to FIGS. 12-14) are arranged within the reservoir receptacle 32, around or along the length direction of the axis A. In such embodiments, the plurality of mechanically movable members or the plurality of linkage-supported, moveable targets are arranged to allow detection of the linear position or rotational position (or both) of the cap 4 (or base/reservoir/cap unit) relative to the axis A of the reservoir receptacle 32. For example, such rotational position detection can be carried out by processing sensor signals from sensors 34 in a manner similar to that described above with respect to the multiple sensor embodiments of FIGS. 4A and 4B.

In embodiments in which two or more (a plurality of) mechanically movable members or linkage-supported, moveable targets are arranged at predefined locations around or along the axis A of the reservoir receptacle 32, a corresponding two or more coils 93 are arranged to detect the position of the cap 4 relative to the infusion pump device 30 (e.g., for detecting a proper connection of the cap 4 or the base/reservoir/cap unit with the infusion pump device 30).

In other embodiments, in addition to or as an alternative to detecting proper connection with the infusion pump device 30, one or more mechanically movable members or linkage-supported, moveable targets are employed to detect one or more other characteristics associated with the cap 4 or the base/reservoir/cap unit or associated infusion set (or components thereof) as discussed above with respect to the process 150 in FIG. 6. Alternatively or in addition, the target signature(s) discussed above that depend on the position (in the linear dimension of the axis A) of the engagement portion 80' may be employed to detect one or more of such characteristics.

In such further embodiments, multiple different engagement portion locations (along the length dimension of the axis A or around the circumference of the axis A, or both) may be parameters associated (on a one-to-one basis or other pre-defined association) with corresponding different predefined characteristics of the cap 4 (or the base/reservoir/cap unit or associated infusion set), for use in a process 150 as described above with respect to FIG. 6. The predefined data may include, but is not limited to, data corresponding to a plurality of different models, sizes, types or styles of caps 4 (or base/reservoir/cap units, reservoirs or associated infusion sets), manufacturers of the caps 4 (or base/reservoir/cap units, reservoirs or associated infusion sets), the type of infusion media in the reservoir 1 (such as, but not limited to the type of insulin, other drug or other media), the concentration of the infusion media in the reservoir 1, the volume amount of infusion media in the reservoir 1, a date (such as, but not limited to a date corresponding to an expiration date, fill date or other date related to the infusion media in the reservoir 1 or the reservoir 1 itself), a location (such as, but not limited to a location corresponding to the place where the reservoir 1, the cap 4, or infusion media in the reservoir 1 (or all) was made, filled, or otherwise processed, or a location for authorized use of the reservoir 1), a lot number (or other code associated with the batch in which the reservoir 1 or infusion media was made, cleaned, filled or otherwise processed), a serial number, a unique ID, a manufacture date, user identification information (for authorized users of the reservoir 1), or other predefined data or characteristic associated with the caps (or base/reservoir/cap units, reservoirs or associated infusion sets). The associations of engagement portion locations and characteristics can be stored in a memory (such as memory 66), as described with respect to 152 in process 150 of FIG. 5.

Figure 6:
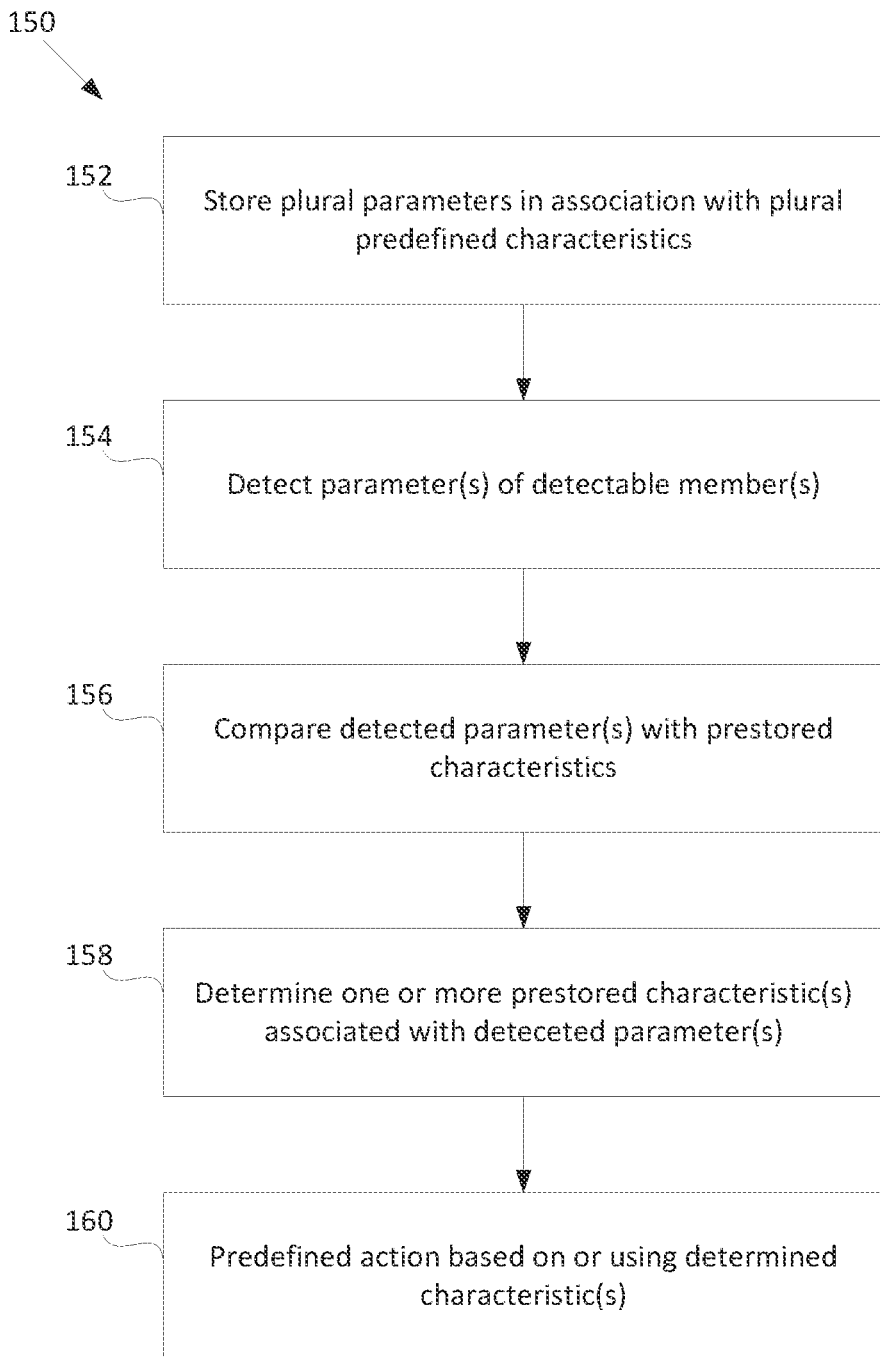
FIG. 6 is a flow diagram of a process performed by the electronic circuit of FIG. 5 according to an embodiment of the present invention.

The stored associations are used by processing electronics (such as processing electronics 62) to compare and determine one or more characteristics of a cap (or base/reservoir/cap unit), reservoir 1 (or its contents), infusion set 50, connection interface 40, or any combination thereof, as described with respect to 156 and 158 in process 150 of FIG. 6. In addition, such processing electronics may be configured to provide a predefined action based on or using the determined characteristic(s), as described with respect to 160 in process 150 of FIG. 6. In this manner, the processing electronics 62 may be configured to detect information (e.g., the associated predefined characteristics) about the cap 4 (or the base/reservoir/cap unit or associated infusion set), by detecting which ones of a plurality of targets 91 are moved and/or the amount of movement of one or more targets 91, when the cap 4 (or the base/reservoir/cap unit) is installed in the reservoir receptacle 32, and by retrieving information associated with the detected target movements or second (moved) positions.

Therefore, a particular characteristic may be associated with the movement of one or more mechanically movable members or linkage-supported, moveable conductive members, or the location or pattern of locations of the particular mechanically movable members or linkage-supported, moveable conductive members that are moved to the second position by the cap 4. In particular embodiments, each different predefined characteristic of the reservoir 1, infusion set 50 or connection interface 40, is associated (for example, on a one-to-one basis or other predefined association) with a respectively different one or more predefined mechanically movable member or linkage-supported, moveable conductive member. In those embodiments, the processing electronics 62 is configured to determine a characteristic of the reservoir 1, infusion set 50 or connection interface 40 from the detectable signals caused by movement of one or more mechanically movable members or linkage-supported, moveable conductive members.

For example, the processing electronics 62 may be configured to compare information received from one or more sensors 34 (in circuits 95 associated with coils 93) with information stored in a table or in another suitable data arrangement. The table or other data arrangement is stored in the electronic memory 66. The table or other data arrangement associates signals produced by movement of different predefined mechanically movable members or linkage-supported, moveable conductive members with a corresponding plurality of predefined characteristics, as described herein with respect to the magnetic, RF, optical and mechanical detection embodiments and incorporated herein by reference.

In particular embodiments, based on one or more of the detectable signals produced by movement of the one or more mechanically movable members or linkage-supported, moveable conductive members, the processing electronics 62 is further configured to determine corresponding characteristics and, based on those characteristics, do one or more predefined actions such as, but not limited to: determine operational settings for the infusion pump device 30, provide signals to the drive device or other components of the infusion pump device 30, provide one or more alarm signals, and record data representing detected states or conditions of one or more of the cap 4, base/reservoir/cap unit, and infusion pump device 30, as described above with regard to magnetic detection, RF detection, optical and mechanical embodiments.

In further embodiments, one or more wireless or wired communication devices is provided on the infusion pump device 30 (or other delivery device) and is configured and controlled to transmit volume information relating to the volume of infusion fluid remaining in or dispensed from the reservoir 1 (or other information corresponding to detected parameters of the one or more targets 91 or associated characteristics) for display on another electronic device separate from or located remote from the infusion pump device 30. In particular embodiments, the wireless communication device(s) are configured to connect for communication on a communication network (such as, but not limited to the Internet), with one or more pre-defined network connected devices. Such one or more pre-defined network connected devices may be located at remote geographic locations relative to the infusion pump device 30 (or other delivery device). In particular embodiments, such network connected devices include a server configured to receive information from the infusion pump device 30 (or other delivery device) or from another network connected device (such as a cradle, user computer, or the like) that communicates with the infusion pump device 30 (or other delivery device). Such information may include, but is not limited to information corresponding to one or more detected parameters or one or more associated characteristics, or other information regarding the reservoir 1, cap 4, base/reservoir/cap unit or infusion set as described above.

In such embodiments, the network connected server may be associated with an entity that records information, supplies associated products such as refills or replacement parts, provides medical treatment or medical insurance to the user or the like. In one example, the network connected server is associated with the Carelink™ system of Medtronic Inc. In other embodiments, the network connected server is one or more other servers and associated entities. Accordingly, such information may be employed by the server (or associated entity) to determine whether or not (or when) to send refills, new or replacement reservoirs, caps, infusion set needle housings, infusion set tubing, or other components of the cap 4, base/reservoir/cap unit, or infusion set. In further embodiments, such information may be provided to the user's doctor or other medical treatment entity associated with the user (for tracking, diagnosing, adjusting treatment plans or other suitable uses). Thus, in such embodiments, refills or replacement components may be sent to users, automatically (without requiring the user to place an order), and usage information can be provided to the user's healthcare provider, insurance provider or other suitable entities, automatically.

In further embodiments, the network connected server is configured to provide (and the infusion pump device 30 or other delivery device is configured to receive) information through the above-noted network communication connection or other network connection. Such information may include, but is not limited to, instructions or recommendations for replacing or refilling a reservoir 1, cap 4, base/reservoir/cap unit or infusion set, messages or notices from healthcare providers, insurance carriers or manufacturers, recall notices or the like. In particular embodiments, electronics (such as electronics 60) in the infusion pump device 30 (or other delivery device) is configured to perform one or more predefined actions (as discussed above) in response to receipt of a predefined instruction, notice or message.

Figure 16:
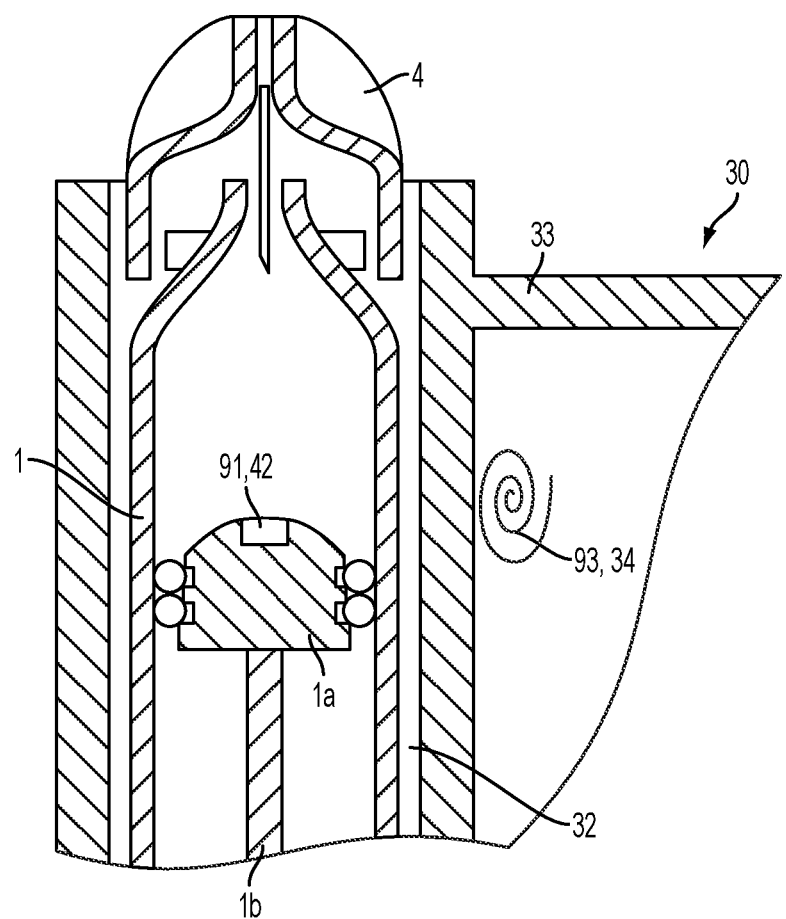
FIG. 16 is a side, cross-section view of a portion of an infusion pump system, with a base/reservoir/cap unit located inside a infusion pump device, according to an embodiment of the present invention.

In embodiments described above, the target(s) 91 is (are) provided on the cap 4 (or base/reservoir/cap unit) or in the infusion pump device 30. In other embodiments as described with reference to FIG. 16, at least one target 91 is provided on a moveable plunger of the reservoir 1. FIG. 16 shows an enlarged, partial, side cross-section view of a portion of the infusion pump device 30, with a base/reservoir/cap unit (only a portion of which is shown in the drawing) received within the reservoir receptacle 32. In FIG. 16, the at least one target 91 is provided on the plunger within the reservoir 1 (e.g., on the head 1$a$ of the reservoir plunger or the shaft 1$b$ of the reservoir plunger). In such embodiments, one or more coils 93 may be arranged in the infusion pump device 30 (e.g., within or in the vicinity of the reservoir receptacle 32), to detect linear positions of the target 91 relative to the axis A, when the base/reservoir/cap unit is installed in the reservoir receptacle 32. Accordingly, based on the detected position of the target 91, processing electronics (such as processing electronics 62) connected to an electronic detection circuit associated with each coil 93 may be configured to detect the linear position of the plunger head 1$a$ and, thus, the amount of infusion media remaining in the reservoir 1.

In particular embodiments, the processing electronics is configured to detect the linear position of the plunger head 1$a$ and determine whether or not the plunger head 1$a$ is in a filled position (corresponding to a filled or un-used reservoir 1), or whether or not the plunger head 1$a$ is in the last position from the previous use of the infusion pump device 30. In such embodiments, the processing electronics may be configured to perform a predefined action in response to a determination that the plunger head is not in a filled position or is not in its last position (which may indicate that a used or re-used reservoir has been installed in the infusion pump device). Such predefined action may include, but is not limited to, inhibiting infusion media delivery operation of the infusion pump device 30, determining particular operational settings for the infusion pump device 30, providing an alarm or control signals, recording data, providing authentication operations, or performing other predefined tasks.

Similar to embodiments discussed above, the target 91 on the plunger head 1$a$ may have a predefined shape, size, material, or combination thereof, to provide a detectable signal (or signature) that is based at least in part on the shape, size, material or combination thereof. Also similar to embodiments discussed above, a plurality of different reservoirs 1 may include a corresponding plurality of different targets 91 (with different respective shapes, sizes, materials, or combinations thereof), to provide a corresponding plurality of different detectable signals (signatures).

In such embodiments, processing electronics and associated memory (such as processing electronics 62 and memory 66) are configured to compare parameters of detected signals (signatures) with pre-stored signal parameter information, and associate predefined data with the detected signals (signatures) as described above. The predefined data may include, but is not limited to, data corresponding to a plurality of different models, sizes, types or styles of caps 4 (or base/reservoir/cap units, reservoirs or associated infusion sets), manufacturers of the caps 4 (or base/reservoir/cap units, reservoirs or associated infusion sets), the type of infusion media in the reservoir 1 (such as, but not limited to the type of insulin, other drug or other media), the concentration of the infusion media in the reservoir 1, the volume amount of infusion media in the reservoir 1, a date (such as, but not limited to a date corresponding to an expiration date, fill date or other date related to the infusion media in the reservoir 1 or the reservoir 1 itself), a location (such as, but not limited to a location corresponding to the place where the reservoir 1, the cap 4, or infusion media in the reservoir 1 (or all) was made, filled, or otherwise processed, or a location for authorized use of the reservoir 1), a lot number (or other code associated with the batch in which the reservoir 1 or infusion media was made, cleaned, filled or otherwise processed), a serial number, a unique ID, a manufacture date, user identification information (for authorized users of the reservoir 1), or other predefined data or characteristic associated with the caps (or base/reservoir/cap units, reservoirs or associated infusion sets). In this manner, the processing electronics can determine various information about the reservoir 1 or cap 4 (or base/reservoir/cap unit or associated infusion set) from the detected signal (or signature).

While the above description of FIG. 16 refers to inductive sensing, in other embodiments, the reservoir plunger 1a may hold or contain a magnet, RF detectable member, or other detectable feature 42 as described herein (instead of or in addition to a target 91). In such embodiments, a corresponding sensor 34 (magnetic sensor or other sensor as described herein) is carried by the infusion pump device 30 at a location to detect the detectable feature 42 as described herein. Accordingly, FIG. 16 is also referred to herein with respect to other embodiments, in which one or more detectable features 42 are provided on the reservoir plunger 1a, and one or more sensors 34 are located in the infusion pump device 30, for detection of the detectable feature(s).

In any of the inductive sensing embodiments described herein one or more (or each) coil 93 may be provided with a backing or shield for inhibiting electromagnetic interference from other components of the infusion pump device 30 or external sources. For example, in particular embodiments, a shunt backing of ferrite (or other suitable) material is arranged adjacent one side of the coil, to inhibit passage of electromagnetic fields to or from that side of the coil. In further embodiments, the material and shape of the backing or shield is configured to direct a magnetic field of the coil 93 toward the target 91. The backing or shield can be made in any suitable form including, but not limited to a plate-like member provided on one side (a back side) of the coil 93, a cage or enclosure containing the coil 93 and having an opening or other magnetic field guide directing the magnetic field toward the target 91. In embodiments in which the coil 93 is arranged on or in a wall of the infusion pump device 30, the backing or shield may be arranged on the same wall or on an opposite side of the wall, adjacent the location of the coil 93.

In inductive detection embodiments described with reference to FIGS. 10-15, a bias member, such as a coil spring (82 in FIGS. 10 and 11, and bias member 97c in FIG. 15) is provided to impart a bias force. In those embodiments, instead of or in addition to a coil 93 and target 91, the compression of the bias spring is detected by inductive sensing. In such embodiments, changes in the state (or amount) of compression of the bias spring provide detectable changes in an electrical signal in the bias spring, where a circuit (similar to circuit 95, but with the bias spring provided as the coil 91) is connected to the bias spring to detect such changes and perform operations as described above.

Inductive detection configurations described herein can provide various advantages. For example, like magnet detection embodiments described herein, inductive detection can provide a reliable, contactless system that is relatively insensitive to certain environmental conductions, such as dust, dirt, moisture, or the like. Furthermore, particular inductive detection systems do not require magnets. Furthermore, in inductive detection systems the coil 93 may be arranged in proximity to an expected location of the target, but can be separated from the rest of the circuit 95. Accordingly, the circuit 95 and electronics 60 may be arranged near the coil 93 or at other locations on the infusion pump device 30, remote from the coil 93.

In particular embodiments as described above, one (or all) of the cap 4, reservoir 1, and the infusion pump device 30 is provided with at least one sensor element, and the other (or both) of the cap 4 and the infusion pump device 30 is provided with at least one detectable feature that is detected by the sensor element(s) when the cap 4 is properly coupled with the infusion pump device 30. Certain embodiments as described above include one or more magnetic detectable features and magnet detection sensors. In other embodiments described above, each of the one or more detectable features 42 includes an inductive device or structure that can be detected by an inductive sensor, and each sensor element 34 includes an inductive sensor. In yet other embodiments, the one or more detectable features 42 include a combination of magnetic detectable devices and inductive devices, while the one or more sensor elements 34 include a combination of one or more magnetic detection sensors and one or more inductive sensors.

c. RF Detection

In particular embodiments as described above, one (or all) of the cap 4, reservoir 1, and the infusion pump device 30 is provided with at least one sensor, and the other (or all) of the cap 4, reservoir 1, and the infusion pump device 30 is provided with at least one detectable feature that is detected by the sensor when the cap 4 is properly coupled with the infusion pump device 30. Embodiments as described above include one or more magnetic detectable features and magnet detection sensors, or one or more inductively detectable features and inductive sensors (or both).

Other embodiments described herein (e.g., in sections, below) include one or more detectable features that are detected by optical, mechanical or electrical contact sensing configurations. In yet other embodiments, the one or more detectable features 42 includes a radio frequency (RF) detectable device or structure that can be detected by an RF sensor, and the one or more sensor elements 34 includes an RF sensor. Thus, in one example, element 42 represents one or more RFID tags carried by the cap 4, while element 34 represents one or more RF sensor elements in or adjacent the reservoir receptacle 32 of the infusion pump device 30.

Accordingly, arrangements and configurations of magnetic sensors and magnetic detectable features (as the sensors and detectable features 34 and 42) described above and shown in FIGS. 1-6 are incorporated herein by reference to apply to embodiments employing RF detectable features and RF sensors, as the sensors and detectable features 34 and 42. In addition and where applicable, further arrangements and configurations of inductive, optical, mechanical or electrical contact sensors and detectable features (as the sensors and detectable features 34 and 42) described with respect to other embodiments herein are incorporated herein by reference to apply to embodiments employing RF detectable features and inductive sensors, as the sensors and detectable features 34 and 42.

In particular embodiments, an RF detectable feature 42 includes a radio frequency identification data (RFID) tag or any other suitable device that provides an RF signal that is detectable by an RF sensor. The RF detectable feature may be a passive device that does not employ a battery power source. Examples of passive RF detectable devices include inductive devices that are powered and read by RF sensor readers, through electromagnetic induction. In other embodiments, the RF detectable feature is an active device that includes or is connected to a local power source, such as, but not limited to a battery, solar cell, or other local source of energy. In particular embodiments, the RF detectable device includes data storage electronics that stores information readable by a suitable RF sensor. Various types of RFID tags are made by a variety of companies including, but not limited to Impinj and NXP Semiconductors.

In particular embodiments, the RF detectable feature is configured as an RFID tag device that has an antenna coil and an electronic circuit electrically connected to the coil. The electronic circuit may be provided on a circuit board, in an electronic circuit chip (such as, but not limited to a microchip) or in or on another suitable support structure. In certain embodiments, the electronic circuit is a passive circuit that has no power source battery but, instead, receives power through the antenna coil, from inductive coupling with a sensor. In other embodiments, the electronic circuit in the RF detectable feature includes or is connected with a battery power source (or other suitable active power source). In an example embodiment, the RF detectable feature is configured as a stick-on label having an adhesive-backed substrate sheet or base, with an RFID tag supported on the substrate sheet or base (or adhered to, embedded in or inlayed into the substrate sheet or base). In such embodiments, the RF detectable feature can be provided in the form of a smart label that can be adhered directly to a cap 4, reservoir 1, or other component of a base/reservoir/cap unit, or to the infusion pump device housing, or any combination thereof.

The RF detectable feature is configured to communicate RF signals at one or more predefined frequencies or within one or more predefined frequency bands. In particular embodiments, the predefined frequencies or bands are within a UHF band, for example, but not limited to 860-960 MHz. Other embodiments may employ other suitable frequencies or bands. In embodiments in which a plurality of RF detectable devices are employed in the system, each RF detectable devices may be configured to operate in a different predefined frequency or band with respect to each other of the RF detectable device in the system.

Also in particular embodiments, the electronic circuit included in the RF detectable feature is configured to store information and communicate stored information in an RF signal. The RF signal may be communicated through inductive coupling with a sensor (for example, in a passive device embodiment) or by transmission with an active transmitter circuit included in the RF detectable feature (for example, in active device embodiments). Information stored by the RF detectable feature may include, but is not limited to, one or more of: serial number or other identification information, a lot number, a unique ID number/code, EPC or other code, indicia or encoded information representing one or more predefined characteristics of the reservoir, reservoir contents, cap 4 or other component of the base/reservoir/cap unit, the infusion pump device, any of the characteristics of the reservoir 1, infusion set 50, and connection interface 40 discussed in the above Magnetic detection section of the present specification, or the like.

In a passive device embodiment example, the RF detectable feature is an RF detectable device configured to receive an RF signal from a sensor device (when the RF detectable device and the sensor device are in sufficient proximity or alignment, or both), and is powered up by the received signal to communicate stored information back to the sensor device, for example, via a back scatter signal. In an active device embodiment example, the RF detectable device is configured to actively transmit stored information to a sensor device (when the RF detectable device and the sensor device are in sufficient proximity or alignment, or both). For example, the active RF detectable device may be configured to transmit stored information at predefined intervals (or periodic or random intervals) of time. In other embodiments, an active RF detectable device may be configured to receive a request signal from a sensor device when the RF detectable device and the sensor device are in sufficient proximity or alignment (or both), where RF detectable device responds to the request signal by transmitting the stored information.

The RF sensor device(s) may include, but are not limited to, an RF reader that includes electronics having an RF transceiver and modem controlled by a microprocessor (or other suitable processor) and electrically connected with an antenna. In embodiments that employ passive RF detectable devices, the RF sensor device includes an inductive loop antenna and electronic circuitry configured to generate an AC magnetic field that induces a voltage across an antenna of a passive RF detectable device, when the RF detectable device and the sensor device are in sufficient proximity or alignment, or both. In such embodiments, the RF sensor electronics are configured to receive information from the RF detectable device, via a back scattered signal (as described above). In other embodiments, the RF sensor device(s) include other suitable devices that provide a detectable response to the presence or alignment (or both) of an RF detectable device.

In particular embodiments, the RF sensor(s) are configured (or are connected with electronics configured) to detect at least one of: (a) the presence of an RF signal; (b) one or more parameters of an RF signal; and (c) data encoded in the RF signal. Such parameters include, but are not limited to the Received Signal Strength Indication (RSSI) or other RF signal strength, amplitude, phase, or other defined parameter of an RF signal provided (actively or passively). In particular embodiments, such parameters are compared with one or more pre-defined threshold values to detect, for example, whether or not the parameter exceeds the threshold value(s). Data encoded in the RF signal includes, but is not limited to, data representing or associated with one or more characteristics of the cap 4, reservoir 1, base 2, infusion set 50 or the base/reservoir/cap unit, or any combination thereof.

In particular embodiments, one or more RF detectable features 42 and or RF sensors 34, or both, are arranged such that the RF sensor detects the position of the cap 4 relative to the infusion pump device 30 (e.g., for detecting a proper connection of the cap 4 or the base/reservoir/cap unit with the infusion pump device 30). For example, one or more RF shields, directional antennas, wave guides or other configurations may be included in the cap 4, reservoir 1, or infusion pump device 30 (or all), to direct RF signals to or from RF detectable devices or sensors (or both). In particular embodiments, such RF shields, directional antennas, wave guides or other configurations are arranged such that the RF sensor is able to detect the RF detectable device (or one or more predefined parameters, data or both of a signal from the RF detectable device), when the RF sensor and the RF detectable device are in a predefined alignment, proximity (or both), such as when the cap 4 or the base/reservoir/cap unit is properly connected with the infusion pump device 30. In further embodiments, such RF shields, directional antennas, wave guides or other configurations are arranged to inhibit detection of the RF detectable device (or predefined parameter, data, or both), when the cap or the base/reservoir/cap unit is not properly connected with the infusion pump device 30.

In other embodiments, one or more RF detectable features and sensor elements, are employed to detect one or more other characteristics associated with the cap 4 or the base/reservoir/cap unit or components thereof, in addition to or as an alternative to detecting proper connection with the infusion pump device 30. In various embodiments, such other characteristics include but are not limited to characteristics of the reservoir 1 (or its contents), infusion set 50, connection interface 40, or any combination thereof, as described above with respect to magnetic detection.

In those embodiments, each different characteristic may be associated with one or more detectable RF parameters such as, but not limited to: the existence of one or more RF detectable features or sensor elements on the cap 4, the location or pattern of locations of one or more RF detectable features or sensor elements on the cap 4 (circumferential or linearly location relative to the dimension of the axis A), the type of RF detectable feature(s) or sensor devices(s) on the cap 4, the type or content of data stored by the RF detectable feature(s), the polarity, direction or orientation of the signal emitted by the RF detectable feature(s), or the like. In particular embodiments, each different predefined characteristic of the reservoir 1, infusion set 50 or connection interface 40, is associated (for example, on a one-to-one basis) with a respectively different predefined detectable location, pattern of locations, type of RF detectable feature or sensor element, data type or content (code or other indicia) or other detectable parameter in the RF signal read from the RF detectable feature. In those embodiments, the processing electronics 62 is configured to determine a characteristic of the reservoir 1, infusion set 50 or connection interface 40 from the signals received from the sensor element 34 or 42.

For example, the processing electronics 62 may be configured to compare information received from one or more RF sensor elements 34 with one or more predefined, stored threshold, where each threshold is associated with a characteristic as described above. In other embodiments, the processing electronics 62 is configured to compare information received from one or more RF sensor elements 34 with values or information stored in a table or in another suitable data arrangement. The table or other data arrangement associates a plurality of different predefined RF detectable device locations (or a plurality of different predefined patterns of RF detectable device locations on the cap) with a corresponding plurality of predefined characteristics. Alternatively or in addition, the table or other data arrangement associates a plurality of different codes or other data receivable from RF detectable devices with a corresponding plurality of characteristics. The associations may be, for example, but not limited to, a one-to-one correspondence of each different RF detectable device location, code or other data with a different characteristic, respectively. The table or other data arrangement is stored in the electronic memory 66. Examples characteristics for RF detection embodiments include characteristics of the reservoir 1 (or its contents), the infusion set 50 connected to the cap 4, the connection interface 40, as described above with regard to magnetic detection and incorporated herein by reference.

In particular embodiments, based on one or more of the parameters detected from the signals received from the RF sensor, the processing electronics 62 is further configured to determine corresponding characteristics and, based on those parameters or characteristics, do one or more of: determine operational settings for the infusion pump device 30, provide signals to the drive device or other components of the infusion pump device 30, provide one or more alarm signals, and record data representing detected states or conditions of one or more of the cap 4, base/reservoir/cap unit, and infusion pump device 30, as described above with regard to magnetic detection.

As described above, embodiments of the RF detectable feature 42 include electronics for storing data that is readable by an RF sensor element 34. In particular embodiments, such data storage electronics are configured to be writable (to receive data and store received data). In such embodiments, an external writing device, such as, but not limited to, a computer or processing device with a suitable data transmitter, is configured to write data onto the RF detectable feature. In particular embodiments, the RF detectable feature 42 includes multiple electronic storage devices or one or more segmented storage devices, where one or more of the storage devices or segments are writable and can receive and record data written thereto, as described above, while one or more other storage devices or segments store readable data (for example, recorded by a manufacturer or other authorized entity) but are not re-writable. Thus, for example, an RF detectable feature 42 may include a segmented RFID tag having a first segment that stores information readable by electronics in the infusion pump device 30, and a second segment that stores additional information that is written onto the tag by a healthcare provider or other authorized entity, or by electronics in the infusion pump device 30.

In such embodiments, for example, a doctor or other health care provider may write and record information onto the RF detectable feature. Information written onto the RF detectable feature in that manner may include, but is not limited to, data corresponding to the characteristics described above, instructions to be read by electronics in the infusion pump device 30 for controlling an operation of the infusion pump device 30 or for displaying information on a display of the infusions pump device 30, data corresponding to the user of the infusion pump device 30 or a treatment associated with that user, or other data or combinations thereof.

In further embodiments, the infusion pump device 30 includes one or more data writing devices for writing data onto an RF detectable feature 42, when the cap 4 or the base/reservoir/cap unit is properly connected with the infusion pump device 30. In such embodiments, electronics 60 is configured to selectively write data (or read and write data) on the RF detectable feature 42, in accordance with predefined, programmed instructions. In one example embodiment, the electronics 60 includes or is connected with a sensor (not shown) for detecting one or more parameters corresponding to the volume of infusion media dispensed by the infusion pump device 30, and is configured to track the amount of infusion media dispensed from a reservoir 1 from a defined time upon or after the reservoir 1 is installed in the reservoir receptacle 32, and write to record on the RF detectable feature 42 that tracked amount or an associated value representing a volume of infusion media dispensed or remaining in the reservoir 1.

Alternatively or in addition, in further embodiments the infusion pump device 30 is configured to write to record other information on the RF detectable feature 42, such as, but not limited to one or more of a date, time or geographic location at which the base/reservoir/cap unit or components thereof were installed in the infusion pump device 30. In further embodiments, such other information includes one or more of operational information or alarm conditions detected by the electronics 60 during operation of the infusion pump device.

In further embodiments, such other information includes one or more of a date, time or geographic location at which infusion media was dispensed, an occlusion in the infusion set 50 was detected, an alarm condition was detected, or another predefined condition was detected or predefined pump operation occurred. Thus, just as the processing electronics 62 described above may be configured to detect, record (or both) the geographic location of the infusion pump device 30, cap 4, or base/reservoir/cap unit, or the time (or all) when a particular characteristic or event is detected, the processing electronics 62 may also or alternatively be configured to record such information onto the RF detectable feature 42.

In embodiments in which date or time is recorded, the electronics 60 include or are associated with an appropriate clock or other source of date or time information. In embodiments in which geographic location is recorded, the electronics 60 includes or is associated with suitable location detection electronics such as, but not limited to satellite position system electronics (for example, but not limited to a GPS system receiver), configured to detect a geographic location of the infusion pump device 30.

In particular embodiments employing RF detection, the processing electronics 62 is configured to determine operational settings for the infusion pump device 30, provide alarm or control signals, record data, provide authentication operations, or perform other predefined tasks base, at least in part, on detection of (or information provided by a detectable characteristic of) the RF detectable feature 42 in a manner similar to the manner described above with respect to magnet elements(s) as the detectable feature 42. Accordingly, the above description of example configurations and operations of processing electronics 62 applies to the RF detectable feature 42. Thus, Parameters 1-N described above may be characteristics of the RF detectable feature 42, such as, but are not limited to the RSSI or other RF signal strength, amplitude, phase, data encoded in the RF signal or other defined parameter of an RF signal.

Furthermore, in embodiments in which the presence or position (such as rotary position) of the cap 4 or the base/reservoir/cap unit relative to the infusion pump device 30 is detected, an RF detection configuration can provide a relatively precise position detection. For example, in further examples of embodiments described above with respect to FIGS. 4A and 4B, in which a plurality of elements 42 are arranged on the cap 4, at a corresponding plurality of different locations, spaced circumferentially around or linearly along (or both) the axis A, the elements 42 are RF detectable devices, while the elements 34 are RF sensor devices. In other embodiments, the elements 42 are RF sensor devices (or both RF sensor devices and RF detectable devices), while elements 34 are RF detectable devices (or both RF detectable devices and RF sensor devices).

In particular embodiments, RF detectable devices and RF sensor devices can provide a relatively precise detection of proper or improper alignment or proximity (or both), of the base/reservoir/cap unit relative to the reservoir receptacle 32, as described above with respect to FIGS. 4A and 4B. Also, in embodiments in which multiple RF sensors or multiple RF detectable devices (or both) are employed on one or both of the cap 4 and infusion pump device 30, the multiple elements may be arranged to allow detection of various predefined states of the cap 4. Thus, in example embodiments, the multiple elements are arranged spaced apart around the circumference of the axis A to allow detection of the rotational position (or movement) of the cap 4 around the axis A, relative to the infusion pump device 30. Alternatively or in addition, the multiple elements are arranged spaced apart in the axial dimension A of the cap 4 to allow detection of the linear position (or movement) of the cap 4 along the axis A, relative to the infusion pump device 30. In other embodiments, one or more elements are arranged to detect angular differences (or movement) between the axial dimension A of the cap and the axial dimension of the reservoir receptacle 32. Accordingly, in different embodiments, the sensor element(s) provide one or more sensor signals representing a rotational position of the cap 4, a linear position of the cap 4, an angular position of the cap 4, or any combination thereof.

RF detectable features and RF sensors can be configured, according to embodiments of the present invention, to provide a relatively precise position detection. Example configurations are described herein. However, other embodiments employ other suitable configurations that provide levels of precision appropriate for their context of use.

In particular embodiments, presence or position detection (or both) is accomplished by configuring one or more RF sensor devices 34 (or electronics connected to such sensor device(s)) to detect the signal strength of one or more RF detectable feature 42. The signal strength detection may include a detection of the RSSI signal level. In particular embodiments, the electronics 60 connected to the sensor(s) are configured to compare a signal strength (such as RSSI signal level) detected by one or more sensor(s) with one or more predefined threshold values. Such predefined threshold values may be set by a manufacturer or other entity associated with the infusion device pump 30, reservoir 1, cap 4 or other components described above, and stored in memory included in or accessible by the electronics 60, such as memory 66. For example, in particular embodiments, the predefined threshold values include values that correspond to signal strength levels that are received by one or more RF sensor device(s) 34, when one or more RF detectable features 42 are in a proper position or alignment (or both) with the one or more RF sensor devices 34 (corresponding to when the base/reservoir/cap unit is properly or fully received (or both) in the infusion pump device 30).

In further particular embodiments, a single RF sensor device (for example, represented by element 34 in FIGS. 4A and 4B) detects RF signals from multiple RF detectable devices (for example, represented by elements 42A and 42B in FIGS. 4A and 4B). In such embodiments, the RF sensor device is connected with electronics 60 configured to determine the signal strength (for example, RSSI signal level) of each sensor of the multiple sensors, for determining the position of the cap 4 relative to the infusion pump device 30. Also in such embodiments, each of the RF detectable device (e.g., elements 42A and 42B) may be configured to provide a detectably different signal relative to each other of the RF detectable devices. Accordingly, the electronics 60 may be configured to determine which RF detectable device (e.g., element 42A or 42B) is associated with each different detected signal, such that the electronics associates a detected signal strength with each different detected signal (i.e., each different element 42A or 42B). By associating a detected signal strength for multiple RF detectable devices (e.g., elements 42A or 42B), the electronics 60 can determine the position of the cap 4 relative to the infusion pump device 30 with relatively good precision. The electronics 60 may be configured to process information received from the sensor device(s) in any suitable manner, such as, but not limited to, comparing detected signal strength levels of signals received from a plurality of RF detectable devices with a corresponding plurality of predefined threshold values, as described above, for example, with respect to the process 150 in FIG. 6. However, other embodiments employ other suitable processing routines for evaluating signals received from a plurality of RF detectable devices.

In further embodiments, one or more RF detectable features or the one or more RF sensors (or both) include an antenna configuration to enhance detection capabilities or precision of the detection (for example, location or position detection precision). Thus, with reference to embodiments described above with respect to FIGS. 4A and 4B, in which a plurality of sensor devices or detectable devices (or both) are located in a spaced relationship around or along (or both) the axis A, in further embodiments a plurality of antennas are similarly located in a spaced relationship around or along (or both) the axis A (e.g., on the infusion pump device 30 or on the cap 4, or both).

In an example embodiment, one or more RF sensor devices or the RF detectable features (or both) 34 or 42 described above include or are connected with a plurality of antennas, where each antenna is located at a different position around the circumference or length (or both) of the direction of the axis A. In embodiments in which one or more RF sensor devices are on the infusion pump device 30, a plurality of antennas may be mounted in the infusion pump device 30 as part of or connected to the RF sensor device(s), and are arranged in a special array around or along (or both) the direction of the axis A. In embodiments in which the one or more RF detectable features are on the cap 4 or other component of the base/reservoir/cap unit, a plurality of antennas may be mounted in the cap 4 or other component of the base/reservoir/cap unit as part of or connected to the RF detectable feature(s), and are arranged in a spatial array around or along (or both) the direction of the axis A.

For example, each antenna of (or connected to) a sensor device 34 is configured and oriented to communicate signals with (receive signals from or transmit signals to, or both) one or more antennas of (or connected to) an RF detectable feature 42, when that RF detectable feature 42 is in a predefined position relative to the antenna (such as, but not limited to, a position directly adjacent the antenna), but does not sufficiently communicate signals with the RF detectable feature that is not in the predefined position. In particular embodiments, one or more antennas are arranged in locations that correspond to the position of one or more of the RF detectable features when the base/reservoir cap unit is fully or properly received within the infusion pump device 30.

Accordingly, electronics 60 connected with the RF sensor device 34 may be configured to determine whether or not the base/reservoir/cap unit is fully received within or in a proper position relative to the infusion pump device 30 (or determine the position of the cap 4 relative to the infusion pump device 30), based on signals received by one or more antenna. In particular embodiments, the electronics 60 is configured to employ information regarding signals received from a plurality of antennas arranged around or along (or both) the direction of the axis A, to determine the position of the base/reservoir/cap unit (or cap 4) relative to the infusion pump device 30. In further embodiments, the electronics 60 is configured to employ such information to determine the direction or speed (or both) of rotation or other movement of the base/reservoir/cap unit (or cap 4) relative to the infusion pump device 30, for example, to evaluate whether the base/reservoir/cap unit (or cap 4) is being moved in the proper or desired direction, to record information corresponding to the direction or speed (or both) of movement, or a combination thereof.

In further embodiments, one or more antennas of sensor device(s) 34 are configured to receive signals from one or more antennas of the RF detectable features 42, where the signal strength (such as, but not limited to RSSI value) or other characteristic of the signal varies as the relative position of the RF detectable device on the cap varies. In such embodiments, the electronics 60 is configured to employ signal strength or other detected signal characteristic from one or a plurality of antennas to determine the position of the base/reservoir/cap unit (or cap 4) relative to the infusion pump device 30. For example, the signal strength (RSSI or other signal strength value) of a received signal can be stronger as the relative positions of the antennas of the sensor device and detectable device become closer (e.g., as the cap 4 or base/reservoir/cap unit is moved toward a fully inserted position within the reservoir receptacle 32). Thus, the electronics 60 may be configured to analyze detected signal strength from one or more sensor devices or one or more antennas (or both), such as, but not limited to comparing detected signal strength with one or more preset thresholds corresponding to predefined relative positions of the base/reservoir/cap unit (or cap 4) and the infusion pump device 30. Other embodiments may employ other algorithms or routines for determining relative positions from received signals.

Particular embodiments employ a plurality of antennas in a spaced arrangement as described above, and electronics 60 configured to analyze RSSI values or other signal strength values for signals received by or transmitted by (or both) the plurality antennas, to provide position detection or pattern recognition (to identify a detected pattern of locations of the antennas from a plurality of predefined possible patterns), for example, with a high precision relative to a single antenna arrangement. In those or other embodiments that employ a plurality of antennas, the antennas may be configured in a phased array configuration or other suitable configuration for providing a predefined detectable signal directions or patterns.

In particular examples of embodiments that employ a plurality of antennas or a plurality of sensor devices 34 (or both a plurality of antennas and a plurality of sensor devices), the electronics 60 is configured to scan the array of sensors to selectively activate each sensor or read a signal from each sensor (or both), in serial sequence or other predefined sequence or a pseudo random sequence. For example, in particular embodiments, a plurality of antennas is arranged (on the cap 4, the infusion pump device 30, or both) at predefined locations around or along (or both) the circumference of the axis A, where each antenna is configured to provide (or is connected with mutually different detectable devices or sensor devices configured to provide) a different detectable signal relative to each other antenna. By configuring each antenna to provide a relatively narrow beam (narrow angle of transmission or reception beam or both), such as, but not limited to a beam angle of about 1 to 3 degrees, and scanning the antennas, the electronics 60 may be configured to provide a relatively precise detection of the rotational or linear position of the cap 4 (or the base/reservoir/cap unit) relative to the reservoir receptacle 32 of the infusion pump device 30. In other embodiments, other suitable beam angles may be employed, including beam angles of less than 1 degree or beam angles greater than 3 degrees.

In those or other example embodiments that employ a plurality of antennas or a plurality of sensor devices 34 (or both a plurality of antennas and a plurality of sensor devices), the electronics 60 is configured to provide maximum ratio combining of received RF signals, for example, to improve signal-to-noise ratio. In such embodiments, the signals received from a plurality of antennas in an array are combined, but the ratio of the combination is adjusted by the electronics 60, depending upon the strength of the signal. For example, the electronics 60 may weight or increase the contribution of signals from antennas in the array that are receiving stronger signals than antennas in the array that are receiving weaker signals (as determined by the electronics 60).

In particular embodiments, antennas may be calibrated (for example by the factory that manufactures the cap, reservoir, base or infusion pump device or by another authorized entity) for improved sensitivity and accuracy. In further embodiments, detection sensitivity and precision is enhanced by employing any combination of two or more features described above including, but not limited to antenna beam forming configurations, antenna arrays of multiple antennas, different detectable parameters for different antennas in an array, other transmission diversity for different antennas in an array, maximum ratio combining, factory calibration, or the like.

In examples of embodiments described above that employ one or more antennas in or connected with one or more sensor devices 34, the sensor antenna(s) may be mounted in the infusion pump device 30, for example, adjacent the reservoir receptacle 32. In particular embodiments, the sensor antenna(s) is (are) located within the housing structure of the infusion pump device 30, for example, by being embedded in or molded within the plastic material that forms the housing structure or the structure of the reservoir receptacle 32 (or both). In other embodiments, the antenna(s) are attached to the housing or reservoir receptacle structure of the infusion pump device 30 by an adhesive or connective hardware (or both).

The size, position and/or orientation of an antenna can greatly influence the strength of the signal and the detection of various features in an RF detectable feature, including but not limited to, an RFID. With this in mind, in certain embodiments, it can be beneficial to provide as large an antenna area as possible and/or augment an antenna in a cap 4. In particular embodiments, the RFID can include an antenna and/or electrical contacts that engage with an antenna formed on the reservoir. In further embodiments, the antenna is formed along the side of the reservoir. In these embodiments, the antenna placed on the reservoir is oriented and/or provides increased size at a location more ideally suited to engage and work with the corresponding electronics on the infusion pump device. In particular embodiments, more than one antenna may be formed on the side of the reservoir. For instance, this may be useful to assure alignment of the antenna after connection of the cap 4 to the reservoir and insertion and locking of the reservoir (or base/reservoir/cap unit) in the infusion pump device housing. This may simplify operation for the user, such that the user may more easily attach the reservoir to the cap 4 without regard to the orientation of the cap 4 in relation to the reservoir. In particular embodiments, one or more antenna is provided on the side of the reservoir, for example, by printing the antenna directly onto the side of the reservoir with a suitably conductive ink. In other embodiments, the antenna may be provided on the reservoir in outer suitable manners including, but not limited to molding the antenna into the reservoir, attached the antenna to the reservoir by adhesive, applying the antenna to the reservoir as a label or the like.

In other examples of embodiments described above that employ one or more antennas in or connected with one or more RF detectable features 42, the antenna(s) may be mounted in the cap 4, base 2 or reservoir 1. In yet other embodiments, the antenna(s) are mounted in the infusion pump device 30 (as described above), and are arranged to electrically connect with one or more RF detectable features 42 on the cap 4, base 2 or reservoir 1, when the cap 4 (or the base/reservoir/cap unit) is properly or fully received within the reservoir receptacle 32 of the infusion pump device 30. In such embodiments, the cap 4 (or other component of the base/reservoir/cap unit) includes a set of one or more electrically conductive contacts that are included in or electrically connected to the RF detectable feature(s) 42 (e.g., RFID tags or the like) and are arranged to engage a corresponding set of one or more electrically conductive contacts on the infusion pump device 30, when the cap 4 (or base/reservoir/cap unit) is properly and fully received within the reservoir receptacle 32 of the infusion pump device 30. In such embodiments, the electrically conductive contacts on the cap 4 (or base/reservoir/cap unit) are not in electrical communication with the contacts on the infusion pump device 30, when the cap 4 (or base/reservoir/cap unit) is not properly and fully received within the reservoir receptacle 32 of the infusion pump device 30. Accordingly, in those embodiments, the RF detectable feature(s) 42 are electrically connected with one or more antenna(s), only when the cap 4 (or base/reservoir/cap unit) is properly and fully received within the reservoir receptacle 32 of the infusion pump device 30.

In examples of embodiments described above that employ one or more antennas mounted in or on the cap 4 (or another component of the base/reservoir/cap unit), the antenna is arranged in sufficient proximity to a vent opening or port 24 on the cap 4 to contact water or other liquid that may come into contact with (or enter) the opening or port. In such embodiments, the antenna is configured to operate properly when dry (or out of contact with water or other liquid), but does not operate (or operates in a detectably different manner) when in contact with water or other liquid. Accordingly, in such embodiments, the antenna may operate as a moisture sensor that becomes inoperative or operates in a detectably different manner, when in contact with water or other liquid (e.g., when the water or other liquid comes into contact with or enters the opening or vent). For example, electronics 60 may be configured to provide an alarm signal, inhibit operation of one or more functions of the infusion pump device 30 (such as, but not limited to, a fluid dispensing function), transmit a message or perform another predefined task, or any combination thereof, when the antenna is not operative, for example, due to the antenna being in contact with water or other liquid.

In various embodiments described above, one or more RF detectable features 42 are provided on the cap 4 (or other portion of the base/reservoir/cap unit). In particular embodiments, one or more RF detectable features 42 are provided on the plunger of a reservoir 1, and one or more RF detectors are provided on the infusion pump device 30, in sufficient proximity to the reservoir receptacle 32, to interact with the RF detectable feature 42 when the reservoir 1 is installed within the reservoir receptacle. For example, with reference to FIG. 16, at least one RF detectable feature 42 is provided on a moveable plunger of the reservoir 1 (e.g., on the head 1a of the reservoir plunger or the shaft 1b of the reservoir plunger. In such embodiments, one or more RF sensors may be arranged in the infusion pump device 30 (e.g., within or in the vicinity of the reservoir receptacle 32), to detect linear positions of the RF detectable feature 42 relative to the axis A, when the base/reservoir/cap unit is installed in the reservoir receptacle 32. Accordingly, based on the detected position of the RF detectable feature 42, processing electronics (such as processing electronics 62) connected to an electronic detection circuit associated with each coil 93 may be configured to detect the linear position of the plunger head 1a and, thus, the amount of infusion media remaining in the reservoir 1.

In particular embodiments, the processing electronics is configured to detect the linear position of the plunger head 1a and determine whether or not the plunger head 1a is in a filled position (corresponding to a filled or un-used reservoir 1), or whether or not the plunger head 1a is in the last position from the previous use of the infusion pump device 30. In such embodiments, the processing electronics may be configured to perform a predefined action in response to a determination that the plunger head is not in a filled position or is not in its last position (which may indicate that a used or re-used reservoir has been installed in the infusion pump device). Such predefined action may include, but is not limited to, inhibiting infusion media delivery operation of the infusion pump device 30, determining particular operational settings for the infusion pump device 30, providing an alarm or control signals, recording data, providing authentication operations, or performing other predefined tasks.

In a further embodiment, the RF detectable feature 42 includes a passive (or active) RFID chip or other RF detectable feature that is provided with a serial number or other code (unique or not unique among other reservoirs 1). In such embodiments, when the reservoir 1 (or base/reservoir/cap unit) is initially installed in the infusion pump device 30 (or other suitable delivery device), or at a particular time after installation, electronics (such as electronics 60 in FIG. 5) reads the serial number or code. In particular embodiments, the electronics 60 are configured to determine whether or not the serial number or code corresponds to that of reservoir 1 that was previously installed in the infusion pump device 30 (or other delivery device), and perform a predefined action in the event that the correspondence is determined (or not). In such embodiments, the electronics may be configured to store a record of serial numbers or codes of reservoirs used over time in the infusion pump device 30 (or other delivery device), and compare a newly read serial number or code from a reservoir 1 with the pre-stored serial numbers or codes to determine whether or not a match is found. A match can indicate a likelihood that the reservoir 1 had been previously used (or an attempt to re-use a previously used reservoir 1). In such embodiments, the processing electronics may be configured to perform a predefined action in response to a determination that the serial number or code read from the reservoir 1 matches a pre-stored serial number or code (for a previously-used reservoir 1), including, but is not limited to, inhibiting infusion media delivery operation of the infusion pump device 30, determining particular operational settings for the infusion pump device 30, providing an alarm or control signals, recording data, providing authentication operations, or performing other predefined tasks.

In embodiments as in FIG. 16 in which the RF detectable feature 42 is located on the reservoir plunger, the RF detectable feature 42 may be either a passive device or an active device. A passive device can be less costly and more durable than an active device. However, an active device can provide additional features as described herein.

In particular embodiments, the infusion pump device 30 (or other delivery device) is provided with an active RFID chip (or other active RF device), while the plunger of the reservoir 1 is provided with a passive RFID chip (or other passive RF device). In such an arrangement, a magnetic field can exist between the passive chip on the reservoir 1 and the active chip on the infusion pump device 30 (or other deliver device), where the magnitude of the magnetic field is dependent on the relative distance between the passive and active RF devices. In such embodiments, the magnetic field increases as the RF device on the reservoir piston moves closer to the RF device on the infusion pump device (or other delivery device), or decreases as the RF device on the reservoir piston moves further from the RF device on the infusion pump device (or other delivery device).

Accordingly, in such embodiments, the sensor element 34 includes a magnetic field detector, to detect the magnetic field or changes in the magnetic field between the RF devices. Also in such embodiments, electronics (such as electronics 60 in FIG. 5 is configured to perform one or more pre-defined actions, based on the magnetic field, including those described above. In particular embodiments, the electronics is configured to determine a volume of infusion media (level or amount remaining or used) for the reservoir 1, based on the detected magnetic field strength.

In further embodiments, volume is determined in other suitable manners. For example, in particular embodiments, as part of a filling operation in which the reservoir 1 is filled (partially or fully) at a filling station or filling device, information corresponding to the volume (amount filled) is written onto the RFID chip or other RF device on the reservoir plunger (or on another portion of the reservoir). Then, when the reservoir is installed in the infusion pump device (or other delivery device), electronics (such as electronics 60 in FIG. 5) provides a count of motor steps of the pump motor or other detection of the amount of infusion media dispensed after installation. The electronics further calculates a volume of infusion media remaining in the reservoir 1 (for example, by subtracting the amount dispensed from the amount filled).

In particular embodiments, the electronics may be configured to display volume information (including, but not limited to the level or amount of infusion media remaining or used) on a user-perceptible display device on the infusion pump device 30. In embodiments in which the infusion pump device 30 (or other delivery device) is provided with an active RFID chip (or other active RF device), additional information may be written to and read from the active chip or device, where such information may include, but is not limited to volume information as described above, or one or more serial numbers or codes as described above.

In further embodiments, one or more wireless or wired communication devices is provided on the infusion pump device 30 (or other delivery device) and is configured and controlled to transmit volume information (or other information corresponding to detected parameters or associated characteristics) for display on another electronic device separate from or located remote from the infusion pump device 30. In particular embodiments, the wireless communication device(s) are configured to connect for communication on a communication network (such as, but not limited to the Internet), with one or more pre-defined network connected devices. Such one or more pre-defined network connected devices may be located at remote geographic locations relative to the infusion pump device 30 (or other delivery device). In particular embodiments, such network connected devices include a server configured to receive information from the infusion pump device 30 (or other delivery device) or from another network connected device (such as a cradle, user computer, or the like) that communicates with the infusion pump device 30 (or other delivery device). Such information may include, but is not limited to volume information, serial numbers or codes or other information regarding the reservoir 1, cap 4, base/reservoir/cap unit or infusion set as described above.

In such embodiments, the network connected server may be associated with an entity that records information, supplies associated products such as refills or replacement parts, provides medical treatment or medical insurance to the user or the like. In one example, the network connected server is associated with the Carelink™ system of Medtronic Inc. In other embodiments, the network connected server is one or more other servers and associated entities. Accordingly, such information may be employed by the server (or associated entity) to determine whether or not (or when) to send refills, new or replacement reservoirs or other components of the cap 4, base/reservoir/cap unit, or infusion set. In further embodiments, such information may be provided to the user's doctor or other medical treatment entity associated with the user (for tracking, diagnosing, adjusting treatment plans or other suitable uses). Thus, in such embodiments, refills or replacement components may be sent to users, automatically (without requiring the user to place an order), and usage information can be provided to the user's healthcare provider, insurance provider or other suitable entities, automatically.

In further embodiments, the network connected server is configured to provide (and the infusion pump device 30 or other delivery device is configured to receive) information through the above-noted network communication connection or other network connection. Such information may include, but is not limited to, instructions or recommendations for replacing or refilling a reservoir 1, cap 4, base/reservoir/cap unit or infusion set, messages or notices from healthcare providers, insurance carriers or manufacturers, recall notices or the like. In particular embodiments, electronics (such as electronics 60) in the infusion pump device 30 (or other delivery device) is configured to perform one or more predefined actions (as discussed above) in response to receipt of a predefined instruction, notice or message.

In further embodiments, a predefined plurality (or lot) of reservoirs 1 (or base/reservoir/cap units, infusion sets or components thereof) are supplied to a user, where the RFID chips (or other RF devices) store one or more serial numbers or codes (unique to each reservoir, base/reservoir/cap units, infusion sets or component thereof. In such embodiments, electronics (such as electronics 60) in the infusion pump device 30 (or other delivery device) may be configured to detect the serial numbers or codes of the reservoirs 1 (or base/reservoir/cap units, infusion sets or components thereof) when used in the infusion pump device 30 (or other delivery device). The detected serial numbers or codes are tracked (by the infusion pump device 30 or other delivery device, by a remote server as discussed above) to determine when a predefined number of the plurality (lot) of reservoirs 1 (or base/reservoir/cap units, infusion sets or components thereof) has been used, and to trigger an order (or re-order) of more reservoirs 1 (or base/reservoir/cap units, infusion sets or components thereof).

In yet further embodiments, volume detection as described above can be employed to detect a possible occlusion or blockage in the delivery path between the infusion pump device 30 (or other delivery device) and the user. In such embodiments, electronics (such as electronics 60) may be configured to perform volume detections as described above, to determine the actual displacement or position of the reservoir plunger (for example, by detection of the magnetic field strength as described above) and the motor count. In addition, the electronics 60 is configured to determine whether the motor count corresponds to the actual displacement of the reservoir plunger. An actual displacement of the reservoir plunger that is less than the amount of displacement that is supposed to occur with the detected number of motor counts may be an indication of an occlusion or blockage in the delivery path. In particular embodiments, upon detection of a possible occlusion or blockage (e.g., upon detection of the plunger displacement associated with the motor count exceeding the actual displacement of the reservoir plunger by a predefined threshold amount), the electronics is configured to perform a predefined action, such as, but not limited to one or more of the actions discussed above.

In particular embodiments as described above, one (or all) of the cap 4, reservoir 1 and the infusion pump device 30 is provided with at least one sensor element, and the other (or all) of the cap 4, reservoir 1 and the infusion pump device 30 is provided with at least one detectable feature that is detected by the sensor element(s) when the cap 4 (or base/reservoir/cap unit) is properly coupled with the infusion pump device 30. Certain embodiments as described above include one or more magnetic detectable features and magnet detection sensors, or one or more inductive members and inductive sensors. In other embodiments described above, each of the one or more detectable features 42 includes an RF detectable device or structure that can be detected by an RF sensor, and each sensor element 34 includes an RF sensor. In yet other embodiments, the one or more detectable features 42 include any combination of magnetic detectable devices, inductive detectable devices and RF detectable devices, while the one or more sensor elements 34 include any combination of one or more magnetic detection sensors, inductive sensors and RF sensors. Any of the embodiments described herein with respect to use involving RFID also may be implemented with physical wired connection, in lieu of a wireless RFID connection, between the reservoir 1, infusion set 50, and/or connection interface 40 and the infusion pump device 30 (or other device(s)).

In further embodiments, one or more (or a plurality of) RF detectable features 42 is included in a label (or smart label) that is adhered to, embedded in or otherwise attached to the reservoir 1, cap 4 or other component of the base/reservoir/ cap unit. In particular embodiments, the label includes an adhesive-backed substrate or other support layer on which an RFID tag or other RF detectable feature (including antenna) is mounted. The substrate may be made of any suitable material, such as a flexible sheet material made of plastic, silicone, paper or fiber board, or the like. In other embodiments, the substrate is made of other suitable material such as, but not limited to other flexible materials or a rigid or semi-rigid material made of metal, plastic, ceramic, composite material or the like. In particular embodiments, the label can be directly adhered to the cap 4, reservoir 1, or other component of the base/reservoir/cap unit by an adhesive material on a back surface of the substrate. In other embodiments, the label is attached to the reservoir 1, cap 4 or other component of the base/reservoir/cap unit with another suitable attachment mechanism such as, but not limited to crimping, welding, magnetic connection, screws, bolts, clamps or other mechanical connection devices. The RFID device, and parts thereof, may span across multiple components and be part of, e.g., the reservoir 1, infusion set 50, tubing 52, connection interface 40, etc., or wholly integrated into any single one of the above-mentioned components.

In yet further embodiments, the label is configured in the form of a data strip having a lengthwise dimension and one or more (or a plurality of) RF detectable features along its lengthwise dimension. In other embodiments, the data strip has one or more (or a plurality of) other types of detectable features 42 as described herein (such as, but not limited to magnetic, inductive, optical, and mechanical detectable features) as an alternative or in addition to one or more RF detectable features 42 along its lengthwise dimension. In particular embodiments, the detectable features 42 include one or more optically detectable features in a pattern, such as, but not limited to a bar code pattern or other optically detectable pattern of elements having dark and light (or low or high reflective) characteristics.

In particular embodiments, the data strip is configured to extend around the cap 4, reservoir 1, or other component of the base/reservoir/cap unit (around the circumference or axis A), such that the one or more (or plurality of) detectable features 42 extend around the cap 4, reservoir 1, or other component of the base/reservoir/cap unit (around the circumference or axis A). In such embodiments, one or more sensors 34 are mounted in or to the infusion pump device 30. The sensor(s) 34 are supported at one or more fixed locations on the infusion pump device 30 for detecting the detectable feature(s) on the data strip, when the cap 4 (or base/reservoir/cap unit) is installed in the reservoir receptacle 32 of the infusion pump device 30.

In particular embodiments, one or more sensor(s) 34 are arranged around the circumference of the reservoir receptacle 32 and axis A for detection of one or more detectable features 42 on the label (or data strip). In such embodiments, the sensor(s) 34 and associated electronics (such as electronics 60 in FIG. 5) are configured to detect one or both of the presence or position (such as rotary position) of the cap 4 or the base/reservoir/cap unit relative to the infusion pump device 30, where an array of detectable features 42 on a label (or data strip) can provide a relatively precise position detection. For example, a label or data strip can be configured to provide a plurality of detectable elements arranged around the cap 4, reservoir 1, or other component of the base/reservoir/cap unit, at a corresponding plurality of different locations, spaced circumferentially around or linearly along (or both) the axis A. In such embodiments, one or more sensor(s) 34 may be arranged around the reservoir receptacle 32 and axis A as described above with respect to FIGS. 4A and 4B.

In particular embodiments, an array of detectable features 42 on a label or data strip as described above can provide a relatively precise detection of proper or improper alignment or proximity (or both), of the cap 4, reservoir 1, or other component of the base/reservoir/cap unit relative to the reservoir receptacle 32, as described with respect to FIGS. 4A and 4B. Also, in particular embodiments multiple detectable features may be arranged to allow detection of various predefined states of the cap 4, reservoir 1, or other component of the base/reservoir/cap unit.

Thus, in example embodiments in which the base/reservoir/cap unit is installed in the reservoir receptacle 32 by rotating the base/reservoir/cap unit around the axis A while inserting the base/reservoir cap unit into the reservoir receptacle 32, rotational position detection or linear position detection (or both) can be accomplished. In such embodiments, multiple detectable elements 42 are arranged on the label or data strip and spaced apart from each other around the circumference of the axis A, to allow detection of the rotational position (or movement) of the cap 4, reservoir 1, or other component of the base/reservoir/cap unit around the axis A, relative to the infusion pump device 30. Alternatively or in addition, the multiple elements are arranged spaced apart in the axial dimension A of the cap 4, reservoir 1, or other component of the base/reservoir/cap unit to allow detection of the linear position (or movement) of the cap 4, reservoir 1, or other component of the base/reservoir/cap unit along the axis A, relative to the infusion pump device 30. Accordingly, in different embodiments, the sensor element(s) 34 provide one or more sensor signals representing a rotational position of the cap 4, reservoir 1, or other component of the base/reservoir/cap unit, a linear position of the cap 4, reservoir 1, or other component of the base/reservoir/cap unit, or a combination thereof.

In particular embodiments, each detectable feature comprises an RFID tag or other RF detectable feature or other type of detectable feature 42 as described herein (such as, but not limited to magnetic, inductive, optical, and mechanical detectable features) and is configured to represent a data value that is detectable by one or more (or each of a plurality of) sensor elements 34. In particular embodiments, the detectable features are printed in magnetically detectable ink, polarized or optically detectable ink, or other materials that can be readily applied to a label or data strip. In other embodiments, the detectable features are discrete elements that are attached to the label or data strip by adhesive or other suitable attachment mechanism. In particular embodiments, the detectable features (or the label or data strip) is made to be transparent or partially transparent, or colored to be invisible, partially invisible or camouflaged on the cap 4, reservoir 1 or other component of the base/reservoir/cap unit. In other embodiments, the detectable features (or the label or data strip) are configured to be viewable.

In further embodiments, the data value represented by each detectable feature 42 has one of two detectable states (for example, one of "0" or "1", or one of positive or negative, or one of two other pre-defined values). In such embodiments, a label or data strip having a plurality of detectable features can be configured as a data strip having a plurality of detectable features 42, where each detectable feature represents one of the two detectable states (e.g., a "0" or a "1"). In particular examples of such embodiments, a plurality of the detectable features on the label or data strip pass adjacent to (and are read in series by) one or more sensor elements (34) fixed to the infusion pump device 30, as the cap 4, reservoir 1, or other component of the base/reservoir/cap unit is inserted into the reservoir receptacle 32 or rotated relative to the reservoir receptacle 32 (or both).

In particular embodiments, the detectable states of the detectable features 42 on the label or data strip represent particular information associated with the cap 4, reservoir 1, or other component of the base/reservoir/cap unit or infusion set connected thereto, such as, but not limited to, the characteristics of the cap 4, reservoir 1, or other component of the base/reservoir/cap unit or infusion set described above. Thus, for example, each possible characteristic can be associated with (on a one-to-one basis or other predefined association) a particular pattern of detectable features 42 or a particular pattern of detectable values (such as, but not limited to "0's" and "1's") of the detectable features 42 on the label or data strip. In such embodiments, such associations may be stored in a memory (such as memory 66 in FIG. 5), for use by processing electronics (such as processing electronics 62) performing a process (such as process 150 in FIG. 6) to determine a characteristic of the cap 4, reservoir 1, or other component of the base/reservoir/cap unit or infusion set, based on the pattern of detectable features or values detected by the sensor element(s) 34, and perform a predefined action based on or using the characteristic.

In further embodiments, a label or data strip is configured with two or more tracks of detectable features 42, where each track includes a series of two or more detectable features arranged in a linear row (or other predefined pattern). In one example, the two or more tracks are parallel to each other, such that two or more linear rows (or other patterns) of detectable features are arranged around the circumference of the cap 4, reservoir 1, or other component of the base/reservoir/cap unit. In such embodiments, each of the plural track includes a plurality of detectable features 42 that have a pattern or values (or both) representing one or more characteristics of the cap 4, reservoir 1, or other component of the base/reservoir/cap unit or infusion set.

In particular embodiments, one or more of the plural tracks is a clock track that provides a series of detectable elements evenly spaced (or spaced at predefined intervals) along the track. In particular embodiments, the detectable elements in the clock track are arranged in alternating fashion (such as, but not limited to, alternating "0's" and "1's"). In such embodiments, processing electronics (such as processing electronics 62 in FIG. 5) may be configured to detect the alternating (or other predefined pattern) of detectable values to determine a timing of motion (such as timing of rotational motion or linear motion) of the cap 4, reservoir 1, or other component of the base/reservoir/cap unit or infusion set, relative to the reservoir receptacle 32 (or axis A), as the cap 4, reservoir 1, or other component of the base/reservoir/cap unit is installed in the reservoir receptacle 32. By determining the timing of the detection of the detectable features 32, the speed of rotation or speed of insertion, as well as the rotational position and insertion position of the reservoir 1, cap 4 or base/reservoir/cap unit can be determined by the processing electronics (as a function of the timing of detection of the detectable features and the spacing between detectable features 42 in the timing track)

In particular embodiments, the label or data strip includes a predefined detectable feature 42 having a predefined detectable value, or a predefined pattern of detectable features 42, for example, at the end of track of detectable features. In such embodiments, the predefined detectable feature, value or pattern is arranged at a location corresponding to a fully installed or final position state of the cap 4, reservoir 1, or other component of the base/reservoir/cap unit in the reservoir receptacle 32. In other words, the predefined detectable feature, value or pattern is arranged at a location on the track to align with and be read by one or more sensor element(s) 34, when the cap 4, reservoir 1, or other component of the base/reservoir/cap unit is in a proper, fully installed position within the reservoir receptacle 32 (but not read, when the cap, reservoir or base/reservoir/cap unit is not properly or fully installed).

d. Mechanical Detection

Certain embodiments as described above include one or more magnetic, RF, or inductively detectable features and one or more magnet, RF or inductive detection sensors, and other embodiments include combinations thereof. In yet other embodiments, a mechanical detection is employed, where the one or more detectable features 42 include a mechanically detectable feature while the one or more sensor elements 34 include a mechanism that mechanically interacts with the mechanically detectable feature(s). In yet other embodiments, the one or more detectable features 42 include a combination of two or more of a magnetically detectable feature, an inductively detectable feature, an RF detectable feature and a mechanically detectable feature, while the one or more sensor elements 34 include a combination of two or more of a magnetic sensor, an inductive sensor, an RF sensor and a mechanical sensor.

Accordingly, arrangements and configurations of magnetic detectable features and sensors, inductively detectable features and inductive sensors and RF detectable features and sensors (as the detectable features and sensors 34 and 42) as described above and shown in FIGS. 1-16 are incorporated herein by reference to apply to embodiments employing mechanically detectable features and associated mechanical sensors, as the sensor elements and detectable features 34 and 42. Any suitable mechanical or electromechanical sensor and detectable feature may be employed as the one or more sensor elements and detectable features 34 and 42 for mechanical detection of the presence or position (or both) or other characteristic of the cap 4 (or base/reservoir/cap unit).

Figure 17:
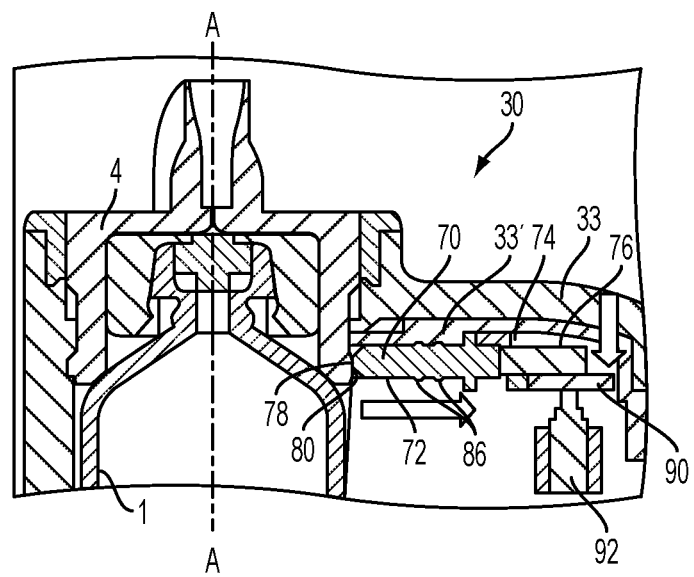
FIG. 17 is a side, plan cut-away view of a portion of an infusion pump device in which a base/reservoir/cap unit is installed, according to an embodiment of the present invention.

One example embodiment of a mechanical detection configuration is described with reference to FIG. 17. The drawing in FIG. 17 shows a partial, cross-section view of a portion of an infusion pump device 30, with a reservoir 1 and cap 4 of a base/reservoir/cap unit (only a portion of which is in view) installed within the reservoir receptacle 32. The infusion pump device 30 includes a housing 33 that includes the reservoir receptacle 32 and that contains components such as a drive device, and one or more sensor device(s) or detectable devices (or both) and associated electronics, as described herein. The drawing in FIG. 18 shows an enlarged partial cross-section view of a similar portion of the infusion pump device 30, but with the reservoir receptacle 32 free of the reservoir 1 and cap 4 (base/reservoir/cap unit)

In embodiments in which the one or more sensor element (s) or detectable features are configured for mechanical detection, either the infusion pump device 30 or the cap 4 (or other component of the base/reservoir/cap unit), or both, holds a sensor device that includes a mechanically moveable member or actuator. The mechanically moveable member (actuator) is arranged to engage an engagement portion of the other of the infusion pump device 30 or the cap 4 (or other component of the base/reservoir/cap unit) and to be moved from a first position to a second position, when the cap 4 (or base/reservoir/cap unit) is being properly and fully received within the reservoir receptacle 32 of the infusion pump device 30. In such embodiments, the mechanically moveable member engages the engagement portion and is moved from the first position to the second position, as a result of a manual movement of the cap 4 (or base/reservoir/cap unit) into the reservoir receptacle 32 and to a proper and fully received position within the reservoir receptacle 32.

The mechanically moveable member is arranged to engage and activate an electrical switch, when the mechanically moveable member is moved to the second position, but is arranged to disengage and not activate the electrical switch when in the first position. Accordingly, a manual movement of the cap 4 (or base/reservoir/cap unit) into the reservoir receptacle 32 and to a proper and fully received position within the reservoir receptacle 32 causes the mechanically moveable member to move to the second position and engage and activate the electrical switch. The electrical switch is connected to electronics (such as electronics 60 discussed above) for detecting whether or not the switch is activated. Accordingly, by detecting the activation state of the electrical switch, the electronics determines whether or not the cap 4 (or base/reservoir/cap unit) is properly and fully received within the reservoir receptacle 32.

Figure 18:
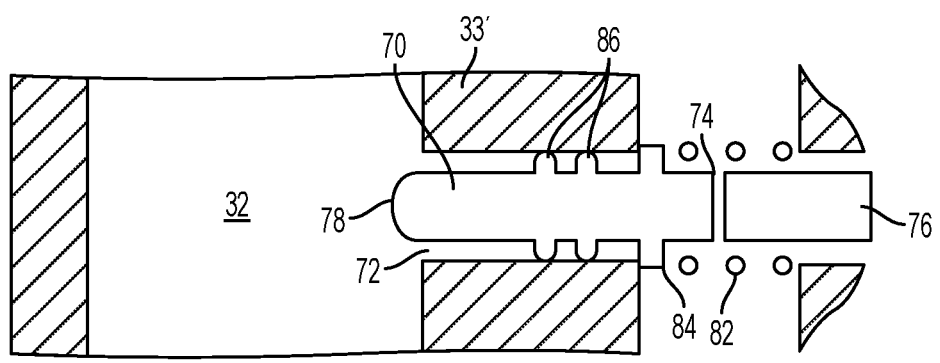
FIG. 18 is an enlarged side, plan cut-away view of the portion of the infusion pump device shown in FIG. 17, but without a base/reservoir/cap unit.

In the embodiment of FIGS. 17 and 18, a mechanically moveable member 70 is supported for movement within a channel 72 located in the infusion pump device 30. The moveable member 70 in FIGS. 17 and 18 has a generally elongated shaft or cylinder shape and is made of a suitably rigid material that holds its shape during normal operation such as, but not limited to plastic, metal, ceramic, wood, composite material, or any combination thereof. In other embodiments, the moveable member 70 may have any other suitable shape or form.

The channel 72 may be formed within the structure of the housing 33 of the infusion pump device 30 or within a further structure located within the housing 33. A first end of the channel 72 is open into the reservoir receptacle 32. A second end of the channel 72 is open into another portion of the interior of the housing 33 of the infusion pump device 30. In the illustrated embodiment, the channel 72 is linear along a longitudinal dimension (horizontal dimension in FIGS. 17 and 18), and the moveable member 70 has a corresponding longitudinal shape that extends along the longitudinal dimension of the channel 72. In other embodiments, the channel 72 (and the moveable member 70) may have correspondingly curved shapes or other suitable shapes that allow the moveable member 70 to move between first and second positions within the channel 72.

As shown in FIG. 17, the moveable member 70 has a first end 74 (the end on the right side of the moveable member 70 in FIG. 17) that is arranged to engage an electrical switch 76. The moveable member 70 has a second end 78 (the end on the left side of the moveable member 70 in FIG. 17) that is arranged to be engaged by an engagement portion 80 of the cap 4 (or other component of the base/reservoir/cap unit) when the cap 4 (or base/reservoir/cap unit) is properly and fully received within the reservoir receptacle 32.

More specifically, the engagement portion 80 of the cap 4 (or other component of the base/reservoir/cap unit) has a surface that comes into contact with and engages a surface of the second end 78 of the moveable member 70, as the cap 4 (or the base/reservoir/cap unit) is manually inserted and moved into a proper and fully inserted position within the reservoir receptacle 32 of the infusion pump device 30.

As the cap 4 (or the base/reservoir/cap unit) is manually moved toward the proper and fully inserted position within the reservoir receptacle 32, the engagement portion 80 engages the second end 78 of the moveable member 70. Then, further movement of the cap 4 (or the base/reservoir/cap unit) toward the a proper and fully inserted position causes the engagement portion 80 to push the second end 78 of the moveable member 70 and move the moveable member 70 from a first position (shown in FIG. 18) to a second position (shown in FIG. 17). The movement of the moveable member 70 from the first position (FIG. 18) to the second position (FIG. 17) causes the first end 74 of the moveable member 70 to push against and activate the electrical switch 76. In contrast, when the moveable member 70 is in the first position (FIG. 18), the first end 74 of the moveable member 70 is out of contact with the switch 76 (or is in contact with the switch 76, but does not apply sufficient mechanical force to activate the switch 76). Accordingly, the switch 76 is activated by the moveable member 70, when the cap 4 (or the base/reservoir/cap unit) is in the proper and fully inserted position within the reservoir receptacle 32, but is not activated by the moveable member 70, when the cap 4 (or the base/reservoir/cap unit) is not in a proper and fully inserted position within the reservoir receptacle 32. In further embodiments, the first end 74 of the moveable member 70 is connected to or arranged adjacent a linkage structure that communicates movement of the first end 74 to the switch 76.

In particular embodiments, the second end 78 of the moveable member 70 extends a small distance into the reservoir receptacle 32, when the moveable member 70 is in the first position (FIG. 18). In that position, the second end 78 of the moveable member 70 is arranged in a location to be contacted by the engagement portion 80 of the cap 4 (or the base/reservoir/cap unit) as the cap 4 (or the base/reservoir/cap unit) is moved toward a proper and fully inserted position within the reservoir receptacle 32. In particular embodiments, the second end 78 of the moveable member 70 is rounded, tapered or provided with another suitable shape that helps to transfer the linear motion of the cap 4 or the base/reservoir/cap unit (e.g., downward motion in the direction of the reservoir receptacle 32 in FIGS. 17 and 18) to linear motion of the moveable member 70 along the longitudinal dimension of the channel 72, as the cap 4 (or the base/reservoir/cap unit) is moved toward a proper and fully inserted position within the reservoir receptacle 32.

In particular embodiments, the second end 78 of the moveable member 70 extends into the channel of the reservoir receptacle 32 by a distance sufficient to contact an outer surface of the cap 4 (or the base/reservoir/cap unit) and ride along that outer surface (allow that outer surface to slide over the second end 78 of the moveable member 70) without moving to the second position and, thus, without actuating the switch 76, as the cap 4 (or the base/reservoir/cap unit) is manually inserted into the reservoir receptacle 32 and rotated toward a proper position. When the cap 4 (or base/reservoir/cap unit) is properly and fully received (inserted and rotated into proper position) in the reservoir receptacle 32, the engagement portion 80 on the cap 4 (or the base/reservoir/cap unit) comes into engagement with the second end 78 of the moveable member 70 and imparts a sufficient force onto the moveable member 70 to push the first end 74 of the moveable member 70 against the switch 76 with enough force to activate the switch 76.

In particular embodiments, the second end 78 of the moveable member 70 (or the entire moveable member 70) is made of a material that is sufficiently compliant, flexible and resilient to be compressed at least at the second end 78 by the engagement portion 80, when the second end 78 of the moveable member 70 is contacted by the engagement portion 80. For example, the material may be sufficiently compliant and flexible to accommodate for different cap 4 sizes or for manufacturing tolerances (or both). Thus, the second end 78 of the moveable member 70 may extend into the reservoir receptacle 32 by a distance sufficient to contact a cap 4 having any size outer diameter (within a predefined range), by compressing sufficiently to accommodate larger diameters within that range.

In particular embodiments, the moveable member 70 is sufficiently compliant, flexible and resilient to transfer at least a portion of the compression force on the second end 78, through the moveable member 70, to produce a resulting expansion or outward bulging of the first end 74 by an amount that applies a force on the switch 76 sufficient to activate the switch 76. Thereafter, when the engagement portion 80 is moved away from the second end 78 of the moveable member 70 (for example, when the cap 4 or base/reservoir/cap unit is being withdrawn from the reservoir receptacle 32), the second end 78 of the moveable member 70 is no longer compressed and, due to the natural resilience of the material of the moveable member 70, the first end 74 returns to a state in which it is not imparting an activation force on the switch 76, to cause the switch to change state (for example, turn off).

Thus, in certain embodiments, the moveable member 70 may be arranged to move from the first position to the second position, without physically shifting toward the switch 76 other than by the action of compressing at the second end 78 to cause the first end 74 to bulge out or expand toward or against the switch 76, as described above. In such embodiments, the moveable member 70 may be configured to avoid or minimize movement of seal structures 86 (described further, below) during movement of the moveable member 70, thus reducing wear on the seal structures 86 and improving sealing functions. In other embodiments, the entire moveable member 70 is also shifted toward the switch 76 while the first end 74 is expanded to activate the switch 76, when the second end 78 of the moveable member 70 is contacted by the engagement portion 80. In yet other embodiments, the moveable member 70 is not compressed or expanded, but, instead, is shifted without expansion toward the switch 76, when the second end 78 of the moveable member 70 is contacted by the engagement portion 80.

In particular embodiments in which the moveable member 70 shifts toward the switch 76 when moving from the first position to the second position, the moveable member 70 includes or is engaged by a bias member 82 that imparts a bias force on the moveable member 70 to bias the moveable member 70 toward the first position (FIG. 18 position). The bias member 82 may be any suitable structure or device that imparts a force on the moveable member 70 in the direction of the first position, such as, but not limited to a coil spring, a leaf spring, other spring configuration, a magnet, balloon or other pressurized expandable container, or the like. In the drawings of FIG. 18, a coil spring is shown as one example of a bias member 82.

In such embodiments, the moveable member 70 includes a protrusion, extension or other structure that provides a stop surface for stopping further motion of the moveable member 70 in the direction of the first position, when the moveable member 70 reaches the first position. In the embodiment of FIGS. 17 and 18, the moveable member 70 includes a protruding shoulder 84 that provides the stop surface. In the illustrated embodiment, the protruding shoulder 84 is arranged outside of the channel 72 and adjacent the second end of the channel 72. The protruding shoulder 84 is configured to be larger (wider) than a dimension (e.g., the width dimension) of the channel 72, so that the protruding shoulder is not able to pass through the channel. Accordingly, the protruding shoulder 84 provides a stop surface (e.g., a surface of the shoulder 84) that engages a surface of the structure in which the channel 72 is located, when the moveable member 70 is in the first position (FIG. 18). However, the protruding shoulder 84 is spaced apart from that surface of the structure in which the channel 72 is located, when the moveable member 70 is in the second position (FIG. 17), or is between the first and second positions.

In particular embodiments, one or more seals or other features are provided for inhibiting the passage of moisture, liquid or other fluid through the channel 72, for example, in the event that moisture, liquid or other fluid enters the reservoir receptacle 32. Thus, the passage of moisture, liquid or other fluid from the reservoir receptacle 32 to other areas within the infusion pump housing 33 can be inhibited, for example, in the event that the infusion pump device 30 is exposed to moisture, liquid or other fluid (such as, for example, rain, pool water, shower water, or the like).

In the embodiment of FIGS. 17 and 18, the moveable member 70 is provided with one or more (two shown in the drawings) seal structures 86, for sealing against the interior surface of the channel 72. In the illustrated embodiment, two seal structures 86 are provided on the moveable member 70. In other embodiments, a single one or more than two seal structures 86 may be employed. In particular embodiments, each seal structure 86 includes a protruding extension or ring of material around the movable member 70 (e.g., around the circumference of the shaft or cylindrical structure of the moveable member 70). In certain embodiments, one or more seal structures 86 are formed of the same material as the moveable member 70 and is either formed as part of the moveable member 70 (e.g., molded or machined, or the like, with the moveable member 70) or formed separately and attached to the moveable member 70. In certain embodiments, one or more seal structures 86 are composed of an O-ring made of the same material as the moveable member. In other embodiments, one or more seal structures 86 are composed of an O-ring made of a different material as the moveable member, such as a flexible, compliant material suitable for sealing functions, including, but not limited to a rubber, plastic or other compliant material.

The switch 76 may be any suitable electrical switch that has a first state (not activated) and a second state (activated), and that is configured to change states when pushed or contacted by the moveable member 70. In one embodiment, the switch 76 is a push-button type switch that has a button structure that can be pushed (e.g., by the moveable member 70) to change the state of the switch. In other embodiments, other suitable switch configurations may be employed. In certain embodiments, the moveable member 70 can form part of the electrical switch, where the moveable member 70 is made of an electrically conductive material (or includes an electrically conductive material at the first end 74) and makes electrical contact with one or more electrodes on the switch 76 to change the state of the switch, when the moveable member 70 is in the second position (e.g., FIG. 17 position).

In the embodiment of FIG. 17, the switch 76 is attached to and supported by a circuit board 90 (such as a printed circuit board or other structure that supports electronics 60 or other electronics associated with the switch). The switch 76 and circuit board 90 may be held within a confined volume in the housing 33 of the infusion pump device 30. In particular embodiments, one or more bias members 92 (such as springs, pogo pin structures, flexible and resilient members or the like) are arranged at one or more locations adjacent the circuit board 90 or switch 76 (or both), to impart a bias force onto the circuit board 90 and switch 76 to help locate or maintain the circuit board 90 and switch 76 in a predefined position, with sufficient precision. In this manner, the position of the switch 76 can be sufficiently defined and maintained, for example, for proper alignment with the moveable member 70, to accommodate for manufacturing tolerances, or both.

The embodiment of FIGS. 17 and 18 includes one sensor element (composed of a moveable member 70 and switch 76). In other embodiments, two or more (a plurality of)

sensor elements, each composed of a respective moveable member 70 and associated switch 76, arranged at different respective predefined locations around or along the reservoir receptacle 32 of the infusion pump device 30. In particular embodiments, one or more moveable members 70 and associated switches 76 are arranged to detect the position of the cap 4 relative to the infusion pump device 30 (e.g., for detecting a proper connection of the cap 4 or the base/reservoir/cap unit with the infusion pump device 30).

In other embodiments, one or more moveable members 70 and associated switches 76 are employed to detect one or more other characteristics associated with the cap 4 or the base/reservoir/cap unit or components thereof, in addition to or as an alternative to detecting proper connection with the infusion pump device 30. In various embodiments, such other characteristics include but are not limited to characteristics of the reservoir 1 (or its contents), infusion set 50, connection interface 40, or any combination thereof, as described above with respect to magnetic detection or RF detection.

In those embodiments, a particular characteristic may be associated with one or more mechanical parameters such as, but not limited to: the existence of one or more predefined engagement portions 80 on the cap 4, or the location or pattern of locations of one or more predefined engagement portions 80 on the cap 4 (circumferential or linearly location relative to the dimension of the axis A), the shape or other parameter of the predefined engagement portion 80, or any combination thereof. In particular embodiments, each different predefined characteristic of the reservoir 1, infusion set 50 or connection interface 40, is associated (for example, on a one-to-one basis) with a respectively different predefined location, pattern of locations, or other detectable parameter of the engagement portion 80. In those embodiments, the processing electronics 62 is configured to determine a characteristic of the reservoir 1, infusion set 50 or connection interface 40 from the signals received from the one or more switch(es) 76.

For example, the processing electronics 62 may be configured to compare information received from one or more switches 76 with information stored in a table or in another suitable data arrangement. The table or other data arrangement is stored in the electronic memory 66. The table or other data arrangement associates a plurality of different predefined engagement portion 80 locations (or a plurality of different predefined patterns of engagement portion 80 locations on the cap) with a corresponding plurality of predefined characteristics, as described above with respect to the magnetic, inductive and RF detection embodiments and incorporated herein by reference.

In particular embodiments, based on one or more of the parameters detected from the signals received from the one or more switches 76, the processing electronics 62 is further configured to determine corresponding characteristics and, based on those characteristics, do one or more of: determine operational settings for the infusion pump device 30, provide signals to the drive device or other components of the infusion pump device 30, provide one or more alarm signals, and record data representing detected states or conditions of one or more of the cap 4, base/reservoir/cap unit, and infusion pump device 30, as described above with regard to magnetic detection, inductive detection, and RF detection embodiments.

In further embodiments, one or more wireless or wired communication devices is provided on the infusion pump device 30 (or other delivery device) and is configured and controlled to transmit volume information (or other information corresponding to detected parameters of the RF detectable feature, or associated characteristics) for display on another electronic device separate from or located remote from the infusion pump device 30. In particular embodiments, the wireless communication device(s) are configured to connect for communication on a communication network (such as, but not limited to the Internet), with one or more pre-defined network connected devices. Such one or more pre-defined network connected devices may be located at remote geographic locations relative to the infusion pump device 30 (or other delivery device). In particular embodiments, such network connected devices include a server configured to receive information from the infusion pump device 30 (or other delivery device) or from another network connected device (such as a cradle, user computer, or the like) that communicates with the infusion pump device 30 (or other delivery device). Such information may include, but is not limited to volume information, serial numbers or codes or other information regarding the reservoir 1, cap 4, base/reservoir/cap unit or infusion set as described above.

In such embodiments, the network connected server may be associated with an entity that records information, supplies associated products such as refills or replacement parts, provides medical treatment or medical insurance to the user or the like. In one example, the network connected server is associated with the Carelink™ system of Medtronic Inc. In other embodiments, the network connected server is one or more other servers and associated entities. Accordingly, such information may be employed by the server (or associated entity) to determine whether or not (or when) to send refills, new or replacement reservoirs or other components of the cap 4, base/reservoir/cap unit, or infusion set. In further embodiments, such information may be provided to the user's doctor or other medical treatment entity associated with the user (for tracking, diagnosing, adjusting treatment plans or other suitable uses). Thus, in such embodiments, refills or replacement components may be sent to users, automatically (without requiring the user to place an order), and usage information can be provided to the user's healthcare provider, insurance provider or other suitable entities, automatically.

In further embodiments, the network connected server is configured to provide (and the infusion pump device 30 or other delivery device is configured to receive) information through the above-noted network communication connection or other network connection. Such information may include, but is not limited to, instructions or recommendations for replacing or refilling a reservoir 1, cap 4, base/reservoir/cap unit or infusion set, messages or notices from healthcare providers, insurance carriers or manufacturers, recall notices or the like. In particular embodiments, electronics (such as electronics 60) in the infusion pump device 30 (or other delivery device) is configured to perform one or more predefined actions (as discussed above) in response to receipt of a predefined instruction, notice or message.

In particular embodiments, the engagement portion 80 may be a raised or predefined surface, projection, bump, rib, gradual rise, detent, aperture, groove or other mechanically detectable feature provided in any suitable location on the cap 4 (or other component of the base/reservoir/cap unit) for contacting the second end 78 of the moveable member 70, when the cap 4 (or the base/reservoir/cap unit) is manually inserted and moved into the a proper and fully inserted position within the reservoir receptacle 32 of the infusion pump device 30. The engagement portion 80 may be made sufficiently small or of a size or shape (or both) to align with and engage the moveable member 70 only when the cap 4

(or base/reservoir/cap unit) is fully and properly received within the reservoir receptacle, and not align or engage the moveable member 70 in any other position of the cap 4 (or base/reservoir/cap unit). In such embodiments, the size or shape (or both) of the engagement portion 80 may be configured to provide a relatively precise detection of a proper connection of the cap 4 (or base/reservoir/cap unit) with the infusion pump device 30.

In further embodiments, a plurality of engagement portions 80 are provided at suitable locations on the cap 4 (or other component of the base/reservoir/cap unit) to engage the second end 78 of the moveable member 70 in a corresponding plurality of different insertion positions of the cap 4 (or base/reservoir/cap unit) within the reservoir receptacle 32. Thus, a user may insert the cap 4 (or base/reservoir/cap unit) into the reservoir receptacle 32 in any of the plurality of different insertion positions to cause one of the engagement portions 80 to engage the second end 78 of the moveable member 70. Alternatively or in addition, a plurality of engagement portions 80 may be provided at suitable locations on the cap 4 (or base/reservoir/cap unit) to individually engage the second end 78 of the moveable member 70 at a corresponding plurality of different positions of the cap 4 (or base/reservoir/cap unit) as the cap 4 (or base/reservoir/cap unit) is being inserted or rotated within the reservoir receptacle 32. In such embodiments, the electronics 60 are configured to detect multiple positions of the cap 4 (or base/reservoir/cap unit) relative to the reservoir receptacle 32, for example, to detect an improper connection of the cap 4 (or base/reservoir/cap unit) with the infusion pump device 30 or to detect the movement of the cap 4 (or base/reservoir/cap unit) toward or away from a proper or full connection position relative to the reservoir receptacle 32.

In particular embodiments, the engagement portion 80 is provided on one or more of the threads 19 (see FIG. 2) of the cap 4. In such embodiments, the engagement portion 80 may be provided at a location on a thread 19 that is selected to align with the moveable member 70 when threads 19 are fully and properly threaded into corresponding threads or grooves in the reservoir receptacle 32 of the infusion pump device 30 (such as when the cap 4 or the base/reservoir/cap unit is fully and properly received in the reservoir receptacle 32). In further embodiments, two engagement portions 80 are provided on two respective threads 19, where one thread 19 and engagement portion 80 is provided on an opposite side of the cap 4 or base/reservoir/cap unit (or 180 degrees around the axis A) from the other thread 19 and engagement portion 80. Thus, with two engagement portions and threads on mutually opposite sides of the cap 4 (or base/reservoir/cap unit), or 180 degrees apart, the user may align threads on the cap 4 (or base/reservoir/cap unit) with threads on the reservoir receptacle 32 in either of two different orientations 180 degrees relative to each other, to connect the cap 4 (or base/reservoir/cap unit) to the infusion pump device 30.

In further embodiments, more than two threads 19 and engagement portions 80 is provided at mutually spaced positions around the circumference of the cap 4 (or base/reservoir/cap unit), and a corresponding number of threads or grooves is provided in the reservoir receptacle 32 of the infusion pump device 30, to accommodate more than two different alignment orientations for threading the cap 4 (or base/reservoir/cap unit) into the reservoir receptacle 32. In any of the embodiments employing threads 19, a plurality of engagement portions 80 may be provided on any one or more of the threads 19. In such embodiments, one or more engagement portions 80 may be arranged to engage and then disengage the second end 78 of the moveable member 70, as the cap 4 (or base/reservoir/cap unit) is threaded into the reservoir receptacle 32. The electronics 60 may be configured to detect and count the number of engagements and disengagements, for determining whether or not the cap 4 (or base/reservoir/cap unit) is fully and properly received in the reservoir receptacle 32. Alternatively or in addition, the electronics 60 may be configured to detect a particular rotational position or linear position (or both) of the cap 4 (or base/reservoir/cap unit) within the reservoir receptacle 32, based on the number of detected engagements (or engagements and disengagements) of engagement portions 80 with the moveable member 70.

For example, in embodiments in which two engagement portions 80 are provided on a thread 19, the electronics 60 may be configured to determine that a proper connection of the cap 4 (or base/reservoir/cap unit) is made when the electronics 60 has detected two activations of the switch 76. Alternatively or in addition, the electronics may be configured to determine that the cap 4 (or base/reservoir/cap unit) has been rotated by one half the proper amount (or other particular amount) or moved linearly by one half the proper amount (or other particular amount) within the reservoir receptacle, when only one activation of the switch 76 has occurred. Other embodiments may employ any suitable number of engagement portions 80 on one or more threads 19 (or on another suitable surface of the cap 4 or base/reservoir/cap unit).

As discussed herein, the movable member 70 is supported within a channel 72 located in the housing 33 of the infusion pump device 30. In particular embodiments, the housing 33 includes a housing portion 33' that contains the channel 72 and further contains a volume in which the switch 76 and circuit board 90 are located. In further embodiments, the housing portion 33' also includes at least a portion of or all of the reservoir receptacle 32. For example, with reference to the orientation in FIG. 17, the housing portion 33' may include the upper portion (but not the lower portion) of the reservoir receptacle 32, from the open end to a location below the channel 72. In such embodiments, the position of the channel 72 (and, thus, the position of the second end 78 of the moveable member 70) relative to the reservoir receptacle 32 can be made with sufficiently high precision, for improving or controlling the precision in detecting the position of a cap 4 (or base/reservoir/cap unit) within the reservoir receptacle 32.

In one example embodiment, the housing portion 33' forms part of the reservoir receptacle 32 or has a part that fits into or around the reservoir receptacle 32, and is molded to or otherwise adhered or connected to a further portion of the housing 33 that forms the reservoir receptacle. In particular embodiments, the further portion of the housing 33 that forms the reservoir receptacle is molded over (or adhered to or otherwise connected to) a part of the housing portion 33', for example, during manufacture or assembly of the infusion pump device 30.

e. Optical Detection

Certain embodiments as described above include one or more magnetic detectable features and magnet detection sensors, while other embodiments include one or more inductively, RF, or mechanically detectable features and one or more RF, inductive or mechanical detection sensors, and other embodiments include any combination of one or more magnetic, inductive, RF or mechanical detectable features and sensors. In yet other embodiments, an optical detection is employed, where the one or more detectable features 42 include an optically detectable feature, while the one or more sensors 34 include an optical sensor. In yet other embodiments, the one or more detectable features 42 include a combination of two or more of a magnetically detectable feature, an inductively detectable feature, an RF detectable feature, a mechanically detectable feature and an optically detectable feature, while the one or more sensors 34 include a combination of two or more of a magnetic sensor, an inductive sensor, an RF sensor, a mechanical sensor and an optical sensor.

Accordingly, arrangements and configurations of magnetic, inductive, RF and mechanical sensor elements and detectable features (as the sensor elements and detectable features 34 and 42) as described above and shown in FIGS. 1-18 are incorporated herein by reference to apply to embodiments employing optical sensors and optically detectable features, as the sensor elements and detectable features 34 and 42. According to certain embodiments, any suitable optical sensor and optically detectable feature may be employed as the one or more sensors and detectable features 34 and 42 for optical detection of the presence or position (or both) of the cap 4 (or base/reservoir/cap unit).

Figure 19:
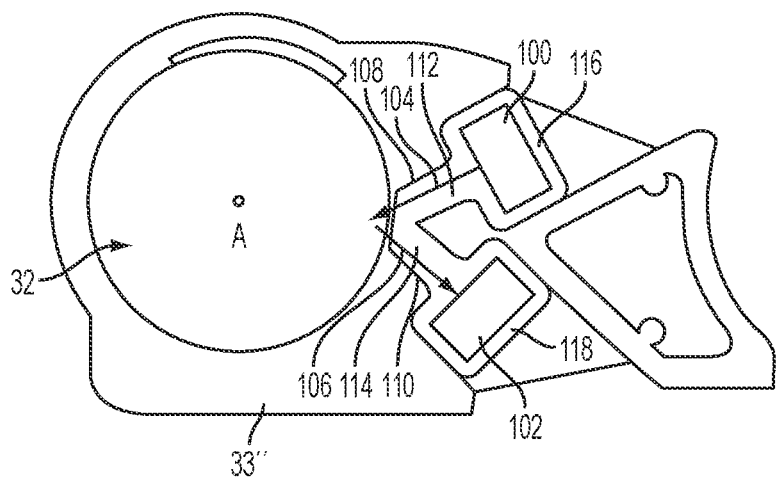
FIG. 19 is a top view of an infusion pump device housing portion according to an embodiment of the present invention.

One example embodiment of an optical detection configuration is described with reference to FIG. 19. The drawing in FIG. 19 shows a partial, top view of a portion 33" of the infusion pump housing 33 of the infusion pump device 30. The housing portion 33" may be similar to the housing portion 33' described above with respect to FIG. 17, but is configured with one or more optical sensors instead of one or more mechanical sensors described with reference to FIG. 17.

In the embodiment in FIG. 19, the housing portion 33" includes at least a part of the reservoir receptacle 32. In particular embodiments, the housing portion 33" includes the upper part of the reservoir receptacle 32 and may be molded with or otherwise coupled to the rest of the reservoir receptacle, similar to the housing portion 33' described above. In other embodiments, the housing portion 33" includes the entire reservoir receptacle 32. In yet other embodiments, the housing portion 33" is a separate housing portion configured to be mounted to or supported adjacent the reservoir receptacle 32.

As shown in FIG. 19, an optical emitter device 100 and an optical detector device 102 are supported and held by the housing portion 33". The optical emitter device 100 is configured and arranged to emit an optical beam or other optical output signal in a first direction (represented by arrow 104 in FIG. 19), toward the reservoir receptacle 32. The optical detector device 102 is configured and arranged to receive an optical beam or other optical signal along a second direction (represented by arrow 106 in FIG. 19), from the reservoir receptacle 32. In the embodiment of FIG. 19, the first direction and second direction are arranged at an angle relative to each other, but are aligned such that an optical signal transmitted in the direction of arrow 104 can be reflected from a predefined location on a cap 4 (or other portion of a base/reservoir/cap unit), along the direction of arrow 106. In other embodiments, the optical emitter device 100 and the optical detector device 102 are supported in other suitable positions relative to each other that allow an optical signal to be emitted from the optical emitter device 100 and, then, received by the optical detector device 102 after having been reflected from a surface of the cap 4 (or other portion of the base/reservoir/cap unit).

The housing portion 33" includes one or more passages through which an optical signal transmitted in the direction of arrow 104 is communicated, and through which a reflected optical signal in the direction of arrow 104 is communicated. In the embodiment of FIG. 19, the passages include a first channel 108 having longitudinal dimension extending between the optical emitter device 100 and the reservoir receptacle 32, and a second channel 110 having a longitudinal dimension extending between the optical receiver device 102 and the reservoir receptacle 32. In other embodiments, the passage(s) may have other suitable forms such as, but not limited to one or more windows, openings, open or transparent (or partially transparent) sides of the reservoir receptacle or the like.

In particular embodiments, each of the channels includes a seal (for example, seal 112 in channel 108 and seal 114 in channel 110) configured to inhibit the passage of moisture, liquid or other fluid from the interior of the reservoir receptacle 32 into the housing portion 33". In the embodiment of FIG. 19, the seals 112 and 114 are in the form of an optically transparent (or partially transparent) material that fills at least a portion of the length of the channels 108 and 110 and seals with contact against the interior surfaces of the channels. In further embodiments, additional sealing features are arranged on or around the optically transparent (or partially transparent) material within the channels 108 and 110, such as, but not limited to, one or more O-rings, sleeves or other structures made of a compressible or other seal-enhancing material. The optically transparent (or partially transparent) material of the seals 112 and 114 may be any suitable material that sufficiently passes optical signals as described herein, including but not limited to plastic, glass or other ceramic material, or the like. As an alternative or in addition to the seals 112 and 114, a window covered by an optically transparent (or partially transparent) material may be arranged at the end of the channel(s) that interface with the reservoir receptacle 32. In particular embodiments, the optically transparent (or partially transparent) material of the window is composed of the material from which the housing portion 33" is made, such that the window material is integral with the housing portion 33". In other embodiments, the window material is formed separate from and then attached to the housing portion 33".

In the embodiment of FIG. 19, the seal 112 is part of a unitary structure 116 that surrounds and encases (or partially surrounds and encases) the optical transmitter device 100. Similarly, the seal 114 is part of a unitary structure 118 that surrounds and encases (or partially surrounds and encases) the optical transmitter device 102. In particular embodiments, the structures 116 and 118 form housings that seal or partially seal the optical emitter device 100 and optical detector device 102 against moisture, liquid or other fluid. Thus, in certain embodiments, the optical transmitter device 100 and the optical receiver device 102 are encased (or partially encased) within structures 116 and 118 during a manufacturing step, and can be stored or shipped for later assembly within the housing portion 33" as part of another manufacturing step.

Figure 20:
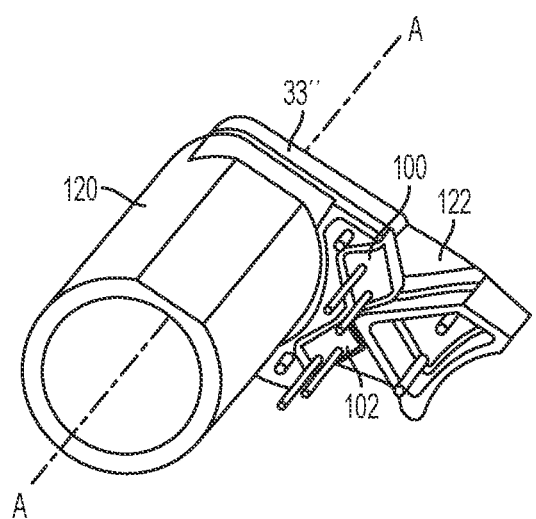
FIG. 20 is a perspective view of the infusion pump device housing portion of the embodiment of FIG. 19.

In particular embodiments, the housing portion 33" is formed separate from other portions of the housing 33 (for example, as shown in FIG. 20) and then is molded or otherwise connected to another other portion of the housing 33. FIG. 20 shows a perspective view of a housing portion 33" that includes optical sensor features as described herein. In other embodiments, the housing portion 33" is molded or otherwise formed as a unitary structure with the rest of the housing 33. In the embodiment of FIG. 20, the housing portion 33" includes a hollow, generally cylindrical section 120 that forms a portion of the reservoir receptacle 32 (for example, the upper portion of the reservoir receptacle 32 relative to the orientation in FIG. 17).

In addition, the housing portion 33" in FIG. 20 includes a support section 122 that holds and supports the optical emitter device 100 and the optical detector device 102 in predefined, proper orientations relative to the reservoir receptacle 32. The support section 122 is fixed with respect to the reservoir receptacle. In particular embodiments, the support section 122 is molded or formed integral with reservoir receptacle 32. In other embodiments, the support section 122 is formed separately and then fixedly secured to the reservoir receptacle 32. By assembling the housing portion 33" with the optical emitter and detector devices 100 and 102 as a unitary structure, the orientation of those devices can be set at a factory or assembly plant (or by another authorized entity) for relatively precise aim and optical detection, prior to assembly of the housing portion 33" with the rest of the housing 33 of the infusion pump device 30.

The cap 4 (or other portion of the base/reservoir/cap unit) includes one or more (or a plurality of) features that affect an optically detectable characteristic of an optical signal emitted onto the feature(s). More specifically, when the cap 4 (or the base/reservoir/cap unit) is inserted into the reservoir receptacle 32, the outer surface of the cap 4 (or other portion of the base/reservoir cap unit) is moved into a position at which it is illuminated by the optical signal beam emitted from the optical emitter device 100. In particular embodiments, as the cap 4 (or base/reservoir/cap unit) is manually inserted into the reservoir receptacle 32, the cap 4 (or base/reservoir/cap unit) is rotated or moved linearly (or both) along axis A relative to infusion pump device 30, toward a fully installed position within the reservoir receptacle 32. During that action, portions of the outer surface of the cap 4 (or other portion of the base/reservoir/cap unit) move past the optical signal passage(s) in the housing portion 33". Accordingly, different regions or areas of the outer surface of the cap 4 (or base/reservoir/cap unit) become aligned with the optical signal passage(s) and are illuminated (at least temporarily) by an optical signal from the optical emitter 100, as the cap 4 (or base/reservoir/cap unit) is moved to its fully installed position within the reservoir receptacle 32. In addition, once the cap 4 (or base/reservoir/cap unit) is in the fully and properly installed position within the reservoir receptacle 32, a particular (predefined) region or area of the cap 4 (or other portion of the base/reservoir/cap unit) is aligned with the optical signal passage(s) and is illuminated by an optical signal from the optical emitter 100.

Some or all of the surface of the cap 4 (or base/reservoir/cap unit) that becomes illuminated during installation of the cap 4 (or base/reservoir/cap unit) is provided with one or more features that affect or alter the optical signal in a detectable manner. In particular embodiments, a plurality of detectable features are provided on the surface of the cap 4 (or base/reservoir/cap unit) at locations that align with the optical signal passage(s) in the housing portion 33" (and, thus, become illuminated by an optical signal from the optical emitter 100) at different instantaneous positions of the cap 4 (or base/reservoir/cap unit) as the cap 4 (or base/reservoir/cap unit) is moved towards and into its fully and properly installed position within the reservoir receptacle 32. In such embodiments, the electronics 60 are configured to detect multiple different positions of the cap 4 (or base/reservoir/cap unit) relative to the reservoir receptacle 32, including a fully and properly installed position, based on optical signals affected or altered by detectable features at the multiple different positions, as detected by the detector 102.

In particular embodiments, portions of the outer surface of the cap 4 (or base/reservoir/cap unit) include an optically reflective feature that reflects an optical signal emitted by the optical emitter 100. For example, the outer surface of the cap 4 (or base/reservoir/cap unit) may be formed of or coated with an optically reflective material. Alternatively or in addition, an optically reflective material may be adhered to the cap 4 (or base/reservoir/cap unit). In such embodiments, one or more confined regions or areas on the cap 4 (or base/reservoir/cap unit) is provided with a feature that is not optically reflective or has a detectably different optical reflective characteristic than other areas on the cap 4 (or base/reservoir/cap unit). Accordingly, when the cap 4 (or base/reservoir/cap unit) is initially inserted into the reservoir receptacle 32, an optical signal from the optical emitter 100 may illuminate the reflective material on the cap 4 (or base/reservoir/cap unit) and be reflected to the optical detector 102. Electronics 60 may be configured to detect the presence of the cap 4 (or base/reservoir/cap unit) within the reservoir receptacle 32, in response to the detection of the reflected signal by (and output signal of) the optical detector 102.

Then, as the cap 4 (or base/reservoir/cap unit) is rotated or linearly moved (or both) toward its full and proper installation position within the reservoir receptacle 32, one or more of the regions or areas provided with the feature that does not reflect (or alters a reflection characteristic) is moved into alignment with the optical signal passage(s) in the housing portion 33". As a result, the optical signal from the optical emitter 100 is not reflected (or is reflected in a detectably different manner relative to other portions of the cap 4 or base/reservoir/cap unit) and the optical detector 102 provides a corresponding output signal to the electronics 60. In such embodiments, the electronics 60 is configured to determine the position of the cap 4 (or base/reservoir/cap unit), based on the output signal from the optical detector 102.

By arranging the optically detectable features at predefined locations on the cap 4 (or base/reservoir/cap unit) that align with the optical signal passage(s) in the housing portion 33" when the cap 4 (or base/reservoir/cap unit) is at predefined, corresponding positions within the reservoir receptacle 32, the electronics 60 may be configured to determine the position of the cap 4 (or base/reservoir/cap unit) within the reservoir receptacle 32 by counting the detected optical features detected by (or otherwise evaluating the output signal received from) the optical detector 102 as the cap 4 (or base/reservoir/cap unit) is moved into the reservoir receptacle 32. Furthermore, by arranging at least one optically detectable feature at a predefined location on the cap 4 (or base/reservoir/cap unit) that aligns with the optical signal passage(s) in the housing portion 33" when the cap 4 (or base/reservoir/cap unit) is at the fully and properly installed position within the reservoir receptacle 32, the electronics 60 may be configured to determine that the cap 4 (or base/reservoir/cap unit) is fully and properly installed within the reservoir receptacle 32, based on an output signal from the optical detector 102 corresponding to the detection of that feature.

In the above embodiments in which the outer surface of the cap 4 (or base/reservoir/cap unit) has an optically reflective outer surface and the detectable feature(s) include one or more features that are not optically reflective or have a different reflective characteristic (detectable parameter), the one or more features may include, but are not limited to, a material, coating, surface contour or pattern (ribs, grooves, undulations, roughness, abrasions, apertures, or the like) or attached article that inhibits or changes optical reflective characteristics. In particular embodiments, the one or more optically detectable features include one or more apertures or detents in the reflective outer surface of the cap 4 (or base/reservoir/cap unit). In yet further embodiments, the one or more optically detectable features include the existence of one or more optically detectable feature on the cap; the location or pattern of locations of one or more optically detectable feature on the cap; the type of optically detectable feature on the cap; the type or content of data stored by the optically detectable feature; or the polarity, direction or orientation of the signal emitted by the optically detectable feature. In yet further embodiments, the optically detectable feature includes a machine-readable pattern of optically detectable regions, such as, but not limited to a bar code or 2D data matrix or liner code. In such embodiments, the pattern of optically detectable regions represents encoded information that can be read by electronics 60. In particular embodiments, the one or more optically detectable features include one or more adhesive-backed tags that are adhered to the cap 4 (or base/reservoir/cap unit) at one or more predefined locations and that have an outer surface has an optically detectable feature as described herein or otherwise inhibits or detectably alters reflection of an optical signal from the optical emitter 100.

In other embodiments, the outer surface of the cap 4 (or base/reservoir/cap unit) is configured to inhibit optical reflection, while the one or more optically detectable features are configured to be detectably reflective. In such embodiments, the electronics 60 is configured to detect one or more relative positions of the cap 4 (or base/reservoir/cap unit) within the reservoir receptacle 32 by evaluating signals from the optical detector 102 representing detection of the reflective optically feature(s) on the cap 4 (or base/reservoir/cap unit).

In further embodiments, one or more optically detectable features on the cap 4 (or base/reservoir/cap unit) are configured to alter the optical signal in an optically detectable manner by altering one or more of the wavelength, direction, phase or other detectable parameter of the optical signal. In yet further embodiments, a plurality of different optically detectable features are provided on the cap 4 (or base/reservoir/cap unit) at respectively different predefined locations relative to each other, such that a different respective detectable feature is aligned with the optical signal passage(s) in the housing portion 33" at different respective positions of the cap 4 (or base/reservoir/cap unit) within the reservoir receptacle 32. In such embodiments, each different optically detectable feature can be configured to provide to the optical detector 102 a different detectable reflective signal (relative to the other optically detectable features on the cap 4 or base/reservoir/cap unit), when aligned with the optical signal passage in the housing portion 33". Accordingly, the optical detector 102 is provided a different detectable reflected signal and, thus, provides a different output signal at different respective positions of the cap 4 (or base/reservoir/cap unit). In such embodiments, the electronics 60 is configured to determine the position of the cap 4 (or base/reservoir/cap unit) relative to the reservoir receptacle 32, based on the output signal of the optical detector 102.

The optical emitter device 100 may be any suitable device that emits an optically detectable signal. In particular embodiments, the optical emitter device 100 includes a light emitting diode (LED) device and LED driver circuit that is configured to produce an optical output signal having a predefined wavelength or peak wavelength, radiant intensity, angle of intensity, or ranges thereof. In particular embodiments, the optical emitter device 100 is an infrared (IR) device configured to provide an IR output signal. In other embodiments, other suitable optical emitter devices may be employed including, but not limited to, devices that operate in other wavelengths outside of IR.

The optical detector device 102 may be any suitable device that detects an optical signal output by the optical emitter 100 and reflected from the cap 4 (or base/reservoir/cap unit). In embodiments in which the optical emitter 100 includes an IR LED device, the optical detector device 102 includes an IR phototransistor or other device configured to detect IR radiation. In other embodiments, the optical detector device 102 may include, but is not limited to, one or more of a phototransistor, photoresistor, photodiode, photovoltaic cell, photomultiplier, photo Schmitt Trigger, charge-coupled device (CCD), active-pixel sensor (APS) or other suitable device that reacts in a detectable matter to an optical signal.

The embodiment of FIGS. 19 and 20 includes one optical sensor composed of an optical emitter-detector pair 100, 102. In other embodiments, two or more (a plurality of) optical sensors (composed of two or more optical emitter-detector pairs 100, 102) are arranged at predefined locations around or along the reservoir receptacle 32. In particular embodiments, one or more optical sensors (optical emitter-detector pairs) are arranged to detect the position of the cap 4 relative to the infusion pump device 30 (e.g., for detecting a proper connection of the cap 4 or the base/reservoir/cap unit with the infusion pump device 30).

In other embodiments, one or more optical sensors (optical emitter-detector pairs) are employed to detect one or more other characteristics associated with the cap 4 or the base/reservoir/cap unit or components thereof, in addition to or as an alternative to detecting proper connection with the infusion pump device 30. In various embodiments, such other characteristics include but are not limited to characteristics of the reservoir 1 (or its contents), infusion set 50, connection interface 40, or any combination thereof, as described above with respect to magnetic detection, RF detection or mechanical detection.

In those embodiments, a particular characteristic may be associated with one or more detectable parameters of the optically detectable elements, such as, but not limited to: the existence of one or more optically detectable elements on the cap 4, the location or pattern of locations of one or more optically detectable elements on the cap 4 (circumferential or linearly location relative to the dimension of the axis A), the optically detectable pattern, shape, wavelength or peak wavelength, radiant intensity, angle of intensity or other detectable parameter of the optically detectable elements, or any combination thereof. In particular embodiments, each different predefined characteristic of the reservoir 1, infusion set 50 or connection interface 40, is associated (for example, on a one-to-one basis) with a respectively different predefined detectable parameter of the optically detectable elements. In those embodiments, the processing electronics 62 are configured to determine a characteristic of the reservoir 1, infusion set 50 or connection interface 40 from the signals received from the one or more optical sensors (optical emitter-detector pairs), for example, using a process as described with respect to process 150 in FIG. 6.

For example, the processing electronics 62 may be configured to compare information received from one or more optical sensors (optical emitter-detector pairs) with information stored in a table or in another suitable data arrangement. The table or other data arrangement is stored in the electronic memory 66. The table or other data arrangement associates a plurality of different predefined optically detectable elements, or locations or patterns of locations of one or more optically detectable elements, the optically detectable pattern, shape or other parameter of the optically detectable elements, or any combination thereof with a corresponding plurality of predefined characteristics, as described above with respect to the magnetic, RF and mechanical detection embodiments and incorporated herein by reference.

In particular embodiments, based on one or more of the parameters (or optical signature) detected from the signals received from the one or more optical sensors (optical emitter-detector pairs), the processing electronics 62 is further configured to determine corresponding characteristics and, based on those characteristics, do one or more of: determine operational settings for the infusion pump device 30, provide signals to the drive device or other components of the infusion pump device 30, provide one or more alarm signals, and record data representing detected states or conditions of one or more of the cap 4, base/reservoir/cap unit, and infusion pump device 30, as described above with regard to magnetic detection, RF detection and mechanical embodiments.

In further embodiments, one or more wireless or wired communication devices is provided on the infusion pump device 30 (or other delivery device) and is configured and controlled to transmit volume information relating to the volume of infusion fluid remaining in or dispensed from the reservoir 1 (or other information corresponding to detected parameters of the one or more optically detectable elements or associated characteristics) for display on another electronic device separate from or located remote from the infusion pump device 30. In particular embodiments, the wireless communication device(s) are configured to connect for communication on a communication network (such as, but not limited to the Internet), with one or more pre-defined network connected devices. Such one or more pre-defined network connected devices may be located at remote geographic locations relative to the infusion pump device 30 (or other delivery device). In particular embodiments, such network connected devices include a server configured to receive information from the infusion pump device 30 (or other delivery device) or from another network connected device (such as a cradle, user computer, or the like) that communicates with the infusion pump device 30 (or other delivery device). Such information may include, but is not limited to information corresponding to one or more detected parameters or one or more associated characteristics, or other information regarding the reservoir 1, cap 4, base/reservoir/cap unit or infusion set as described above.

In such embodiments, the network connected server may be associated with an entity that records information, supplies associated products such as refills or replacement parts, provides medical treatment or medical insurance to the user or the like. In one example, the network connected server is associated with the Carelink™ system of Medtronic Inc. In other embodiments, the network connected server is one or more other servers and associated entities. Accordingly, such information may be employed by the server (or associated entity) to determine whether or not (or when) to send refills, new or replacement reservoirs, caps, infusion set needle housings, infusion set tubing, or other components of the cap 4, base/reservoir/cap unit, or infusion set. In further embodiments, such information may be provided to the user's doctor or other medical treatment entity associated with the user (for tracking, diagnosing, adjusting treatment plans or other suitable uses). Thus, in such embodiments, refills or replacement components may be sent to users, automatically (without requiring the user to place an order), and usage information can be provided to the user's healthcare provider, insurance provider or other suitable entities, automatically.

In further embodiments, the network connected server is configured to provide (and the infusion pump device 30 or other delivery device is configured to receive) information through the above-noted network communication connection or other network connection. Such information may include, but is not limited to, instructions or recommendations for replacing or refilling a reservoir 1, cap 4, base/reservoir/cap unit or infusion set, messages or notices from healthcare providers, insurance carriers or manufacturers, recall notices or the like. In particular embodiments, electronics (such as electronics 60) in the infusion pump device 30 (or other delivery device) is configured to perform one or more predefined actions (as discussed above) in response to receipt of a predefined instruction, notice or message.

f. Electrical Contact Detection

Certain embodiments as described above include one or more magnetic detectable features and magnet detection sensors, while other embodiments include one or more inductively, RF, mechanically or optically detectable features and inductive, RF, mechanical or optical detection sensors. Other embodiments include any combination of one or more magnetic, inductive, RF, mechanical or optical detectable features and sensors. In yet other embodiments, an electrical contact detection is employed, where the one or more detectable features 42 include a first electrical contact feature, while the one or more sensors 34 include an electrical contact sensor having a further electrical contact feature arranged to selectively make electrical contact with the first electrical contact feature. In yet other embodiments, the one or more detectable features 42 include a combination of two or more of a magnetically detectable feature, an inductively detectable feature, an RF detectable feature, a mechanically detectable feature, an optically detectable feature, or an electrical contact feature while the one or more sensors 34 include a combination of two or more of a magnetic sensor, an inductive sensor, an RF sensor, a mechanical sensor, an optical sensor and an electrical contact sensor.

Accordingly, arrangements and configurations of magnetic, inductive, RF, mechanical and optical sensor elements and detectable features (as the sensor elements and detectable features 34 and 42) as described above and shown in FIGS. 1-20 are incorporated herein by reference to apply to embodiments employing electrical contact sensors and electrical contact features, as the sensor elements and detectable features 34 and 42. According to certain embodiments, any suitable electrical contact sensor and electrical contact feature may be employed as the one or more sensors and detectable features 34 and 42 for electrical contact detection of the presence or position (or both) of the cap 4 (or base/reservoir/cap unit).

Figure 21:
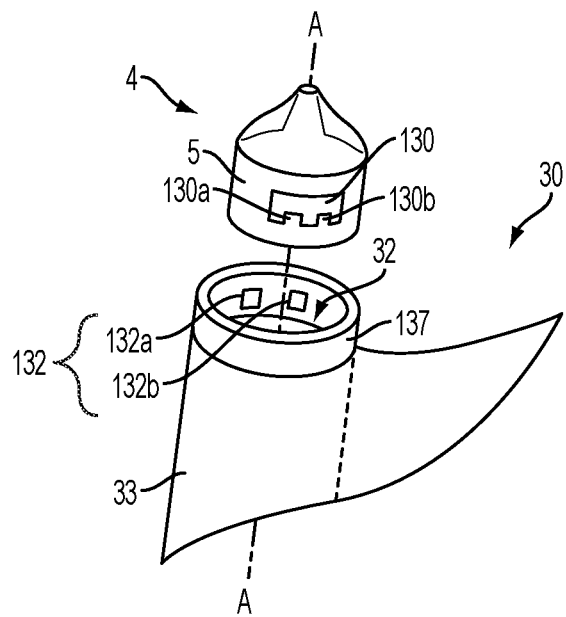
FIG. 21 is a perspective view of portions of an infusion pump system including a cap outside of a portion of an infusion pump device, according to an embodiment of the present invention.

Example embodiments of electrical contact detection configurations are described with reference to FIGS. 21-27. The drawing in FIG. 21 shows a partial, top view of a portion of the infusion pump housing 33 of the infusion pump device 30, including the open end portion of the reservoir receptacle 32. The cap 4 is provided with a first electrical contact feature 130 attached to the body 5 of the cap 4. The first electrical contact feature 130 is provided at a location on the cap body 5 to engage and make electrical contact with a second electrical contact feature 132 on the infusion pump device 32, when the cap 4 (or base/reservoir/cap unit) is installed in the reservoir receptacle of the infusion pump device 32.

Each of the electrical contact features 130 and 132 may include one or more of any suitable electrically conductive material, including, but not limited to, an electrically conductive metal member, plating, coating, ink, or other material suitable for making an electrical contact as described herein. The electrical contact feature 130 may be attached to, embedded in, molded in, applied onto or otherwise affixed to a wall portion of the cap body 5. Similarly, the electrical contact feature 132 may be attached to, embedded in, molded in, applied onto or otherwise affixed to a wall portion of the housing 33 within the reservoir receptacle 32.

Figure 22:
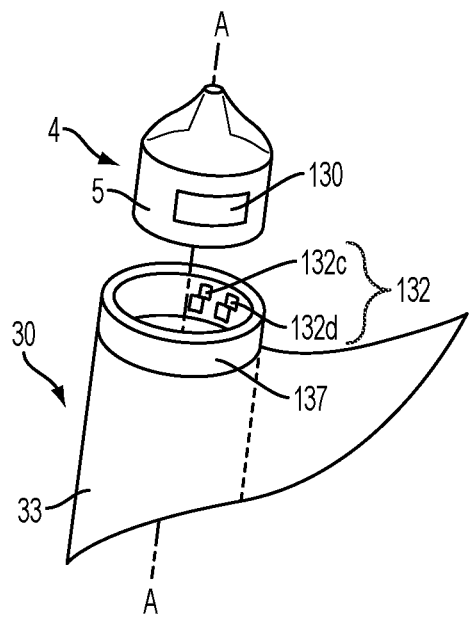
FIG. 22 is a perspective view of portions of an infusion pump system including a cap outside of a portion of an infusion pump device, according to another embodiment of the present invention.

In particular embodiments, one or both of the electrical contact features 130 and 132 includes a biased portion that is biased in a radial direction relative to the axis A, for example, where the first electrical contact feature 130 is biased radially outward (away from the axis A), or the second electrical contact feature 132 is biased radially inward relative to the axis A (or both electrical contact features are biased). In particular embodiments, at least one of the electrical contact features 130 and 132 has smooth, strip or pad configuration. In the embodiment in FIG. 21, the electrical contact feature 130 includes two biased contact portions 130*a* and 130*b*, while the electrical contact feature 132 includes two contact pads 132*a* and 132*b*. In other embodiments, as shown in FIG. 22, the electrical contact feature 130 includes an electrically conductive strip or elongated pad, while the electrical contact feature 132 includes two biased, electrically conductive members 132*c* and 132*d*. In other embodiments, the electrical contact features 130 and 132 have other suitable configurations.

Figure 23A:
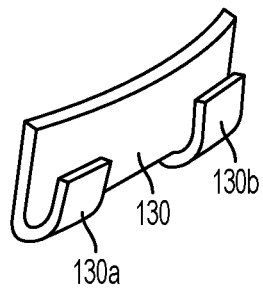
FIG. 23A is an enlarged perspective view of an embodiment of an electrical contact member on a cap of FIG. 21.

Example electrical contact feature configurations 130 (detached from the cap body 5) are shown in FIGS. 23A-23E. In the embodiment of FIG. 23A, the electrical contact feature 130 includes first and second biased extension portions 130*a* and 130*b*, similar to the electrical contact feature 130 in FIG. 21. The electrical contact feature 130 in FIG. 23A may be made of a sheet or strip of electrically conductive metal material having extension portions 130*a* and 130*b* that are bent or folded partially to extend outward from the rest of the sheet or strip. The material has sufficient flexibility to allow the extension portions 130*a* and 130*b* to bend or fold further inward toward the rest of the sheet or strip when a pressing force is applied to the extension portions 130*a* and 130*b*. In addition, the material has a natural spring force sufficient to bias the extension portions 130*a* and 130*b* toward a non-pressed state (as shown in FIG. 23A), when a pressing force is applied.

Figure 23B:
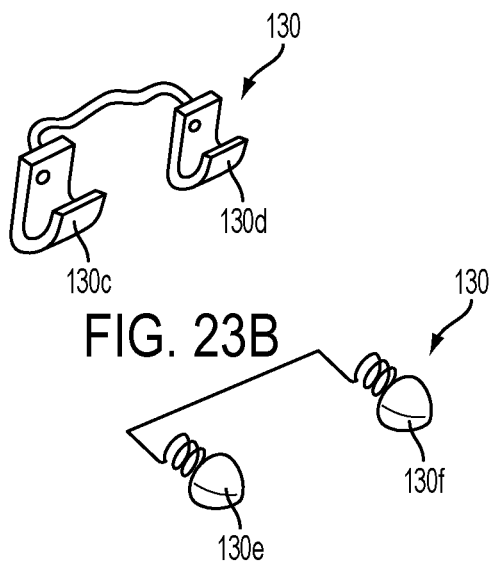
FIG. 23B is an enlarged perspective view of another embodiment of an electrical contact member for a cap of FIG. 21 or 22.
Figure 23C:
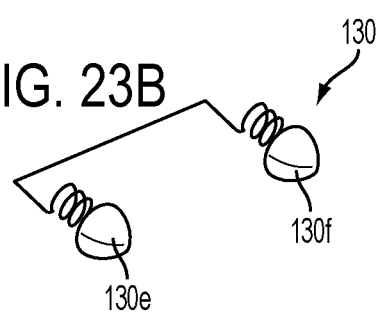
FIG. 23C is an enlarged perspective view of another embodiment of an electrical contact member for a cap of FIG. 21 or 22.
Figure 23D:
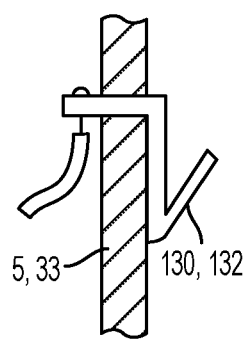
FIG. 23D is an enlarged, side, cross-section view of another embodiment of an electrical contact member for a cap or an infusion pump device of FIG. 21 or 22.
Figure 23E:
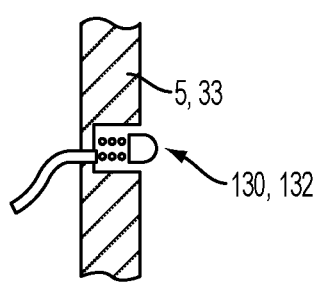
FIG. 23E is an enlarged, side, cross-section view of another embodiment of an electrical contact member for a cap or an infusion pump device of FIG. 21 or 22.

In the embodiments of FIGS. 23B and 23C, the electrical contact feature 130 includes a plurality (two, in the illustrated embodiments) of separate biased members (130*c* and 130*d* in FIGS. 23B and 130*e* and 130*f* in FIG. 23C). In the embodiment of FIG. 23B, each of the biased members 130*c* and 130*d* may be formed of a strip or sheet of electrically conductive metal that is bent or folded similar to the extension portions 130*a* and 130*b* of FIG. 23A. However, the biased members 130*c* and 130*d* are separate members that are electrically coupled together by an electrical conductor 134, such as, but not limited to a conductive wire or conductive trace on the cap body 5. Each biased member 130*c* and 130*d* may be supported on a wall portion of the cap body 5, for example, as shown in FIG. 23E.

In the embodiment of FIG. 23C, each biased member 130*e* and 130*f* includes an electrically conductive body 136 engaged or connected with a bias spring 138, and is biased outward (e.g., outward from the cap body 5) by the bias spring 138. Each biased member 130*e* and 130*f* may be supported on a wall portion of the cap body 5, for example, within a recess or groove in the cap body 5, as shown in FIG. 23E. The biased members 130*e* and 130*f* are separate members that are electrically connected together by an electrical conductor 139, such as, but not limited to a conductive wire or conductive trace on the cap body 5. In particular embodiments, the bias springs 138 are made of an electrically conductive material and are electrically coupled to the electrical conductor 139 and the respective electrically conductive bodies 136, to electrically couple the bodies 136 together.

In the embodiment of FIG. 21, when the cap 4 (or base/reservoir/cap unit) is moved in the direction of axis A, into the reservoir receptacle 32, the biased members 130*a* and 130*b* engage and slide along the inner surface of the reservoir receptacle 32. When the cap 4 (or base/reservoir/cap unit) reaches a fully installed position within the reservoir receptacle, the biased members 130*a* and 130*b* align with and electrically contact the pads 132*a* and 132*b*, respectively. Because the biased members 130*a* and 130*b* are electrically connected together, the pads 132*a* and 132*b* become electrically connected together (through the electrical contact feature 130), when the biased members 130*a* and 130*b* contact the pads 132*a* and 132*b*.

Prior to being contacted by the biased members 130*a* and 130*b*, the pads 132*a* and 132*b* are electrically separated from each other, but connected to a sensor circuit that is configured to detect electrical connection (or shorting) of the pads 132*a* and 132*b*. Accordingly, the sensor circuit 34 is configured to detect a condition of the pads 132*a* and 132*b* being electrically connected together (or shorted) when the pads 132*a* and 132*b* are contacted by the biased members 130*a* and 130*b*, respectively.

Figure 26:
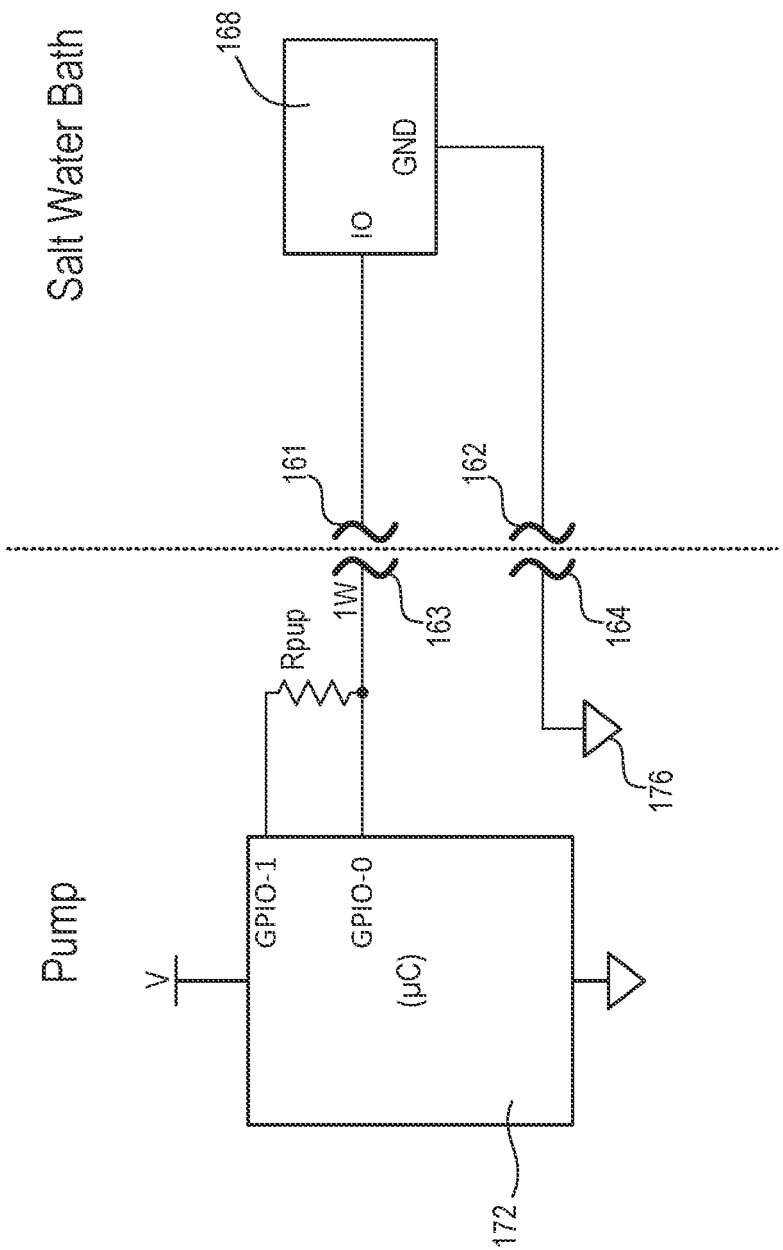
FIG. 26 is a schematic diagram of a detection circuit according to an embodiment of the present invention.
Figure 27:
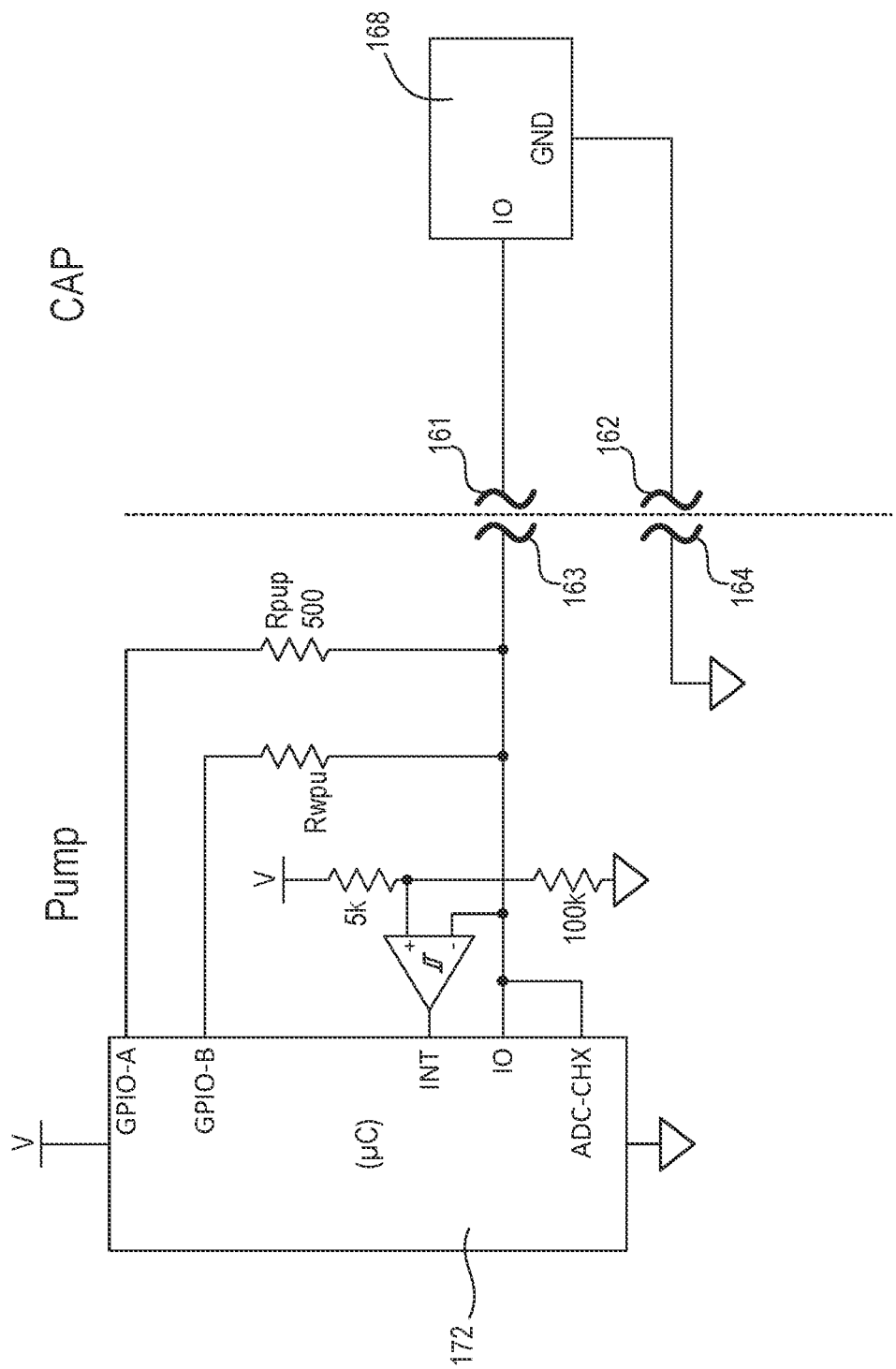
FIG. 27 is a schematic diagram of a detection circuit according to another embodiment of the present invention.

In the embodiment of FIG. 22, biased members 132*c* and 132*d* are provided on or in the interior wall of the reservoir receptacle 32, as described above. FIGS. 26 and 27 may also represent examples of biased members 132 on a wall portion of the housing 33 of the infusion pump device. While the embodiments of FIGS. 21 and 22 show an electrical contact feature 130 on the body 5 of the cap 4, in other embodiments, the electrical contact feature 130 is provided on the body of the reservoir 1 in a similar manner as described with respect to the cap body 5. In such embodiments, the electrical contact feature 132 is arranged further into the reservoir receptacle (relative to the arrangement in FIG. 21) to align with the electrical contact feature on the body of the reservoir 1, when the base/reservoir/cap unit is properly installed in the reservoir receptacle.

In particular embodiments, the electrical contact feature 132 is provided in a wall portion of the housing 33 of the infusion pump device 30. In other embodiments, the electrical contact feature 132 is provided in an upper ring member 137 that is connected to the housing 33 of the infusion pump device, at the upper end (the open end) of the reservoir receptacle 32. The upper ring member 137 may be made of any suitably rigid material, such as, but not limited to plastic, metal, ceramic, wood, composite material, or any combination thereof, and may be connected to the housing 33 in any suitable manner, including, but not limited to threads, screws, bolts, clamps, adhesive materials, welds, slot and groove connectors or the like. In such embodiments, the upper ring member 137 may include some or all of the electronics 60.

Alternatively, the upper ring member 137 may include one or more electrical contacts that electrically connect with corresponding electrical contacts on the housing 33, to electrically couple the electrical contact feature 132 with electronics 60 located in the infusion pump device 30.

In particular embodiments, electronics 60 (coupled with the sensor circuit is 34) is configured to detect the presence of the cap 4 (or base/reservoir/cap unit) in a properly installed position within the reservoir receptacle, in response to a detection of the pads 132a and 132b being electrically connected together (or shorted) by the electrical contact feature 130 on the cap 4. In other embodiments, the electronics 60 is configured to detect other parameters associated with the electrical contact feature 130 and associate the detected parameters with one or more characteristics of the cap 4 (or associated reservoir 1 or base/reservoir/cap unit, or infusion set connected thereto).

In particular embodiments of FIGS. 21-23E, one or more portions of the outer surface of the cap 4 (or base/reservoir/cap unit) include an electrical contact feature 130. In such embodiments, one or more other regions or areas on the cap 4 (or base/reservoir/cap unit) is not electrically conductive or conducts in a detectably different manner than the electrical contact feature 130. Accordingly, when the cap 4 (or base/reservoir/cap unit) is in a fully installed position within the reservoir receptacle 32 such that the electrical contact features 130 and 132 engage each other, the first electrical contact feature 130 completes or closes an electrical circuit between conductive elements (pads 132a and 132b, or biased members 132c and 132d) of the second electrical contact feature 132. Electronics 60 may be configured to detect the presence of the cap 4 (or base/reservoir/cap unit) within the reservoir receptacle 32, in response to the detection of the closed electrical circuit between conductive elements (pads 132a and 132b, or biased members 132c and 132d) of the second electrical contact feature 132.

If the cap 4 (or base/reservoir/cap unit) is rotated or linearly moved (or both) away from a fully installed position within the reservoir receptacle 32, the electrical contact feature 130 on the cap 4 (or base/reservoir/cap unit) is moved out of engagement with the electrical contact feature 132 on the reservoir receptacle 32. As a result, the electrical circuit is broken or disconnected between the conductive elements (pads 132a and 132b, or biased members 132c and 132d) of the second electrical contact feature 132. Electronics 60 may be configured to detect the movement of the cap 4 (or base/reservoir/cap unit) from a fully installed position within the reservoir receptacle 32, in response to the detection of the electrical circuit being broken between conductive elements (pads 132a and 132b, or biased members 132c and 132d) of the second electrical contact feature 132.

In further embodiments, a plurality of electrical contact features 130 are arranged at a corresponding plurality of different predefined locations on the cap 4 (or base/reservoir/cap unit), such that one or more electrical contact features 130 align with one or more electrical contact features 132 in the reservoir receptacle 32, when the cap 4 (or base/reservoir/cap unit) is at predefined, corresponding positions within the reservoir receptacle 32. In such embodiments, the electronics 60 may be configured to determine the position of the cap 4 (or base/reservoir/cap unit) within the reservoir receptacle 32 by counting electrical circuit connections (shorts) or disconnections (breaks) detected as the cap 4 (or base/reservoir/cap unit) is moved into the reservoir receptacle 32.

In further embodiments, one or more electrical contact features on the cap 4 (or base/reservoir/cap unit) are configured to have a predetermined electrically detectable characteristic or parameter, such as, but not limited to, a particular electrical resistance or impedance characteristic or parameter. In such embodiments, the electronics 60 is configured to detect the one or more characteristics or parameters of the electrical contact feature 130 and associate the detected characteristic(s) or parameter(s) with one or more characteristics of the cap 4 (or base/reservoir/cap unit), or with the reservoir 1 (or its contents), infusion set 50, connection interface 40, or any combination thereof, as described above with respect to magnetic detection, RF detection, mechanical detection or optical detection.

In yet further embodiments, a plurality of different electrical contact features 130, each having a different electrically detectable characteristic relative to the others, are provided on the cap 4 (or base/reservoir/cap unit) at respectively different predefined locations relative to each other. In such embodiments, a different respective electrical contact feature 130 on the cap (or base/reservoir/cap unit) is aligned with the electrical contact feature 132 in the reservoir receptacle 32 at different respective positions of the cap 4 (or base/reservoir/cap unit) within the reservoir receptacle 32. Accordingly, the electronics 60 may be configured to determine the position of the cap 4 (or base/reservoir/cap unit) relative to the reservoir receptacle 32, based on the particular electrical connection(s) (short(s)) or disconnection(s) (break(s)) detected as the cap 4 (or base/reservoir/cap unit) is moved relative to the reservoir receptacle 32

In particular embodiments, each different predefined characteristic of the cap 1, base/reservoir/cap unit, reservoir 1, infusion set 50 or connection interface 40, is associated (for example, on a one-to-one basis or other predefined association) with a respectively different predefined detectable location, pattern of locations, or other detectable characteristic or parameter of the electrical contact feature(s) 130. In those embodiments, the processing electronics 62 are configured to determine a characteristic of the cap 4, base/reservoir/cap unit, reservoir 1, infusion set 50 or connection interface 40 from the signals received from the sensor 34 connected with the electrical contact feature(s) 132.

For example, the processing electronics 62 may be configured to compare information received from one or more sensors 34 with information stored in a table or in another suitable data arrangement. The table or other data arrangement is stored in the electronic memory 66. The table or other data arrangement associates a plurality of different predefined electrically detectable characteristics or parameters, or locations or patterns of locations of one or more electrical contact feature(s) 130, or any combination thereof with a corresponding plurality of predefined characteristics of the cap 4, base/reservoir/cap unit, reservoir 1, infusion set 50 or connection interface 40.

In particular embodiments, based on one or more of the characteristics or parameters detected from the electrical contact feature 130, the processing electronics 62 is further configured to determine corresponding characteristics (for example, using a process 150 as described with respect to FIG. 6) and, based on those characteristics, do one or more of: determine operational settings for the infusion pump device 30, provide signals to the drive device or other components of the infusion pump device 30, provide one or more alarm signals, and record data representing detected states or conditions of one or more of the cap 4, base/reservoir/cap unit, and infusion pump device 30, as described above with regard to magnetic detection, inductive detection, RF detection, mechanical embodiments and optical detection.

In further embodiments, one or more wireless or wired communication devices is provided on the infusion pump device 30 (or other delivery device) and is configured and controlled to transmit volume information relating to the volume of infusion fluid remaining in or dispensed from the reservoir 1 (or other information corresponding to detected parameters of the one or more electrical contact detectable elements or associated characteristics) for display on another electronic device separate from or located remote from the infusion pump device 30. In particular embodiments, the wireless communication device(s) are configured to connect for communication on a communication network (such as, but not limited to the Internet), with one or more pre-defined network connected devices. Such one or more pre-defined network connected devices may be located at remote geographic locations relative to the infusion pump device 30 (or other delivery device). In particular embodiments, such network connected devices include a server configured to receive information from the infusion pump device 30 (or other delivery device) or from another network connected device (such as a cradle, user computer, or the like) that communicates with the infusion pump device 30 (or other delivery device). Such information may include, but is not limited to information corresponding to one or more detected parameters or one or more associated characteristics, or other information regarding the reservoir 1, cap 4, base/reservoir/cap unit or infusion set as described above.

In such embodiments, the network connected server may be associated with an entity that records information, supplies associated products such as refills or replacement parts, provides medical treatment or medical insurance to the user or the like. In one example, the network connected server is associated with the Carelink™ system of Medtronic Inc. In other embodiments, the network connected server is one or more other servers and associated entities. Accordingly, such information may be employed by the server (or associated entity) to determine whether or not (or when) to send refills, new or replacement reservoirs, caps, infusion set needle housings, infusion set tubing, or other components of the cap 4, base/reservoir/cap unit, or infusion set. In further embodiments, such information may be provided to the user's doctor or other medical treatment entity associated with the user (for tracking, diagnosing, adjusting treatment plans or other suitable uses). Thus, in such embodiments, refills or replacement components may be sent to users, automatically (without requiring the user to place an order), and usage information can be provided to the user's healthcare provider, insurance provider or other suitable entities, automatically.

In further embodiments, the network connected server is configured to provide (and the infusion pump device 30 or other delivery device is configured to receive) information through the above-noted network communication connection or other network connection. Such information may include, but is not limited to, instructions or recommendations for replacing or refilling a reservoir 1, cap 4, base/reservoir/cap unit or infusion set, messages or notices from healthcare providers, insurance carriers or manufacturers, recall notices or the like. In particular embodiments, electronics (such as electronics 60) in the infusion pump device 30 (or other delivery device) is configured to perform one or more predefined actions (as discussed above) in response to receipt of a predefined instruction, notice or message.

Figure 24:
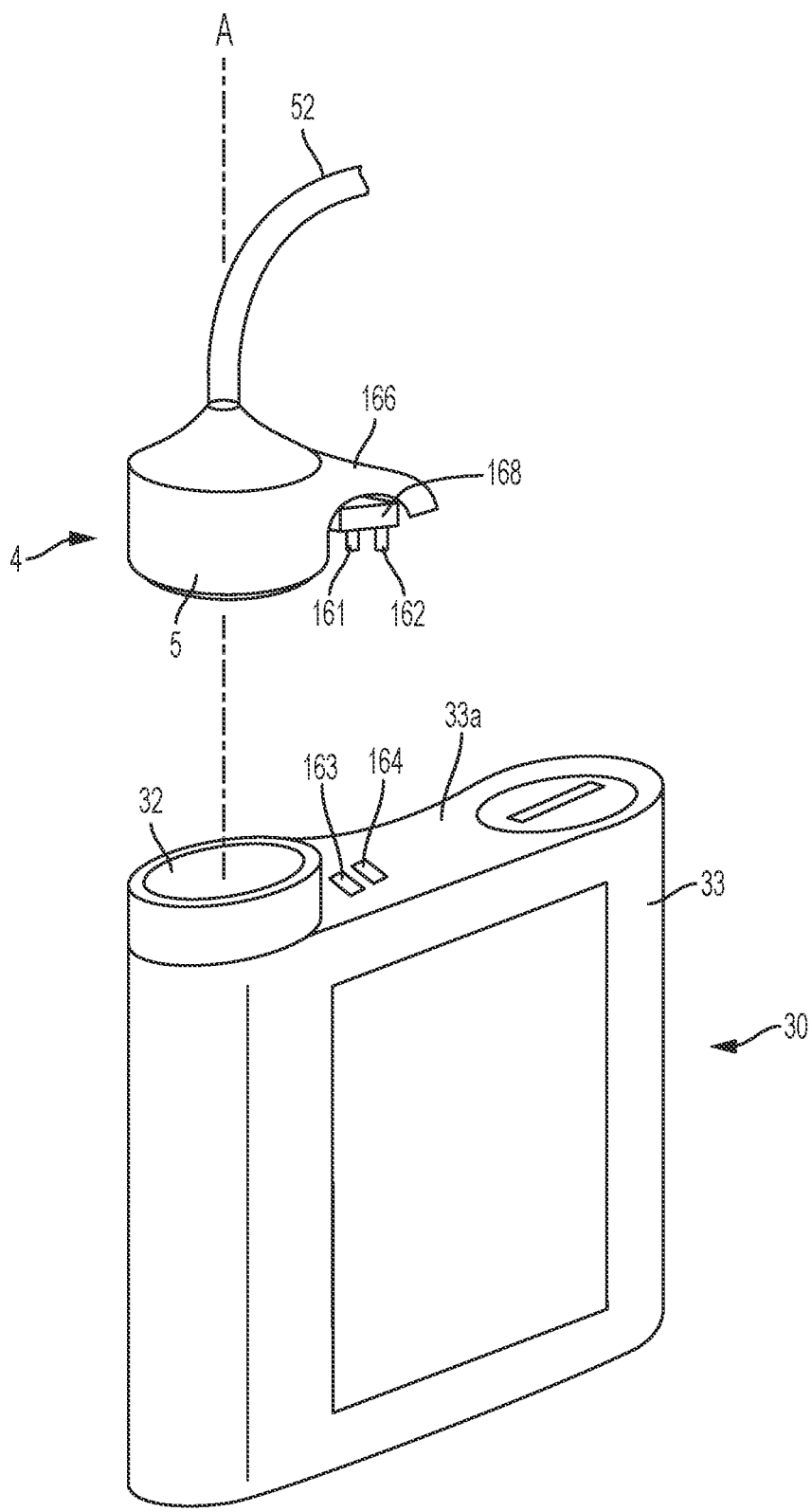
FIG. 24 is a perspective view of an infusion pump system including a cap outside of the infusion pump device, according to another embodiment of the present invention.
Figure 25:
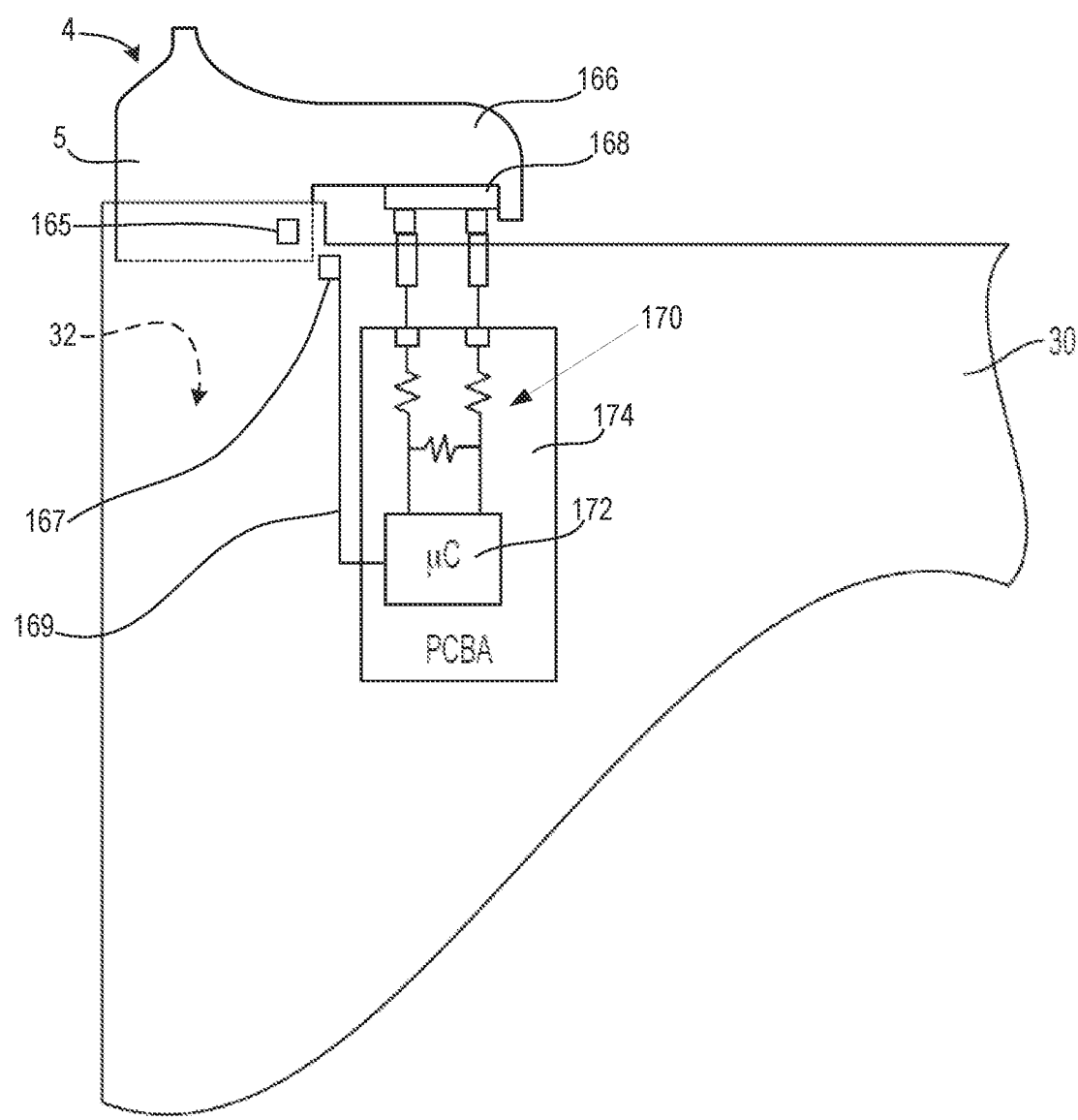
FIG. 25 is a schematic diagram representing a portion of the infusion pump system of FIG. 24, with the cap on the infusion pump device.

Another example embodiment of electrical contact detection configuration is shown in FIGS. 24 and 25. The drawing in FIG. 24 shows a cap 4 that is provided with a pair of first electrical contact features 161 and 162 and an infusion pump device 30 that is provided with a second pair of electrical contact features 163 and 164. The drawing in FIG. 25 shows a portion of the infusion pump device 30, with the cap 4 of FIG. 24 (or base/reservoir/cap unit including the cap 4 of FIG. 24) in an installed state.

The first electrical contact features 161 and 162 are arranged to engage and make electrical contact with a pair of second electrical contact feature 163 and 164 on the infusion pump device 30, when the cap 4 (or base/reservoir/cap unit) is installed in the reservoir receptacle of the infusion pump device 32. However, the second electrical contact features 163 and 164 are arranged at a location on the housing 33 of the infusion pump device 30, external to the reservoir receptacle 32. Accordingly, the first and second contact features 161-164 engage with each other, outside of the reservoir receptacle 32, when the cap 4 (or base/reservoir/cap unit) is installed in the reservoir receptacle of the infusion pump device 32.

In the embodiment in FIG. 24, the second electrical contact features 163 and 164 are arranged on a surface 33*a* of the housing 33, where the surface 33*a* faces in the same direction (or substantially in the same direction) as axis A and the open end of the reservoir receptacle 32 of the infusion pump device 30. In other embodiments, the second electrical contact features 163 and 164 may be located at other suitable surfaces of the housing 33 or other suitable locations on the infusion pump device 30.

In the embodiment in FIG. 24, the first electrical contact features 161 and 162 are supported on an extension portion 166 of the cap 4. The extension portion extends outward from the axis A, over the surface 33*a* of the housing 33, when the cap 4 (or base/reservoir/cap unit) is installed in the reservoir receptacle of the infusion pump device 32. In particular embodiments, the extension portion 166 is an integral portion of the housing 5 of the cap. For example, the extension portion 166 may be formed with (and with the same material as) the rest of the housing 5, for example, in a molding process or the like. In other embodiments, the extension portion 166 is formed separate from the housing 5 of the cap 4 and, then, is attached to the housing 5 by any suitable connection mechanism including, but not limited to adhesive, welding, soldering, connectors or the like.

In particular embodiments, the first electrical contact features 161 and 162 are arranged to engage and make electrical contact with a pair of second electrical contact feature 163 and 164, when the cap 4 (or base/reservoir/cap unit) is in a fully and properly installed position within the reservoir receptacle 32 of the infusion pump device 30, but do not engage and make electrical contact with a pair of second electrical contact feature 163 and 164, when the cap 4 (or base/reservoir/cap unit) is not in a fully and properly installed position within the reservoir receptacle 32. More specifically, when the cap 4 (or base/reservoir/cap unit) is fully and properly installed, the one first electrical contact feature 161 is arranged to engage one second electrical contact feature 163, while the other first electrical contact feature 162 is arranged to engage the other second electrical contact feature 164. In this manner, an electrical contact between the first and second pairs of electrical contact features is made, only when the cap 4 (or base/reservoir/cap unit) is in a fully and properly installed position within the reservoir receptacle 32.

In particular embodiments, the first and second electrical contact features 161-164 may be configured and operate similar to the first and second contact features 130 and 132 described above. In further embodiments, the first electrical contact features are part of (or are electrically connected with) electrical terminals of an electronic circuit such as, but not limited to an integrated circuit (IC) chip 168, carried by the cap 4. In such embodiments, the IC chip 168 includes an EPROM, ROM, PROM or other suitable electronic storage device that stores electronic data and/or programming. In such embodiments, electronics within the infusion pump device 30 (e.g., electrical circuit 170 described below and/or electrical circuit 60 described above with respect to FIG. 5) may be configured to read data from the electronic storage device, when an electrical contact between the first and second pairs of electrical contact features is made. In further embodiments, such electronics within the infusion pump device 30 may be configured to write data to the electronic storage device (e.g., the IC chip 168).

Data stored on or written to the electronic storage device (e.g., the IC chip 168) may include any suitable data, such as, but not limited to data associated with one or more characteristics of the cap 4 (or other component of the base/reservoir/cap unit, or the infusion set, infusion pump device 30 or user), including, but not limited to one or more of: a type or identity of a manufacturer of the reservoir, cap or infusion pump device; a size of the reservoir, cap or infusion pump device; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir, cap or infusion pump device; a location corresponding to a place where the reservoir or infusion media in the reservoir was made, filled, or otherwise processed; a location corresponding to a place where the cap or infusion pump device was made, assembled or otherwise processed; a location corresponding to a place where the reservoir, infusion media in the reservoir, cap or infusion pump device is authorized to be used; a lot number or code associated with a batch in which the reservoir, cap, infusion pump device or infusion media was made, cleaned, filled or otherwise processed; a serial number; a unique ID; user identification information for authorized users.

In the embodiment in FIGS. 24 and 25, the second electrical contact features 163 and 164 on the infusion pump device 30 are electrically connected with (or are part of) an electrical circuit 170 contained within the housing 33 of the infusion pump device 30. In particular embodiments the electrical circuit 170 may be part of or include an electrical circuit 60 as described above with respect to FIG. 5, where the sensor element 34 in FIG. 5 represents the second electrical contact features 163 and 164, or is connected with the second electrical contact features 163 and 164, to detect electrical connection of the first electrical contact features 161 and 162 making electrical contact with the second electrical contact features 163 and 164. In such embodiments, detection of electrical contact of the first and second electrical contact features 161-164 may be similar to the detection of electrical contact between electrical contact features in the embodiments of FIGS. 21-23E. In other embodiments, detection of electrical contact of the first and second electrical contact features 161-164 may be carried out by other suitable detection electronics.

In particular embodiments, the electrical circuit 170 includes a controller circuit, such as, but not limited to a microcontroller (μc) 172 and a resistor circuit and/or other circuit components. Also in particular embodiments, the electrical circuit 170 may be provided on a printed circuit board assembly (PCBA) 174 located within the housing 33 of the infusion pump device 30.

The first and second electrical contact features 161-164 may be formed as pads of metal or other electrically conductive material. In other embodiments, the first electrical contact features 161 and 162, or the second electrical contact features 163 and 164 (or each of the first and second electrical contact features 161-164) may include an electrically conductive member that is spring biased or otherwise supported for movement against a bias force, such as, but not limited to a pogo connector, spring biased connector or the like. In such embodiments, one or both of the pair of first electrical contact features 161-162 and the pair of second electrical contact features 163-164 are arranged to press against the other pair of the first or second electrical contact features and move against the bias force (e.g., spring force), such that the first and second electrical contact features are positively engaged with each other, by the bias force, when the cap 4 (or base/reservoir/cap unit) is in a fully and properly installed position within the reservoir receptacle 32. In other embodiments, other suitable electrical connectors may be employed with or for the first and second electrical contact features 161-164, including, but not limited to snap connectors that snap together and make electrical contact, slide connectors that slide together to make electrical contact, or the like.

In further embodiments, one or more additional electrical contact features 165 is located on the cap 4 (or other portion of the base/reservoir/cap unit) for electrical contact with one or more additional electrical contact features 167 on the infusion pump device 30, within the reservoir receptacle 32 of the infusion pump device 30, when the cap 4 (or base/reservoir/cap unit) is fully and properly installed in the reservoir receptacle 32. The additional electrical contact 167 on the infusion pump device 30 may be electrically connected to the microcontroller 172 (or other portion of the electronics 170) through one or more electrical leads 169. In such embodiments, the electronics (such as electrical circuit 170 and/or electrical circuit 60 described above with respect to FIG. 5) may be configured to detect an electrical connection of the additional electrical contact features 165 and 167, in addition to or as an alternative to detection of an electrical connection between the pairs of first and second electrical contact features 161-164. In such embodiments, the electronics may be configured to verify a proper position of the cap 4 (or base/reservoir/cap unit) within the reservoir receptacle 32, only upon detection of an electrical connection between the additional electrical contact features 165 and 167, and also between the pairs of first and second electrical contact features 161-164. In other embodiments, detection of an electrical connection between the additional electrical contact features 165 and 167, and a detection of an electrical connection between the pairs of first and second electrical contact features 161-164 may be employed as a redundant detection system.

In particular embodiments, the second electrical contact features 163 and 164 are mounted on the housing 33 of the infusion pump device 30 and sealed with respect to the housing 33 in a manner that inhibits leakage of fluid (water or other fluid) through the housing 33. In such embodiments, the infusion pump device 30 may be configured for use in damp conditions or, in further embodiments, in certain submerged or underwater environments. For example, embodiments may be configured for use in wet conditions (e.g., while the user is bathing, showering, or swimming), sea water or other salt water or ionic solution conditions, or high humidity or rain conditions. In such embodiments, a further reliable seal may be provided on the cap 4 (or base/reservoir/cap unit) or on the open end of the reservoir receptacle 32 of the infusion pump device 30, or both, to inhibit fluid from entering into the reservoir receptacle 32, when the cap 4 (or base/reservoir/cap unit is installed in the reservoir receptacle. Also in such embodiments, the rest of the housing 33 of the infusion pump device may be made to be sufficiently sealed or water-tight, to inhibit water from entering the housing 33. Thus, in particular embodiments, each of the electrical connections between electrical contact features on the cap 4 (or base/reservoir/cap unit) and contact features on the infusion pump device 30 are made outside of the reservoir receptacle 32 (e.g., via the pairs of first and second electrical contact features 161-164, where the second electrical contact features 163 and 164 are sealed with the housing 33 to inhibit passage of fluid through the contact features).

In particular embodiments, the electronics (such as electrical circuit 170 and/or electrical circuit 60 described above with respect to FIG. 5) may be configured to detect a condition in which the infusion pump device is present in a wet environment or in an ionic solution environment. In such embodiments, the electronics may be configured to provide a signal to and detect a response from the electronic device (e.g., the IC chip 168) on the cap 4 (or base/reservoir/cap unit), where the response is different in wet (or ionic solution) conditions relative to dry conditions.

The electronics in the infusion pump device (such as electrical circuit 170 and/or electrical circuit 60 described above with respect to FIG. 5) may be configured to read data from (and/or write data to) the electronic device (e.g., the IC chip 168) on the cap 4 (or base/reservoir/cap unit) as discussed above, when the infusion pump device (and the connected cap 4 or base/reservoir/cap unit) are in a dry environment. In particular embodiments, the electronics may be further configured to detect the presence of the cap 4 (or base/reservoir/cap unit) in an installed position, as discussed above, but is disabled from reading or writing to the electronic device (e.g., the IC chip 168) on the cap 4 (or base/reservoir/cap unit), when the infusion pump device (and the connected cap 4 or base/reservoir/cap unit) are in a wet or ionic solution environment. In such embodiments, the electronics in the infusion pump device may be configured to operate in accordance with the Table 3.

TABLE 3

| Connection Environment | Read Data | Confirm Presence |
|---|---|---|
| Wet | No | Yes |
| Dry | Yes | Yes |

In embodiments that operate in accordance with Table 3, data may be read from or written to the electronic device (e.g., the IC chip 168) on the cap 4 (or base/reservoir/cap unit), when the infusion pump device (and connected cap 4 or base/reservoir/cap unit) are in a dry environment, for example, to system setup or other activities that typically occur in dry environments. For example, data relating to the model number, cannula length, infusion set tubing length or other characteristics as described herein may be read from the electronic device (e.g., the IC chip 168) on the cap 4 (or base/reservoir/cap unit) in a dry environment, to assist with initial or updated settings of the infusion pump device to allow proper priming or filing of the infusion set tubing and cannula and conduct other operations. Then, at a later time, the infusion pump device may be located in a wet (or ionic solution) environment that could inhibit accurate reading and writing date from or to the electronic device on the cap 4 (or base/reservoir/cap unit), yet still detect the presence of the cap 4 (or base/reservoir/cap unit) and continue to operate as previously set (initially or by update) if the presence of the cap 4 (or base/reservoir/cap unit) is detected. In particular embodiments, upon detection of a wet (or ionic solution) environment, the electronics (such as electrical circuit 170 and/or electrical circuit 60 described above with respect to FIG. 5) may be configured to inhibit operation of a read or write operation, as exposure of the electrical contact features 161-164 to moisture or ionic solutions may cause communication bit errors to occur.

An example of a circuit configuration for detecting a wet (or ionic solution) condition is shown in FIG. 26, where the electronic device (e.g., the IC chip 168) on the cap 4 (or base/reservoir/cap unit) is connected, through the first and second electrical contact features 161-164 to a ground terminal 176 and to a pair of input/output terminals (GPIO-1 and GPIO-2) of a microprocessor chip (e.g., corresponding to the microcontroller 172). In that embodiment, the microcontroller 172 may selectively transmit a test signal through the electrical contact features 163 and 161 to the IC chip 168, and then receive a response signal back from the IC chip 168, where the response signal through the electrical contact features 163 and 161, where the response signal has a value or parameter that differs when the IC chip 168 is in a wet (or ionic solution) environment than when the IC chip 168 is in a dry environment. The microcontroller 172 may be configured to detect the response signal and determine whether or not the IC chip 168 is in a wet or dry environment.

Another example of a circuit configuration that further operates to detect the attachment or detachment of a cap 4 (or base/reservoir/cap unit) to the infusion pump device 30 is shown in FIG. 27. In the embodiment of FIG. 27, the microcontroller 172 includes further input terminals INT and ADC-CHX and a further input/output terminal IO, where the electrical contact feature 163 is connected to the terminal IO and to one input of a comparator (the other input of the comparator being connected to a reference potential, and the output of the comparator being connected to the INT input). In the embodiment in FIG. 27, when the cap 4 (or base/reservoir/cap unit) is installed such that the IC chip 168 is connected to the electrical contact features 163 and 164, through the electrical contact features 161 and 162, then the INT input receives a signal output from the comparator, indicating a weak or a strong load. However, when the cap 4 (or base/reservoir/cap unit) is not fully installed such that the IC chip 168 is not connected to the electrical contact features 163 and 164, then the INT input receives a signal output from the comparator, indicating no load. The microcontroller 172 may be configured to detect the load condition and determine whether or not the IC chip 168 is connected (to detect whether or not the cap 4 or base/reservoir/cap unit is fully installed).

3. Reservoir/Cap/Infusion-Set Units

In embodiments as described above, the connection interface 40 is configured to connect and interface the reservoir 1 with the infusion set 50 and with the infusion pump device 30, using releasable couplers including a first releasable coupler that removably attaches the cap 4 to the base 2 (and, thus, to the reservoir 1) and a second releasable couple that removably attaches the cap 4 to the infusion pump device 30. In particular examples of such embodiments, the cap 4 may be configured to allow the cap 4 to be selectively and manually connected and disconnected from a reservoir 1 and an infusion pump device 30, for example, to allow the reservoir 1 to be stored, shipped, sold, or otherwise provided to a user (or healthcare provider or other authorized person), separate and independent of the infusion pump device, the connection interface 40 and the infusion set 50, and then connected with the cap 4 and infusion pump device by the user (or healthcare provider or other authorized person).

In further examples of such embodiments, the releasable couplers may be configured to allow the user (or healthcare provider or other authorized person) to replace a first reservoir 1 with a second reservoir 1 (or a re-filled first reservoir 1) and continue to use the same connection interface 40, by allowing the cap 4 to be disconnected from the first reservoir 1 and reconnected to the second reservoir 1 (or re-filled first reservoir 1). For example, the first reservoir 1 may be removed from the reservoir receptacle 32 of the infusion pump device 30 (e.g., after the first reservoir 1 is fully or partially empty or otherwise ready for replacement), the cap 4 (or the cap 4 and base 2) is removed from the first reservoir 1 and then connected to a second reservoir 1. The second reservoir 1 is, then, installed in the reservoir receptacle 32 of the infusion pump device 30. In this manner, the reservoir 1 may be replaced, while the infusion set 50 remains secured to a patient (without withdrawing the needle 56 from the patient's skin).

In other embodiments as described with reference to FIGS. 28a-34, a reservoir (201 or 301) and an infusion set (250 or 350) are assembled as a combined unit and stored, shipped, sold, or otherwise provided to a user (or healthcare provider or other authorized person), as an assembled unit. Such embodiments may include a connection interface that connects the infusion set (250 or 350) to the reservoir (201 or 301) permanently or other manner in which the connection is maintained in a desired manner.

In particular embodiments, the reservoirs 201 and 301 and infusion sets 250 and 350 correspond to (and operate similar to) the reservoir 1 and infusion set 50 described above, and are employed with an infusion pump device 30 in a manner as described herein. However, in the embodiments described with reference to FIGS. 28A-34, a transfer guard 200 or 300 is further provided for interfacing the reservoir 201 with a supply container (203 in FIG. 31), to allow a user (or healthcare provider or other authorized person) to fill the reservoir 201 or 301 (completely or partially) with infusion media from the supply container 203, for example, prior to installing (or re-installing) the reservoir 201 or 301 into the infusion pump device 30.

Embodiments described with reference to FIGS. 28A-34 may be employed with any one or more of the detection embodiments (magnetic detection, RF detection, mechanical detection and optical detection) described above. Thus, in further embodiments of FIGS. 28A-34, the reservoir 201 or 301, or the cap 204 or 304 (or both the reservoir and the cap) is provided with one or more detectable elements 42, as described above.

a. Twist and Lock Embodiment

Embodiments described with reference to FIGS. 28A-31 employ a transfer guard 200 for interfacing the reservoir 201 with a supply container 203. The transfer guard 200 is a structure configured to interface the reservoir 201 with a supply container (a bottle, second reservoir or other container, for example, to fill or re-fill the reservoir 201 with fluidic media from the bottle, second reservoir or other container. Once filled (or re-filled), the reservoir 201 is separated from the transfer guard 200 and, then, may be installed in an infusion pump device 30 and operated as described above. Examples of transfer guards are described in U.S. Pat. No. 8,356,644 titled "Transfer Guard System and Methods", which is incorporated herein by reference in its entirety. Other embodiments may employ other suitable transfer guard structures.

In the embodiment in FIGS. 28A-31 the transfer guard 200 includes a generally cylindrical body 202 configured of a suitably rigid material such as, but not limited to plastic, metal, ceramic, wood, paper or card stock, composite material, or the like. The body 202 of the transfer guard 202 has a first end 205 for interfacing with the infusion media port of the reservoir 201, and a second end 206 for interfacing with an infusion media port of a supply container 203. In the embodiment of FIGS. 28A-31, the first end 205 has an opening and a cavity with an interior volume for receiving at least a portion of the infusion media port of the reservoir 201. Also in that embodiment, the second end 206 has an opening and a cavity with an interior volume for receiving at least a portion of the infusion media port of the supply container.

When the infusion media ports of the reservoir 201 and the supply container 203 are received in the cavities at the first and second ends of the transfer guard 200, one or more hollow needles in the transfer guard 200 connect the interior volume of the supply container in fluid flow communication with the interior volume of the reservoir 201. In that state, the reservoir piston may be withdrawn (pulled outward relative to the body of the reservoir 201), to create a sufficient pressure differential between the interior of the reservoir 201 and the interior of the supply container, to draw infusion media from the supply container, through the hollow needle(s) and into the reservoir 201.

Once the reservoir 201 is sufficiently filled, the supply container 203 may be removed from the second end 206 of the transfer guard 200. Alternatively or in addition, the first end 205 of the transfer guard 200 may be removed from the reservoir 201, for example by rotating the transfer guard 200 about the axis AA relative to the reservoir 201 and then pulling the transfer guard 200 and reservoir 201 apart along the direction of the axis AA, as described below. The axis AA corresponds to the longitudinal axis of the reservoir 201, as well as the longitudinal axis of the container 203 and of the transfer guard 200, when the container 203 and transfer guard 200 are connected to the port of the reservoir 201 in the arrangement shown in FIG. 31. The transfer guard 200 may be configured to be disposed of after removal from the reservoir 201. Alternatively, the transfer guard 200 may be configured to be re-connected to another or the same reservoir 201, after removal from the reservoir 201, for one or more further filling operations.

Figure 29A:
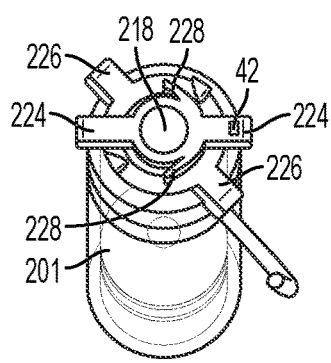
FIGS. 29A and 29B are a perspective view and a cut-away side view of the cap and reservoir of FIG. 28A in a first or fill state.
Figure 29B:
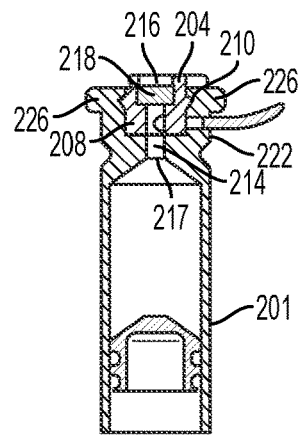
Figure 30A:
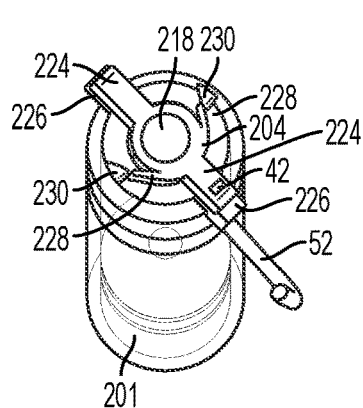
FIGS. 30A and 30B are a perspective view and a cut-away side view of the cap and reservoir of FIG. 28A in a second or delivery state.
Figure 30B:
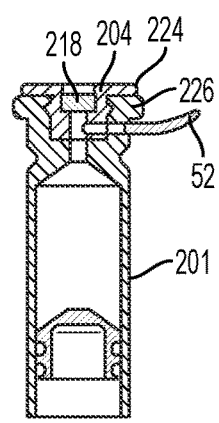
Figure 31:
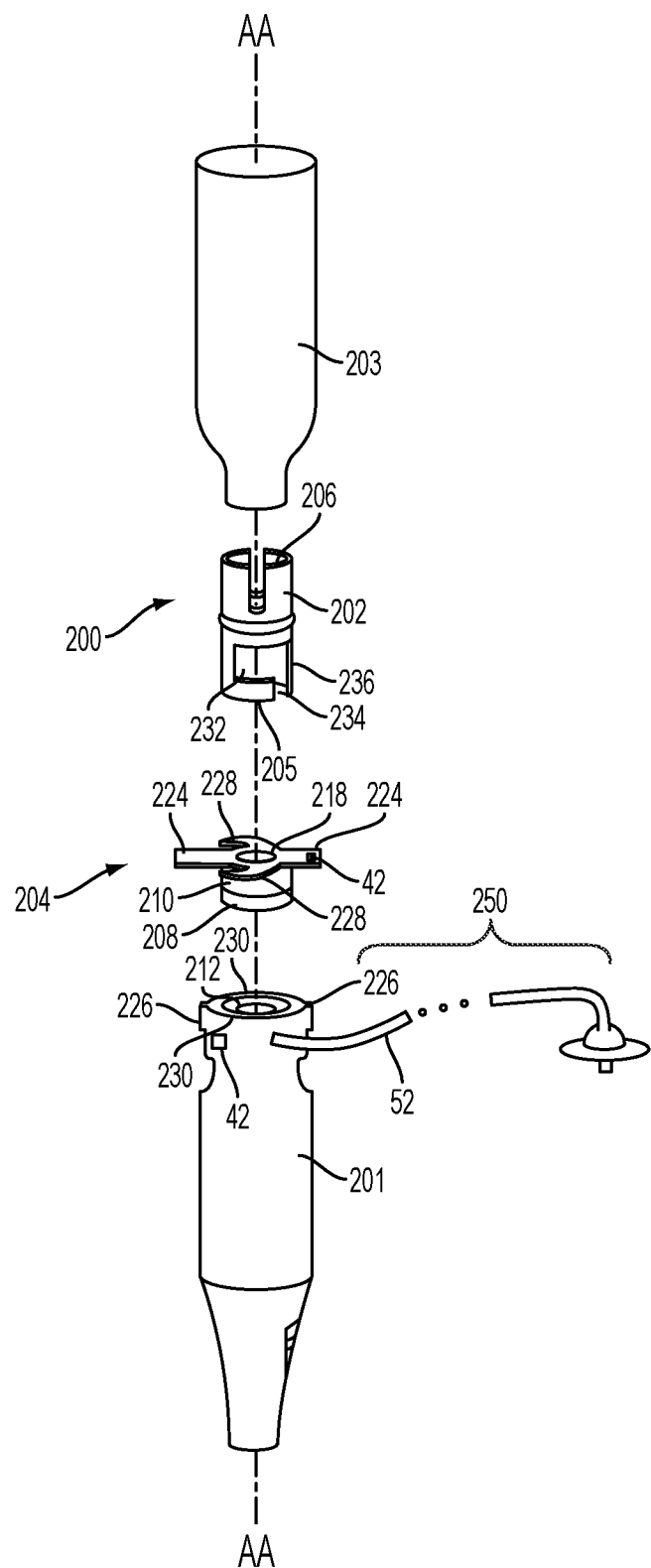
FIG. 31 is a partial exploded view of the cap, reservoir and transfer guard of FIG. 28A, with a supply container.

A cap 204 that connects to the infusion media port of the reservoir 201, and is rotatable around the axis AA relative to the reservoir 201 when connected to the port of the reservoir 201. As described herein, when connected to the reservoir 201, the cap 204 is rotatable at least to and between a first position (or fill position) as shown in FIGS. 29A and 29B, and a second position (or deliver position) as shown in FIGS. 30A and 30B.

In the embodiment of FIGS. 29A-31, the cap 204 has a generally cylindrical portion 208 that extends coaxially with the axis AA when the cap 204 is connected to the port of the reservoir 201. The cap 204 includes a protruding rib 210 that extends around the axis AA on the outer surface of the generally cylindrical portion 208. The protruding rib 210 fits into a correspondingly shaped groove 212 in the port of the reservoir 201, to secure the cap 204 to the reservoir 201, yet allow the cap 204 to rotate around the axis AA relative to the reservoir 201. In other embodiments, two or more protruding ribs are provided on the outer surface of the cylindrical portion 208 of the cap 204, and a corresponding number (two or more) grooves 212 are provided in the port of the reservoir 201 for receiving the two or more ribs when the cap 204 is connected to the port of the reservoir 201.

In particular embodiments, the cap 204 or the port of the reservoir 201 (or both) is made of a material that has sufficient rigidity to secure the cap 204 to the reservoir 201 when the rib(s) 210 is in the groove(s) 212, but is sufficiently flexible and resilient to allow the cap 204 to be snapped into the port of the reservoir 201. In such embodiments, during assembly, the cylindrical portion 208 is configured to be inserted into the port of the reservoir 201 and pushed along the direction of the axis AA, causing the rib(s) 210 to ride along and partially compress against the inner surface of the port of the reservoir 201, until the rib(s) 210 engage the groove(s) 212 in the port of the reservoir 201 and then expand from their compressed state to fill or partially fill the groove(s) 212. In particular embodiments, the cap 204 is configured to provide a snap sound or snap-like feel that is perceptible to a person assembling the cap 204 with the reservoir 201, when the rib(s) 210 engage the groove(s) 212. Once snapped into place, the rib(s) 210 can ride within the groove(s) 212 to allow the cap 204 to rotate around the axis AA relative to the reservoir 201, while remaining connected to the reservoir 201.

In embodiments shown in FIGS. 29A-31, one or more ribs 210 are provided on the cap 204 and one or more grooves 212 are provided in the port of the reservoir 201. In other embodiments, the relative locations of the ribs and grooves are reversed such that one or more ribs is provided on the port of the reservoir 201 and one or more grooves is provided on the cap 204. In yet other embodiments, each of the cap 204 and the port of the reservoir 201 includes at least one rib and at least one groove.

A channel 214 extends through the cylindrical portion 208 of the cap 204, along the direction of the axis AA. The channel 214 is open on both ends 216 and 217. However, the channel 214 is sealed by a septum 118 that is held by the cap 204, adjacent the end 216. In the embodiment in FIGS. 29A-31, the septum 218 is supported within the cap 204, in a position adjacent, but recessed from the end 216 of the channel 214. The septum is made of a material that provides a fluid seal and, in particular embodiments, a hermetic seal, to seal the channel 214, but that can be pierced by the needle(s) in the transfer guard 200, when the port of the reservoir 201 is received within the first end 205 of the transfer guard 201. In particular embodiments, the septum 218 is made of a material that automatically reseals itself after a needle has pierced the material and then is withdrawn from the septum.

The channel 214 has an opening 220 at a location along its longitudinal dimension, between the first and second ends 216 and 217 of the channel 214. The opening 220 is arranged to align in fluid flow communication with an open end 221 of a further channel 222 in the port of the reservoir 201, when the cap 204 is connected to the reservoir and the cap 204 is rotated to the second position (or deliver position) as shown in FIGS. 30A and 30B. However, when the cap 204 is in the first position (or fill position) as shown in FIGS. 29A and 29B, the opening 220 is out of alignment and out of fluid flow communication with the channel 222 in the port of the reservoir.

The channel 222 in the port of the reservoir 201 has a longitudinal dimension that extends in a direction transverse to the longitudinal dimension of the channel 214 and the axis AA when the cap 204 is connected to the reservoir 201. In the embodiment in FIGS. 29A-31, the channel 222 extends generally perpendicular to the channel 214, when the cap 204 is connected to the reservoir 201. The channel 222 is connected in fluid flow communication with tubing 252 of the infusion set 250. In particular embodiments, the tubing 252 is connected to the reservoir 201 (at the channel 222) permanently or other manner in which the connection is maintained. In the embodiment of FIGS. 29A-31, the tubing 252 is connected with an infusion needle, as described above with respect to tubing 52 and infusion needle 56.

In particular embodiments, the open end 221 of the channel 222 is sealed by the cap 204 to inhibit the passage of fluid into or out of the channel 222, when the cap is in the first position (or other positions between the first and second position). In one example, the outer surface of the cylindrical portion 208 of the cap 204 is configured to fit sufficiently closely with the inner surface of the port of the reservoir 201 to seal the open end 221 of the channel 222, when the cap 204 is in the first position (or other positions between the first and second position). In further examples, one or more seals or seal material is arranged on the outer surface of the cylindrical portion 208 of the cap 204, to seal the open end 221 of the channel 222, when the cap 204 is in the first position (or other positions between the first and second position).

The cap 204 includes one or more extension arms 224 that extend over the port end of the reservoir 201, when the cap 204 is connected to the reservoir 201. In the embodiment of FIGS. 29A-31, the cap 204 has two extension arms 224 extending from the cylindrical portion 208 of the cap 204. The extension arms 224 extend from the cylindrical portion 208 at locations opposite each other (180 degree apart) relative to the axis AA and are thinner than the cylindrical portion 208 in the dimension of the axis AA. Accordingly, when the cap 204 is connected to the port of the reservoir 201, the arms 224 extend outward and transverse to the axis AA, over the port end of the reservoir 201, as shown in FIGS. 29A-30B.

The port of the reservoir 201 also includes one or more extension arms 226 that extend outward and transverse to the axis AA. In the embodiment of FIGS. 28A-31, the reservoir 201 has two extension arms 226 extending from the port end of the reservoir 201, at locations opposite each other (180 degree apart) relative to the axis AA. The extension arms 226 on the port of the reservoir 201 are arranged to align with the extension arms 224 (such that extension arms 224 are directly on top of the extension arms 226 in the direction of the axis AA) when the cap 204 is rotated to the second position (or deliver position) as shown in FIGS. 30A and 30B. The extension arms 226 are arranged to not align with the extension arms 224 (such that extension arms 224 are not directly on top of the extension arms 226 in the direction of the axis AA) when the cap 204 is in the first position (or fill position) as shown in FIGS. 29A and 29B, or when the cap 204 is in other positions between the first and second positions. As described herein, the extension arms 224 provide surfaces that can be engaged to receive a force for rotating the cap 204 from a first position (or fill position) as shown in FIGS. 29A and 29B, to a second position (or deliver position) as shown in FIGS. 30A and 30B.

In particular embodiments, the cap 204 or the port of the reservoir 201 (or both) are provided with a latch or other structure that locks the cap 204 in the second position (or deliver position), after the cap 204 has been rotated to the second position. In the embodiment in FIGS. 29A-31, the cap includes a pair of flexible pawls 228 that are arranged to engage a corresponding pair of stop members 230 on the port of the reservoir 201. In particular embodiments, the flexible pawls 228 are flexible extensions of the cap 204, formed as a unitary (for example, molded) structure with the cylindrical portion 208 and the arms 224 of the cap 204. The flexible pawls 228 are arranged around the outer periphery of the cylindrical portion 208 of the cap 204, to ride adjacent an end surface of the port of the reservoir 201, as the cap 204 is rotated in a first direction (for example, clockwise) between the first position (or fill position) and the second position (or deliver position).

The stop members 230 are arranged on that end surface of the port of the reservoir 201, to engage the flexible pawls 228, as the cap 204 is rotated in the first direction between the first position (or fill position) and the second position (or deliver position). As the cap 204 is rotated from the first position (or fill position) toward the second position (or deliver position), the flexible pawls 228 engage and slide along the stop members 230. The engagement with the stop members 230 causes the flexible pawls 228 to flex inward toward the axis AA as they ride along the stop members 230. As the cap 204 is rotated to the second position (or deliver position), the flexible pawls 228 are moved past the stop members 230 and flex back outward, away from the axis AA, due to their natural resilience.

In particular embodiments, the stop members 230 are shaped or otherwise configured to inhibit rotation of the cap 204 out of the second position (or deliver position), once the cap 204 has been rotated to that position. In the embodiment of FIGS. 29A-31, each stop member 230 has a sloping or ramp surface that that faces a flexible pawl 228 when the cap 204 is in the first position (or fill position) and a stop surface that faces the flexible pawl 228 when the cap 204 is in the second position (or deliver position). The sloping or ramp surface of the stop member 230 slopes inward toward the axis AA in the direction of cap rotation from the first position to the second position, while the stop surface of the stop member 230 has a more abrupt radial dimension. In other embodiments, each stop member 230 has other shapes suitable for allowing the flexible pawls 228 to pass as the cap 204 is rotated toward the second position (or deliver position) and to engage the flexible pawls 228 to inhibit reverse rotation of the cap 204 toward the first position (or fill position) once the cap 204 has been rotated to the second position. In the embodiment in FIGS. 29A-31, the cap 204 is provided with two flexible pawls 228 and the reservoir 201 is provided with two stop members 230. In other embodiments, the cap 204 is provided with only one flexible pawl or with more than two flexible pawls, the reservoir 201 is provided with only one stop member or with more than two stop members, or any combination thereof.

In the embodiment of FIGS. 28A-31, the transfer guard 200 includes a window opening 232 for each extension arm 226 of the reservoir 201. Accordingly, in the embodiment of FIGS. 28A-31, the transfer guard 200 has two window openings 232. In addition, a slot 234 is provided at or near one side edge 236 of each window opening 232. Each slot 234 extends parallel to the direction of the axis AA, from one of its window openings 232 to the first end 205 of the transfer guard 200. The window openings 232 and the slots 234 open to the reservoir-receiving cavity in the first end 205 of the transfer guard 200, such that, when the port of the reservoir 201 is received within the cavity in the first end 205 of the transfer guard, each extension arm 226 on the port of the reservoir 201 extends through a respective one of the window openings 232.

Figure 28A:
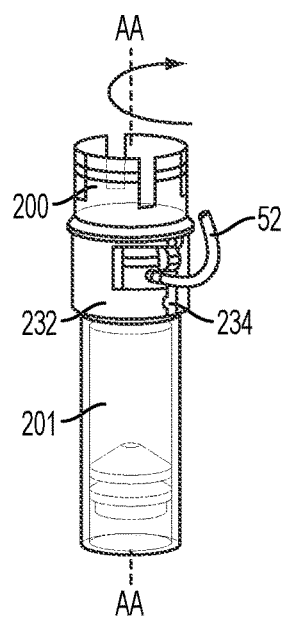
FIG. 28A is a perspective view of a cap and reservoir connected with a transfer guard and FIG. 28B is a perspective view of the same cap and reservoir with the transfer guard in the state of being removed, according to an embodiment of the present invention.

In the embodiment of FIGS. 28A-31, the reservoir 201, infusion set 250 and transfer guard 200 may be assembled together as a single unit, and packaged, stored, and provided to a user (or healthcare provider or other authorized person) as a pre-assembled unit (reservoir/infusion-set/transfer-guard unit). Initially, the cap 204 is in the first position (or fill position) as shown in FIGS. 29A and 29B, but with the port of the reservoir 201 received within the first end 205 of the transfer guard 200 as shown in FIGS. 28A and 28B. In that state, the extension arms 224 of the cap 204 and the extension arms 226 of the reservoir 201 extend through the openings 232 in the transfer guard 200, but with the extension arms 226 out of alignment with the slot 234.

With the port of the reservoir received within the first end 205 of the transfer guard 200 and the cap 204 in the first position (or fill position), a supply container that contains a supply of infusion media may be received in the cavity in the second end 206 of the transfer guard 200. In particular embodiments, the reservoir/infusion-set/transfer-guard unit is provided to a user (or healthcare provider or other authorized person) in a pre-assembled state, but without a supply container connected to the transfer guard 200. In such embodiments, the reservoir 201 may be filled (partially or fully) before installation in an infusion pump device, by installing a supply container in the second end 206 of the transfer guard 200 and withdrawing (partially or fully) the piston in the reservoir 201 to draw a desired volume of infusion media fluid from the supply container, through the transfer guard needle(s), and into the reservoir 201. Once the reservoir 201 has received the desired volume of infusion media fluid, the user (or healthcare provider or other authorized person) releases the reservoir 201 from the transfer guard 200 and installs the reservoir 201 into the reservoir receptacle 32 of the infusion pump device 30, for operation as described above.

Figure 28B:
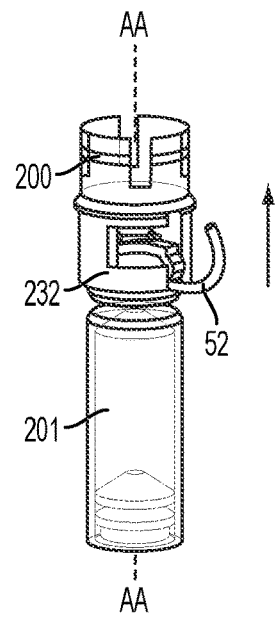

In particular embodiments, to release the reservoir 201 from the transfer guard, the user (or healthcare provider or other authorized person) rotates one of the transfer guard 200 and reservoir 201 relative to the other in a first direction (for example, the clockwise in the embodiment of FIG. 28A) about the axis AA, to a release position (shown in FIG. 28B). As the transfer guard 200 and reservoir 201 are rotated relative to each other, the side edge 236 of each window opening 232 engages one of the arms 224 of the cap 204 and applies a force on the arm 224. Further relative rotation of the transfer guard 200 and reservoir 201 in the first direction forces the arms 224 to rotate the cap 204 toward and to the second position (or deliver position) shown in FIGS. 30A and 30B.

When the cap 204 reaches the second position (or deliver position), the arms 224 are aligned with (adjacent and directly on top of) the extension arms 226 on the port of the reservoir 201. In addition, the aligned arms 224 and 226 are aligned with the slots 234 in the transfer guard. In that state, the reservoir 201 may be withdrawn from the transfer guard 200, by manually separating the reservoir 201 from the transfer guard 200 in the direction of the axis AA, as shown by the arrow in FIG. 28B. As the reservoir 201 is withdrawn from the transfer guard 200, the aligned extension arms 224 and 226 pass through the slots 234, to allow the port of the reservoir 201 to be removed from the cavity in the first end 205 of the transfer guard 200. Upon removal from the transfer guard 200, the cap 204 in the port of the reservoir 201 is in the second position (or deliver position) as shown in FIGS. 30A and 30B. Thus, rotation of the transfer guard 200 and reservoir 201 relative to each other to a release position (FIG. 28B) also causes the cap 204 to rotate to the second position (or deliver position).

Accordingly, in particular embodiments, the reservoir/infusion-set/transfer-guard unit is provided with the cap 204 in a first position (or fill position) in which the fluid pathway to the infusion set 250 is closed, to prevent introduction of air. In that state, a supply container may be connected to the transfer guard 200 to fill (partially or fully) the reservoir 201. Once the reservoir is filled to a desired level, the transfer guard is used to assist rotation of the cap 204 to the second position (or deliver position), in which the fluid pathway to the infusion set 250 is opened to the interior of the reservoir 201. In particular embodiments, the cap 204 is latched or locked into the second position (or deliver position), once it is rotated to that position. In that state, the reservoir 201 is removed from the transfer guard 200 and is installed in the reservoir receptacle 32 of the infusion pump 30 for operation as described above.

Embodiments described with reference to FIGS. 28A-31 may be employed with any one or more of the detection embodiments (magnetic detection, RF detection, mechanical detection and optical detection) described above. In such embodiments, the reservoir 201 or cap 204 (or both) is provided with one or more detectable elements 42 described above, as shown in FIG. 31.

In particular examples of such embodiments, one or more detectable elements is arranged on one or more extension arms 224 of the cap 204, and one or more corresponding sensors is arranged on the infusion pump device 30 at locations to detect whether or not the extension arm 224 has been sufficiently rotated to the second position (or deliver position). In such embodiments, electronics 60 in the infusion pump device may be configured to provide one or more predefined operations, upon the detection of an extension arm 224 that is not sufficiently rotated to the second position (or deliver position), where such predefined operations include, but are not limited to one or more of stopping or inhibiting pumping operation, allowing only a limited pumping operation, providing a warning message, or recording data indicating the detection. Alternatively or in addition, the electronics 60 may be configured to provide one or more predefined operations, at least partially based on (or in response to) a determination that the extension arm 224 is properly rotated to the second position, where such predefined operations include, but are not limited to one or more of allowing or providing pumping operation, allowing a predefined pumping operation, providing a predefined message, and recording data indicating the detection.

b. Spring-Loaded Plunger

Figure 32:
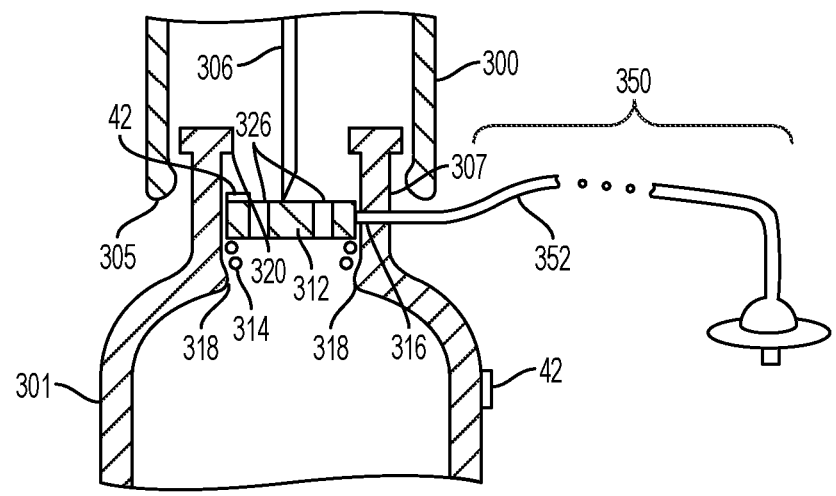
FIG. 32 is an enlarged, partial cross-section view of a portion of a transfer guard engaged with a reservoir having a cap according to a further embodiment of the present invention.
Figure 33:
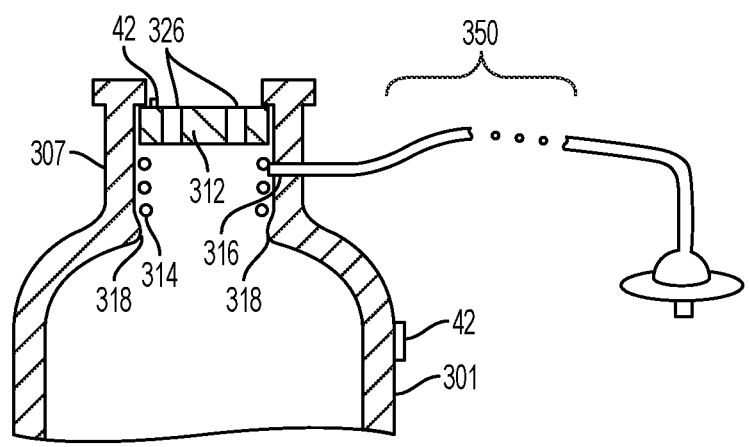
FIG. 33 is an enlarged, partial cross-section view of a portion of the reservoir and cap according to the embodiment of FIG. 32, but with the transfer guard removed.
Figure 34:
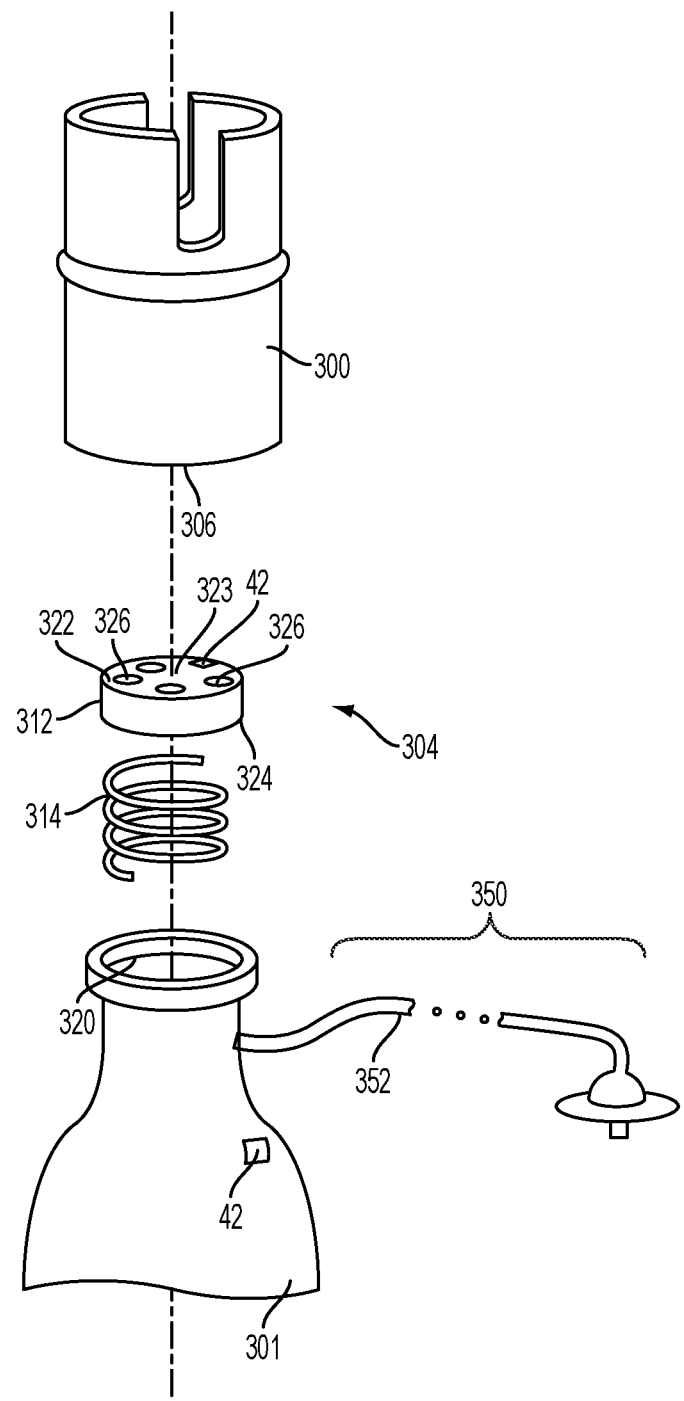
FIG. 34 is an enlarged, partial exploded view of the cap, reservoir and transfer guard of FIG. 32.

Embodiments described with reference to FIGS. 32-34 employ a transfer guard 300 for interfacing the reservoir 301 with a supply container (e.g., similar to supply container 203 discussed above). FIG. 32 show a partial cross-section view of a neck portion of the reservoir 301 received within (and interfacing with) a portion of the transfer guard 300. FIG. 33 shows a partial cross-section view of the neck portion of the reservoir 301, when the transfer guard 300 is detached and removed from the neck portion. FIG. 34 shows an exploded, perspective view of the reservoir, cap and transfer guard system. Only a portion of the transfer guard 300 (i.e., the first end 305 portion, including a portion of a hollow needle 306) is shown in FIG. 32.

In the embodiment of FIGS. 32-34, the reservoir 301 has an infusion media port arranged within a neck portion 307 of the reservoir 301. In addition, a cap structure 310 is arranged within the neck portion 307 of the reservoir 301. The cap structure 310 includes a moveable plunger 312 and a bias member 314, such as, but not limited to, a coil spring or other spring structure.

The neck portion 307 of the reservoir 301 includes a channel 316 that is open on one end to the interior volume of the neck portion 307 and is connected at its other end to tubing 352 of an infusion set 350. In particular embodiments, the tubing 352 is connected to the reservoir 301 (at the channel 316) permanently or other manner in which the connection is maintained. The infusion set 350 and tubing 352 may be similar to the infusion set 50 or 250 and tubing 52 or 252 described above.

The neck portion 307 of the reservoir 301 also includes one or more first projections or other stop surfaces 318 and one or more second stop surfaces 320 arranged to hold the moveable plunger 312 within the interior volume of the neck portion 307. In particular embodiments, the first projection or stop surface 318 includes a ring-shaped projection arranged at or adjacent the bottom of the neck portion 307 (where the interior volume of the neck portion 307 opens into the rest of the interior volume of the reservoir). In particular embodiments, the second projection or stop surface 320 includes a ring-shaped projection arranged at or adjacent the reservoir port or top of the neck portion 307 (where the interior volume of the neck portion 307 opens to the environment outside of the reservoir). In particular embodiments, the first and second projections or stop surfaces 318 and 320 are formed integral with the body of the reservoir 301, for example, as a unitary molded structure. In other embodiments, the one or both of the first and second projections or stop surfaces 318 and 320 is formed as a separate element that is fixed to the reservoir 301.

In the embodiment in FIGS. 32-34, the moveable plunger 312 includes a generally cylindrical shaped body having first and second opposed surfaces 322 and 324. The first surface 322 faces upward in FIGS. 32-34, toward the open end in the port of the reservoir 301. The second surface 324 faces downward in FIGS. 32-34, toward the interior volume of the reservoir 301. The plunger 312 includes one or more fluid flow passages that allow fluid to pass through the plunger 312. In the embodiment of FIGS. 32-34, four fluid flow passages 326 are provided in the form of channels extending through the plunger 312 (from the side of the first surface 322 to the side of the second surface 324). In other embodiments, any suitable number of channels or other fluid flow passages are provided through the moveable plunger 312. The moveable plunger 312 may be made of any suitable material having sufficient rigidity and strength to operate in the manner described herein, such as, but not limited to plastic, rubber, metal, ceramic, wood or composite material, or any combination thereof.

Similar to embodiments described above, the reservoir 301, infusion set 350 and transfer guard 300 in the embodiment of FIGS. 32-34 may be assembled together as a single unit, and packaged, stored, and provided to a user (or healthcare provider or other authorized person) as a pre-assembled unit (reservoir/infusion-set/transfer-guard unit).

In other embodiments, the reservoir 301 and transfer guard 300 are provided separately, and then assembled together, at or before use.

When the transfer guard 300 is assembled with the reservoir 301, the port portion of the reservoir 301 is received within a cavity at the first end 305 of the transfer guard 300, and the transfer guard needle 306 is received within the open end of the port of the reservoir 301, as shown in FIG. 32. In that state, the transfer guard needle 306 engages the first surface 322 of the plunger 312 and applies a force on the plunger that overcomes the bias force of the bias member 314, to push the plunger 312 into a first position (or a fill position), as shown in FIG. 32. In the embodiment of FIGS. 32-34, the surface 322 of the plunger 312 has a central region 323 that is spaced from the flow passages 326 and provides an engagement surface for engaging the transfer guard needle 306.

In the first position (or fill position), the cylindrical outer surface of the plunger 312 is aligned with the open end of the channel 316, to block fluid flow to or from the channel 316, to seal the channel 316. However, the flow passages 326 in the plunger 312 allow fluid to pass through the plunger 312, and into the interior volume of the reservoir 301. Accordingly, in the first position (or fill position) shown in FIG. 32, the plunger 312 blocks the channel 316 to inhibit fluid from passing into or out of the infusion set tubing 352, yet allows fluid to flow from the needle 306 of the transfer guard 300, through the flow passages 326 and into the interior of the reservoir, to fill (partially or fully) the reservoir.

In one example, the outer surface of the plunger 312 is configured to fit sufficiently closely with the inner surface of the neck of the reservoir 201 to seal the open end of the channel 316, when the plunger 312 is in the first position. In further examples, one or more seals or seal material is arranged on the outer cylindrical surface of the plunger 316, to seal the open end of the channel 316, when the plunger 316 is in the first position. In such embodiments, the one or more seals or seal material may include, for example, but not limited to, a silicone or soft plastic or rubber material affixed to the outer cylindrical surface of the plunger 316, at a location to align with and block or seal against the open end of the channel 316.

After filling of the reservoir 301, the port end of the reservoir 301 is removed from the transfer guard 300, so that the reservoir 301 may be installed within a reservoir receptacle 32 of an infusion pump device 30 as described above. Upon removal of the reservoir 301 from the transfer guard 300, the transfer guard needle 306 is withdrawn from the port of the reservoir 301. This allows the moveable plunger 312 to move, under the force of the bias member 314 toward its second position (or deliver position) shown in FIG. 33. In the second position (or deliver position), the plunger 312 abuts against the second stop surface 320.

In the second position (or deliver position), the plunger 312 is separated from the open end of the channel 316, to allow fluid flow communication between the channel 316 and the interior of the reservoir 301. As a result, the infusion set tubing 352 of the infusion set 350 is in flow communication with the interior of the reservoir, to allow fluid delivery. In this state, the reservoir 301 may be installed in the reservoir receptacle 32 of an infusion pump device 30 and operated as described above.

Accordingly, in the embodiment of FIGS. 32-34, the reservoir 301, infusion set 350 and transfer guard 300 may be provided as an assembled unit, where the needle of the transfer guard forces the plunger to a first position (or fill position) against the bias force of the bias member. In that first position (or fill position), the plunger seals the channel 316 and, thus, closes off the fluid flow path between the interior of the reservoir and the infusion set before and during a filling operation. The flow passages 326 in the plunger 312 allow fluid to flow from the transfer guard needle (from a supply container), into the interior of the reservoir 301, when the plunger 312 is in the first position (or fill position). Once filling is sufficiently complete, the reservoir 301 is removed from the transfer guard 300, causing the biased plunger 312 to move to the second position (or deliver position), where the plunger 312 no longer seals the channel 316. In that position, the channel 316 is in fluid flow communication with the interior of the reservoir 301, and the reservoir 301 is installed in an infusion pump device 30 for controlling delivery of infusion media to the infusion set tubing 352, through the channel 316.

In further examples of the embodiments of FIGS. 32-34, the reservoir 301 includes a septum (not shown) at or adjacent the open port end of the reservoir, for sealing the open port end of the reservoir. The septum (not shown) may be made of any suitable material, such as, but not limited to, a silicone, plastic or rubber material, that is compatible with infusion media contained within the reservoir 301 and that can be pierced by the needle 306 (and through which the needle 306 extends) when the transfer guard 300 is connected to the neck portion of the reservoir 301. In particular embodiments, the septum (not shown) has a disk or plug shape configured to fit within the neck portion of the reservoir 301, and is secured to the neck portion of the reservoir 301 (for example, secured to the second stop surface 320. In particular embodiments, the septum is made of a re-sealable material that seals itself after removal of the needle 306.

Embodiments described with reference to FIGS. 32-34 may be employed with any one or more of the detection embodiments (magnetic detection, RF detection, mechanical detection and optical detection) described above. In such embodiments, the reservoir 301 or plunger 312 (or both) is provided with one or more detectable elements 42 described above, as shown in FIG. 32.

In particular examples of such embodiments, one or more corresponding sensors is arranged on the infusion pump device 30 at locations to detect whether or not the plunger 312 has moved to the second position (or deliver position). In such embodiments, electronics 60 in the infusion pump device may be configured to provide one or more predefined operations, upon the detection that the plunger 312 has not sufficiently moved to the second position (or deliver position), where such predefined operations include, but are not limited to one or more of stopping or inhibiting pumping operation, allowing only a limited pumping operation, providing a warning message, or recording data indicating the detection. Alternatively or in addition, the electronics 60 may be configured to provide one or more predefined operations, at least partially based on (or in response to) a determination that the plunger 312 has sufficiently moved to the second position (or deliver position), where such predefined operations include, but are not limited to one or more of allowing or providing pumping operation, allowing a predefined pumping operation, providing a predefined message, and recording data indicating the detection.

4. Mechanical Interface of Cap or Reservoir with Pump

As described above, the second releasable coupler releasably secures the cap 4 (or base/reservoir/cap unit) to the housing of the infusion pump device 30, when the base/reservoir/cap unit is received in the reservoir receptacle 32 of the infusion pump device 30. In the embodiment of FIGS. 1 and 2, the second releasable coupler includes threads 19 on the housing 5 of the cap 4 that are arranged to engage corresponding threads (not shown) in a reservoir receptacle 32 of the infusion pump device 30 in order to releasably secure the base/reservoir/cap unit to the infusion pump device 30.

In other embodiments, the second releasable coupler includes other suitable coupling structures for coupling the cap 4 to the infusion pump device 30 in a selectively releasable manner, such as, but not limited to the coupling structures described with reference to FIGS. 35-75. The embodiments described with reference to FIGS. 35-75 and 78-81 include caps 404, 504, 704, 804, 904a-e, 964, 974, 984, 994, 1004 and 1014, that connect to reservoirs 1 (e.g., to form base/reservoir/cap units as described above) and that are received in reservoir receptacles 32 and operate with infusion pump devices 30 in a manner similar to that described above with respect to cap 4.

Embodiments described with reference to FIGS. 35-75 and 78-81 may be employed with any one or more of the detection embodiments (magnetic detection, RF detection, mechanical detection and optical detection) described above. Thus, in further embodiments of FIGS. 35-75, the reservoir or the cap 404, 504, 704, 804, 904a-e, 964, 974, 984, 994, 1004 and 1014 (or both) is provided with one or more detectable elements 42, as described above.

a. Push-Fit, Pinch Release On Cap

In particular embodiments, the second releasable coupler includes one or more resilient extensions that engage stop surfaces in the reservoir receptacle 32 to retain the cap (or base/reservoir/cap unit) within the reservoir receptacle. The one or more resilient extensions are flexible to selectively disengage the stop surfaces sufficiently to allow removal of the cap (or base/reservoir/cap unit) from the reservoir receptacle 32.

Figure 35:
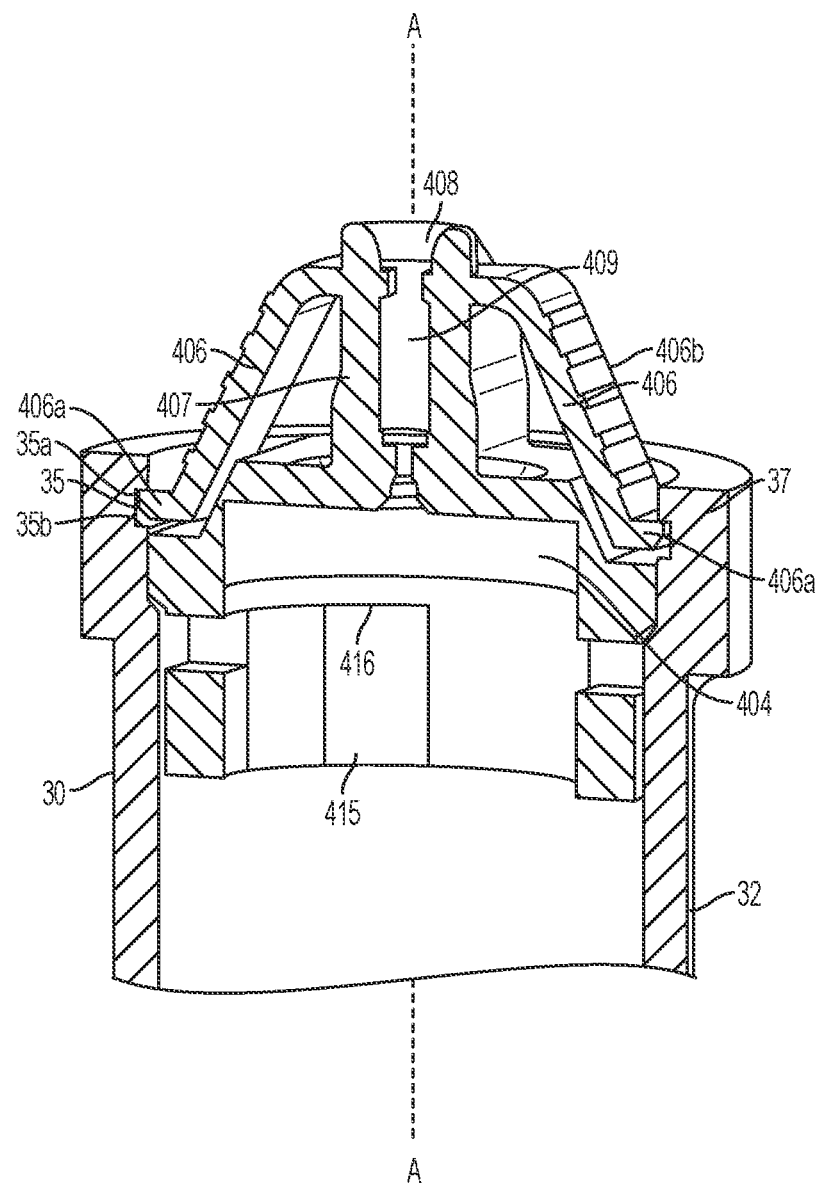
FIG. 35 is an enlarged, partial cut-away view of a cap and reservoir receptacle according to a further embodiment of the present invention.

For example, in the embodiment described with reference to FIG. 35, the second releasable coupler includes two flexible, resilient extensions (arms or wings) 406 on the cap 404. The extensions 406 are configured to be received with a channel 35 in the reservoir receptacle 32, as shown in FIG. 35. When engaged with the channel 35, the resilient extensions 406 inhibit removal of the cap 404 (or base/reservoir/cap unit) from the reservoir receptacle 32 of the infusion pump device 30. However, from the state shown in FIG. 35, the two extensions 406 may be manually squeezed toward each other (for example, by placing a thumb and first finger on different respective ones of the two extensions 406 and squeezing the extensions toward each other), to withdraw the extensions 406 from the channel 35 by a sufficient amount to allow the user to pull the cap 404 (or base/reservoir/cap unit) out of the reservoir receptacle 32.

In the embodiment of FIG. 35, the cap 404 is configured to be coupled to a reservoir (or base and reservoir) as described above with respect to cap 4, base 2 and reservoir 1. The drawing in FIG. 35 shows a cut-away view of the cap 404 and a portion of the reservoir receptacle 32 of the infusion pump device 30, without the base and reservoir, to better illustrate the manner in which the cap 404 engages the housing of the infusion pump device 30. However, in particular embodiments, the cap 404 is configured to be received within the reservoir receptacle 32, when the cap 404 is already assembled with the reservoir 1 (for example, as part of a base/reservoir/cap unit as described above).

The cap 404 includes a port 408 for connection with an infusion set tubing such as, but not limited to, an infusion set tubing 52 of an infusion set 50 as described above. The cap 404 also includes a body portion 407 through which a channel 409 extends. The channel 409 connects to a hollow needle (not shown) similar to needle 9 described above, and provides a fluid flow communication path from the hollow needle to the port 408 (and to an infusion set tubing, when connected to the port 408). The cap 404 also includes one or more connection features (of the first releasable coupler) for coupling the cap 404 to a reservoir (or to a base/reservoir unit). In the embodiment in FIG. 35, the connection features include detent openings 410 (similar to detent openings 10 described above), entry slots 415 (similar to entry slots 15 described above) and a stop shoulder 416 (similar to the stop shoulder 16 described above). Connection features 410, 415 and 416 may be configured and may operate to connect the cap 404 to a reservoir 1 (or base/reservoir unit) in a manner similar to openings 10, slots 15 and stop shoulder 16 described above.

The cap 404 may be made of any one or more suitable materials having sufficient rigidity and strength to operate as described herein, including, but not limited to plastic, metal, ceramic, composite or other suitable material. In one example, the cap 404 (including the resilient extensions 406, body 407 and port 408) is made of a molded plastic material, as a single, unitary, molded structure. In other embodiments, the cap 404 may be made by other processes or in multiple parts that are assembled together (or both).

In the embodiment shown in FIG. 35, each of the resilient extensions 406 has an engagement portion 406a. The engagement portion 406a of each extension 406 is shaped to be at least partially received within the channel 35 in the reservoir receptacle 32 of the infusion pump device 30, when the cap 404 (or base/reservoir/cap unit) is installed in the reservoir receptacle 32. When received within the channel 35, the engagement portions 406a of the resilient extensions 406 inhibit removal of the cap 404 (or base/reservoir/cap unit) from the reservoir receptacle 32 of the infusion pump device 30. However, when engaged with the channel 35, the two extensions 406 may be manually squeezed toward each other (for example, by placing a thumb and first finger on different respective ones of the two extensions 406 and squeezing the extensions toward each other), to withdraw the engagement portions 806a from the channel 35 by a sufficient amount to allow the user to pull the cap 404 (or base/reservoir/cap unit) out of the reservoir receptacle 32.

The channel 35 defines a lip portion 37 around the rim of the open end of the reservoir receptacle 32, where the channel 35 and the lip portion 37 have a first stop surface 35a (the downward-facing surface of the channel 35 in FIG. 35) against which a first surface of each engagement portion 406a (the upward-facing surfaces of the extensions 406 in FIG. 35) engages to inhibit removal of the cap 404 from the reservoir receptacle 32, when the engagement portions 406a of the extensions are received in the channel 35. A second stop surface 35b (the upward facing surface of the channel 35 in FIG. 35) against which a second surface of each engagement portion 406a engages to inhibit further insertion of the cap 404 (or base/reservoir/cap unit) further into the reservoir receptacle 32, once the engagement portions 406a of the extensions are received in the channel 35.

In particular embodiments, the cap 404 is provided to the user (or medical technician or other authorized person) either separate from or connected to a reservoir 1. If received separately, the user (or medical technician or other authorized person) assembles the cap 404 with the reservoir 1 (or with the base 2 and reservoir 1 to form a base/reservoir/cap unit) as described above.

Once assembled, the base/reservoir/cap unit is inserted into the reservoir receptacle 32, along the direction of the axis A. In particular embodiments, while inserting the base/reservoir/cap unit into the reservoir receptacle 32, the user (or medical technician or other authorized person) squeezes the extensions 406 inward in the radial direction, toward each other (or toward the axis A). With the extensions 406 squeezed inward sufficient to allow the engagement portions 406a to clear the lip 37 of the port of the reservoir receptacle 32, the user (or medical technician or other authorized person) inserts the base/reservoir/cap unit into the reservoir receptacle 32. Once the engagement portions 406a are inserted past the lip 37, the user (or medical technician or other authorized person) releases the squeezing force on the extensions 406, to allow the extensions 406 to move back outward in the radial direction toward their pre-squeezed state.

As the extensions 406 return toward their pre-squeezed state, the engagement portions 406a move outward in a radial direction relative to the axis A to engage the inner surface of the reservoir receptacle 32. Then, if needed, the user (or medical technician or other authorized person) can make adjustments to the position of the cap 404 in the direction of the axis A to align the engagement portions 406a with the channel 35, to allow the engagement portions to be received within the channel 35. As the engagement portions 406a align with the channel 35, the resilient return force of the extensions 406 causes the engagement portions 406a to move into the channel 35 and lock the cap 404 (and base/reservoir/cap unit) to the reservoir receptacle 32 of the infusion pump device 30.

Thus, in particular embodiments, the user (or medical technician or other authorized person) squeezes the extensions 406 toward each other when inserting the cap 404 (or base/reservoir/cap unit) into the reservoir receptacle 32. In other embodiments, the engagement portions 406a are shaped to allow the user (or medical technician or other authorized person) to insert the cap 404 (or base/reservoir/cap unit) into the reservoir receptacle 32 without the user also applying a separate squeezing force on the extensions 406. For example, in such embodiments, the engagement portions 406a may be rounded or angled at their tip, to allow the movement of the cap 404 (or base/reservoir/cap unit) along the axis A into the reservoir receptacle 32 to force the extensions toward each other.

In particular embodiments, the resilient return force of the extensions 406 and the shape of the engagement portions 406a are configured to provide a snap-fit action between the engagement portions 406a and the channel 35. In such embodiments, the extensions 406 and the shape of the engagement portions 406a are configured to provide an audible or tactile (or both) snap sound or feel (or both) that is perceptible to the user (or medical technician or other authorized person) as the user (or medical technician or other authorized person) inserts the cap 404 (or base/reservoir/cap unit) into the reservoir receptacle 32. The snap-fit action provides the user (or medical technician or other authorized person) with an audible or tactile (or both) indication that the cap 404 (or base/reservoir/cap unit) has been sufficiently or properly received within the reservoir receptacle 32.

The cap 404 (or base/reservoir/cap unit) may be removed from the reservoir receptacle 32 by squeezing the two extensions 406 toward each other to withdraw the engagement portions 806a from the channel 35 by a sufficient amount to allow the user to pull the cap 404 (or base/reservoir/cap unit) out of the reservoir receptacle 32. With the extensions 406 squeezed toward each other, the user (or medical technician or other authorized person) pulls the cap 404 (or base/reservoir/cap unit) in the direction of the axis A, out of the reservoir receptacle 32. In particular embodiments, no twisting or rotational motion on the cap 404 is needed to remove the cap 404 (or base/reservoir/cap unit) from the reservoir receptacle 32.

In the embodiment of FIG. 35, each extension 406 has a squeeze surface 406b that is exposed or otherwise accessible to the user (or medical technician or other authorized person) when the cap 404 (or base/reservoir/cap unit) is installed in the reservoir receptacle 32. In particular embodiments, the surfaces 608b are located outside of and above the port of the reservoir receptacle 32 when the cap 404 (or base/reservoir/cap unit) is installed in the reservoir receptacle 32. The surfaces 406b are provided for a user (or medical technician or other authorized person) to grip or otherwise operate the extensions 406 to selectively squeeze and release the extensions, and to pull the cap 404 (or base/reservoir/cap unit) in the direction of the axis A, out of the reservoir receptacle 32, as described above. In particular embodiments, the surfaces 406b have a friction enhancing feature, to improve the grip of the user (or medical technician or other authorized person) and to provide a tactile indication to the user (or medical technician or other authorized person) of the surface 406b. In the illustrated embodiment, the friction enhancing feature includes a plurality of ridges or grooves formed in the surfaces 406b. In other embodiments, other suitable friction enhancing features are provided on the surfaces 406b such as, but not limited to, other patterns of raised or recessed surface contours, a layer of rubber or other material of higher friction than the material of the extensions 406, or the like.

In particular embodiments, the reservoir receptacle 32 of the infusion pump device 30 includes a spring or other bias member that imparts a bias force on the cap 404 or the reservoir 1 in the direction of the axis A and outward from the reservoir receptacle 32, when the base/reservoir/cap unit is installed in the reservoir receptacle 32. In one example embodiment, the infusion pump device 30 includes a coil spring located at the bottom of the reservoir receptacle 32, to impart a bias force on the reservoir 1 and the cap 404 in the upward direction with respect to FIG. 35, when the base/reservoir/cap unit is installed in the reservoir receptacle 32. In other embodiments, the bias member includes a spring located to engage a predefined surface of the cap 404 when the base/reservoir/cap unit is installed in the reservoir receptacle 32. In yet further embodiments, the bias member is a spring or other bias device attached to the cap 404 or to the reservoir 1, to engage a predefined surface in the reservoir receptacle 32 of the infusion pump device when the base/reservoir/cap unit is installed in the reservoir receptacle 32. The bias force causes the first surface (upper surface in FIG. 35) of the engagement portion 406a to press against the first stop surface 35a of the channel 35. In such embodiments, the bias force helps to lock and maintain the cap 4 (and base/reservoir/cap unit) in a predefined position within the reservoir receptacle 32.

In the embodiment shown in FIG. 35, the cap 404 has two resilient extensions 406 arranged on opposite sides of the axis A relative to each other (e.g., about 180 degrees apart). In other embodiments, the two extensions 406 may be arranged at other suitable locations relative to the each other and the axis A. In yet other embodiments, the cap 404 includes only one resilient extension 406. In yet other embodiments, the cap 404 includes more than two resilient extensions 406. For example, in a further embodiment, the cap 404 includes four resilient extensions 406 arranged in two pairs, such that two hands are used to squeeze all four of the extensions (i.e., one hand for squeezing two of the four extensions, and the other hand for squeezing the other two extensions).

In various embodiments described above, the resilient extensions 406 are formed integral with the body 407 of the cap 404 and are made of a material having a natural flexibility and resilience. In other embodiments, the extensions 406 are separate members that are attached to the body 407 of the cap 404 with resilient connectors, such as, but not limited to springs or material having a natural spring force.

In the embodiment of FIG. 35, channel 35 is an annular channel in the housing of the infusion pump device 30 (or a housing portion 33, 33', 33" as described above). The channel 35 is located within the reservoir receptacle 32, a small distance from the open end of the reservoir receptacle 32 and extends around the axis A of the cap 404 (or base/reservoir/cap unit), when the cap 404 (or base/reservoir/cap unit) is located within the reservoir receptacle 32. The annular shape of the channel 35 allows the cap 404 to be inserted into the reservoir receptacle 32 in any rotational orientation (about the axis A) relative to the infusion pump device 30, and still allow the engagement portions 406*a* to align with and engage the first and second stop surfaces of the channel. However, other suitable configurations of one or more stop surfaces may be employed in other embodiments. For example, other embodiments may employ stop surfaces formed by surfaces of one or more indentations or recesses in the inner surface of the reservoir receptacle 32, at locations for receiving one or more engagement portions 406*a*, instead of surfaces of an annular channel. Yet other embodiments, one or more of the stop surfaces is provided by one or more raised features on the inner surface of the reservoir receptacle 32.

Embodiments described with reference to FIG. 35 may be employed with any one or more of the detection embodiments (magnetic detection, inductive detection, RF detection, mechanical detection, optical detection and electrical contact detection) described above. In such embodiments, the cap 404 or the reservoir 1 (or both) is provided with one or more detectable elements 42 described above.

In particular examples of such embodiments, one or more detectable elements 42 is provided on one or each extension 406. For example, one or more detectable elements 42 may be provided on the engagement portion 406*a* of one or more of the extensions 406. In such embodiments, one or more corresponding sensors is arranged on the infusion pump device 30 at locations to detect whether or not the extensions 406 (or engagement portions 406*a*) is located in a proper position, for example, within the channel 35. In other embodiments, the sensor(s) are arranged to detect other possible positions of the extension 406 (or engagement portion 406*a*) within the reservoir receptacle 32.

In such embodiments, electronics 60 in the infusion pump device may be configured to provide one or more predefined operations, upon the detection of an extensions 406 (or engagement portions 406*a*) that is not in a proper location (for example, upon detection of an engagement portion 406*a* that is outside of or not sufficiently located within the channel 35. Such predefined operations include, but are not limited to one or more of stopping or inhibiting pumping operation, allowing only a limited pumping operation, providing a warning message, or recording data indicating the detection.

Alternatively or in addition, the electronics 60 may be configured to provide one or more predefined operations, at least partially based on (or in response to) a determination that an extensions 406 (or engagement portions 406*a*) is in a proper location (for example, upon detection of an engagement portion 406*a* that is sufficiently located within the channel 35). Such predefined operations include, but are not limited to one or more of allowing or continuing pumping operation, allowing a limited pumping operation, providing a predefined message, or recording data indicating the detection.

b. Push-Fit with Oblong Ring Release

In other embodiments, the second releasable coupler includes one or more moveable or resilient (or both) ring-shaped members on or in the housing of the infusion pump device 30 that engage one or more corresponding grooves or stop surfaces in or on the cap (or other portion of the base/reservoir/cap unit), when the cap (or base/reservoir/cap unit) is installed within the reservoir receptacle 32 of the infusion pump device 30. When engaged with the groove(s) or stop surface(s), the ring-shaped member(s) lock the cap (or other portion of the base/reservoir/cap unit) in a predefined position within the reservoir receptacle 32, and inhibit removal of the cap (or other portion of the base/reservoir/cap unit) from the predefined position within the reservoir receptacle 32.

The ring shaped member(s) include or are connected with one or more buttons or other interface on the outside of the housing of the infusion pump device 30. The button(s) or other interface(s) are configured to be selectively operated by a user (or medical technician or other authorized person) to selectively expand the ring-shaped member in at least one dimension. The expansion of the ring-shaped member releases the cap (or other portion of the base/reservoir/cap unit) from the locked state and allows the user (or medical technician or other authorized person) to remove the cap (or other portion of the base/reservoir/cap unit) from the reservoir receptacle. In particular embodiments, the ring-shaped member is also expanded to install a cap (or other portion of the base/reservoir/cap unit) in the reservoir receptacle 32 of the infusion pump device 30.

For example, in the embodiment described with reference to FIGS. 36-38, the second releasable coupler includes a ring member 502 that is made of a material that is sufficiently rigid and strong, yet also flexible and resilient to operate as described herein. In particular embodiments, the ring member 502 is made of a compliant plastic material or a silicone rubber material. The ring member 502 is configured to engage a groove in a cap 504 (or other portion of the base/reservoir/cap unit), when the cap 504 (or base/reservoir/cap unit) is installed within the reservoir receptacle 32 of the infusion pump device 30.

Figure 38:
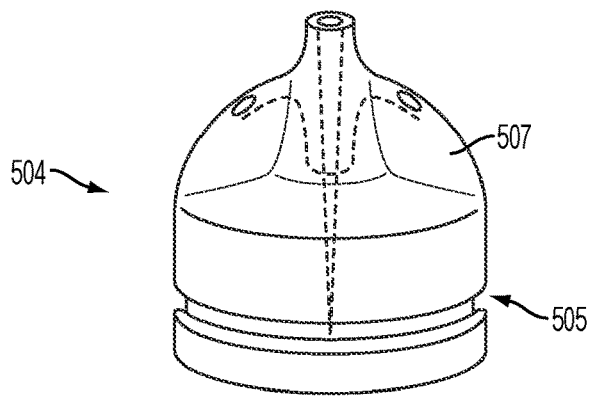
FIG. 38 is an enlarged, perspective view of a cap that may be employed with the embodiment of FIGS. 36 and 37.

An example of a cap 504 is shown in FIG. 38. As shown in FIG. 38, the cap 503 includes a groove 505 on an outer surface of the body 507 of the cap 504. In various other respects, the cap 504 may be similar to the cap 4 or other caps 404, 704 or 804 described herein.

The ring member 502 includes an annular, ring portion 503, an anchor portion 506, and a button portion 508. The ring portion 503 has an inner opening 510, and is arranged within or over the reservoir receptacle 32 with axis A of the reservoir receptacle 32 extending through the inner opening 510. In particular embodiments, the ring member 502 is held by a portion of the housing of the infusion pump device 30, in the region of the reservoir receptacle 32, with a central point or axis of the ring portion 503 arranged at or near (or coaxial with) the axis A of the reservoir receptacle 32. The button portion 508 of the ring member 502 extends through an opening or slot in housing of the infusion pump device 30, at the reservoir receptacle 32. The anchor portion 506 of the ring member 502 is received within a receptacle opening, slot, or indentation within the housing of the infusion pump device 30, at the reservoir receptacle 32. In the embodiment in FIGS. 36-38 the anchor portion 506 and button portion 508 are provided on mutually opposite sides of the ring portion 503 and the axis A.

When the button portion 508 of the ring member 502 is not operated, the ring member 502 is in a first state (released state). In the first state (released state), the opening 510 in the ring portion 503 has a first width (or diameter) D1 in a first direction, where the first direction extends along the anchor portion 506 and the button portion 508. Also in the first state (released state), the opening 510 has a second width (or diameter) D2 in a second direction, where the second direction extends transverse to the first direction. In the embodiment in FIGS. 36-38, the second direction (of the second width D2) is approximately perpendicular to the first direction (of the first width D1). In other embodiments, the first direction is transverse, but not perpendicular, to the second direction.

When the button portion 508 of the ring member 502 is operated (for example, is pushed by a finger 511 of a user, healthcare provider or other authorized person), the ring member 502 is in a second state (expanded state). In the second state (expanded state), the second width (or diameter) D2' of the opening 510 is expanded in a second direction relative to the second width (or diameter) D2 in the first state (released state). Also in the second state (expanded state), the first width (or diameter) D1' of the opening 510 in the ring member 502 is reduced in a first direction relative to the first width (or diameter) D1 in the first state (released state).

The ring portion 503 is configured to be at least partially received within the groove 505 in the cap 504, when the cap 504 (or base/reservoir/cap unit) is installed in the reservoir receptacle 32 of the infusion pump device 30 and the ring member 502 is in the first state (released state). When received within the groove 505, the ring portion 503 inhibits removal of the cap 504 (or base/reservoir/cap unit) from the reservoir receptacle 32 of the infusion pump device 30. However, from the state shown in FIG. 36, the button portion 508 of the ring member 502 may be manually pushed to expand the second width of the ring portion 503 from D2 to D2' (the second or expanded state). By expanding the second width of the ring portion 503 from D2 to D2', the ring portion 503 is withdrawn from the groove 505 by a sufficient amount to allow the user to pull the cap 504 (or base/reservoir/cap unit) out of the reservoir receptacle 32.

In particular embodiments, the cap 504 includes a port for connection with an infusion set tubing such as, but not limited to, an infusion set tubing 52 of an infusion set 50 as described above. The cap 504 also includes a channel through the body portion 507 that connects to a hollow needle (not shown) similar to needle 9 described above, and provides a fluid flow communication path from the hollow needle to the port (and to an infusion set tubing, when connected to the port). The cap 504 also includes one or more connection features as described above for coupling the cap 504 to a reservoir (or to a base/reservoir unit). The cap 504 may be made of any one or more suitable materials having sufficient rigidity and strength to operate as described herein, including, but not limited to plastic, metal, ceramic, composite or other suitable material. In one example, the cap 504 is made of a molded plastic material, as a single, unitary, molded structure. In other embodiments, the cap 504 may be made by other processes or in multiple parts that are assembled together (or both).

In particular embodiments, the cap 504 is provided to the user (or medical technician or other authorized person) either separate from or connected to a reservoir 1. If received separately, the user (or medical technician or other authorized person) assembles the cap 504 with the reservoir 1 (or with the base 2 and reservoir 1 to form a base/reservoir/cap unit) as described above.

Once assembled, the base/reservoir/cap unit is inserted into the reservoir receptacle 32, along the direction of the axis AA. In particular embodiments, while inserting the base/reservoir/cap unit into the reservoir receptacle 32, the user (or medical technician or other authorized person) pushes the button portion 508 of the ring member 502 to expand the second diameter of the opening 510 from D2 to D2'. With the second diameter of the opening 510 expanded from D2 to D2', the cap 504 (or base/reservoir/cap unit) can be inserted into the reservoir receptacle 32 and through the opening 510 in the ring member 502.

Once the cap 504 (or base/reservoir/cap unit) is inserted into the reservoir receptacle 32 a sufficient distance, the button portion 508 may be released to allow the ring member 502 to return toward the first state (released state), but with a portion of the body 507 of the cap 504 extending through the opening 510 of the ring member 502. In that position, a portion of the inner surface of the opening 510 of the ring member 502 abuts a portion of the outer surface of the body 507 of the cap 504. Then, if needed, the user (or medical technician or other authorized person) can make adjustments to the position of the cap 504 in the direction of the axis A to align the groove 505 with the ring member 502, to allow the ring portion 503 to be received within the groove 505. As the groove 505 aligns with the ring portion 503 of the ring member 502, the resilient return force of the ring member 502 causes the ring portion 503 to move into the groove 505 and lock the cap 504 (and base/reservoir/cap unit) to the reservoir receptacle 32 of the infusion pump device 30.

Thus, in particular embodiments, the user (or medical technician or other authorized person) pushes the button portion 508 when inserting the cap 504 (or base/reservoir/cap unit) into the reservoir receptacle 32. In other embodiments, the cap 504 (or base/reservoir/cap unit) is shaped to allow the user (or medical technician or other authorized person) to insert the cap 504 (or base/reservoir/cap unit) into the reservoir receptacle 32 without the user also pushing the button portion 508. For example, in such embodiments, the cap 504 (or base/reservoir/cap unit) may have an outer surface that is tapered to a smaller diameter toward the bottom end of the cap 504 (or base/reservoir/cap unit) relative to the upper end, such that the tapered outer surface engages the inner surface of the ring portion 503 and expands the ring portion 503 in the second direction as the cap 504 (or base/reservoir/cap unit) is moved further into the reservoir receptacle 32 in the direction of axis A.

In particular embodiments, the resilient return force of the ring member 502 and the shape of the groove 505 are configured to provide a snap-fit action between the ring member 502 and the groove 505. In such embodiments, the ring portion 503 and the groove 505 are configured to provide an audible or tactile (or both) snap sound or feel (or both) that is perceptible to the user (or medical technician or other authorized person) as the user (or medical technician or other authorized person) inserts the cap 504 (or base/reservoir/cap unit) into the reservoir receptacle 32. The snap-fit action provides the user (or medical technician or other authorized person) with an audible or tactile (or both) indication that the cap 504 (or base/reservoir/cap unit) has been sufficiently or properly received within the reservoir receptacle 32.

The cap 504 (or base/reservoir/cap unit) may be removed from the reservoir receptacle 32 by pushing the button 508 to expand the second width of the opening 510 from D2 to D2', to withdraw the ring portion 503 from the groove 505 by a sufficient amount to allow the user to pull the cap 504 (or base/reservoir/cap unit) out of the reservoir receptacle 32. With the button portion 508 pushed, the user (or medical technician or other authorized person) pulls the cap 504 (or base/reservoir/cap unit) in the direction of the axis A, out of the reservoir receptacle 32. In particular embodiments, no twisting or rotational motion on the cap 504 is needed to remove the cap 504 (or base/reservoir/cap unit) from the reservoir receptacle 32.

In particular embodiments, the reservoir receptacle 32 of the infusion pump device 30 includes a spring or other bias member that imparts a bias force on the cap 504 or the reservoir 1 in the direction of the axis AA and outward from the reservoir receptacle 32, when the base/reservoir/cap unit is installed in the reservoir receptacle 32. In such embodiments, the spring or bias member may be similar to the spring or bias member described above with respect to the cap 404. The bias force causes a surface (lower surface in FIG. 38) of the groove 505 to press against the a surface of the ring portion 503. In such embodiments, the bias force helps to lock and maintain the cap 504 (and base/reservoir/cap unit) in a predefined position within the reservoir receptacle 32.

Figure 36:
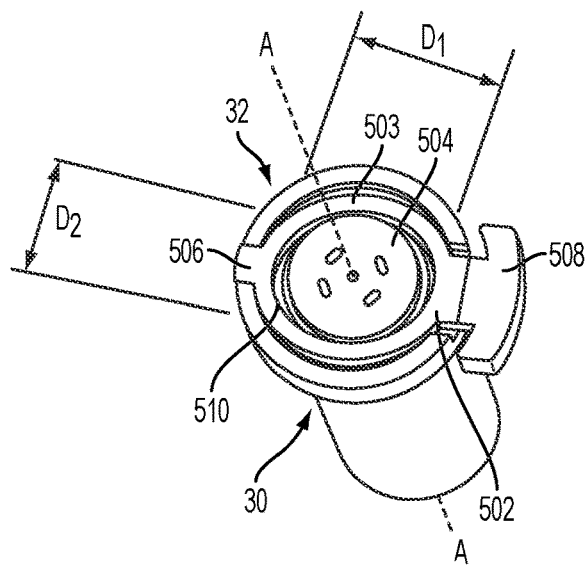
FIG. 36 is a partial perspective view of a cap and reservoir receptacle according to a further embodiment of the present invention.
Figure 37:
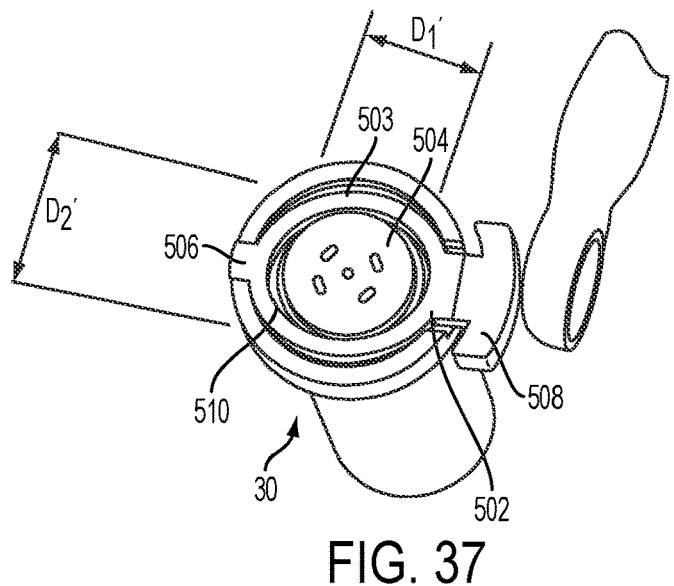
FIG. 37 is a partial perspective view of the cap and reservoir receptacle of the embodiment of FIG. 18, but with a user's finger pressing a button portion.

In the embodiment shown in FIGS. 36-38, the ring member 502 has one button portion 508. In other embodiments, the ring member 502 includes a second button portion (not shown) in place of the anchor portion 506, where the second button portion extends out from the housing of the infusion pump device in a manner similar to the button portion 508. In particular embodiments, the second button portion is arranged on the opposite side of the ring member 502 (and the axis A) relative to the first button portion 508. In such embodiments, a user (or medical technician or other authorized person) may grip and squeeze the two button portions 508 with one hand (for example, by placing a thumb on one button portion and a first finger on the other button portion and squeezing the button portions toward each other) to expand the ring member to the second state (expanded state).

In the embodiment of FIGS. 36-38, the groove 505 in the cap 504 is an annular groove that extends around the entire body 507 of the cap 504. The annular shape of the groove 505 allows the cap 504 to be inserted into the reservoir receptacle 32 in any rotational orientation (about the axis A) relative to the infusion pump device 30, and still allow the ring member to align with and engage the groove 505. However, other suitable configurations of one or more stop surfaces may be employed in other embodiments. For example, other embodiments may employ one or more indentations or recesses on the outer surface of the cap 504 body 507 that form stop surfaces for engaging the ring portion 503, when the ring member 502 is in the first state (released state) and the cap 504 (or base/reservoir/cap unit) is received in the reservoir receptacle 32.

The embodiment shown in FIGS. 36-38 includes one ring-shaped member 502 with one button portion 508. In other embodiments, two (or more) ring-shaped members are supported on or in the housing of the infusion pump device 30, in the region of the reservoir receptacle, similar to the ring-shaped member 502 in FIGS. 36-38. In such embodiments, the multiple ring-shaped members may be arranged generally coaxially with the reservoir receptacle 32 (with the axis A extending through the inner opening of each ring-shaped member), but arranged with their respective button portions 508 at different respective locations around the circumference of the reservoir receptacle 32. In embodiments that employ multiple ring-shaped members, the cap 504 includes a corresponding number (multiple) grooves 505, one for each ring-shaped member.

Figure 39:
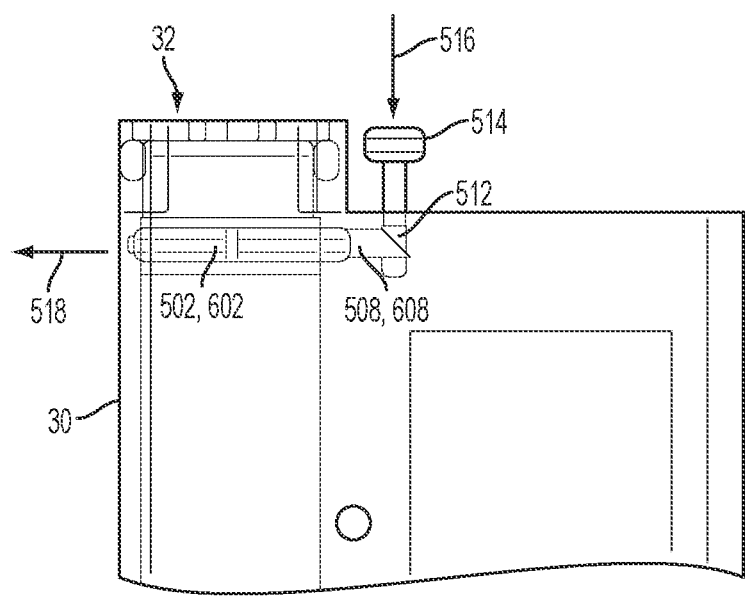
FIG. 39 is a schematic diagram of a button configuration according to embodiments of the present invention.

In the embodiment of FIGS. 36-38, the one or more ring-shaped members 502 are arranged with the button portion(s) 508 positioned adjacent the reservoir receptacle 32 portion of the infusion pump device 30, and moveable in a lateral direction (perpendicular or otherwise transverse to the axis A). In other embodiments, as represented by FIG. 39, the button portion 508 of each ring-shaped member 502 is engaged with a linkage structure 512. The linkage structure 512 connects to a further button portion 514 that is either located at a different (remote) location relative to the button portion 508 or is oriented in a different direction relative to the button portion 508, or both. In the embodiment of FIG. 39, the further button portion 514 is located adjacent the reservoir receptacle 32, but is oriented to move in the direction of the axis A (upon receiving a manual pushing force in the downward direction relative to FIG. 39). In particular embodiments, the further button portion 514 is also configured to be returned to an extended (un-pushed) state, when a manual pushing force is not received or is released, for example, by the return of the ring-shaped member 502 to its first state (released state) under the natural return (resilient) force of the ring-shaped member 502.

In the embodiment of FIG. 39, the linkage structure 512 includes a ramped or wedge-shaped surface on the button portion 508 that slidingly engages a surface of the further button portion 514, when the further button portion 514 is pressed. As the further button portion 514 depresses, the sliding engagement with the ramped or wedge-shaped surface causes the button portion 508 to move toward its pressed state (and ring-shaped member 502 to expand to its second or expanded state). Accordingly, when the button portion 514 is pushed in the direction of arrow 516, the linkage structure 512 transfers the axially directed motion of the button portion 514 to a radially directed motion of the button portion 508 in the direction of arrow 518.

By releasing the button portion 514, the ring-shaped member 502 returns to its first state (released state), which causes the further button to be moved back to its initial (un-depressed) state. In other embodiments, the ramped or wedge-shaped surface is provided on the further button portion 514 at the interface of the further button portion 504 and the linkage structure 512. In yet further embodiments, both the linkage structure 512 and the further button portion 514 have ramped or wedge-shaped surfaces at their interface. In yet further embodiments, other suitable linkage structure for operatively connecting the further button portion 514 to the button portion 508 is employed.

Embodiments described with reference to FIGS. 36-38 may be employed with any one or more of the detection embodiments (magnetic detection, inductive detection, RF detection, mechanical detection, optical detection and electrical contact detection) described above. In such embodiments, the cap 504 or the reservoir 1 (or both) is provided with one or more detectable elements 42 described above.

Alternatively or in addition, the ring shaped member 502 is provided with one or more detectable elements 42 described above. In embodiments that employ multiple ring-shaped members, a plurality of those ring-shaped members (or each of the multiple ring-shaped members) may be provided with one or more detectable elements described above. For example, one or more detectable elements 42 may be provided on the ring portion 503 or the button portion 508.

In such embodiments, the infusion pump device 30 may include one or more corresponding sensor elements 32 described above, arranged to detect the detectable elements 42, for example, when the ring-shaped member 502 is in one or more of the first state (released state) or second state (expanded state), to detect the position of the ring-shaped member relative to the housing of the infusion pump device 30. In further embodiments, the detectable element(s) 42 and sensor element(s) are arranged such that one or more sensor elements detect one or more detectable elements, if the ring portion 503 of the ring-shaped member is received within the groove 505 of the cap 504.

In further examples of such embodiments, one or more additional detectable elements 42 are provided on the cap 504 (or other portion of the base/reservoir/cap unit), and one or more further sensor elements 32 are arranged on the infusion pump device 30 to detect those detectable elements 42 if the cap 504 (or base/reservoir/cap unit) is properly received within the reservoir receptacle 32 of the infusion pump device 30 (or not properly received within the reservoir receptacle 32). Accordingly, the electronics 60 in those embodiments may be configured to determine whether or not the cap 504 (or base/reservoir/cap unit) is properly received within the reservoir receptacle 32 and properly engaged with the ring-shaped member 502, based at least in part on signals provided by sensor elements 32.

In such embodiments, electronics 60 in the infusion pump device may be configured to provide one or more predefined operations, at least partially based on (or in response to) one or more of: (1) a determination that the cap 504 (or base/reservoir/cap unit) is not properly received within the reservoir receptacle 32, and (2) a determination that the ring portion 503 of the ring-shaped member is not properly received within the groove 505 of the cap 504. Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap 504 (or base/reservoir/cap unit) is properly received within the reservoir receptacle 32, and (2) a determination that the ring portion 503 of the ring-shaped member is received within the groove 505 of the cap 504. Such predefined operations include, but are not limited to one or more of allowing or providing pumping operation, allowing a predefined pumping operation, providing a predefined message, and recording data indicating the detection.

c. Push-Fit with U-Shaped Release

In other embodiments, the second releasable coupler includes one or more moveable U-shaped members on or in the housing of the infusion pump device 30 that engage one or more corresponding grooves or stop surfaces in or on the cap (or other portion of the base/reservoir/cap unit), when the cap (or base/reservoir/cap unit) is installed within the reservoir receptacle 32 of the infusion pump device 30. When engaged with the groove(s) or stop surface(s), the U-shaped member(s) lock the cap (or other portion of the base/reservoir/cap unit) in a predefined position within the reservoir receptacle 32, and inhibit removal of the cap (or other portion of the base/reservoir/cap unit) from the predefined position within the reservoir receptacle 32.

The U-shaped member(s) include or are connected with one or more buttons or other interface on the outside of the housing of the infusion pump device 30. The button(s) or other interface(s) are configured to be selectively operated by a user (or medical technician or other authorized person) to selectively move (slide, shift or otherwise move) the U-shaped member in at least one predefined direction. The movement of the U-shaped member in the predefined direction releases the cap (or other portion of the base/reservoir/cap unit) from the locked state and allows the user (or medical technician or other authorized person) to remove the cap (or other portion of the base/reservoir/cap unit) from the reservoir receptacle. In particular embodiments, the U-shaped member is also selectively moved (slid, shifted or otherwise moved) in the predefined direction to install a cap (or other portion of the base/reservoir/cap unit) in the reservoir receptacle 32 of the infusion pump device 30.

For example, an embodiment of a second releasable coupler that includes a U-shaped member 602 is described with reference to FIGS. 40-42. The embodiment in FIGS. 40-42 is configured to operate with a cap having a groove, such as, but not limited to the cap 504 with the groove 515 described herein with reference to FIG. 38.

Figure 40:
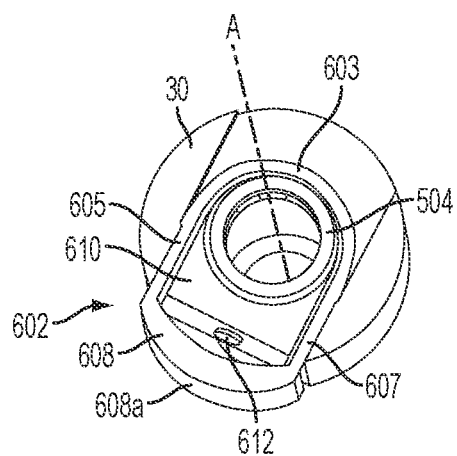
FIG. 40 is a partial perspective view of a portion of a cap and a portion of a reservoir receptacle according to a further embodiment of the present invention.
Figure 41:
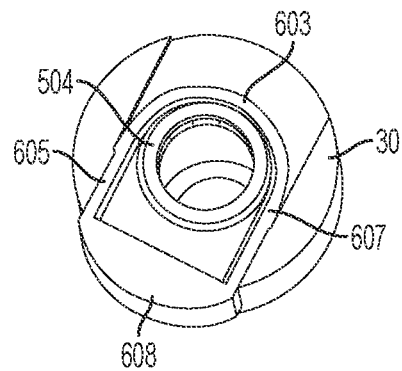
FIG. 41 is a partial perspective view of the portion of the cap and the portion of the reservoir receptacle of the embodiment of FIG. 40, but with a button portion in the pressed state.
Figure 42:
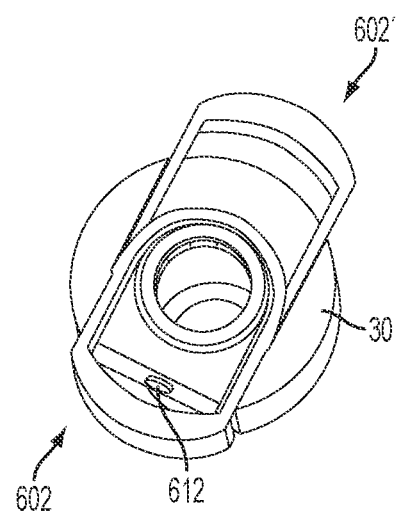
FIG. 42 is a partial perspective view of a portion of a cap and a portion of a reservoir receptacle according to a further embodiment of the present invention.

In the embodiment of FIGS. 40-42, the U-shaped member 602 that is made of a material that is sufficiently rigid and strong to operate as described herein. In particular embodiments, the U-shaped member 602 is made of a plastic, metal, ceramic, composite material or other suitable material. The U-shaped member 602 is configured to engage the groove 515 in the cap 504 (FIG. 38), or in another portion of the base/reservoir/cap unit, when the cap 504 (or base/reservoir/cap unit) is installed within the reservoir receptacle 32 of the infusion pump device 30.

The U-shaped member 602 includes a curved portion 603, a first generally linear portion 605 extending from one end of the curved portion 603, and a second generally linear portion 607 extending from a second end of the curved portion 603, where the combination of the curved portion 603 and first and second generally linear portions 605 and 607 form a U-shape. In other embodiments, the portions 605 and 607 are not linear and, instead, have a curvature along their respective length dimensions. The U-shaped member 602 also includes a button portion 608, connecting ends of the generally linear portions 605 and 607.

The U-shaped member 602 has an inner opening 610 located between the two generally linear portions 605 and 607 and between the curved portion 603 and the button portion 608. The U-shaped member is arranged on or in the reservoir receptacle 32 of the infusion pump device 30 (in a manner similar to the manner in which the ring-shaped member 502 is supported on or in the reservoir receptacle 32, as described above with respect to FIGS. 36-37). In particular, the U-shaped member is supported in a position within or over the reservoir receptacle 32, with axis AA of the reservoir receptacle 32 extending through the inner opening 610.

In particular embodiments, the U-shaped member 602 is held by a portion of the housing of the infusion pump device 30, in the region of the reservoir receptacle 32, with a central point of the inner opening 610 arranged at or near (or coaxial with) the axis AA of the reservoir receptacle 32. The button portion 608 of the U-shaped member 602 extends through an opening or slot in housing of the infusion pump device 30, at the reservoir receptacle 32.

The U-shaped member 602 (including the button portion 608) is moveable between a first position (as shown in FIG. 40) and a second position (as shown in FIG. 41). In particular embodiments, the U-shaped member 602 is biased toward the first position (shown in FIG. 40), for example, by a separate spring or other bias member, or by the shape and natural spring force of the material from which the U-shaped member 602 is made. In the embodiment in FIGS. 40-42, a bias member such as, but not limited to, a coil spring 612 is interposed between the button portion 608 and the housing of the infusion pump device 30. In other embodiments, a bias member may be interposed between the curved portion 603 of the U-shaped member and a portion of the housing of the infusion pump device 30 (or between the infusion pump device 30 and one or both of the linear portions 608 of the U-shaped member 602).

The button portion 608 has a surface 608a located external to the housing of the infusion pump device, in the region of the reservoir receptacle. The surface 608a of the button portion 608 is arranged for receiving a manual force to overcome the force of the bias member 612 and selectively move the U-shaped member 602. Thus, for example, a user (or medical technician or other authorized person) may apply a manual force on the surface 608a of the button portion 608, to move the U-shaped member 602 from the first position (FIG. 40) to the second position (FIG. 41), by pressing the surface 608a with a finger or thumb.

When the button portion 608 is not operated, the U-shaped member 602 is in the first position. When the U-shaped member 602 is in the first position while a cap 504 (or base/reservoir/cap unit) is properly received in the reservoir receptacle 32, the curved portion 603 of the U-shaped member 602 engages the groove 505 of the cap 504 to inhibit movement of the cap 504 (and base/reservoir/cap unit) relative to the reservoir receptacle 32, in the direction of the axis AA. In particular embodiments, the curved portion 603 is configured to be at least partially received within the groove 505 in the cap 504, when the cap 504 (or base/reservoir/cap unit) is installed in the reservoir receptacle 32 of the infusion pump device 30 and the U-shaped member 602 is in the first position (FIG. 40). When received within the groove 505, the curved portion 603 inhibits removal of the cap 504 (or base/reservoir/cap unit) from the reservoir receptacle 32 of the infusion pump device 30.

However, from the state shown in FIG. 39, the button portion 608 of the U-shaped member 602 may be manually pushed to move the U-shaped member 602 from the first position toward the second position. As the U-shaped member 602 moves toward the second position, the curved portion 603 is withdrawn from the groove 505 by a sufficient amount to allow the user to pull the cap 504 (or base/reservoir/cap unit) out of the reservoir receptacle 32.

As described above, the base/reservoir/cap unit is inserted into the reservoir receptacle 32, along the direction of the axis AA. In particular embodiments, while inserting the base/reservoir/cap unit into the reservoir receptacle 32, the user (or medical technician or other authorized person) pushes the button portion 608 of the U-shaped member 602 to move the U-shaped member 602 toward the second position (FIG. 41). When the U-shaped member 602 is moved sufficiently toward the second position, the cap 504 (or base/reservoir/cap unit) can be inserted into the reservoir receptacle 32 and through the opening 610 in the U-shaped member 602.

Once the cap 504 (or base/reservoir/cap unit) is inserted into the reservoir receptacle 32 a sufficient distance, the button portion 608 may be released to allow the U-shaped member 602 to return toward the first state (released state), for example, via a return force from the bias member 612, but with a portion of the body 507 of the cap 504 extending through the opening 610 of the U-shaped member 602. In that position, a portion of the inner surface of the curved portion 603 in the opening 610 of the U-shaped member 602 abuts and presses against a portion of the outer surface of the body 507 of the cap 504. Then, if needed, the user (or medical technician or other authorized person) can make adjustments to the position of the cap 504 in the direction of the axis A to align the groove 505 with the curved portion 603 of the U-shaped member 602, to allow the curved portion 603 to be received within the groove 505. As the groove 505 aligns with the curved portion 603 of the U-shaped member 602, the resilient return force of the curved portion 603 causes the curved portion 603 to move into the groove 505 and lock the cap 504 (and base/reservoir/cap unit) to the reservoir receptacle 32 of the infusion pump device 30.

Thus, in particular embodiments, the user (or medical technician or other authorized person) pushes the button portion 608 when inserting the cap 504 (or base/reservoir/cap unit) into the reservoir receptacle 32. In other embodiments, the cap 604 (or base/reservoir/cap unit) is shaped to allow the user (or medical technician or other authorized person) to insert the cap 504 (or base/reservoir/cap unit) into the reservoir receptacle 32 without the user also pushing the button portion 608. For example, in such embodiments, the cap 504 (or base/reservoir/cap unit) may have an outer surface that is tapered to a smaller diameter toward the bottom end of the cap 504 (or base/reservoir/cap unit) relative to the upper end, such that the tapered outer surface engages the inner surface of the curved portion 503 and pushes the U-shaped member 602 toward the second position as the cap 504 (or base/reservoir/cap unit) is moved further into the reservoir receptacle 32 in the direction of axis A.

In particular embodiments, the return force of the bias member 612 and the shapes of the curved portion 603 and the groove 505 are configured to provide a snap-fit action between the U-shaped member 602 and the groove 505. In such embodiments, the curved portion 603 and the groove 505 are configured to provide an audible or tactile (or both) snap sound or feel (or both) that is perceptible to the user (or medical technician or other authorized person) as the user (or medical technician or other authorized person) inserts the cap 504 (or base/reservoir/cap unit) into the reservoir receptacle 32. The snap-fit action provides the user (or medical technician or other authorized person) with an audible or tactile (or both) indication that the cap 504 (or base/reservoir/cap unit) has been sufficiently or properly received within the reservoir receptacle 32.

The cap 504 (or base/reservoir/cap unit) may be removed from the reservoir receptacle 32 by pushing the button portion 608 to move the U-shaped member 602 toward the second position, to withdraw the curved portion 503 from the groove 505 by a sufficient amount to allow the user to pull the cap 504 (or base/reservoir/cap unit) out of the reservoir receptacle 32. With the button portion 608 pushed, the user (or medical technician or other authorized person) pulls the cap 504 (or base/reservoir/cap unit) in the direction of the axis A, out of the reservoir receptacle 32. In particular embodiments, no twisting or rotational motion on the cap 504 is needed to remove the cap 504 (or base/reservoir/cap unit) from the reservoir receptacle 32.

In particular embodiments, the reservoir receptacle 32 of the infusion pump device 30 includes a spring or other bias member that imparts a bias force on the cap 504 or the reservoir 1 in the direction of the axis A and outward from the reservoir receptacle 32, when the base/reservoir/cap unit is installed in the reservoir receptacle 32. In such embodiments, the spring or bias member may be similar to the spring or bias member described above with respect to the cap 404. The bias force causes a surface (lower surface in FIG. 38) of the groove 505 to press against the a surface of the curved portion 603. In such embodiments, the bias force helps to lock and maintain the cap 504 (and base/reservoir/cap unit) in a predefined position within the reservoir receptacle 32.

The embodiment shown in FIGS. 40-41 includes one U-shaped member 602 with one button portion 608. In other embodiments, two (or more) U-shaped members are supported on or in the housing of the infusion pump device 30, in the region of the reservoir receptacle, similar to the U-shaped member 602 in FIGS. 40-41. In such embodiments, the multiple U-shaped members may be arranged generally coaxially with the reservoir receptacle 32 (with the axis A extending through the inner opening 610 of each U-shaped member), but arranged with their respective button portions 608 at different respective locations around the circumference of the reservoir receptacle 32.

For example, in the embodiment represented by FIG. 42, two U-shaped members 602 and 602' are arranged over a reservoir receptacle 32 of an infusion pump device 30, with the U-shaped member 602 arranged adjacent (above) the U-shaped member 602' or spaced apart from the U-shaped member 602' in the direction of the axis A. The button portion 608 of the U-shaped member 602 is arranged on the opposite side of the axis A (180 degrees apart) relative to the button portion 608a of the U-shaped member 608. In that configuration, a user (or medical technician or other authorized person) may operate both U-shaped members simultaneously (to move both U-shaped members from their respective first positions to their respective second positions), with one hand, by placing a thumb on one of the button portions and a first finger on the other button portion and squeezing the thumb and finger toward each other. In other embodiments, more than two U-shaped members (and button portions) may be employed, such that more than one hand would be used to operate (move) all of the U-shaped members, simultaneously, to unlock the cap 504.

In embodiments that employ two or more U-shaped members 602, 602', etc., the cap 504 includes a corresponding number (two or more) grooves 505 in cap 504. In such embodiments, each U-shaped member 602, 602', etc., is arranged to align with and be received in a different respective one of the grooves 505, when the cap 504 (or base/reservoir/cap unit) is properly installed in the reservoir receptacle 32, as described above. In that state, the two or more U-shaped members 602, 602', etc. inhibit removal of the cap 503 (or base/reservoir/cap unit) from the reservoir receptacle 32. From that state, the button portions 608, 608', etc. of each of the U-shaped members 602, 602', etc., may be operated simultaneously (manually pushed at the same time), to move the U-shaped members 602, 602', etc. toward their respective second positions. As a result, the curved portion 603 of each U-shaped member 602, 602', etc. withdraws from its corresponding groove 505 by a sufficient amount to allow the user to pull the cap 504 (or base/reservoir/cap unit) out of the reservoir receptacle 32.

In the embodiment of FIGS. 40-42, the one or more U-shaped members 602, 602', etc. are arranged with the button portion(s) 608 positioned adjacent the reservoir receptacle 32 portion of the infusion pump device 30, and moveable in a lateral direction (perpendicular or otherwise transverse to the axis A). In other embodiments, similar to that represented by FIG. 39, the button portion 608 of each U-shaped member 602 is engaged with a linkage structure 512. The linkage structure 512 connects to a further button portion 514 that is either located at a different (remote) location relative to the button portion 608 or is oriented in a different direction relative to the button portion 608, or both. In the embodiment of FIG. 39, the further button portion 514 is located adjacent the reservoir receptacle 32, but is oriented to move in the direction of the axis A (upon receiving a manual pushing force in the downward direction relative to FIG. 39). In particular embodiments, the further button portion 514 is also configured to be returned to an extended (un-pushed) state, when a manual pushing force is not received or is released, for example, by the return of the U-shaped member 602 to its first state (released state) under the return bias force of the bias member 612.

Embodiments described with reference to FIGS. 40-42 may be employed with any one or more of the detection embodiments (magnetic detection, inductive detection, RF detection, mechanical detection, optical detection and electrical contact detection) described above. In such embodiments, the cap 504 or the reservoir 1 (or both) is provided with one or more detectable elements 42 described above.

In particular embodiments, the U-shaped member 602 is provided with one or more detectable elements 42 described above. In embodiments that employ multiple U-shaped members 602, 602', etc., a plurality of those U-shaped members (or each of the multiple U-shaped members) may be provided with one or more detectable elements described above. For example, one or more detectable elements 42 may be provided on the curved portion 603, the button portion 608 or any one (or both) of the linear portions 605 of the U-shaped member 602, 602', etc.

In such embodiments, the infusion pump device 30 may include one or more corresponding sensor elements 32 described above, arranged to detect the detectable elements 42, for example, when the U-shaped member (602, 602', etc.) is in one or more of the first position, the second position or other positions between the first and second position, to detect the position of the U-shaped member relative to the housing of the infusion pump device 30. In further embodiments, the detectable element(s) 42 and sensor element(s) are arranged such that one or more sensor elements detect one or more detectable elements, if the curved portion 603 of the U-shaped member is received within the groove 505 of the cap 504.

In further examples of such embodiments, one or more additional detectable elements 42 are provided on the cap 504 (or other portion of the base/reservoir/cap unit), and one or more further sensor elements 32 are arranged on the infusion pump device 30 to detect those detectable elements 42 if the cap 504 (or base/reservoir/cap unit) is properly received within the reservoir receptacle 32 of the infusion pump device 30 (or not properly received within the reservoir receptacle 32). Accordingly, the electronics 60 in those embodiments may be configured to determine whether or not the cap 504 (or base/reservoir/cap unit) is properly received within the reservoir receptacle 32 and properly engaged with the U-shaped member (602, 602', etc.), based at least in part on signals provided by sensor elements 32.

In such embodiments, electronics 60 in the infusion pump device may be configured to provide one or more predefined operations, at least partially based on (or in response to) one or more of: (1) a determination that the cap 504 (or base/reservoir/cap unit) is not properly received within the reservoir receptacle 32, and (2) a determination that the curved portion 603 of the U-shaped member is not properly received within the groove 505 of the cap 504. Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap 504 (or base/reservoir/cap unit) is properly received within the reservoir receptacle 32, and (2) a determination that the curved portion 603 of the U-shaped member is received within the groove 505 of the cap 504. Such predefined operations include, but are not limited to one or more of allowing or providing pumping operation, allowing a predefined pumping operation, providing a predefined message, and recording data indicating the detection.

d. Twist-Lock with Push Button Release

In other embodiments as described with reference to FIGS. 43-47, the second releasable coupler includes one or more resilient extensions 700 on a cap 704. The extension(s) 700 are configured to engage and be deflected inward by the inner surface 32c of the reservoir receptacle 32, as the cap 704 (or base/reservoir/cap unit) is moved into the reservoir receptacle 32, until the resilient extension(s) engage one or more grooves, indentations or other stop surfaces 32d in the reservoir receptacle 32. When engaged with the stop surface(s) 32d, the resilient extension(s) retain and lock the cap 704 (or base/reservoir/cap unit) within the reservoir receptacle.

In particular embodiments, the one or more resilient extensions 700 are flexible to selectively disengage the stop surfaces sufficiently to allow removal of the cap (or base/reservoir/cap unit) from the reservoir receptacle 32. For example, in FIGS. 43-47, the infusion pump device 30 includes one or more (two in FIGS. 36-40) button members 708 that are configured to be manually pressed by a user (or medical technician or other authorized person) to selectively move the resilient extension(s) 700 an amount to sufficiently disengage the stop surfaces 32d. In other examples, the one or more resilient extensions 700 may be configured to flex to sufficiently disengage the stop surfaces 32d when a manual force (rotary or linear, or both) greater than a predefined amount is applied to the cap 704 (or other portion of the base/reservoir/cap unit) by a user (or medical technician or other authorized person).

Each extension 700 has an engagement portion 702 that is configured to engage a respective sloped or ramped section 32c on the inner surface 32b of the reservoir receptacle 32, when the cap 700 (or base/reservoir/cap unit) is initially moved into the reservoir receptacle 32. In FIGS. 43-47, the cap 704 has two extensions 700, and the inner surface 32b of the reservoir receptacle 32 has a corresponding number of (two) ramped surface section 32c, one for each extension 700. Each ramped surface section 32c has a surface that slopes inward toward the axis A, from a first circumferential location 32c' to a second circumferential location 32c" along the ramped section 32c. A stop surface 32d is located at the second circumferential location 32c" of each ramped section 32c. In the embodiment of FIGS. 43-47, each stop surface 32d includes an indentation in the inner surface 32b of the reservoir receptacle, located at one end of each ramped section 32c.

The ramped sections 32c are configured to align with the engagement portions 702 of the extensions 700 on the cap 704, when the cap 704 (or base/reservoir/cap unit) is initially received within the reservoir receptacle. The cap 704 (or base/reservoir/cap unit) is configured to be rotated in a first direction (e.g., the direction of arrow 706 in FIGS. 43 and 44) around the axis A, once the cap 704 (or base/reservoir/cap unit) is initially received within the reservoir receptacle. The cap 704 includes an extended grip portion 705 that provides a surface for allowing a user (or medical technician or other authorized person) to grip the cap 704 and apply a manual force in the rotational direction of arrow 706. As the cap 704 (or base/reservoir/cap unit) is rotated, the engagement portions 702 of the extensions 700 on the cap 704 ride along the surfaces of the ramp sections 32c. The inward slope of the ramp sections causes the extensions 700 to flex inward (toward the axis A) as the cap 704 (or base/reservoir/cap unit) is rotated in the direction of arrow 706.

The extensions 700 are configured to continue to ride along the surfaces of the ramp sections 32c and flex inward until the extensions 700 align with and engage the stop surfaces 32d. When engaged with the stop surfaces 32d, the resilient extensions 700 retain and lock the cap (or base/reservoir/cap unit) within the reservoir receptacle. In the embodiment of FIGS. 43-47, the stop surfaces 32d include indentations that allow the resilient extensions 700 to flex outward slightly and the engagement portions 702 to extend at least partially into the indentations, upon alignment of the engagement portions 702 with the indentations (as shown in FIG. 44).

In particular embodiments, the extensions 700, engagement portions 702 and the stop surfaces 32d (or both) are made of materials that have sufficient rigidity to secure the cap 704 to the infusion pump device 30 when the engagement portions 702 are in the indentations of the stop surfaces 32d, but sufficiently flexible and resilient to allow the engagement portion 702 to be snapped into indentations of the stop surfaces 32d. In such embodiments, as the cap 704 is rotated, the engagement portions 702 ride along the ramp portion 32c as the extensions 700 flex, until the engagement portions 702 align with and snap into the indentations of the stop surfaces 32d. In particular embodiments, the cap 704 is configured to provide a snap sound or snap-like feel that is perceptible to a person installing the cap 704 (or base/reservoir/cap unit) in the reservoir receptacle 32.

When engaged with the indentations of the stop surfaces 32d, the resilient extensions 700 inhibit removal of the cap 704 (or base/reservoir/cap unit) from the reservoir receptacle 32 of the infusion pump device 30. However, from the state shown in FIG. 43, the two extensions 700 may be manually flexed inward (toward the axis A) by operating a pair of button members 708 (one shown in view in FIG. 43, the other being out of view, on the opposite side of the reservoir receptacle 32, relative to the axis A). The button members 708 are operated to flex the extensions 700 inward, to withdraw the extensions 700 from the indentations of the stop surfaces 32d by a sufficient amount to allow the user to remove the cap 704 (or base/reservoir/cap unit) from the reservoir receptacle 32. In particular embodiments, the reservoir receptacle 32 and cap 704 are configured to allow the cap 704 (or base/reservoir/cap unit) to be pulled outward in the linear direction of the axis A, without requiring rotating or twisting, to remove the cap 704 (or base/reservoir/cap unit) from the reservoir receptacle 32, when the button members 708 are operated to withdraw the extensions 700 from the indentations by a sufficient amount.

In the embodiment of FIGS. 43-47, each button member 708 includes a body that is supported in an indentation in the housing of the infusion pump device 30, adjacent the open port of the reservoir receptacle. The body of each button member 708 has a surface 708a that is exposed from outside of the housing of the infusion pump device 30 in a position at which it may be pressed by a finger or thumb of a user (or medical technician or other authorized person), to operate the button member 708. The body of each button member 708 also includes a linkage portion 708b that extends through a passage or opening in the housing of the infusion pump device 30 and has a surface 708c located adjacent or partially within an indentations of one of the stop surfaces 32d, on the inside of the reservoir receptacle 32. In particular embodiments, each button member 708 includes spring or other bias member 714 arranged to bias the button member 708 outward in the radial direction relative to the axis A. Each button member 708 is configured to be manually pressed on its surface 708a, to move the linkage portion 708b inward in the radial direction relative to the axis A. If an engagement portion 702 of an extension 700 is in the indentation of the stop surface 32d associated with the button member 708, then the surface 708c of the button member 708 forces the extension arm 700 inward, as the button member 708 is pushed. By pushing the button member 708 a sufficient distance, the extension 700 is flexed inward an amount to withdraw the engagement portion 702 of the extension 700 out of the indentation of the stop surface 32d a sufficient amount to allow the cap 704 (or base/reservoir/cap unit) to be removed from the reservoir receptacle 32, as described above.

In particular embodiments, the cap 704 includes one or more alignment features 710 that align with one or more corresponding or mating features 712 located on the infusion pump device 30, in the region of the port of the reservoir receptacle 32, to align the cap 704 in one or more predefined rotated positions relative to the axis A, when the cap 704 (or base/reservoir/cap unit) is initially received in the reservoir receptacle 32. The one or more predefined positions are locations at which the engagement portions 702 of the extensions 700 engage the ramp portion 32c, at or near the first location 32c', when the cap 704 (or base/reservoir/cap unit) is initially received by the reservoir receptacle 32.

Figure 43:
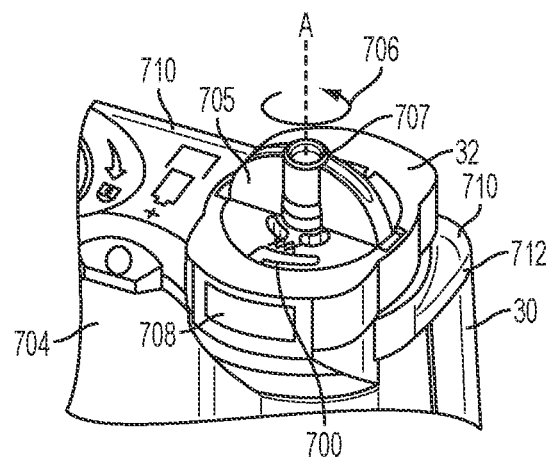
FIG. 43 is a partial perspective view of a cap and a portion of a reservoir receptacle of an infusion pump device according to a further embodiment of the present invention.
Figure 44:
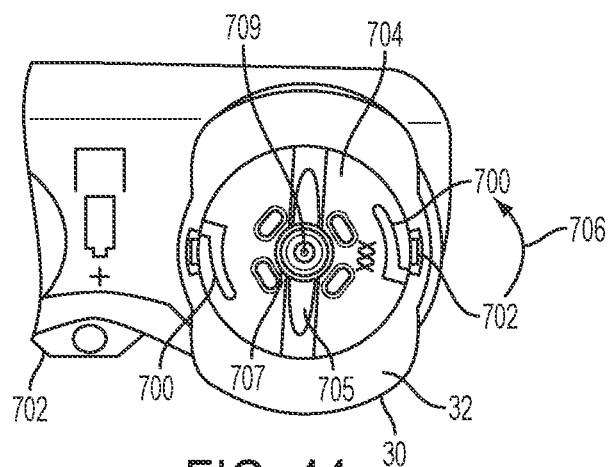
FIG. 44 is a partial perspective view of the cap and reservoir receptacle of the embodiment of FIG. 43, but in a locked or latched state.
Figure 45:
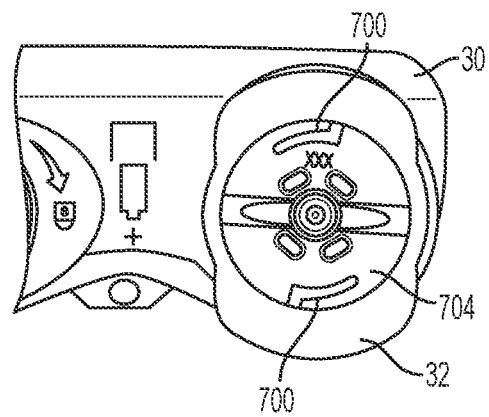
FIG. 45 is a partial perspective view of the cap and reservoir receptacle of the embodiment of FIG. 43, but in an unlocked or unlatched state.
Figure 46:
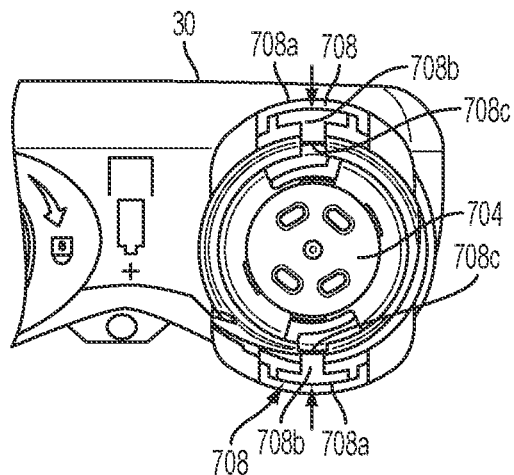
FIG. 46 is a partial cut-away, perspective view of the cap and reservoir receptacle of the embodiment of FIG. 43, showing button members.
Figure 47:
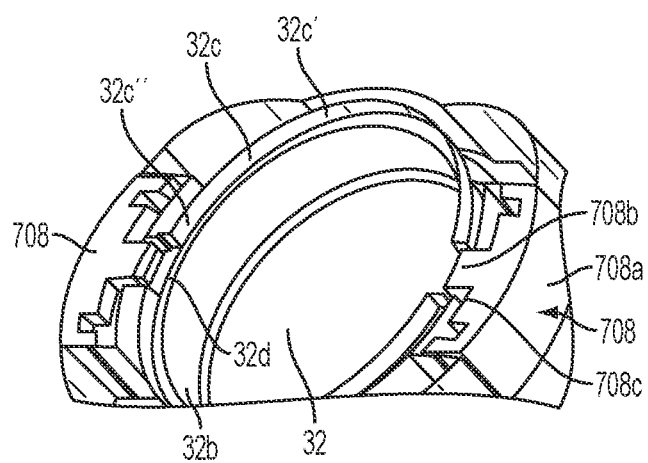
FIG. 47 is a partial perspective view of a portion of the reservoir receptacle of the embodiment of FIGS. 43-46.
Figure 48:
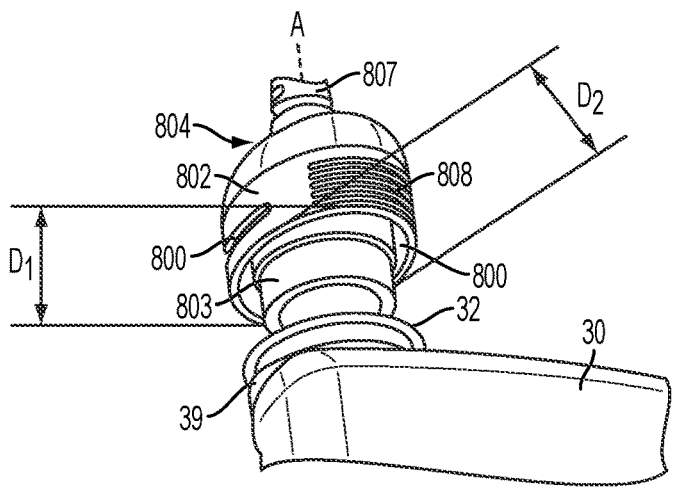
FIGS. 48 and 49 are partial perspective views of a cap and a portion of a reservoir receptacle of an infusion pump device according to a further embodiment of the present invention.
Figure 49:
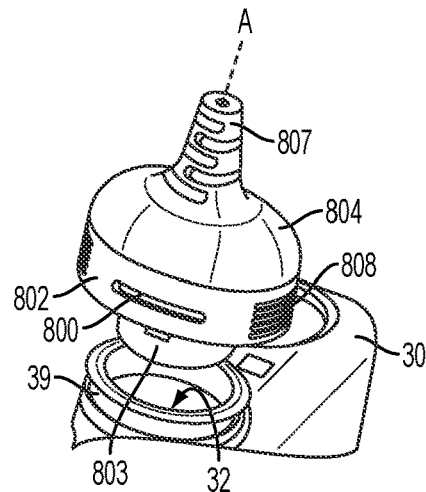
Figure 50:
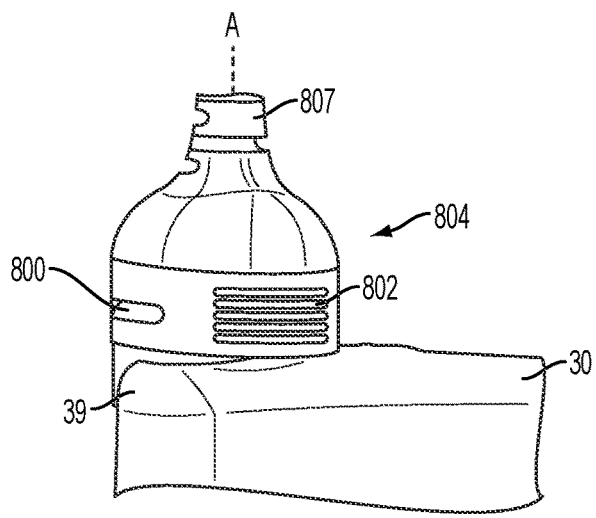
FIGS. 50 and 51 are partial perspective views of the cap and reservoir receptacle of the embodiment of FIGS. 48 and 49, but in a locked or latched state.
Figure 51:
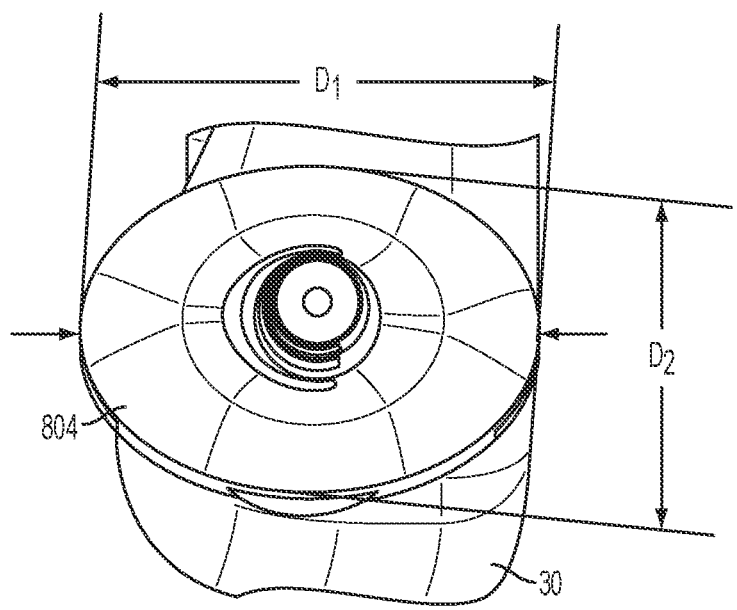

Accordingly, the cap 704 (or base/reservoir/cap unit) may be installed in the infusion pump device 30 by inserting cap 704 (or base/reservoir/cap unit) through the open port of the reservoir receptacle and manually aligning the alignment features 710 and 712, as shown in FIG. 43. In that state, the extensions 700 engage the sloping surface of the ramp portion 32c, at or near the first location 32c' of the ramp portions 32c. From that state, the cap 704 may be manually rotated in the direction of the arrow 706 to cause the engagement portions 702 of the extensions 700 to ride along the sloped surfaces of the ramp sections 32c until the engagement portions 702 align with the indentations of the stop surfaces 32d. At that state, the engagement portions 702 are received (at least partially) within the indentations of the stop surfaces 32d and the extensions 700 flex outward to retain and lock the cap 704 (and base/reservoir/cap unit) in an operating position within the reservoir receptacle 32.

As discussed above, the cap 704 (and base/reservoir/cap unit) may be removed from the reservoir receptacle 32 by manually pressing all of the button members 708 at the same time, to flex the extensions 700 inward to withdraw the engagement portions 702 from the indentations sufficient to allow the cap 704 (and base/reservoir/cap unit) to be manually pulled outward (along the direction of the axis A) from the reservoir receptacle 32.

In the embodiment of FIGS. 43-47, the cap 704 is configured to be coupled to a reservoir (or base and reservoir) as described above, for operation with the infusion pump device 30 in manner similar to the operation of the cap 4 and reservoir 1 as described above. The cap 704 includes a port 707 for connection with an infusion set tubing such as, but not limited to, an infusion set tubing 52 of an infusion set 50 as described above. The cap 704 also includes a body portion through which a channel 709 extends. The channel 709 connects to a hollow needle (not shown) similar to needle 9 described above, and provides a fluid flow communication path from the hollow needle to the port 707 (and to an infusion set tubing, when connected to the port 707). The cap 704 also includes one or more connection features (e.g. of the first releasable coupler as described above) for coupling the cap 704 to a reservoir (or to a base/reservoir unit).

The cap 704 may be made of any one or more suitable materials having sufficient rigidity and strength to operate as described herein, including, but not limited to plastic, metal, ceramic, composite or other suitable material. In one example, the cap 704 (including the resilient extensions 700, grip 705, port 707 and the cap body) is made of a molded plastic material, as a single, unitary, molded structure. In other embodiments, the cap 704 may be made by other processes or in multiple parts that are assembled together (or both).

In the embodiment of FIGS. 43-47, the alignment features 710 are outwardly extending tabs on the cap 704, while the alignment features 712 are inward extending slots in the housing of the infusion pump device 30, at the open port of the reservoir receptacle, where the slots are shaped to receive the tabs, when aligned. In other embodiments, the mating alignment features 710 and 712 have other suitable configurations that allow the cap 704 to be received by the reservoir receptacle 32 in one or more predefined positions, where such other configurations include one or more other tabs and slots, keyed surfaces, surface shapes or other shape features.

In the embodiment of FIGS. 43-47, each stop surface 32a includes an indentation shaped to align with and receive at least a portion of the engagement portion 702 of an extension 700. In other embodiments, the stop surface 32a includes one or more other features provided in the reservoir receptacle, such as, but not limited to, an extension, protrusion, groove, or other structural feature provided on an inner surface 32b of the reservoir receptacle 32.

The embodiment of FIGS. 43-47 includes two extensions 700, two ramp portions 32c, two stop surfaces 32d and two button members 708. Other embodiments employ only one of each of those features. Yet other embodiments employ more than two of each of those features.

In the embodiment of FIGS. 43-47, the two extensions 700 are located on opposite sides of the cap 704 and the axis A relative to each other and, similarly, the two button members 708 are located on opposite sides of the cap and the axis A relative to each other. In addition, the two ramp portions 32c and two stop surfaces 32d are located, relative to each other, on opposite sides of the reservoir receptacle and axis A. That configuration allows the two button members 708 to be operated simultaneously, with one hand, for example, by pressing one button member 708 with a thumb and the other button member 708 with the first finger of the same hand. In other embodiments, the extensions, button members, ramp portions and stop surfaces are located in other suitable locations.

Embodiments described with reference to FIGS. 43-47 may be employed with any one or more of the detection embodiments (magnetic detection, inductive detection, RF detection, mechanical detection, optical detection and electrical contact detection) described above. In such embodiments, the cap 704 or the reservoir 1 (or both) is provided with one or more detectable elements 42 described above.

In particular embodiments, one or more (or all) of the extensions 700 of the cap is provided with one or more detectable elements 42 described above. In such embodiments, the infusion pump device 30 may include one or more corresponding sensor elements 32 described above, arranged to detect the detectable elements 42, for example, when extensions 700 are engaged with the ramp portion 32c, or when the extensions are engaged with the stop surface 32d, or when the extensions are flexed (or any combination thereof). In further embodiments, one or more (or all) of the tabs or other alignment features 710 is provided with one or more detectable elements 42 described above. In such embodiments, the infusion pump device 30 may include one or more corresponding sensor elements 32 described above, arranged to detect the detectable elements 42, for example, when alignment features 710 on the cap 704 are properly aligned with or mated with corresponding alignment features on the infusion pump device 30.

In further examples of such embodiments, one or more additional detectable elements 42 are provided on the cap 704 (or other portion of the base/reservoir/cap unit), and one or more further sensor elements 32 are arranged on the infusion pump device 30 to detect those detectable elements 42 if the cap 704 (or base/reservoir/cap unit) is properly received within the reservoir receptacle 32 of the infusion pump device 30 (or not properly received within the reservoir receptacle 32). Accordingly, the electronics 60 in those embodiments may be configured to determine whether or not the cap 704 (or base/reservoir/cap unit) is properly received within the reservoir receptacle 32, or whether or not the extensions 700 are properly engaged with the stop surfaces 32d, or both.

In such embodiments, electronics 60 in the infusion pump device may be configured to provide one or more predefined operations, at least partially based on (or in response to) one or more of: (1) a determination that the cap 704 (or base/reservoir/cap unit) is not properly received within the reservoir receptacle 32, and (2) a determination that the extensions 700 are not properly received within the indentations of the stop surfaces 32c. Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap 704 (or base/reservoir/cap unit) is properly received within the reservoir receptacle 32, and (2) a determination that the extensions 700 are properly received within the indentations of the stop surfaces 32c. Such predefined operations include, but are not limited to one or more of allowing or providing pumping operation, allowing a predefined pumping operation, providing a predefined message, and recording data indicating the detection.

e. Push-In Lock with Pinch Release

In other embodiments as described with reference to FIGS. 48-51, the second releasable coupler includes one or more features 800 on a skirt portion 802 of a cap 804, that engage and mate with one or more features 39 on the housing of the infusion pump device 30, in the region of the open port of the reservoir receptacle 32. In the embodiment of FIGS. 48-51, the feature(s) 800 include a pair of open slots in the skirt portion 802 of the cap 804, and the feature(s) 39 include an outward extending annular lip around the open port of the reservoir receptacle 32.

The cap 804 includes a body portion 803 configured to couple to a reservoir 1 (for example, with a first releasable coupler as described above, or other suitable coupling structure), and to fit at least partially within the reservoir receptacle 32, when the cap 804 (or base/reservoir/cap unit) is installed within the reservoir receptacle 32 (for example, as described above with respect to caps 4, 204, 404, 504, 604 and 704, or in another suitable manner). The skirt portion 802 of the cap 804 extends over the outside of a body portion 803 of the cap 804 and has one end (the end of the skirt portion 802 that is adjacent to the reservoir-coupling end of the body portion 803 of the cap 804) that is open to a space 806 between the interior surface 802a of the skirt portion 802 and the exterior surface 803a of the body portion 803.

When the cap 804 (or base/reservoir/cap unit) is installed in the reservoir receptacle 32, the body portion 803 of the cap 804 fits at least partially within the reservoir receptacle 32 (for example, as described above with respect to caps 4, 204, 404, 504, 604 and 704, or in another suitable manner) while the skirt portion 802 extends at least partially over the outside of the open port of the reservoir receptacle 32. In particular, when the cap 804 (or base/reservoir/cap unit) is installed in the reservoir receptacle 32, an end portion of the port of the reservoir receptacle 32 fits at least partially into the space 806 between the skirt portion 802 and the body portion 803 of the cap 804.

In the embodiment in FIGS. 48-51, the skirt portion 802 of the cap 804 has an oblong or oval-shape at its open end, and is wider in one dimension ($D_1$) than in a second dimension ($D_2$). In particular embodiments, the width of the interior surface of the skirt in the second dimension $D_2$ is smaller than the diameter of the open port end of the reservoir receptacle 32, while the width of the interior surface of the skirt in the first dimension $D_1$ is larger than the diameter of the open port end of the reservoir receptacle 32. In such embodiments, the skirt portion 802 is configured of a material or structure (or both) that is sufficiently resilient and flexible to expand in the second dimension ($D_2$) when a sufficient squeezing force is applied to the skirt in the direction of the first dimension ($D_1$). Furthermore, in such embodiments, the skirt portion 802 is sufficiently resilient to return to the un-squeezed configuration, when the squeezing force is released.

The shape and size of the skirt portion 802 and of the engagement features (slots) 800 are configured to allow the skirt portion 802 to fit over the end of the port of the reservoir receptacle 32 when the skirt portion 802 is expanded in the second dimension $D_2$ (for example, by manually squeezing the skirt portion 802 in the first dimension $D_1$). In the expanded (squeezed) state, the skirt portion 802 of the cap 804 may be fitted over the end portion of the port of the reservoir receptacle 32 as the cap 804 (or base/reservoir/cap unit) is moved into the reservoir receptacle 32.

Once the cap 804 (or base/reservoir/cap unit) is sufficiently inserted into the reservoir receptacle 32, the skirt portion 802 may be returned to its unexpanded state (for example, by releasing the manual squeezing force on the skirt portion 802). As the skirt portion 802 returns to the unexpanded, the engagement features (slots) 800 on the skirt portion 802 engage and receive the engagement feature (lip) 39 around the port of the reservoir receptacle 32. In that state, the cap 804 (or base/reservoir/cap unit) is retained and locked in the reservoir receptacle 32, in an operating position.

From that state, the cap 804 (or base/reservoir/cap unit) may be removed from the reservoir receptacle 32, by applying a squeezing force on the skirt portion 802 in the first dimension $D_1$ to cause the skirt portion 802 to expand in the second dimension $D_2$ to withdraw the engagement features (slots) 800 from the engagement feature (lip) 39 by a sufficient amount to unlock the cap 804 and allow the cap 804 (or base/reservoir/cap unit) to be manually pulled out of the reservoir receptacle 32.

In the embodiment of FIGS. 48-51, the cap 804 is configured to be coupled to a reservoir (or base and reservoir) as described above, for operation with the infusion pump device 30 in manner similar to the operation of the cap 4 and reservoir 1 as described above. The cap 804 includes a port 807 for connection with an infusion set tubing such as, but not limited to, an infusion set tubing 52 of an infusion set 50 as described above. The body portion 803 of the cap 804 includes a channel 809 that connects to a hollow needle (not shown) similar to needle 9 described above, and provides a fluid flow communication path from the hollow needle to the port 807 (and to an infusion set tubing, when connected to the port 807).

The cap 804 may be made of any one or more suitable materials having sufficient rigidity and strength to operate as described herein, including, but not limited to plastic, metal, ceramic, composite or other suitable material. In one example, the cap 804 (including the resilient skirt portion 802) is made of a molded plastic material, as a single, unitary, molded structure. In other embodiments, the cap 804 may be made by other processes or in multiple parts that are assembled together (or both).

In the embodiment of FIGS. 48-51, the skirt portion 802 of the cap 804 has an outer surface that includes one or more friction features 808. The friction features 808 are provided to identify a location on the skirt portion 802 to apply a manual squeezing force, as described above. In addition, the friction features 808 are configured to inhibit a finger or thumb from slipping off of the skirt portion 802, when applying a manual squeezing force. In the embodiment in FIGS. 48-51, first and second friction features are provided on the skirt portion 802, at locations along the first dimension $D_1$. In the embodiment in FIGS. 48-51, each friction feature includes a set of raised ribs. In other embodiments, other suitable friction features may be used for enhancing friction between a finger or thumb and the skirt portion 802, including, but not limited to, grooves, protrusions, one or more pads of material having a higher friction coefficient than the material of the skirt portion 802, or the like.

The embodiment of FIGS. 48-51 includes two engagement features (slots) 800 on the skirt portion 802. Other embodiments employ only one engagement feature (slot) 800, while yet other embodiments include more than two engagement features (slots) 800 on the skirt portion 802.

Also, while the embodiment of FIGS. 48-51 includes one engagement feature (lip) 39 on the infusion pump device 30, other embodiments employ more than one engagement features (lip, protrusion or the like) 39 on the infusion pump device 30.

In the embodiment of FIGS. 48-51, the feature(s) 800 include a pair of open slots in the skirt portion 802 of the cap 804. In other embodiments, the engagement features 800 include other suitable structure for engaging the engaging features 39 on the infusion pump device 30, including, but not limited to one or more grooves, indentations, apertures or the like. In other embodiments, the feature(s) 800 include a protruding feature, such as, but not limited to one or more ribs or other protrusions, while the engagement features 39 include mating slots, grooves, indentations, apertures or the like.

In the embodiment of FIGS. 48-51, the feature(s) 39 include an annular, outward-extending lip around the port of the reservoir receptacle 32. In other embodiments, the engagement feature 39 includes other suitable structure for engaging mating engaging features 800 on the cap 804, including, but not limited to one or more protrusions, slots, grooves, indentations, apertures or the like.

Embodiments described with reference to FIGS. 48-51 may be employed with any one or more of the detection embodiments (magnetic detection, inductive detection, RF detection, mechanical detection, optical detection and electrical contact detection) described above. In such embodiments, the cap 804 or the reservoir 1 (or both) is provided with one or more detectable elements 42 described above.

In particular embodiments, the skirt portion 802 of the cap 804 is provided with one or more detectable elements 42 described above. In such embodiments, the infusion pump device 30 may include one or more corresponding sensor elements 32 described above, arranged to detect the detectable elements 42, for example, when engagement features 800 are engaged with the engagement features 39, or when the skirt portion 802 is extended over the port end of the reservoir receptacle 32, or when the port end of the reservoir receptacle 32 is received within the space 806 (or any combination thereof).

In further examples of such embodiments, one or more additional detectable elements 42 are provided on the cap 804 (or other portion of the base/reservoir/cap unit), and one or more further sensor elements 32 are arranged on the infusion pump device 30 to detect those detectable elements 42 if the cap 804 (or base/reservoir/cap unit) is properly received within the reservoir receptacle 32 of the infusion pump device 30 (or not properly received within the reservoir receptacle 32). Accordingly, the electronics 60 in those embodiments may be configured to determine whether or not the cap 804 (or base/reservoir/cap unit) is properly received within the reservoir receptacle 32, engagement features 800 are engaged with the engagement features 39, or whether or not the skirt portion 802 is extended over the port end of the reservoir receptacle 32.

In such embodiments, electronics 60 in the infusion pump device may be configured to provide one or more predefined operations, at least partially based on (or in response to) one or more of: (1) a determination that the cap 804 (or base/reservoir/cap unit) is not properly received within the reservoir receptacle 32, (2) a determination that the engagement features 800 are not sufficiently engaged with the engagement features 39, and (3) a determination that the skirt portion 802 is not sufficiently extended over the port end of the reservoir receptacle 32. Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap 804 (or base/reservoir/cap unit) is properly received within the reservoir receptacle 32, (2) a determination that the engagement features 800 are engaged with the engagement features 39, and (3) a determination that the skirt portion 802 is extended over the port end of the reservoir receptacle 32. Such predefined operations include, but are not limited to one or more of allowing or providing pumping operation, allowing a predefined pumping operation, providing a predefined message, and recording data indicating the detection.

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

f. Pinch to Connect and Release

Figure 52:
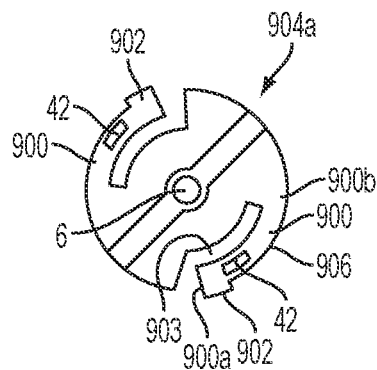
FIG. 52 is a top view of a cap of a reservoir connection interface apparatus according to an embodiment of the present invention.

In further embodiments as described with reference to FIGS. 52-54, the second releasable coupler includes a flexible arm structure that includes one or more flexible arms 900 formed on or attached to the cap 904a. Each flexible arm 900 includes a tab 902 configured to engage a corresponding indentation, opening, groove, stop surface or other engagement feature on the infusion pump device 30, when the cap 904a (or base/reservoir/cap unit) is installed in the reservoir receptacle of the infusion pump device 30. FIG. 52 shows a top-down view of a cap 904a that includes two flexible arms 900, provided on opposite sides of housing 905 of the cap 904a (on opposite sides of the axis A) relative to each other. That arrangement allows the two flexible arms 900 to be manually squeezed toward each other with one hand, to release the cap (or base/reservoir/cap unit) as described below. However, in other embodiments, one or more flexible arms 900 may be arranged in any suitable location on the housing 905 of the cap 904a.

Each flexible arm 900 has a free end portion 900a and extends (at a second end portion 900b) from the rest of the housing 905 in a cantilever manner. In the embodiment of FIGS. 52-54, the housing 905 of the cap 904a has a shape or indentation adjacent each flexible arm 900 to provide a gap 903 between the flexible arm 900 and another portion of the housing 905 of the cap. In such embodiments, each flexible arm 900 has an outer surface 906 that follows the contour of the outer surface of adjacent portions of the housing 905, when the flexible arm 900 is in the un-flexed state (as shown in FIG. 52). In other embodiments, each flexible arm 900 extends outward from the housing 905 of the cap 904a, to form a gap 903 between the flexible arm and the housing 905. Each flexible arm 900 is sufficiently flexible to bend inward, into the gap 903, toward a central portion of the cap 904a, when sufficient inward-directed pressure is applied to the flexible arm 900. In addition, each flexible arm 900 is sufficiently resilient to return to its un-flexed state, when the inward-directed pressure is released.

Each flexible arm 900 has a tab 902 that extends outward (radially outward relative to the axis A) from the free end portion 900a of the flexible arm 900. The tab 902 is shaped to engage or fit into a correspondingly shaped indentation, opening, groove, stop surface or other engagement structure in the reservoir receptacle 32 of the infusion pump device 30, when the cap 904a (or base/reservoir/cap unit) is installed in the reservoir receptacle 32. In the embodiment of FIG. 53, the engagement structure includes apertures 908 in an upper ring member 910 on the open end of the reservoir receptacle 32. Two apertures 908 are shown in FIG. 53, to correspond to the two flexible arms 900 in the embodiment of FIG. 52.

The upper ring member 910 may be attached to the reservoir receptacle 32 in any suitable attachment mechanism including, but not limited to, welding, glue, resin or other adhesive material, screw threads, friction fit, or the like. The upper ring member 910 may be made of any suitably rigid material, such as but not limited to plastic, metal, ceramic, composite material or combinations thereof. In particular embodiments, the upper ring member 910 corresponds to (or is) the upper ring member 94 discussed above with respect to the embodiment in FIG. 7. In other embodiments, the apertures 908 (or other engagement structure) is provided directly in or on the housing 33 of the infusion pump device 30, for example, within or on one or more wall portions that define the reservoir receptacle 32 of the infusion pump device 30.

In particular embodiments, each flexible arm 900 is formed integral with the housing 905 of the cap 4, for example, by being molded with the rest of the housing 905. In such embodiments, the housing 905 of the cap 904a (and, thus, each flexible arm 900) is made of a material having sufficient rigidity to hold a shape and operate as described herein, and sufficient flexibility and resiliency to allow each flexible arm 900 to flex inward and return to an un-flexed state, as described herein. In other embodiments, each flexible arm is a separate element relative to the housing 905 of the cap 904a and is attached to the housing 905 by any suitable attachment mechanism including, but not limited to one or more welds, adhesives, screws, bolts, clamps or the like.

Figure 53:
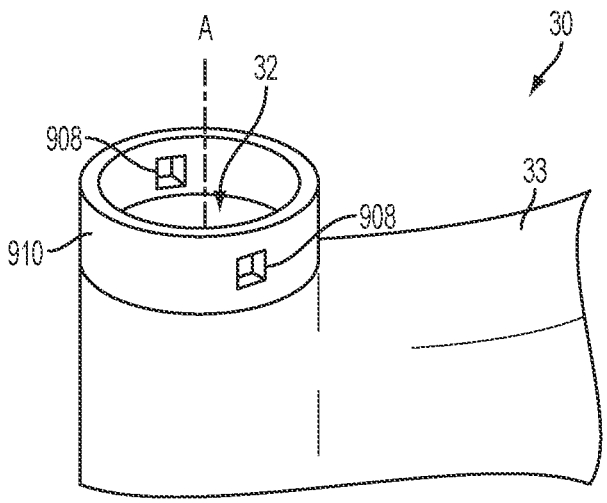
FIG. 53 is a partial perspective view of a portion of a reservoir receptacle of an infusion pump device that operates with a cap of FIG. 52.

In the embodiment of FIGS. 52 and 53, the cap 904a (or base/reservoir/cap unit) is installed in the reservoir receptacle 32 of the infusion pump device by inserting the cap 904a (or base/reservoir/cap unit) into the open end of the reservoir receptacle 32 (or open end of the ring member 910). As the cap 904a is inserted into the reservoir receptacle 32, manual pressure may be applied to the flexible arms 900, to squeeze the flexible arms 900 toward each other (toward the axis A). By that action, the flexible arms 900 flex inward, into the gaps 903 by a sufficient amount to allow the tabs 902 to clear upper edge of the reservoir receptacle 32 (or ring member 910) so that the cap 904a (and base/reservoir/cap unit) can be moved further into the reservoir receptacle 32. As the tabs 902 clear the upper edge and are within the reservoir receptacle 32 (or ring member 910), manual pressure can be released from the flexible arms 900, to allow the resilient, flexible arms 900 to return toward an un-flexed state. However, because the tabs 902 are located within the reservoir receptacle 32 (or ring member 910), the tabs 902 ride or slide along an inner surface of the reservoir receptacle 32 (or ring member 910), as the cap 904a is moved further toward a fully installed position. When the cap 904a (and base/reservoir/cap unit) are in a fully installed position within the reservoir receptacle, 32, the tabs 902 on the cap 4 align with the apertures 908 in the reservoir receptacle 32 (or ring member 910). When the tabs 902 align with the apertures 908, the tabs 902 fit within the apertures 908 and allow the flexible arms 900 to retract at least partially toward their un-flexed states, for example, due to the resiliency of the flexible arms 900. This action causes the tabs 902 to be retained within the apertures 908, to retain the cap 904a (and base/reservoir/cap unit) in the installed position within the reservoir receptacle 32.

Figure 54:
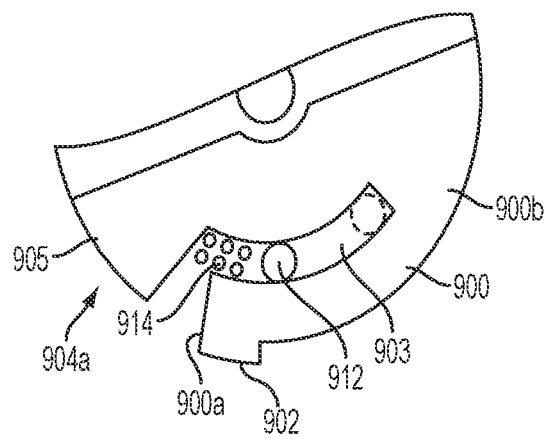
FIG. 54 is an enlarged, partial top view of an embodiment of a cap that operates with an infusion pump device of FIG. 53.

In the embodiment of FIGS. 52-54, to remove the cap 904a (and base/reservoir/cap unit) from an installed position within the reservoir receptacle 32, manual pressure can be applied to ends of tabs 902 extending through the openings 908. For example, a squeezing action can be applied by manually squeezing the tab ends of tabs 902 toward each other, to flex the flexible arms 900 inward sufficiently to release the tabs 902 from the openings 908. In particular embodiments, a combination of manual squeezing pressure as noted above with a linear force (also applied manually) to pull the cap 904a (or base/reservoir/cap unit) in a direction outward from the open end of the reservoir receptacle 32 is applied to release the tabs 902 from the openings 908. Once the tabs 902 are released from the openings 908, further manual force to pull the cap 904a (or base/reservoir/cap unit) in a direction outward from the open end of the reservoir receptacle 32 is applied to withdraw the cap 904a (and base/reservoir/cap unit) from the reservoir receptacle 32.

In particular embodiments, a locking mechanism is provided on one or more (or each) of the flexible arms 900, or within one or more (or each) of the gaps 903, to selectively lock the associated flexible arm 900 from flexing inward. In particular embodiments, the locking mechanism is configured to selectively lock the flexible arm 900, when the tab 902 is engaged with the engagement member (e.g., the aperture 908) in the infusions pump device 30, to inhibit removal (e.g., accidental or unauthorized) removal of the cap 904a (or base/reservoir/cap unit) from the reservoir receptacle 32. In such embodiments, the locking mechanism is also configured to selective unlock the flexible arm 900 and allow the flexible arm to flex, to release the tab 902 from the engagement member. In the embodiment of FIG. 54, the locking mechanism includes a moveable lock member 912 that is located within the gap 903 associated with the flexible arm 900. The moveable lock member 912 is arranged to be moved, in a controlled manner, between first and second positions (shown in solid and broken lines in FIG. 54). In the first position (solid line position in FIG. 54), the moveable lock member 912 is located further toward the free end 900a of the flexible arm 900, as compared to the position of the moveable lock member 912 in the second position (broken line position in FIG. 54). When the lock member 912 is in the first position (solid line position in FIG. 54), the flexible arm 900 is inhibited from flexing inward by the lock member 912. When the lock member 912 is in the second position (broken line position in FIG. 54), the flexible arm 900 is allowed to flex inward, when sufficient inward-directed pressure is applied to the flexible arm 900. In particular embodiments, the lock member 912 is controlled to be in the second position (broken line position in FIG. 54) during installation or removal of the cap 904a (or base/reservoir/cap unit) to or from the reservoir receptacle 32, and is selectively controlled to move to and remain in the first position (solid line position in FIG. 54) when the cap 904a (or base/reservoir/cap unit) is fully installed within the reservoir receptacle 32.

Movement of the lock member 912 is controlled by any suitable mechanism, including, but not limited to a manual lever, magnetic actuator, electronic solenoid or the like. In particular embodiments, the lock member 912 is (or includes) a magnetic or magnetically attractable material that magnetically interacts with an electromagnet or a moveable magnet located on or adjacent the outer surface of the cap 904a. The electromagnet is selectively energized (or the moveable magnet is selectively moved) to cause the lock member 912 to move between locked and unlocked positions (solid and broken line positions in FIG. 54). In further embodiments, the lock member 912 may be coupled to a bias member 914 (such as, but not limited to a coil spring or other spring), to bias the lock member 912 toward the locked position (solid line position in FIG. 54), when the lock member 912 is not controlled to move to the unlocked position. In other embodiments, the bias member 914 biases the lock member 912 toward the unlocked position (broken line position in FIG. 54) when the lock member 912 is not controlled to move to the locked position.

Embodiments described with reference to FIGS. 52-54 may be employed with any one or more of the detection embodiments (magnetic detection, inductive detection, RF detection, mechanical detection and optical detection) described above. In such embodiments, the cap 904a or the reservoir 1 (or both) is provided with one or more detectable elements 42 as described above, while the ring 910 or other portion of the infusion pump device 30 is provided with one or more sensor elements 34 as described above. In particular embodiments, one or more detectable elements 42 are arranged on the flexible arms 900, or are arranged on the moveable lock member 912 (or both). In such embodiments, electronics (such as electronics 60) may be configured to detect the relative position (state of flex) of the flexible arm(s) 900, or to detect the relative position of the lock member 912 (or both), in addition to or as an alternative to detection of the presence of the cap 904a (or base/reservoir/cap unit) or other characteristics and information as described above.

In such embodiments, electronics 60 in the infusion pump device may be configured to provide one or more predefined operations, at least partially based on (or in response to) one or more of: (1) a determination that the cap 904a (or base/reservoir/cap unit) is not properly received within the reservoir receptacle 32, (2) a determination that the tabs 902 are not sufficiently engaged with the engagement members 908, and (3) a determination that the lock member 912 is in an unlocked position. Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap 904a (or base/reservoir/cap unit) is properly received within the reservoir receptacle 32, (2) a determination that the tabs 902 are engaged with the engagement members 908, and (3) a determination that the lock member 912 is in a locked position. Such predefined operations include, but are not limited to one or more of allowing or providing pumping operation, allowing a predefined pumping operation, providing a predefined message, and recording data indicating the detection.

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

g. Pivot to Release

Figure 55:
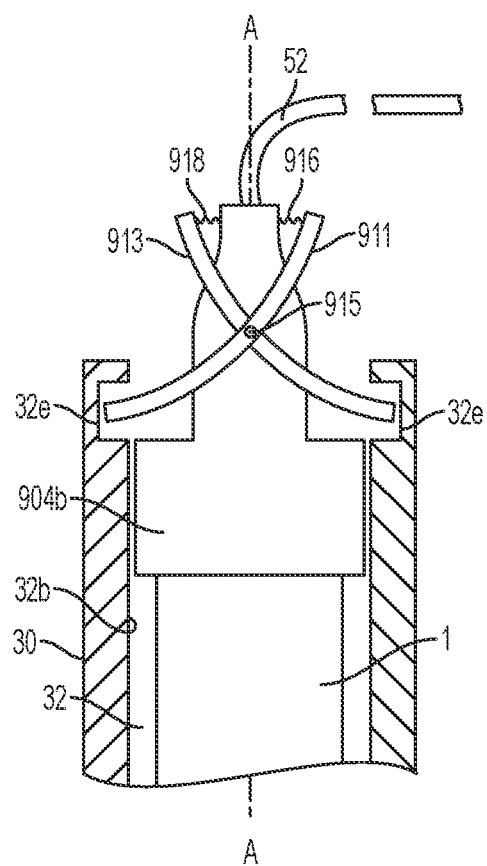
FIG. 55 is a partial side, cross-section view of a portion of a reservoir receptacle of an infusion pump device containing a base/reservoir/cap unit having a cap-to-infusion pump device connection interface according to an embodiment of the present invention.

In a further embodiment as described with reference to FIG. 55, the second releasable coupler includes a pair of pivot members 911 and 913 that are pivotally coupled at a pivot point 915 to the cap 904b. One or more bias members, such as, but not limited to springs 916 and 918 are provided to bias the pivot members 911 and 913 into a latched or locked state. In the latched state, one end (the lower end in FIG. 55) of each pivot member 916 and 918 is received within a groove or indentation 32e in the inner surface 32b of the reservoir receptacle 32. In that state, the cap 904b is latched or locked within the reservoir receptacle 32 of the infusion pump device 30, to inhibit removal of the cap 904b (and base/reservoir/cap unit) from the reservoir receptacle 32.

From that state, one end (the upper end in FIG. 55) of each pivot member 916 and 918 may be manually squeezed toward the other pivot member to cause the other end (lower end in FIG. 55) of each pivot member to withdraw from the groove or indentation 32e by a sufficient amount to allow the user (or medical technician or other authorized person) to pull the cap 904b (and base/reservoir/cap unit) from the reservoir receptacle, in the direction of axis A.

Figure 56:
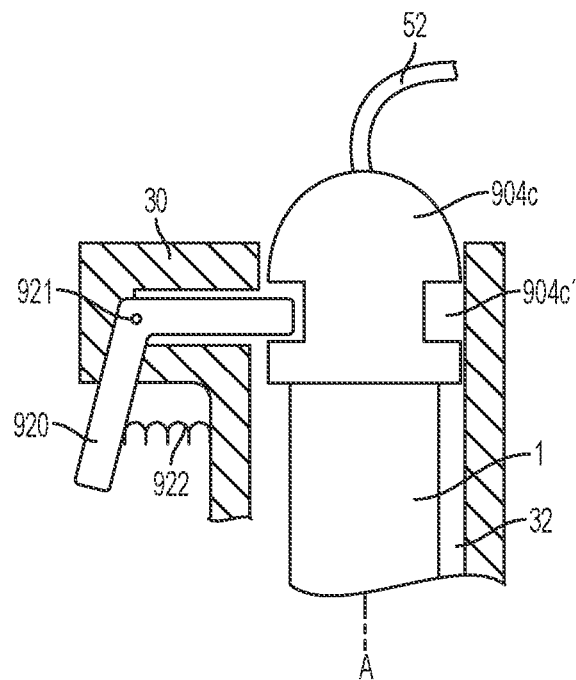
FIG. 56 is a partial side, cross-section view of a portion of a reservoir receptacle of an infusion pump device containing a base/reservoir/cap unit having a cap-to-infusion pump device connection interface according to another embodiment of the present invention.

In a further embodiment as described with reference to FIG. 56, the second releasable coupler includes one or more pivot members 920 that is pivotally connected to the housing of the infusion pump device 30, at a pivot point 921. One or more bias members 922, such as but not limited to a spring, is provided to bias the pivot member(s) 920 into a latched or locked state. In the latched state one end (the lower end in FIG. 55) of each pivot member 916 and 918 is received within a groove or indentation 904c' in the outer surface of the cap 904c. In that state, the cap 904c is latched or locked within the reservoir receptacle 32 of the infusion pump device 30, to inhibit removal of the cap 904c (and base/reservoir/cap unit) from the reservoir receptacle 32.

From that state, one end (the lower end in FIG. 56) of the pivot member 920 may be manually pushed toward the housing of the infusion pump device 30, to cause the other end (upper end in FIG. 56) of the pivot member 920 to withdraw from the groove or indentation 904c by a sufficient amount to allow the user (or medical technician or other authorized person) to pull the cap 904c (and base/reservoir/ cap unit) from the reservoir receptacle, in the direction of axis A. Embodiments described with reference to FIGS. 55-56 may be employed with any one or more of the detection embodiments (magnetic detection, inductive detection, RF detection, mechanical detection, optical detection and electrical contact detection) described above. In such embodiments, the cap 904b or 904c or the reservoir 1 (or both) is provided with one or more detectable elements 42 as described above, while the infusion pump device 30 is provided with one or more sensor elements 34 as described above.

In particular embodiments, one or more detectable elements 42 are arranged on the pivot member(s) 911, 913 or 920, or on the bias members 916, 918 and 922 (or all). In such embodiments, electronics (such as electronics 60) may be configured to detect the relative position of the pivot member(s) or bias member, in addition to or as an alternative to detection of the presence of the cap 904b or 904c (or base/reservoir/cap unit) or other characteristics and information as described above.

In such embodiments, electronics 60 in the infusion pump device may be configured to provide one or more predefined operations, at least partially based on (or in response to) one or more of: (1) a determination that the cap 904b or 904c (or base/reservoir/cap unit) is not properly received within the reservoir receptacle 32, and (2) a determination that the pivot member(s) 911, 913 or 920 are not sufficiently engaged with the groove or indentation 32e or 904c'. Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap 904b or 904c (or base/ reservoir/cap unit) is properly received within the reservoir receptacle 32, and (2) a determination that the pivot member(s) 911, 913 or 920 are sufficiently engaged with the groove or indentation 32e or 904c'. Such predefined operations include, but are not limited to one or more of allowing or providing pumping operation, allowing a predefined pumping operation, providing a predefined message, and recording data indicating the detection.

In a further embodiment as described with reference to FIGS. 57 and 58, the second releasable coupler includes one or more (or a plurality) of biased ball members 930 supported on the infusion pump device 30, and projecting at least partially into the reservoir receptacle 32 of the infusion pump device 30. The ball members 930 are arranged to engage one or more grooves or indentations (one groove is shown at 904d' in FIG. 57) in the outer surface of the housing of the cap 904d, when the cap 904d (or base/ reservoir/cap unit) is installed in the reservoir receptacle 32 of the infusion pump device 30.

h. Push-In Lock with Biased Ball Members

Figure 57:
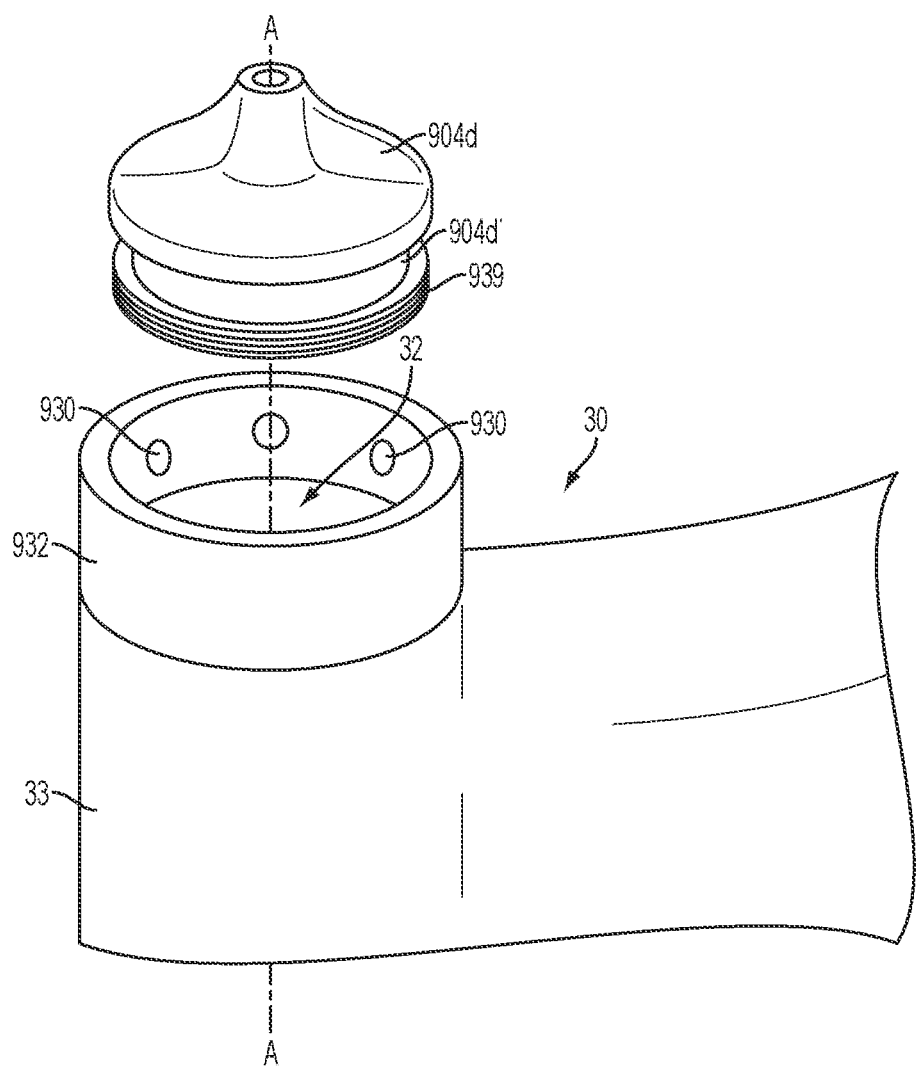
FIG. 57 is an enlarged, partial perspective view of a portion of a reservoir receptacle of an infusion pump device and a cap having a cap-to-infusion pump device connection interface according to another embodiment of the present invention.
Figure 58:
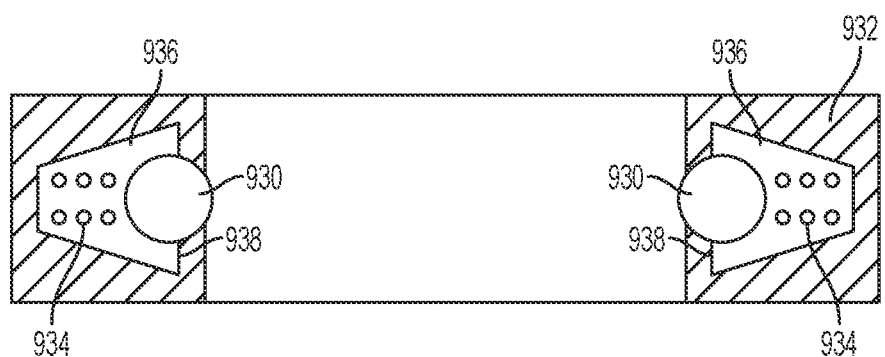
FIG. 58 is an enlarged, side, cross-section view of an upper ring member having a portion of a connection interface of FIG. 57.

In the embodiment in FIGS. 57 and 58, the ball members 930 are supported in an upper ring member 932 on the open end of the reservoir receptacle 32. The upper ring member 932 may be attached to the reservoir receptacle 32 in any suitable attachment mechanism including, but not limited to, welding, glue, resin or other adhesive material, screw threads, friction fit, or the like. The upper ring member 932 may be made of any suitably rigid material, such as but not limited to plastic, metal, ceramic, composite material or combinations thereof. In particular embodiments, the upper ring member 908 corresponds to (or is) the upper ring member 94 discussed above with respect to the embodiment in FIG. 7. In other embodiments, ball members 930 are supported directly in or on the housing 33 of the infusion pump device 30, for example, within or on one or more wall portions that define the reservoir receptacle 32 of the infusion pump device 30.

In particular embodiments, the ball members 930 are biased toward the interior of the reservoir receptacle 32 (toward the axis A), by one or more bias members. In the embodiment in FIGS. 57 and 58, the bias members 934 include springs supported inside of the upper ring member 932, as shown in the cross-section view of FIG. 58. In particular embodiments, the upper ring member 932 includes a ball receptacle 936 in which a ball member 930 and an associated bias member 934 is supported. The receptacle 936 in the embodiment of FIG. 58 has a tapered shape that becomes wider in the direction toward the interior of the reservoir receptacle 32 (or axis A), forming a tapered collar for receiving a ball member.

A lip 938 is provided on the inner-facing end of the receptacle 936, to retain the ball member 930 within the tapered collar of the receptacle 936. The ball member 930 is held within the receptacle 936, but is biased, by the bias member 934, against the lip 938, such that a portion of the ball member 930 extends out of the upper ring member 932, toward the interior of the reservoir receptacle 32. In particular embodiments, the ball member 930 extends into the interior of the reservoir receptacle 32 by a sufficient distance to engage the outer surface of the cap 904 and be received within the groove 904*d*', when the cap 904*d* (or base/reservoir/cap unit) is received within the reservoir receptacle 32.

When biased against the lip 938, the ball member 930 is spaced from the tapered surface of the receptacle 936, but is moveable toward the tapered surface (against the force of the bias member), when a suitable force is applied to the outward extended portion of the ball member.

Accordingly, as the cap 904*d* (or base/reservoir/cap unit) is inserted into the reservoir receptacle 32, the ball members 930 engage and slide or ride along the outer surface of the cap 904*d*, until the ball members 930 engage and are received within the groove 904' of the cap 904*d*. The groove 904*d*' and the ball members 930 are arranged relative to each other, so that the ball members 930 engage and are received within the groove 904*d*', when the cap 904*d* (or base/reservoir/cap unit) reaches its fully installed position within the reservoir receptacle 32.

When engaged with the outer surface of the cap 904 and outside of the groove 904', the ball members 930 are pushed against the bias force of the bias members 934, and move further into the receptacle 936. However, when the ball members 930 are received within the groove 904*d*', the ball members move under the bias force of the bias members 934, toward their extended position. This action causes a portion of the ball members 934 to extend into the groove 904*d*', to retain the cap 904*d* (and base/reservoir/cap unit) in the installed position within the reservoir receptacle 32. To remove the cap 904*d* (and base/reservoir/cap unit) from an installed position within the reservoir receptacle 32, manual force can be applied to pull the cap 904*d* outward from the reservoir receptacle 32 with sufficient force to overcome the bias force of the bias members 934 on the ball members 930 and force the ball members 930 further into the receptacle 936.

In the embodiment of FIGS. 57 and 58, the ball members 930 may be contained within a single ball receptacle 936 that extends annularly within the ring member 932 (or within a wall forming a portion of the reservoir receptacle 32). In other embodiments, each ball member 930 may be contained in a separate receptacle 936. In further embodiments, other shaped members may be used in place of the ball members 930.

In the embodiment of FIGS. 57 and 58, three ball members 930 are shown in view. However, any suitable number of ball members 930 may be employed. In particular embodiments, either four, five or six ball members 930 are employed. In other embodiments, fewer than four or more than six ball members 930 are employed. In addition, the cap 904*d* may include one or more seals 939 (one O-ring seal shown in FIG. 57) on the outer surface of the cap 904*d*, between the groove 904*d*' and the open end of the cap 904*d*. The seal(s) 939 are arranged to engage the inner surface of the reservoir receptacle 32 and provide a moisture seal between the cap 904*d* and the inner surface of the receptacle 32 when the cap 904*d* (or base/reservoir/cap unit) is installed in the reservoir receptacle 32. (Other embodiments of caps described herein may include one or more seals similar to the seal 939.)

Embodiments described with reference to FIGS. 57-58 may be employed with any one or more of the detection embodiments (magnetic detection, inductive detection, RF detection, mechanical detection, optical detection and electrical contact detection) described above. In such embodiments, the cap 904*d* or the reservoir 1 (or both) is provided with one or more detectable elements 42 as described above, while the infusion pump device 30 is provided with one or more sensor elements 34 as described above.

In particular embodiments, one or more detectable elements 42 are arranged on a ball member 930, or on a bias member 934 (or both). In such embodiments, electronics (such as electronics 60) may be configured to detect the relative position of the ball member(s) or bias member(s), in addition to or as an alternative to detection of the presence of the cap 904*d* (or base/reservoir/cap unit) or other characteristics and information as described above.

In such embodiments, electronics 60 in the infusion pump device may be configured to provide one or more predefined operations, at least partially based on (or in response to) one or more of: (1) a determination that the cap 904*d* (or base/reservoir/cap unit) is not properly received within the reservoir receptacle 32, and (2) a determination that the ball member(s) 930 are not sufficiently engaged with the groove 904*d*'. Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: 1) a determination that the cap 904*d* (or base/reservoir/cap unit) is properly received within the reservoir receptacle 32, and (2) a determination that the ball member(s) 930 are sufficiently engaged with the groove 904*d*'. Such predefined operations include, but are not limited to one or more of allowing or providing pumping operation, allowing a predefined pumping operation, providing a predefined message, and recording data indicating the detection.

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

i. Rotatable Ring Lock and Release

Figure 59:
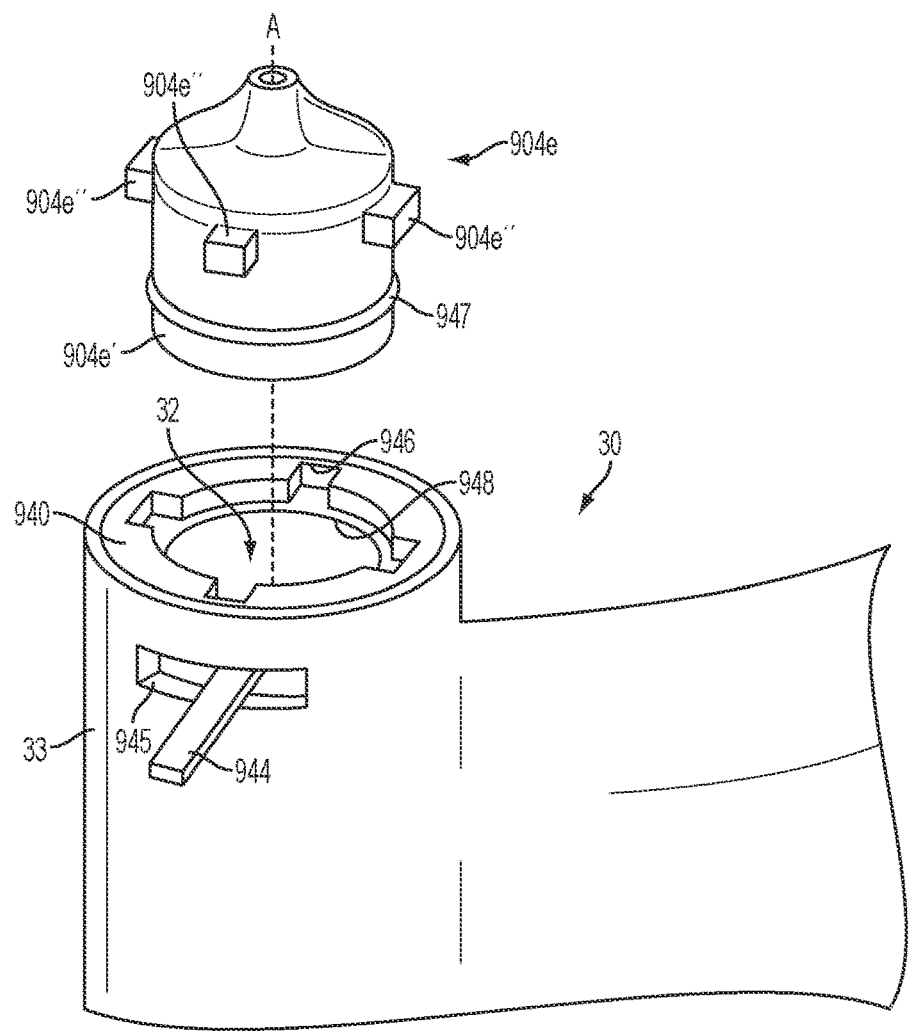
FIG. 59 is an enlarged, partial perspective view of a portion of a reservoir receptacle of an infusion pump device and a cap having a cap-to-infusion pump device connection interface according to another embodiment of the present invention.
Figure 60:
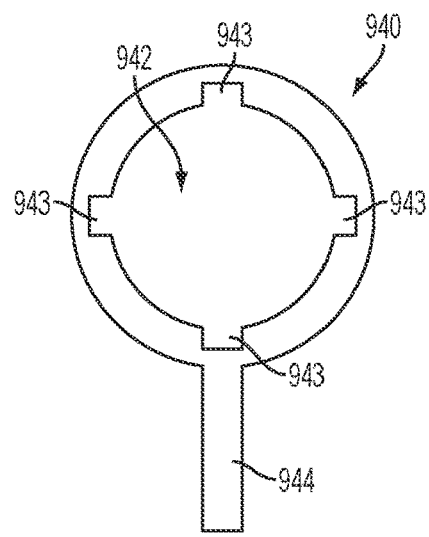
FIG. 60 is an enlarged, top view of rotary ring member of a connection interface of FIG. 59.

In a further embodiment as described with reference to FIGS. 59 and 60, the second releasable coupler includes a rotatable ring member 940 mounted at the open end of the reservoir receptacle 32. In FIG. 59, the rotatable ring member 940 is shown mounted for rotation in the reservoir receptacle 32 of the infusion pump device 30. In FIG. 60, the rotatable ring member 940 is shown separate from the infusion pump device 30.

The rotatable ring member 940 is connected to the infusion pump device 30, but is mounted for rotation around the axis A of the reservoir receptacle 32 (and of the cap 904*e* and base/reservoir/cap unit when installed in the reservoir receptacle 32). For example, an annular edge portion of the rotatable ring member 940 fits within an annular groove in the inner wall of the reservoir receptacle 32 (or in an upper ring member attached thereto), where the groove is dimensioned to receive the annular edge portion of the rotatable ring member 940 and allow rotation of the rotatable ring member 940 about the axis A, relative to the infusion pump device 30. In other embodiments, the rotatable ring member 940 may be mounted for rotation by other suitable rotary coupling mechanisms.

In particular embodiments, the rotatable ring member 940 is formed of a plate having a generally annular shaped portion 941 with a central opening 942 and one or more (or a plurality of) cutouts or slots 943 extending radially outward from the edge of the central opening 942. The embodiment of FIGS. 59 and 60 the rotating ring member 940 also has a handle or lever portion 944 extending radially outward from an outer edge of the annular portion 941. The handle or lever portion 944 extends outward through a slot-shaped (elongated) opening 945 in the infusion pump device 30, in the region of the reservoir receptacle 32, as shown in FIG. 59. The handle or lever portion 944 provides a user interface to allow a user to manually rotate the rotatable ring member 940 relative to the infusion pump device 30, by manually moving the handle or lever portion 944 to one side or the other (to the left or to the right in the drawing of FIG. 59).

The central opening 942 in the rotatable ring member 940 is dimensioned match or correspond to the outer dimension of a body portion 904e' of the cap 904e, to allow the body portion 904e' to pass through the central opening 942, when the cap 904e is inserted into the reservoir receptacle 32, in the direction of the axis A. The cap 904e also includes one or more (or a plurality of) tab portions 904e" extending radially outward from the body portion of the cap 904e. In particular embodiments, the number of tab portions 904e" is equal to or less than the number of cutouts or slots 943 in the rotatable ring 940.

The tab portions 904e" are shaped to align with and fit through the cutouts or slots 943, when the cap 904e (or base/reservoir/cap unit) is inserted into the reservoir receptacle 32. In particular embodiments, the tab portions 904e" also align with and fit in corresponding grooves or slots 946 in the inner surface of the reservoir receptacle 32 (or in an inner surface of an upper ring member attached to the reservoir receptacle 32). In such embodiments, a separate groove or slot 946 in inner wall of the reservoir receptacle 32 is associated with each different one of the cutouts or slots 943 and aligns with a respective one of the cutouts or slots 943, when the cap 904e (or base/reservoir/cap unit) is inserted into the reservoir receptacle 32. When the cap 904e (or base/reservoir/cap unit) is fully inserted into the reservoir receptacle 32 such that the tap portions 904e" have passed through the cutouts or slots 943 in the rotatable ring 940, the tab portions 904e" are abutted against a stop surface or shelf on an interior surface 948 of the reservoir receptacle 32.

Once the cap 904e (or base/reservoir/cap unit) is sufficiently inserted into the reservoir receptacle 32 such that the tab portions 904e" (having passed through the cutouts or slots 943) are located on the stop surface or shelf 948, the rotatable ring member 940 may be rotated to move the cutouts or slots 943 out of alignment with the grooves or slots 946. When the cutouts or slots 943 out of alignment with the grooves or slots 946 (while the tabs 904e" are within the grooves or slots 946, the cap 904e is retained within the reservoir receptacle by the rotatable ring member 940. To release the cap 904e, the rotatable ring member 940 is manually rotated, as described above, to align the cutouts or slots 943 with the grooves or slots 946. When so aligned, the cap 904e may be manually pulled out from the reservoir receptacle 32, such that the tabs 904e pass back through the cutouts or slots 943 as the cap 904e (or base/reservoir/cap unit) is withdrawn from the reservoir receptacle 32.

In particular embodiments, the body portion 904e' of the cap 904e includes one or more (or a plurality of) seal members 947 for sealing against a surface 948 in the reservoir receptacle 32. In the embodiment of FIG. 59, a seal member 947 in the form of an O-ring is provided around the circumference of the body portion 904e' of the cap 904e, between the tabs 904e" and the open end of the cap 904e. The seal member 947 is arranged engage and form a seal against an inner surface of the reservoir receptacle 32 (for example, an inner surface 948 that is raised inward toward the axis A).

In particular embodiments, only caps (such as cap 904e) that have tab portions (such as 904e") that are equal or less in number and arranged in a corresponding pattern as the cutouts or slots 943 in the rotatable ring member 940 are able to be installed within the reservoir receptacle 32 that has the rotatable ring 940. In such embodiments, other caps (not shown) have tab portions that are greater in number or arranged in a different pattern (or both) than the cutouts or slots 943 in the rotatable ring member 940 and, thus, are not able to fit within the reservoir receptacle 32 of the infusion pump device 30 shown in FIG. 59. However, in such embodiments, one or more other infusion pump devices (similar to infusion pump device 30) is provided with a rotatable ring member (similar to rotatable ring member 940), but having cutouts or slots 943 corresponding in number and pattern to the tabs on the other caps, such that, certain caps are configured to fit within certain infusion pump devices (but not others). Accordingly, a cap 904e supplied to a particular user may be configured to correspond to an infusion pump device 30 that is associated with that particular user, but not to an infusion pump device associated with another user. Therefore, a different number and pattern of tabs 904e" and number and pattern of cutouts or slots 943 (among a plurality of possible numbers and patterns) may be associated with each different user (among a plurality of users).

While the embodiment in FIGS. 59 and 60 include four equally spaced cutouts or slots 945 and four corresponding equally spaced tabs 904e", other embodiments may include any other suitable numbers of cutouts or slots 945 and tabs 904e" and/or other suitable spacings thereof.

Figure 61:
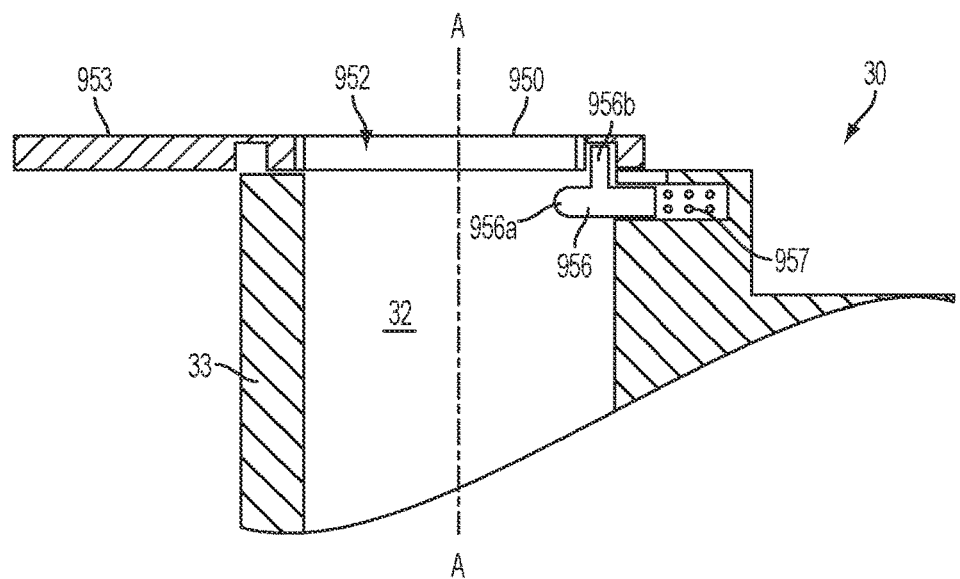
FIG. 61 is an enlarged, partial side, cross-section view of a portion of a reservoir receptacle of an infusion pump device having a cap-to-infusion pump device connection interface according to another embodiment of the present invention.
Figure 62:
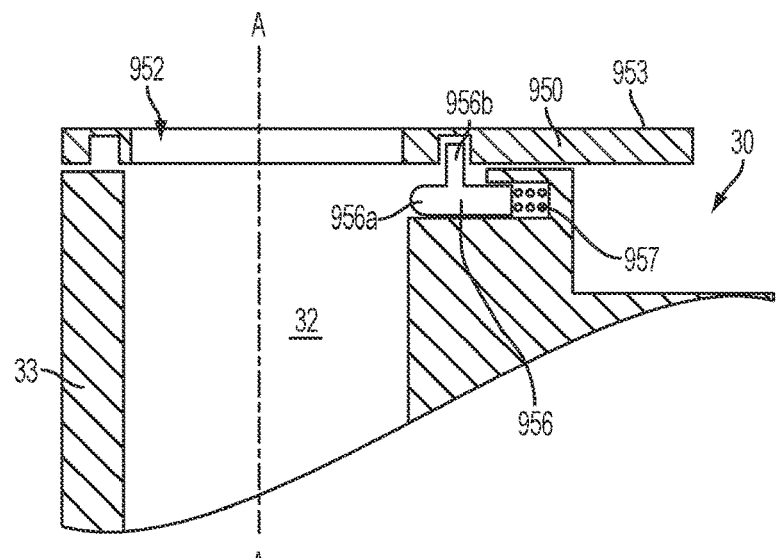
FIG. 62 is an enlarged, partial side, cross-section view of a portion of a reservoir receptacle of an infusion pump device having the cap-to-infusion pump device connection interface of FIG. 61, but in a second rotary position.
Figure 63:
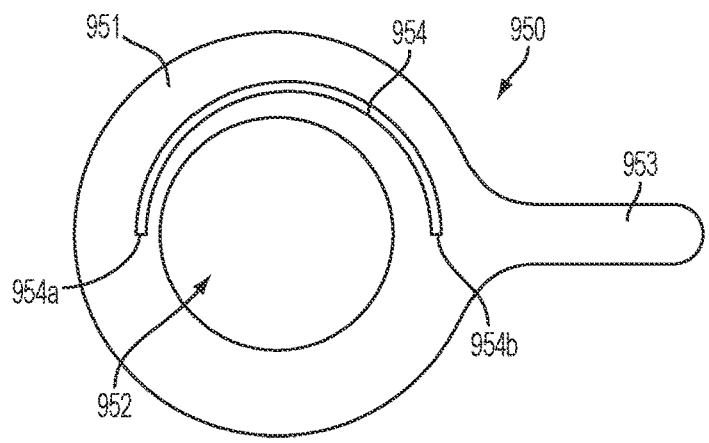
FIG. 63 is an enlarged, top view of rotary ring member of a connection interface of FIGS. 61 and 62.

In a further embodiment as described with reference to FIGS. 61-63, the second releasable coupler includes another form of a rotatable ring member 950 mounted at the open end of the reservoir receptacle 32. In FIG. 61, the rotatable ring member 950 is shown mounted for rotation on the reservoir receptacle 32 of the infusion pump device 30. In FIG. 62, the rotatable ring member 950 is also shown mounted for rotation on the reservoir receptacle 32 of the infusion pump device 30, but rotated 180 degrees relative to the position of the rotatable ring member 950 in FIG. 61. In FIG. 63, the rotatable ring member 950 is shown separate from the infusion pump device 30, with the lower side surface (the surface facing downward in FIGS. 60 and 62) in view.

In the embodiment in FIGS. 61-63, the rotatable ring member 950 has an annular portion 951 with a central opening 952 having a dimension for allowing a cap (or base/reservoir/cap unit) pass through, similar to the central opening 943 in the ring member of FIG. 60. In addition, the rotatable ring member 950 includes a handle or lever portion 953, for manually rotating the ring member, similar to the manner in which handle portion 944 allows for rotation of the ring member 940 in FIG. 60. However, the ring member 950 in FIGS. 61-63 includes a groove or rib feature 954 on one surface (the surface facing downward or towards the reservoir receptacle 32 in FIGS. 61 and 62). The groove or rib feature 954 extends at least partially around the rotatable ring member 950 and forms a partial spiral, where a first end 954a of the groove or rib feature 954 is located radially inward (closer to the axis A) with respect to the second end 954b of the groove or rib feature 954. When the rotatable ring member 950 is mounted for rotation on the reservoir receptacle (as shown in FIGS. 61 and 62), the groove or rib feature 954 faces toward the reservoir receptacle 32.

A moveable pin or locking member 956 is supported by the housing 33 of the infusion pump device 30 for movement between an extended position (shown in FIG. 61) and a retracted position (shown in FIG. 62). In particular embodiments, the moveable pin or licking member 956 is biased by a bias member 957 (such as a spring or the like) toward the extended position. In the extended position (FIG. 61), an end portion 956a of the moveable locking member 956 extends at least partially into the reservoir receptacle 32. In the retracted position (FIG. 62), the end portion 956a of the moveable locking member 956 is retracted out of the reservoir receptacle 32 (or does not extend as far into the reservoir receptacle 32 relative to the extended position).

The moveable locking member 956 has a protrusion or extension 956b that engages the groove or rib feature 954 of the rotatable ring member 950. In FIGS. 61 and 62, the protrusion or extension 956b is shown as extending into a groove 954 in the rotatable ring member 950. The protrusion or extension 956b and the groove or rib feature 954 are configured such that the protrusion or extension 956b rides within or along and is guided by the groove or rib feature 954, as the rotatable ring member 950 rotates (e.g., rotates to and between the positions shown in FIGS. 61 and 62). Because of the spiral shape of the groove or rib feature 954 (extending from a radial inward end 954a to a radial outward end 954b), the moveable locking member 956 is moved to and between the extended and retracted positions shown in FIGS. 61 and 62, as the rotatable ring member 950 rotates to and between the corresponding positions shown in FIGS. 61 and 62.

The moveable locking member 956 is configured to engage a groove, indentation or other stop surface on a cap (or base/reservoir/cap unit), when the cap (or base/reservoir/cap unit) is installed in the reservoir receptacle 32 and the moveable locking member 956 is in the extended position (of FIG. 61). In such embodiments, the cap includes a groove, indentation or other stop surface on the outer surface of the body of the cap (for example, but not limited to a groove similar to the groove 904c' in the cap 904c in FIG. 56, or the groove 904d' in the cap 904d in FIG. 57).

Accordingly, in the embodiment of FIGS. 61-63, to insert a cap (or base/reservoir/cap unit) into the reservoir receptacle 32, the rotatable ring member 950 is rotated to retract the moveable locking member 956 to the retracted position (shown in FIG. 62). With the moveable locking member 956 in the retracted position, the cap (or base/reservoir/cap unit) may be inserted through the opening 952 of the rotatable ring member 950 and at least partially into the reservoir receptacle 32. Once the cap (or base/reservoir/cap unit) is fully inserted into the reservoir receptacle (e.g., to a fully installed position), the rotatable ring member 950 may be rotated to a position as shown in FIG. 61, to move the moveable locking member 956 to the extended position (as shown in FIG. 61). In the extended position, the moveable locking member 956 extends into the groove or indentation (or engages the stop surface) on the cap, to retain the cap (and base/reservoir/cap unit) in the installed position.

To remove the cap (or base/reservoir/cap unit) from the reservoir receptacle, the rotatable ring member 950 is rotated to the position shown in FIG. 62, to move the moveable locking member 956 to the retracted position (as shown in FIG. 62). With the moveable locking member 956 in the retracted position, the cap (or base/reservoir/cap unit) may be withdrawn from the reservoir receptacle 32 by manually pulling the cap (or base/reservoir/cap unit) outward from the reservoir receptacle 32.

Embodiments described with reference to FIGS. 59-63 may be employed with any one or more of the detection embodiments (magnetic detection, inductive detection, RF detection, mechanical detection, optical detection and electrical contact detection) described above. In such embodiments, the cap 904b or 904c or the reservoir 1 (or both) is provided with one or more detectable elements 42 as described above, while the infusion pump device 30 is provided with one or more sensor elements 34 as described above.

In particular embodiments, one or more detectable elements 42 are arranged on the rotatable ring member 940 or 950, on the tabs 904e'', on the moveable locking member 956 or on the bias member 957 (or any combination thereof). In such embodiments, electronics (such as electronics 60) may be configured to detect the relative position of the rotatable ring member, tabs, moveable locking member or bias member, in addition to or as an alternative to detection of the presence of the cap (or base/reservoir/cap unit) or other characteristics and information as described above.

In such embodiments, electronics 60 in the infusion pump device may be configured to provide one or more predefined operations, at least partially based on (or in response to) one or more of: (1) a determination that the cap (or base/reservoir/cap unit) is not properly received within the reservoir receptacle 32, and (2) a determination that the rotatable ring member, movable locking member or bias member is not in a locking position. Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap (or base/reservoir/cap unit) is properly received within the reservoir receptacle 32, and (2) a determination that the rotatable ring member, movable locking member or bias member is in a locking position. Such predefined operations include, but are not limited to one or more of allowing or providing pumping operation, allowing a predefined pumping operation, providing a predefined message, and recording data indicating the detection.

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

j. Pawl Push-In Lock with Pinch Release

In a further embodiment as described with reference to FIGS. 64-66, the second releasable coupler includes one or more (or a plurality) of latch pawls that are arranged on the cap 964, to engage one or more corresponding ribs, grooves, openings, projections or other stop surface structures located on the housing 33 of the infusion pump device, but outside of the reservoir receptacle. When the latch pawls are engaged with the stop surface structures, the latch pawls secure the cap 964 to the housing 33 of the infusion pump device 30. In such embodiments, the cap 964 may be configured of a sufficiently flexible and resilient material (plastic or other suitable material) that can be flexed by manual pressure, to selectively move the latch pawl(s) out of engagement with the stop surface structure(s) on the infusion pump device 30. In such embodiments, when the cap 4 is secured to the housing of the infusion pump device 30, the cap 964 may be squeezed to release the cap 4 from the housing 33.

Figure 64:
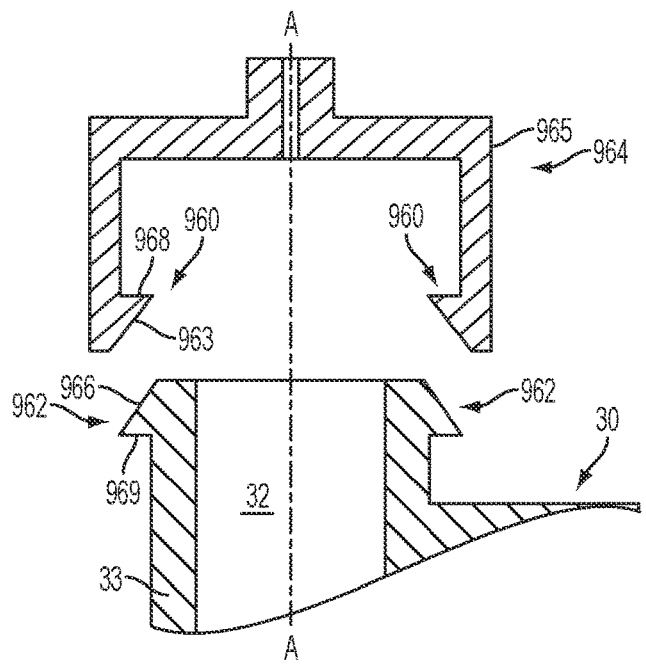
FIG. 64 is an enlarged, partial, side, cross-section view of a portion of a reservoir receptacle of an infusion pump device and a cap having a cap-to-infusion pump device connection interface according to another embodiment of the present invention.
Figure 65:
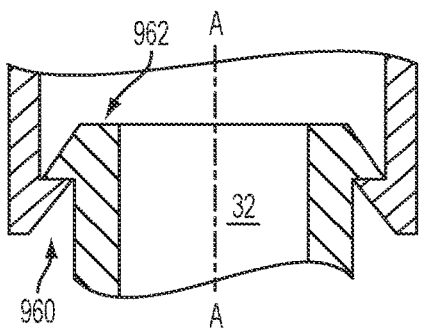
FIG. 65 is an enlarged, side, cross-section view of a portion of the cap of FIG. 64 connected, through the connection interface, to a portion of the infusion pump device of FIG. 64.
Figure 66:
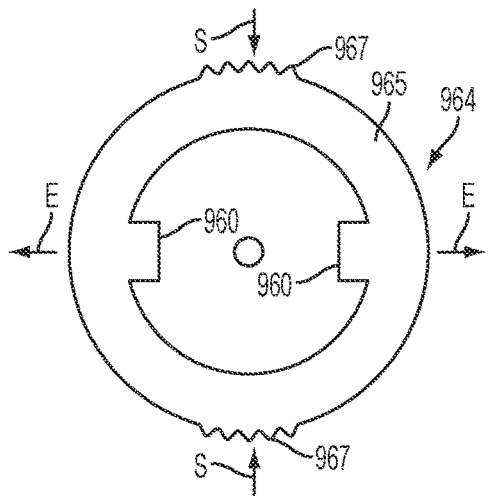
FIG. 66 is an enlarged, bottom view of the cap of FIGS. 64 and 65.

For example, in the embodiment of FIGS. 64-66, a cap 964 is provided with a body portion 965 that is sufficiently flexible and resilient to allow a user to manually squeeze the body portion 965 and cause the body portion 965 to compress in one dimension (the dimension in which the squeezing force is directed) and, as a result, to expand in a second dimension (e.g., a dimension substantially perpendicular to the one dimension). Thus, for example, upon applying a squeezing force in a first dimension (directed into and out of the page in FIG. 64 and directed in the dimension of the arrows S in FIG. 66), the body portion 965 of the cap 964 expands in a second dimension (directed to the right and left in FIG. 64, and directed in the dimension of arrows E in FIG. 66).

Also in the embodiment of FIGS. 64-66, the cap 964 includes a plurality of latch pawls 960 (two latch pawls 960 in the illustrated embodiment) provided on the flexible body portion 965 of the cap 964. While two latch pawls 960 are shown in FIGS. 64-66, other embodiments may have more than two latch pawls spaced around the inner periphery of the cap 964. In the illustrated embodiment, the latch pawls 960 are formed with the cap body 965, as a single, integral structure, such as, but not limited to, a molded structure. In other embodiments, the latch pawls 960 are separate elements that are attached to the cap body 965.

In the embodiment of FIGS. 64-66, the cap body 965 has an open interior and an open end (the downward facing end in FIG. 64) that has an inner diameter that is sufficiently large enough to fit over and outside of an end portion of the reservoir receptacle 32 (or over an upper ring member secured to the end portion of the reservoir receptacle 32, as described above), as shown in FIG. 65. When fitted over the end portion of the reservoir receptacle 32 (or upper ring portion on the reservoir receptacle 32), the pawls 960 engage with a stop surface 962 on the housing 33 of the infusion pump device 30 (or on the upper ring portion), to secure the cap 4 (or base/reservoir/cap unit) to the infusion pump device 30.

In particular embodiment, the pawls 960 have an engagement surface 963 that is configured to engage a further engagement surface 966 on the stop surface 962. The diameter of the body 965 of the cap 964 (at least at the open end of the cap 964) is dimensioned such that the stop surface 964 of each pawl 960 engages the engagement surface 966 of the stop surface 962, when the cap body 965 is placed over the open end of the reservoir receptacle 32. Once the engagement surfaces 963 and 966 are engaged, further movement of the cap 964 toward the reservoir receptacle 32 causes the engagement surface 966 to force the pawls 960 radially outward, as the cap 4 (or base/reservoir/cap unit) is moved toward an installed position with respect to the reservoir receptacle 32. The flexible material of the body 965 of the cap 964 allows the pawls 960 to move radially outward under the force of the engagement surface 966, as the cap 4 (or base/reservoir/cap unit) is moved further toward the installed position, until the pawls 960 clear (pass) the engagement surface 966. Once the pawls 960 clear (pass) the engagement surface 966, the resiliency of the material of the cap body 965 causes the cap body 965 to contract slightly in the dimension in which the pawls 960 are located, so that the pawls 960 move (or snap) back toward each other, to engage the housing 33 of the infusion pump device 30, below the stop surface 962. In that arrangement, the pawls 960 retain the cap 4 on the housing 33 of the infusion pump device 30.

From the installed position (shown in FIG. 65), the cap 964 may be selectively removed from the housing 33 of the infusion pump device 30, by applying a squeezing force on the cap body 965 at a position to expand the cap body 965 in the dimension in which the pawls 960 are located, to selectively move the pawls 960 out of engagement with the stop surface 962. In particular embodiments, the cap body 5 includes surface features 967 at locations at which a squeezing force can be applied (in the direction of arrows S) to selectively expand the cap body 965 (in the direction of arrows E) to release the pawls 960 from the stop surface 962. In this manner, a relatively easy-to-use, and cost efficient connection structure may be provided for selectively connecting a cap 964 (or base/reservoir/cap unit) to the reservoir receptacle 32 of the infusion pump device 30. In particular embodiments, the surface features 967 provide a visually perceptible or a tactile surface to help a user determine locations to apply a squeezing force on the cap body 965, to selectively move the pawls 960. In further embodiments, the surface features 967 may include a series of bumps, ridges, grooves or combinations thereof, or other surface features or added materials that increase friction between a user's fingers and the cap body 965 (relative to other portions of the cap body 965).

In the embodiment in FIGS. 64-66, one or both of the engagement surfaces 963 and 966 of the pawl 960 and the stop surface 962 has a tapered or sloped surface (sloped relative to the axis A or direction of motion of the cap 964 relative to the infusion pump device 30 as the cap 964 is installed in the reservoir receptacle), to help to cause the pawls 960 to move radially outward when the engagement surfaces 963 and 966 are engaged and pressed together with sufficient force. In addition, one or both of the pawl 960 and the stop surface 962 may include a second engagement surface 968 and 969, respectively, that engage each other when the cap 964 (or base/reservoir/cap unit) is in an installed position, as shown in FIG. 65. The second engagement surfaces 968 and 969 are configured to inhibit separation of the cap 964 from the housing 33 of the infusion pump device unless the pawls 960 are moved radially outward a sufficient distance (by squeezing the cap body 965 in the direction of arrows S). In particular embodiments, the second engagement surfaces 968 and 969 are substantially perpendicular to the axis A. In other embodiments, the engagement surfaces of the pawls 960 and the stop surface 962 have other suitable configurations to allow selective engagement, retention when engaged and selective disengagement, as described above.

Embodiments described with reference to FIGS. 64-66 may be employed with any one or more of the detection embodiments (magnetic detection, inductive detection, RF detection, mechanical detection and optical detection) described above. In such embodiments, the cap 964 is provided with one or more detectable elements 42 as described above, while the infusion pump device 30 is provided with one or more sensor elements 34 as described above.

In particular embodiments, one or more detectable elements 42 are arranged on the pawls 960. In such embodiments, electronics (such as electronics 60) may be configured to detect the relative position of the pawls 960, in addition to or as an alternative to detection of the presence of the cap (or base/reservoir/cap unit) or other characteristics and information as described above.

In such embodiments, electronics 60 in the infusion pump device may be configured to provide one or more predefined operations, at least partially based on (or in response to) one or more of: (1) a determination that the cap (or base/reservoir/cap unit) is not properly received within the reservoir receptacle 32, and (2) a determination that the pawls 960 are not in a locking position (or cap-installed position). Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap (or base/reservoir/cap unit) is properly received within the reservoir receptacle 32, and (2) determination that the pawls 960 are in a locking position (or cap-installed position). Such predefined operations include, but are not limited to one or more of allowing or providing pumping operation, allowing a predefined pumping operation, providing a predefined message, and recording data indicating the detection.

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

k. Push-In Lock with Expandable Ring Member

In a further embodiment as described with reference to FIGS. 67-68, the second releasable coupler includes an expandable ring member 970 that is arranged in or on the reservoir receptacle 32 of the infusion pump device 30 (or in or on an upper ring member attached to the reservoir receptacle 32 as described herein). The expandable ring member 970 is arranged to be engaged by an engagement feature 972 on the cap 974 (or base/reservoir/cap unit), as the cap 974 (or base/reservoir/cap unit) is moved into the reservoir receptacle 32 of the infusion pump device 30. In such embodiments, the expandable ring member 970 expands to allow the engagement feature 972 on the cap 974 to move through a gap 973 in the ring member 970 and clear (pass) the ring member 970, as the cap 974 (or base/reservoir/cap unit) is moved into the reservoir receptacle 32, toward an installed position. Once the engagement feature 972 clears (passes) through the gap 973 in the ring member 970, the ring member 970 contracts back to its original (unexpanded) state and inhibits the engagement feature 972 from passing back through the gap 973, to retain the cap 974 (or base/reservoir/cap unit) in the reservoir receptacle 32.

Figure 67:
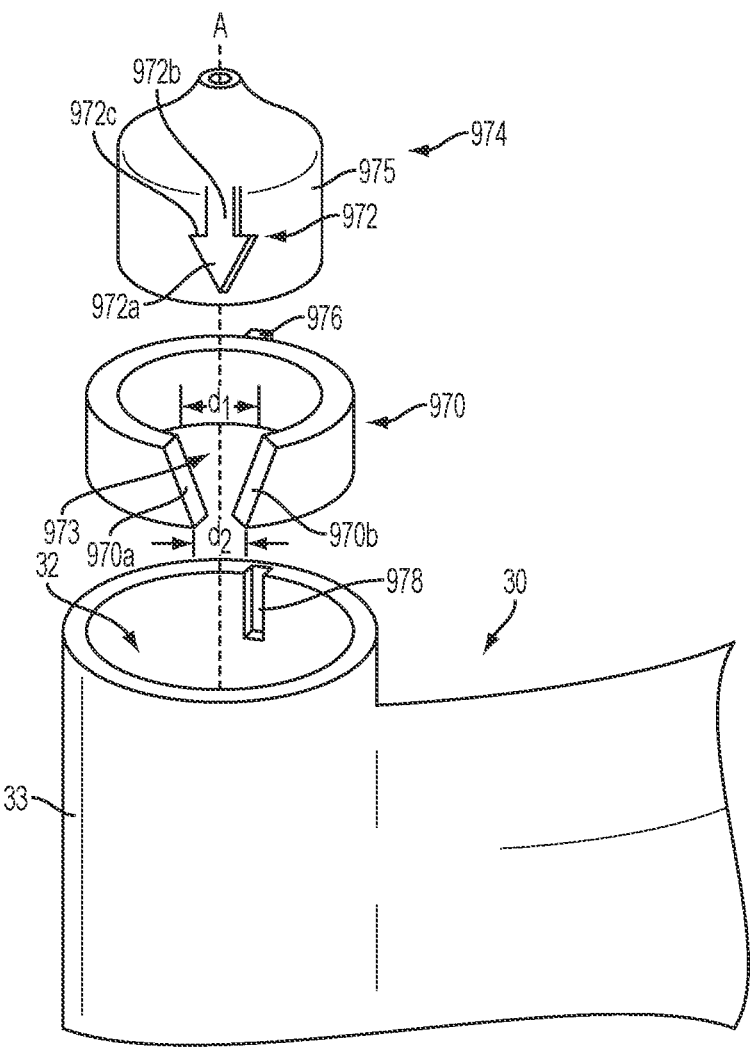
FIG. 67 is an enlarged, partial exploded, partial perspective view of a portion of a reservoir receptacle of an infusion pump device and a cap having a cap-to-infusion pump device connection interface according to another embodiment of the present invention.
Figure 68:
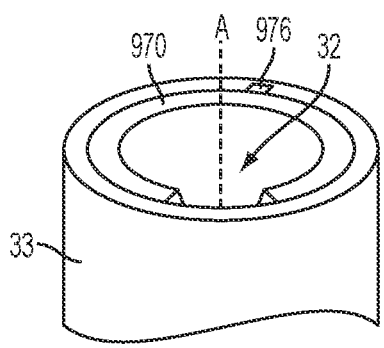
FIG. 68 is an enlarged, partial perspective view of a portion of a reservoir receptacle of an infusion pump device of FIG. 67, with the ring member of the connection interface within the reservoir receptacle.

In the embodiment of FIGS. 67-68, the expandable ring member 970 has a generally annular shape, with a gap 973 provided between two ends 970*a* and 970*b*. The ring member 970 is made of a material that is resiliently expandable and can expand from a first state to open the gap 973 further (increase the width of the gap 973) relative to the first state when a sufficient force is applied to the two ends 970*a* and 970*b* of the ring member 970 in a direction of spreading the two ends 970*a* and 970*b* apart. In addition, the ring member 970 is sufficiently resilient, to return to its first state (unexpanded state), when the force is released from the two ends 970*a* and 970*b* of the ring member 970. The ring member 970 may be made of any suitable material that is sufficiently flexible and resilient to expand and contract as described herein, such as, but not limited to a spring metal or other metal, plastic, ceramic or composite material, or any combination thereof.

The ring member 970 is held within the reservoir receptacle 32 and, in particular embodiments, is fixed to the interior surface of the reservoir receptacle 32 (or to an upper ring member attached to the upper end of the reservoir receptacle). The ring member 970 may be secured to the housing 33 of the infusion pump device 30 (or upper ring member) by any suitable securing mechanism and, in particular embodiments, is keyed with the housing 33 of the infusion pump device 30 to inhibit rotation of the ring member 970 relative to the housing 33. In the illustrated embodiment, the ring member 970 includes a key tab or protrusion 976 that fits within a correspondingly shaped key slot or indentation 978 in the housing 33 of the infusion pump device 30, to inhibit rotation of the ring member 970. In other embodiments, the placement of the key tab and the key slot is reversed, such that the key tab is on the housing 33 and the key slot is on the ring member 970. In other embodiments, other suitable keyed engagement features are provided on the ring member 970 and the housing 33 of the infusion pump device 30, to inhibit rotation of the ring member 970.

In the embodiment of FIG. 67, the engagement feature 972 on the cap 974 includes a protruding portion that protrudes outward from the surface of the cap housing 975. The protruding portion of the engagement feature 972 includes a tapered section 972*a* that has a relatively smaller width or pointed end toward the open end of the cap 974 (the lower end of the cap 974 in FIG. 67) and increases in width toward the port 6 end of the cap 974. In the illustrated embodiment, the tapered section 972*a* has a triangular or arrow-head like shape. Also in the illustrated embodiment, the protruding portion of the engagement feature 972 includes a generally linear section 972*b* that extends from the tapered section 972*a*, toward the port 6 end of the cap 974. The generally linear section 972*b* has a width dimension that is greater than the width of the smallest width or pointed end of the tapered section 972*a*, and smaller than the greatest width end of the tapered section 972*a*. In particular embodiments, the engagement feature 972 is formed with the rest of the body 975 of the cap 974, as a single, integrated structure, for example, but not limited to, a molded structure. In other embodiments, the engagement feature 972 is a separate element that is attached to the body 975 of the cap 974.

The tapered section 972*a* of the engagement feature 972 is configured to fit into and through the gap 973, as the cap 974 (or base/reservoir/cap unit) is moved into the reservoir receptacle 32, toward an installed position. The tapered shape of the tapered section 972*a* helps to align the tapered section 972*a* with the gap 973 (and to align the cap 974 or base/reservoir/cap unit in a proper installation alignment position with the infusion pump device 30. The widest end of the tapered section 972*a* (the end closes to the port 6 end of the cap 4) has a stop surface 972*c* that engages the ring member 970, after the tapered section 972*a* passes through the gap 973. The stop surface 972*c*, when engaged with the ring member 970, inhibits removal of the cap 974 (or base/reservoir/cap unit) from the reservoir receptacle 32. When the tapered section 972*a* is passed through the gap 973, the linear section 972*b* of the engagement feature is disposed within the gap 973 and inhibits rotation of the cap 974 (and base/reservoir/cap unit) relative to the ring member 970 (and, thus, relative to the infusion pump device 30).

In the embodiment of FIGS. 67-68, the ends 970a and 970b on either side of the gap 973 are tapered or sloped relative to the direction of the axis A. As shown in FIGS. 67-68, the tapered or sloped ends 970a and 970b form a gap 973 that has a first width $d_1$ and a second width $d_2$, where the first width $d_1$ is located further into the reservoir receptacle 32 and is smaller than the second width $d_2$. The tapered or sloped ends 970a and 970b further help to align the engagement feature 972 on the cap 974 with the gap 974 and help to convert linear motion of the cap 974 (or base/reservoir/cap unit) in the installation direction of axis A into a force to expand the ring member 970, as the engagement feature 972 passes through the gap 973.

In particular embodiments, the ring member 970 is provided with one or more arms or levers (not shown) or other features that are manually operable by a user to selectively expand the gap 973. In such embodiments, once the cap 974 (or base/reservoir/cap unit) has been installed in the reservoir receptacle 32 such that the engagement feature 972 has passed through the gap 973 in the ring member 970, the ring member 970 may be selectively expanded (with manual force on the arms or levers) to allow the cap 974 to be manually pulled outward from the reservoir receptacle 32 to remove the cap 974 (or base/reservoir/cap unit) from the reservoir receptacle 32.

Embodiments described with reference to FIGS. 67-68 may be employed with any one or more of the detection embodiments (magnetic detection, inductive detection, RF detection, mechanical detection, optical detection and electrical contact detection) described above. In such embodiments, the cap 974 is provided with one or more detectable elements 42 as described above, while the infusion pump device 30 is provided with one or more sensor elements 34 as described above.

In particular embodiments, one or more detectable elements 42 are arranged on the ring member 970 or the engagement feature 972 (or both). In such embodiments, electronics (such as electronics 60) may be configured to detect the relative position of the ring member 970 or engagement feature 972, in addition to or as an alternative to detection of the presence of the cap (or base/reservoir/cap unit) or other characteristics and information as described above.

In such embodiments, electronics 60 in the infusion pump device may be configured to provide one or more predefined operations, at least partially based on (or in response to) one or more of: (1) a determination that the cap (or base/reservoir/cap unit) is not properly received within the reservoir receptacle 32, and (2) a determination that the ring member 970 or engagement feature 972 is not in a locking position (or cap-installed position). Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap (or base/reservoir/cap unit) is properly received within the reservoir receptacle 32, and (2) determination that the ring member 970 or engagement feature 972 is in a locking position (or cap-installed position). Such predefined operations include, but are not limited to one or more of allowing or providing pumping operation, allowing a predefined pumping operation, providing a predefined message, and recording data indicating the detection.

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

l. Slot and Tab Connection

In a further embodiment as described with reference to FIGS. 69-71, the second releasable coupler includes a compressible ring member 980 that is held within the interior of the reservoir receptacle 32 of the infusion pump device 30, adjacent the open end of the reservoir receptacle 32. In the illustrated embodiment, the compressible ring member 980 fits within an annular groove or notch 981 provided on the inner surface of the reservoir receptacle 32. The compressible ring member 980 has an uncompressed state (shown in FIG. 69) and a compressed state (shown in FIG. 70). In the uncompressed state (FIG. 69), the compressible ring member 980 includes a central opening 980a through which at least a portion of the cap 984 (or base/reservoir/cap unit) pass, as the cap 984 (or base/reservoir/cap unit) is installed in or withdrawn from the reservoir receptacle 32. The compressible ring member 980 may be made of any suitable compressible material, such as, but not limited to, a resiliently compressible rubber, silicone rubber, or plastic material, or the like.

An upper ring member 982 is configured to fit over the open end of the reservoir receptacle 32 and includes threads 983 (or other suitable connection structure) to secure to the outer surface of the housing 33 of the infusion pump device 30, adjacent the open end of the reservoir receptacle 32, for example. The upper ring member 982 may be made of any suitably rigid material such as, but not limited to a generally rigid plastic, metal, ceramic, wood or composite material, or any combination thereof. The upper ring member 982 includes a central opening 982a through which at least a portion of the cap 984 (or base/reservoir/cap unit) pass, as the cap 984 (or base/reservoir/cap unit) is installed in or withdrawn from the reservoir receptacle 32. The upper ring member 982 also includes a ledge or lip portion 982b that surrounds the central opening 982a and overlaps and abuts at least a portion of the compressible ring member 980.

The threads 983 on the upper ring member 982 are arranged to threadingly engage corresponding threads 986 on the outer surface of the housing 33 of the infusion pump device 30, around the open end of the reservoir receptacle 32. Accordingly, the upper ring member 982 secures to the housing 33 of the infusion pump device 30 (via threads 983 and 986, or other suitable connection structure) and helps retain the compressible ring member 980 within the groove or notch 981 in the reservoir receptacle 32. Furthermore, as described herein the upper ring member 982 may be rotated about the axis A in a first direction and selectively threaded further onto the housing 33 to selectively compress the compressible ring member 980 between the ridge or lip 982b of the upper ring member 982 and the groove or notch 981 in the reservoir receptacle 32. From that state, the upper ring member 982 may be rotated about the axis A in a second direction opposite to the first direction, to selectively decompress the compressible ring member 980.

Figure 69:
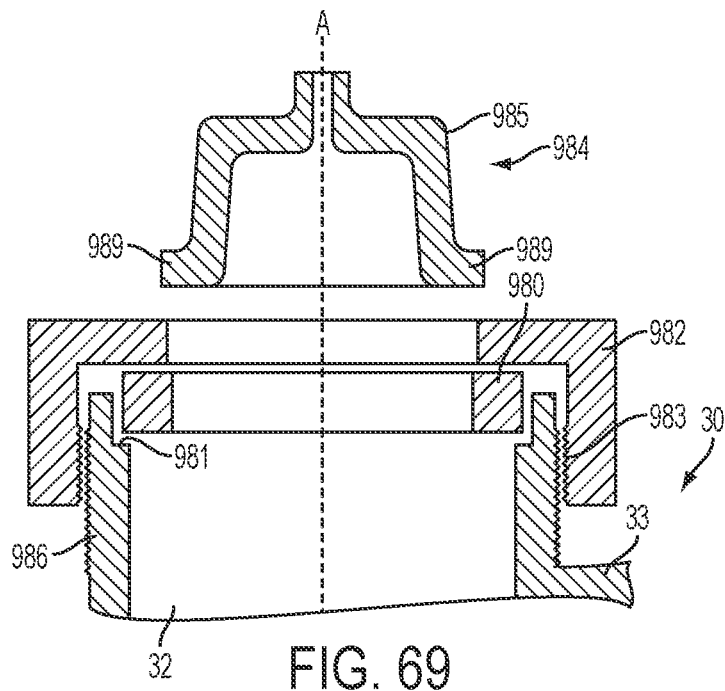
FIG. 69 is an enlarged, partial side, cross-section view of a cap and a portion of a reservoir receptacle of an infusion pump device having a cap-to-infusion pump device connection interface according to another embodiment of the present invention.

When the compressible ring member 980 is in an uncompressed state (as shown in FIG. 69), the central opening 980a in the compressible ring member 980 has a diameter large enough (e.g., larger than the outer diameter of the cap 984 and base/reservoir/cap unit) to allow the cap 984 (and base/reservoir/cap unit) to pass at least partially through the central opening 980a, to install or withdraw the cap 984 (or base/reservoir/cap unit) to or from the reservoir receptacle 32. In the uncompressed state, the cap 984 (or base/reservoir/cap unit) may be moved into the reservoir receptacle 32, by passing the cap (or base/reservoir/cap unit) through the central openings 980a and 982a in the compressible ring member 980 and the upper ring member 982, to a position at which a portion of the body 985 of the cap 984 is laterally adjacent to the compressible ring member 980. Then, the upper ring member 982 is rotated in a direction to compress the compressible ring member 980 in the direction of the axis A.

Figure 70:
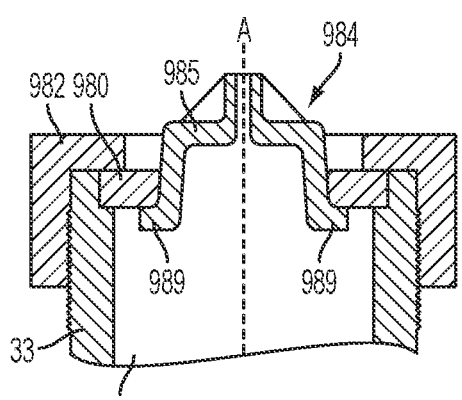
FIG. 70 is an enlarged, partial side, cross-section view of a cap within a portion of a reservoir receptacle of an infusion pump device of FIG. 69.
Figure 71:
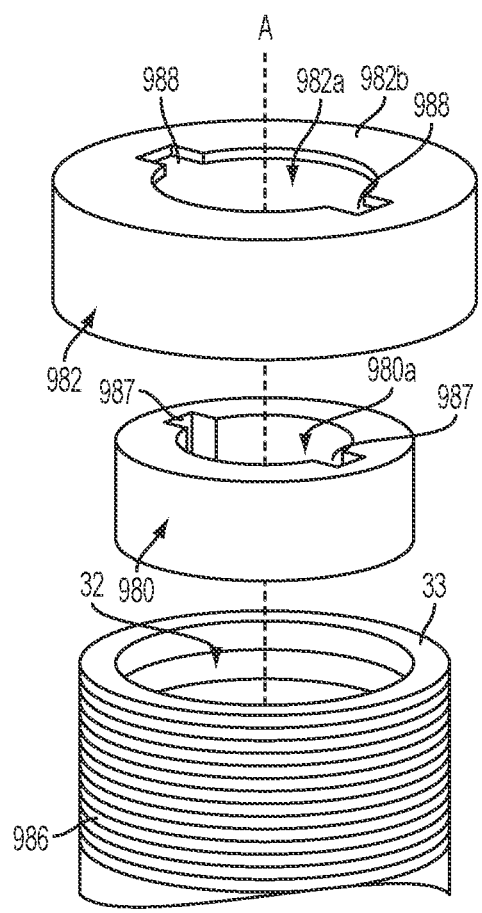
FIG. 71 is an enlarged, exploded perspective view of a portion of a reservoir receptacle of an infusion pump device of FIG. 69.

When the compressible ring member 980 is in a compressed state (as shown in FIG. 70), the compressible ring member 980 is compressed in the direction of the axis A, but is expanded inward toward the axis A, to reduce the diameter of the central opening 980a. By threading the upper ring member 982 a sufficient amount onto the housing 33 of the infusion pump device 30, the upper ring member 982 compresses the compressible ring member 980 to reduce the diameter of the central opening 980a by an amount to cause the ring member 980 to engage and abut the outer surface of the cap body 985 with sufficient force to retain the cap 984 (or base/reservoir/cap unit) within the reservoir receptacle 32 (as shown in FIG. 70).

In particular embodiments, one or both of the upper ring member 982 and the compressible ring member 980 is provided with one or more (or a plurality) of notches or slots 988 and 987, respectively, that have a shape and size that receive a corresponding one or more (or a plurality) of tabs or protrusions 989 on the body 985 of the cap 984. In the illustrated embodiment, the upper ring member 982 and the compressible ring member 980, each have two slots, while the cap 984 has two corresponding tabs 989. In other embodiments, more than two slots and tabs may be provided on the respective components. In yet other embodiments, the locations of the slots and tabs are reversed, such that the slots are on body 985 of the cap 984 and the tabs or projections are on the upper ring member 982 and the compressible ring member 980. The slots and tabs help to align the cap 984 (and base/reservoir/cap unit) in a predefined rotational position relative to the axis A, during installation or removal of the cap 984 (or base/reservoir/cap unit) in or from the reservoir receptacle 32. Accordingly, the slots and tabs may be arranged to orient the cap 984 (and base/reservoir/cap unit) in a proper rotational or angular orientation relative to the axis A, when the cap 984 (or base/reservoir/cap unit) is installed in the reservoir receptacle 32.

In a further embodiment as described with reference to FIGS. 72 and 73, the second releasable coupler includes an upper ring member 990 that is attached to the open end of the reservoir receptacle 32 of the infusion pump device 30, for example, in a manner similar to the manner in which other upper ring members described herein are attached to the infusion pump device, or other suitable manner. The upper ring member 990 includes a central opening 990a, through which at least a portion of the cap 994 (or base/reservoir/cap unit) pass, as the cap 994 (or base/reservoir/cap unit) is installed in or withdrawn from the reservoir receptacle 32. The upper ring member 990 may be made of any suitably rigid material such as, but not limited to a generally rigid plastic, metal, ceramic, wood or composite material, or any combination thereof.

Figure 72:
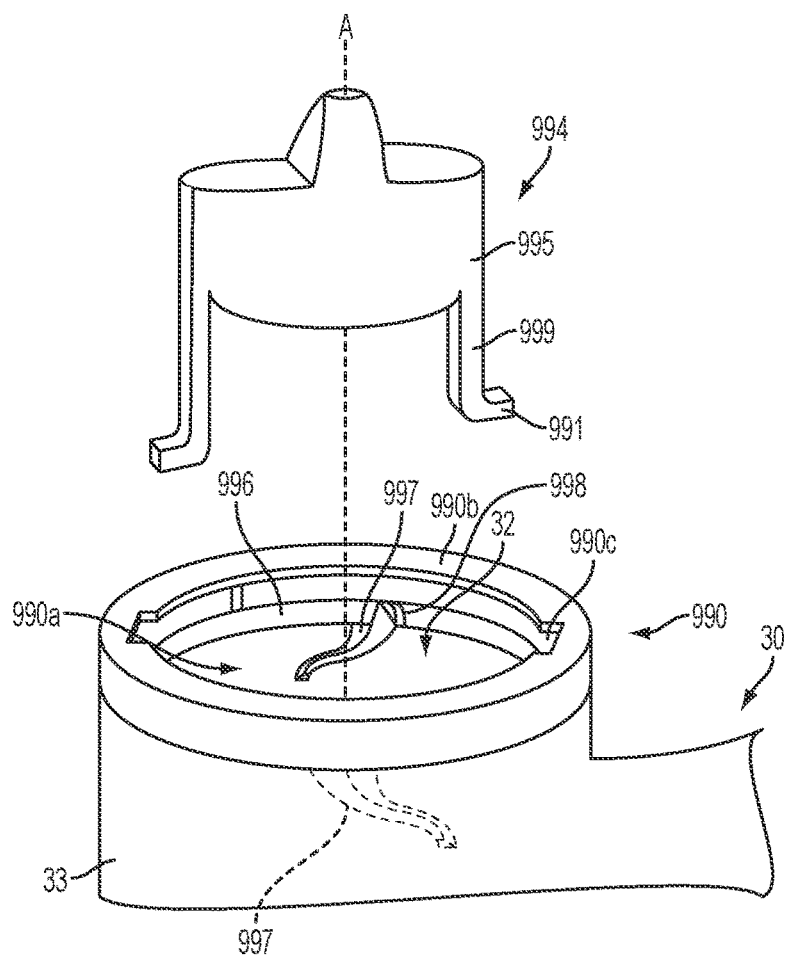
FIG. 72 is an enlarged, partial perspective view of a cap and a portion of a reservoir receptacle of an infusion pump device having a cap-to-infusion pump device connection interface according to another embodiment of the present invention.

In the embodiment of FIG. 72, the upper ring member 990 has a ridge or lip portion 990b provided with one or more (or a plurality) of notches or slots 990c, respectively, that have a shape and size that receive a corresponding one or more (or a plurality) of tabs or protrusions 991 on the body 995 of the cap 994, when the cap 994 (or base/reservoir/cap unit) is passed at least partially through the central opening 990a of the upper ring member 990. In the illustrated embodiment, the upper ring member 990 has two slots, while the cap 994 has two corresponding tabs 991. In other embodiments, more than two slots and tabs may be provided on the respective components.

In the embodiment of FIG. 72, the portion of the housing 33 of the infusion pump device 30 that defines the interior wall of the reservoir receptacle 32 is provided with an annular shelf 996 and one or more (or a plurality) of channels 997 extending through the annular shelf 996 and into the interior wall of the reservoir receptacle 32 below the annular shelf 996. The annular shelf 996 extends around the axis A and may be formed as part of the upper rim of the housing 33 at the reservoir receptacle, or may be formed as a further surface feature on the inner wall of the reservoir receptacle 32 below the upper rim of the housing 33. In the embodiment of FIG. 72, two channels 997 are provided (one shown in view, and the other out of view but shown in broken lines as if being viewed through the housing 33 of the infusion pump device 30). In other embodiments, more than two channels 997 may be provided.

To install the cap 994 (or base/reservoir/cap unit) in the reservoir receptacle 32, the cap 994 (or base/reservoir/cap unit) is moved along the direction of the axis A, through the opening 990 in the upper ring member 990. As the cap 994 is moved along the direction of the axis A, the cap 994 is manually rotated about the axis A to align the tabs 991 on the cap 994 with the slots 990c in the upper ring member 990, so that the tabs 991 pass through the slots 990c. Once the tabs 991 pass through the slots 990c, the tabs 991 engage the shelf 996 and inhibit further movement of the cap 994 into the reservoir receptacle 32, until the tabs 991 are aligned with the open ends of the channels 997. More specifically, once the tabs are engaged with the shelf 996, the cap 994 is manually rotated further manually rotated about the axis A, while the tabs ride along the top of the shelf 996, to align the tabs 991 with the open ends of the channels 997. In particular embodiments, one or more protrusions, walls or other features 998 is provided at one or more locations along the shelf 996, to be engaged by the tabs 991 and stop further rotational motion of the cap 994 (or base/reservoir/cap unit) in one direction around the axis A. The stop feature(s) 998 inhibit further rotation in one direction, to help the user align the tabs 991 with the open ends of the channels 997.

Once the tabs 991 are aligned with the open ends of the channels 997, the cap 994 (and base/reservoir/cap unit) is manually moved in the direction of axis A, further into the reservoir receptacle 32, toward a fully installed position. As shown in FIGS. 72, the channels 997 extend from their open ends, downward, further into the reservoir receptacle 32 and partially around the axis A. Accordingly, the tabs 991 follow the channels 997 downward and partially around the axis A, as the cap 994 (and base/reservoir/cap unit) is rotated partially about the axis A and moved toward an installed position.

When the tabs 991 reach the lower end of the channels 997, the cap 994 (and base/reservoir/cap unit) is in the fully installed position within the reservoir receptacle 32. In particular embodiments, the lower end of the channels 997 includes a further recess or stop surface that is engaged by the tabs 991, when the tabs reach the lower end of the channels 997, and provides tactile feedback to the user, indicating that the tabs 991 have reached the end of the channels 997 (and the cap or base/reservoir/cap unit is in the fully installed position).

From the fully installed position, the cap 994 (and base/reservoir/cap unit) may be removed from the reservoir receptacle by manually rotating the cap 994 about the axis A in a direction to cause the tabs 991 to follow the channels 997 toward the open end of the channels 997, while simultaneously pulling the cap 994 outward from the reservoir receptacle 32. When the tabs 991 reach the open ends of the channels 997, the cap 994 is further manually rotated about the axis A to align the tabs 991 with the slots 990c. Once the tabs 991 are aligned with the slots 990c, further pulling of the cap 994 outward from the reservoir receptacle 332 causes the cap 994 (and base/reservoir/cap unit) to be withdrawn from the reservoir receptacle 332, through the opening 990a in the upper ring member 990.

In the embodiment of FIG. 72, the tabs 991 may be arranged on leg portions 999 that extend from the body 995 of the cap 994, below the open end (lower end in FIG. 72) of the cap 994. The leg portions 999 locate the tabs 991 a sufficient distance from the open end of the cap 994, to engage the channels 997 in the reservoir receptacle 32 (below the upper ring member 990), while a portion of the cap 994 extends outward from the opening 990a of the upper ring member 990.

In other embodiments, the legs 999 are omitted and the tabs 991 are arranged on the body 995 of the cap 994. In such embodiments, the channels 997 may be located in the upper ring member 990 (instead of the housing 33 of the infusion pump device 30), and the lip 990b of the upper ring member 990 may be omitted, as shown in FIG. 73.

Figure 73:
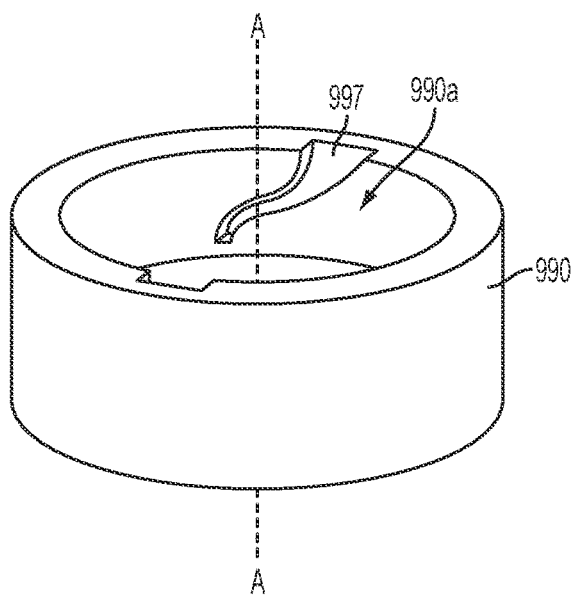
FIG. 73 is an enlarged, perspective view of an upper ring member having a cap-to-infusion pump device connection interface according to another embodiment of the present invention.

In the embodiments of FIGS. 72 and 73, the open, upper ends of the channels 997 are tapered or flared to be wider than other portions of the channels. The tapered or flared upper ends of the channels 997 can help the user to align the tabs 991 with the open ends of the channels during installation of the cap 994 (or base/reservoir/cap unit) in the reservoir receptacle 32.

Embodiments described with reference to FIGS. 69-73 may be employed with any one or more of the detection embodiments (magnetic detection, inductive detection, RF detection, mechanical detection, optical detection and electrical contact detection) described above. In such embodiments, the cap 984 or 994 is provided with one or more detectable elements 42 as described above, while the infusion pump device 30 is provided with one or more sensor elements 34 as described above.

In particular embodiments, one or more detectable elements 42 are arranged on the tabs 989, compressible ring member 980, or upper ring member 982. In such embodiments, electronics (such as electronics 60) may be configured to detect the relative position of the tabs 989, compressible ring member 980 or upper ring member 982, in addition to or as an alternative to detection of the presence of the cap (or base/reservoir/cap unit) or other characteristics and information as described above.

In such embodiments, electronics 60 in the infusion pump device may be configured to provide one or more predefined operations, at least partially based on (or in response to) one or more of: (1) a determination that the cap (or base/reservoir/cap unit) is not properly received within the reservoir receptacle 32, and (2) a determination that the tabs 989, compressible ring member 980 or upper ring member 982 is not in a locking position (or cap-installed position). Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap (or base/reservoir/cap unit) is properly received within the reservoir receptacle 32, and (2) determination that the tabs 989, compressible ring member 980, or upper ring member 982 is in a locking position (or cap-installed position). Such predefined operations include, but are not limited to one or more of allowing or providing pumping operation, allowing a predefined pumping operation, providing a predefined message, and recording data indicating the detection.

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

m. Spring Connection

In a further embodiment as described with reference to FIGS. 74 and 75, the second releasable coupler includes one or more (or a plurality of) moveable members 1000 supported by the housing 33 of the infusion pump device 30, and arranged to at least partially extend into the reservoir receptacle 32. The embodiment of FIG. 74 includes two moveable members 1000. Other embodiments include more than two moveable members 1000 arranged around the axis A, within the reservoir receptacle 32. Each moveable member 1000 is supported on or in an interior wall portion of the reservoir receptacle, and is biased by a bias member 1002 toward the center of the reservoir receptacle 32 (toward the axis A). In particular embodiments, the bias member 1002 is a spring, such as, but not limited to, a coil spring, a leaf spring, or the like, arranged between the moveable member 1000 and a portion of the housing 33 of the infusion pump device 30. Each moveable member 1000 may be composed of a rigid body having a pin or pellet shape (or other suitable shape), and made of any suitably rigid material such as, but not limited to plastic, metal, ceramic, wood, composite material or any combination thereof.

In the illustrated embodiment, each moveable member 1000 is located within a groove, depression, or indentation 1003 in an interior wall portion of the reservoir receptacle 32. In the illustrated embodiment, the grooves, depressions, or indentations 1003 are provided in the housing 33 of the infusion pump device. In other embodiments, the grooves, depressions, or indentations 1003 (and the moveable members 1000 and bias members 1002) are located in an upper ring member (not shown) that connects to the upper end of the housing 33 at the reservoir receptacle 32, for example, similar to the manner in which other upper ring members described herein connect to the housing 33.

Each moveable member 1000 is arranged to engage and contact a flexible spring member 1006 on the outer surface of the body 1005 of a cap 1004, when the cap 1004 (or base/reservoir/cap unit) is moved into the reservoir receptacle 32, in the direction of the axis A. The flexible spring member 1006 is connected to the cap body 1005 and extends away from the open end (lower end in FIGS. 74 and 75) of the cap 1004, while inclining or flaring outward. In particular embodiments, a single spring member 1006 extends around the cap body 1005 (around the axis A), to engage the moveable members 1000 in any rotary position of the cap 1004 (and base/reservoir/cap unit) relative to the reservoir receptacle 32 (and axis A). In other embodiments, a plurality of spring members 1006 corresponding in number and location to a plurality of moveable members 1000 are arranged around the perimeter of the cap body 1005, to engage the corresponding plurality of moveable members 1000 when the cap 1004 (or base/reservoir/cap unit) is moved into the reservoir receptacle 32, in the direction of the axis A.

In particular embodiments, one or more pairs of spring members 1006 are arranged on the cap body 1005 such that the two spring members 1006 in each pair are located on opposite sides of the axis A relative to each other. In such embodiments, the two spring members 1006 in a given pair provide radially-directed spring forces in opposite directions, to help retain the cap 1004 (or base/reservoir/cap unit) stable within the reservoir receptacle. In yet other embodiments, each different cap 1004 has a different arrangement of spring members 1006 (e.g., a different number or pattern of locations on the cap body 1005) with respect to other caps 1004, where the different arrangements correspond to different respective characteristics of the cap 1004 (or base/reservoir cap unit or infusion set connected thereto), as described above with respect to other embodiments having different features corresponding to different characteristics.

Figure 74:
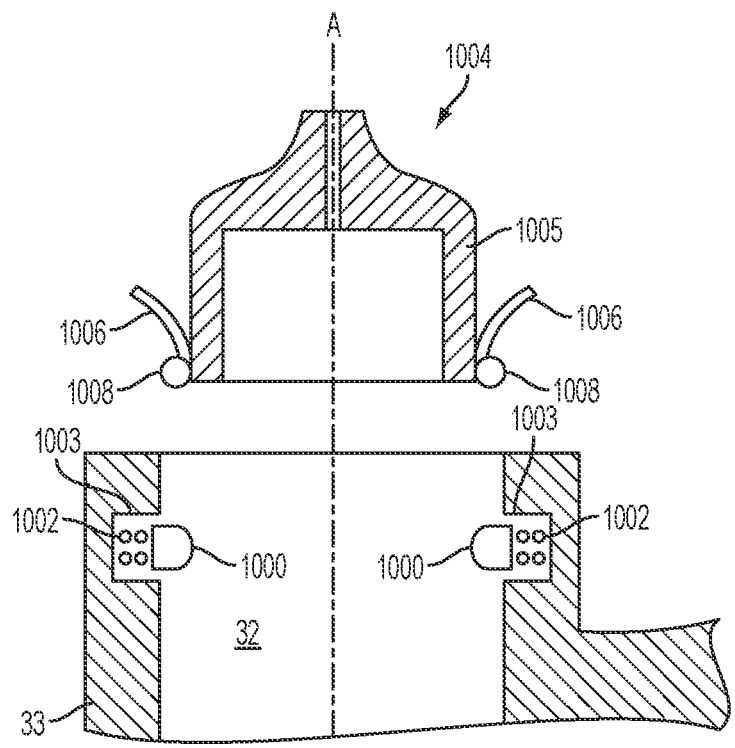
FIG. 74 is an enlarged, partial, side, cross-section view of a portion of a reservoir receptacle of an infusion pump device and a cap having a cap-to-infusion pump device connection interface according to another embodiment of the present invention.
Figure 75:
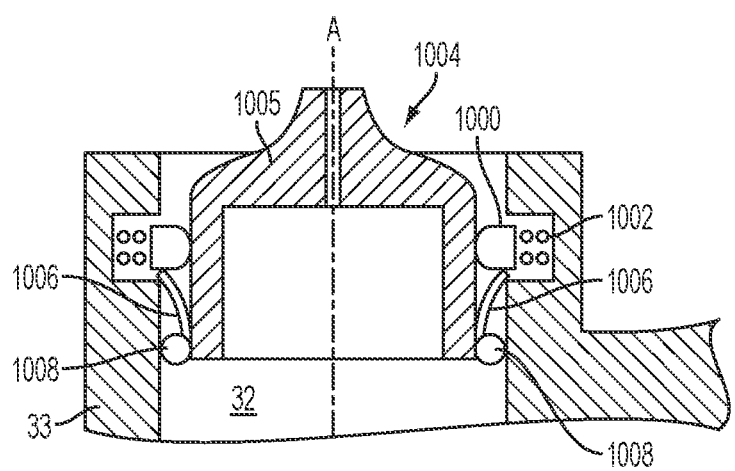
FIG. 75 is an enlarged, side, cross-section view of a cap within a portion of a reservoir receptacle of FIG. 74.

In the embodiment of FIGS. 74 and 75, when the cap 1004 (or base/reservoir/cap unit) is inserted into the reservoir receptacle 32 and moved in the direction of the axis A toward an installed position, the moveable members 1000 in the reservoir receptacle 32 engage the flexible springs 1006 on the cap 1004. As the cap 1004 (or base/reservoir/cap unit) is moved further into the reservoir receptacle toward the installed position, the moveable members 1000 press against the spring member(s) 1006 and force the outward extending of flared end(s) of the spring member(s) toward the cap body 1005, until the spring member(s) 1006 are moved past the moveable members 1000. When the cap 1004 (or base/reservoir/cap unit) has moved to a fully installed position in the reservoir receptacle 32, the spring member(s) 1006 on the cap body 1005 have moved past the moveable members 1000, and the spring member(s) 1006 have returned to their non-pressed state, as shown in FIG. 75. In that state, the moveable members 1000 are biased (by the bias members 1002) outward, over the spring member(s) 1006, to a position to engage the spring member(s) 1006 and inhibit movement of the cap 1004 (or base/reservoir/cap unit) in a direction to withdraw the cap (or base/reservoir/cap unit) from the reservoir receptacle 32.

From the installed position, the cap 1004 (or base/reservoir/cap unit) may be selectively withdrawn from the reservoir receptacle, by selectively moving the moveable members 1000 radially outward a sufficient distance to allow the spring member(s) 1006 to pass by the moveable members 1000, while applying a manual force to pull the cap 1004 in the direction of axis A, outward from the reservoir receptacle 32. In particular embodiments, a mechanism for selectively moving the moveable members 1000 radially outward is provided in the housing 33 of the infusion pump device 30, where such mechanism may include, but is not limited to, a magnetic or electromagnetic solenoid, a manually movable lever on the bias members 1002 or other suitable mechanism.

The moveable members 1000 are configured with a first surface facing toward the open end of the reservoir receptacle (facing upward in FIGS. 74 and 75) and a second surface facing inward, into the reservoir receptacle 32 (facing downward in FIGS. 74 and 75). In particular embodiments, the first surface of the moveable member 1000 is tapered, sloped or curved (forming one or more oblique angles relative to the axis A) to enhance the ability of the spring member(s) 1006 to engage and move the moveable members radially outward, as the cap 1004 (or base/reservoir/cap unit) is moved in the direction of axis A into the reservoir receptacle 32. In further embodiments, the second surface of the moveable member 1000 is generally perpendicular to the axis A (or has another suitable shape) to inhibit movement of the spring member(s) 1006 past the moveable members 1000, when the cap 1004 (or base/reservoir/cap unit) is in the fully installed position (as shown in FIG. 75).

In particular embodiments, one or more seal members 1008 is provided on the cap 1004, for example, around the perimeter of the cap body 1005, adjacent to the open end of the cap body 1005. In such embodiments, the one or more seal members 1008 are configured to contact and seal against an interior surface of the reservoir receptacle 32, when the cap 1004 (or base/reservoir/cap unit) is installed within the reservoir receptacle 32. The seal member 1008 may be any suitable seal structure including, but not limited to an O-ring or band of seal material as described herein.

Embodiments described with reference to FIGS. 74-75 may be employed with any one or more of the detection embodiments (magnetic detection, inductive detection, RF detection, mechanical detection, optical detection and electrical contact detection) described above. In such embodiments, the cap 1004 is provided with one or more detectable elements 42 as described above, while the infusion pump device 30 is provided with one or more sensor elements 34 as described above.

In particular embodiments, one or more detectable elements 42 are arranged on the tabs 991, legs 999, moveable members 1000, bias members 1002 or spring members 1006. In such embodiments, electronics (such as electronics 60) may be configured to detect the relative position of the tabs 991, legs 999, moveable members 1000, bias members 1002 or spring members 1006, in addition to or as an alternative to detection of the presence of the cap (or base/reservoir/cap unit) or other characteristics and information as described above.

In such embodiments, electronics 60 in the infusion pump device may be configured to provide one or more predefined operations, at least partially based on (or in response to) one or more of: (1) a determination that the cap (or base/reservoir/cap unit) is not properly received within the reservoir receptacle 32, and (2) a determination that the tabs 991, legs 999, moveable members 1000, bias members 1002 or spring members 1006 are not in a locking position (or cap-installed position). Such predefined operations include, but are not limited to one or more of stopping or inhibiting pumping operation, allowing only a limited pumping operation, providing a warning message, and recording data indicating the detection.

Alternatively or in addition, the electronics 60 may be configured to provide one or more predefined operations, at least partially based on (or in response to) one or more of: (1) a determination that the cap (or base/reservoir/cap unit) is properly received within the reservoir receptacle 32, and (2) determination that the tabs 991, legs 999, moveable members 1000, bias members 1002 or spring members 1006 is in a locking position (or cap-installed position). Such predefined operations include, but are not limited to one or more of allowing or providing pumping operation, allowing a predefined pumping operation, providing a predefined message, and recording data indicating the detection.

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

n. Push-Fit with Spring-Loaded Reservoir or Cap

In further examples of any of the embodiments described herein, the reservoir receptacle 32 of the infusion pump device 30 may include a spring or other bias member (such as bias member 1000 in FIGS. 76 and 77) that imparts a bias force on a reservoir (e.g., reservoir 1, 201 or 301 or other suitable reservoir) or a cap (e.g., cap 4, 204, 404, 504, 704, 804, 904a-e, 964, 974, 984, 994, 1004, or other suitable cap) in the direction of the longitudinal axis of the reservoir receptacle 32 (axis A) and outward from the reservoir receptacle 32, when the base/reservoir/cap unit is installed in the reservoir receptacle 32. The user (or medical technician or other authorized person) installs a base/reservoir/cap unit in the reservoir receptacle 32 by inserting the base/reservoir/cap unit, reservoir-end first, into the reservoir receptacle 32 and pushing the cap against the force of the spring or other bias member, to move the base/reservoir/cap unit further into the reservoir receptacle 32.

In such further examples, the cap includes a latching or locking structure to latch or lock the cap to the infusion pump device 30, against the bias force of the spring or other bias member, when the cap (or base/reservoir/cap unit) is fully and properly received in the reservoir receptacle 32. Various examples of such latching or locking structure are described herein, where a predefined manual action can be carried out to selectively unlatch or unlock the cap (or base/reservoir/cap unit) from a latched or locked state, to allow the cap (or base/reservoir/cap unit) to be withdrawn from the reservoir receptacle 32. In particular embodiments, when the cap (or base/reservoir/cap unit) is in a latched or locked state, the force of the spring or other bias member helps to lock and maintain the cap (and base/reservoir/cap unit) in a predefined position within the reservoir receptacle 32.

According to certain embodiments, the spring or other bias member is configured such that the cap (or base/reservoir/cap unit) is at least partially ejected from the reservoir receptacle 32 by the force of the spring or other bias member, upon unlatching or unlocking of the cap (or base/reservoir/cap unit) from the latched or locked state. By partially ejecting the cap (or base/reservoir/cap unit) from the reservoir receptacle 32, the reservoir 1, 201, 301 is moved out of operative alignment with the drive mechanism within the reservoir receptacle 32 and, thus, will not be operated by the infusion pump device (unless and until the cap or base/reservoir/cap unit is again placed in a latched or locked state). Alternatively or in addition, by partially ejecting the cap (or base/reservoir/cap unit) from the reservoir receptacle 32, the cap (or base/reservoir/cap unit) can be easier to manually grip to further withdraw the cap (or base/reservoir/cap unit) from the reservoir receptacle 32.

Figure 76:
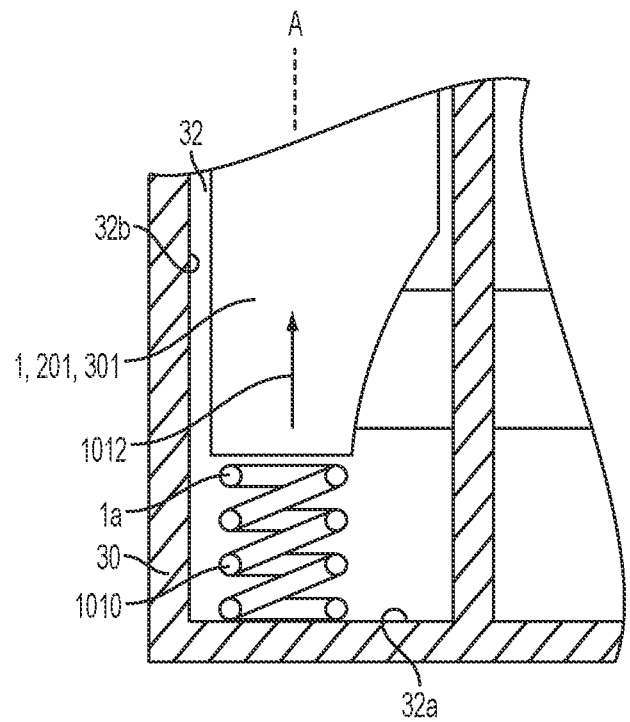
FIGS. 76 and 77 are partial perspective views of a base/reservoir/cap unit or reservoir within a reservoir receptacle according to various embodiments of the present invention.

FIG. 76 shows a portion of the reservoir receptacle 32 of an infusion pump device 30, with a base/reservoir/cap unit received in the interior volume of the reservoir receptacle 32. Only an end portion of the reservoir of the base/reservoir/cap unit is shown in FIG. 76. The reservoir in FIG. 76 may be the reservoir 1, 201 or 301 coupled to or including any of the cap embodiments (4, 204, 404, 504, 704, 804, 904a-e, 964, 974, 984, 994, 1004) described herein. In the example embodiment of FIG. 76, the infusion pump device 30 includes a bias member 1010 in the form of a coil spring located at or near the closed end (the bottom end in FIG. 76) of the reservoir receptacle 32, to impart a bias force on the reservoir (and to the cap coupled to the reservoir) toward the port end of the reservoir receptacle 32, in the direction of arrow 1012 and the axis A (upward in FIG. 76), when the base/reservoir/cap unit is installed in the reservoir receptacle 32.

In the embodiment of FIG. 76, the bias member 1010 engages and imparts a bias force on an end surface 1c of the reservoir 1, 201, 301. The bias member 1010 is supported by a stop surface 32a of the reservoir receptacle 32. Thus, in the example embodiment in FIG. 76, one end of the coil spring that forms the bias member 1010 is arranged to abut against and impart a bias force on the end surface 1c of the reservoir 1, while a second end of coil spring is arranged to abut against and be supported by the stop surface 32a. In other embodiments, an engagement member is interposed between the bias member 1010 and the end surface 1c of the reservoir 1 or the stop surface 32a of the reservoir receptacle 32 (or both), such that the bias member 1010 does not make direct contact with the end surface 1c or the stop surface 32a (or both).

In the embodiment of FIG. 76, the stop surface 32a is the end surface of the reservoir receptacle at the close end thereof. In other embodiments, the stop surface 32a is another surface provided in the reservoir receptacle, such as, but not limited to, a surface of an extension, protrusion, groove, indentation, or other structural feature provided on an inner surface 32b of the reservoir receptacle 32, or on the inner surface of the end of the reservoir receptacle 32.

Figure 77:
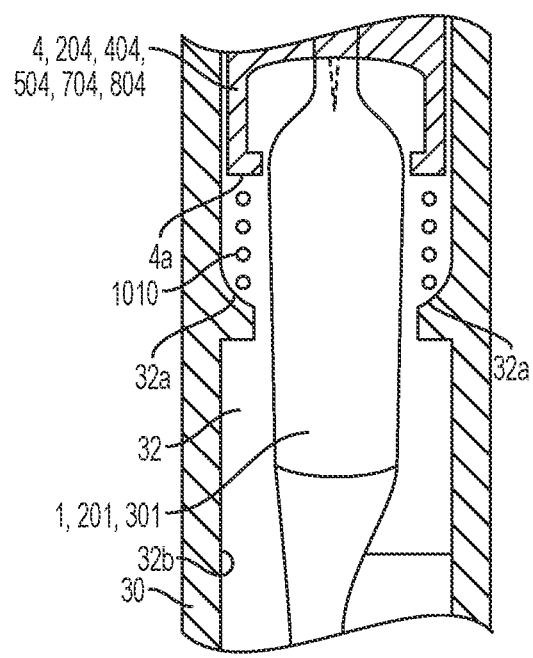

In further example embodiments, as shown in FIG. 77, the bias member 1010 engages and imparts a bias force on a surface 4a of a cap 4 (or 204, 404, 504, 704, 804, 904a-e, 964, 974, 984, 994, or 1004). Only a portion of the cap, reservoir and the reservoir receptacle 32 is shown in FIG. 77. The cap in FIG. 76 may be any of the caps described herein (e.g., cap 4, 204, 404, 504, 704, 804, 904a-e, 964, 974, 984, 994, or 1004) or other suitable cap.

In FIG. 77, the surface 4a is an end surface of the cap (adjacent the cap open end that receives the reservoir). In other embodiments, the surface 4a may be any other predefined surface of the cap, or an extension or other structural feature of the cap. The bias member 1010 in FIG. 77 is supported by a stop surface 32a of the reservoir receptacle 32, as described above. However, in the example embodiment of FIG. 77, the stop surface 32a is an annular protrusion on the inner surface 32b of the reservoir receptacle 32.

In the embodiments of FIGS. 76 and 77 the bias member 1010 includes a coil spring. Other embodiments employ other types of bias members, such as, but not limited to other forms of springs, magnetic or electromagnetic bias members, compressed fluid bias members, or any combination thereof, with or without a coil spring.

o. Other Connection Configurations

In other embodiments, the second releasable coupler includes one or more other features, that engage and mate with one or more other features on the housing of the infusion pump device 30, in the region of the open port of the reservoir receptacle 32. In particular embodiments, the infusion pump device 30 is provided with an electronic solenoid device that selectively moves a solenoid plunger from a first position to a second position, when energized (or when de-energized). In such embodiments, the second releasable coupler includes one or more grooves, indentations, apertures, projections or other stop surfaces on the cap (e.g., cap 4, 404, 504, 704, 804 or on any other suitable cap configurations) that are arranged to engage with the solenoid plunger, when the solenoid plunger is in the second position (i.e., when the solenoid is energized, or de-energized, to move the plunger to the second position). When engaged with the stop surface on the cap, the solenoid plunger locks and retains the cap within the reservoir, When the solenoid plunger is in the second position, the plunger is withdrawn from the stop surface on the cap by an amount sufficient to unlock the cap from the reservoir receptacle and allow the cap to be removed from the reservoir receptacle (e.g., by manually pulling the cap in the direction of axis A, out of the reservoir receptacle 32).

p. Side-Loading Reservoir Receptacle

In various embodiments described above, the reservoir receptacle 32 of the infusion pump device 30 has an end opening (an open end) through which the axis A extends, for receiving a cap (or base/reservoir/cap unit) inserted into the open end of the reservoir receptacle, along the direction of the axis A. In further embodiments, the housing 33 of the infusion pump device 30 has a side opening into the reservoir receptacle 32 for receiving, from the side, a cap (or base/reservoir/cap unit), such as any of the caps (or base/reservoir/cap units) described herein, or other suitable cap (or base/reservoir/cap unit). In such embodiments, the cap 4 (or base/reservoir/cap unit) is inserted in a direction transverse (for example, generally perpendicular) to the axis A, through an open side of the reservoir receptacle 32.

Figure 78:
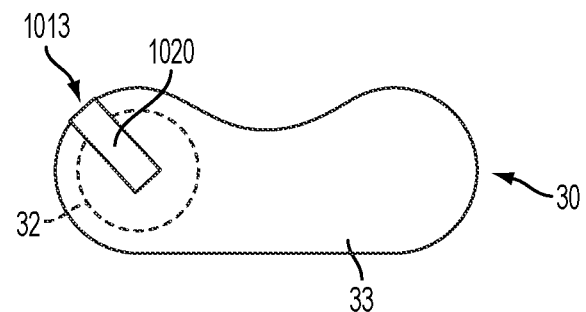
FIG. 78 is a top view of an infusion pump device having a side-entry reservoir receptacle according to an embodiment of the present invention.
Figure 79:
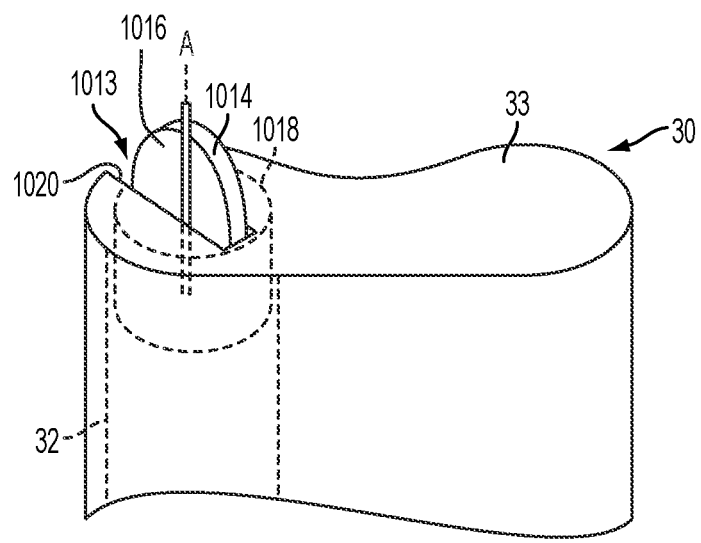
FIG. 79 is a partial perspective view of the infusion pump device of FIG. 78, with a portion of a cap extending through an opening in the infusion pump device housing.

For example, in the embodiment of FIGS. 78 and 79, the housing 33 of the infusion pump device 30 includes a side opening 1013 (facing out of view in the drawings)) having a size and a shape to receive a cap 1014 (or base/reservoir/cap unit), laterally, through the side opening. In particular embodiments, a door or closure structure is provided to close the side opening 1013 of the housing 33, once the cap 1014 (or base/reservoir/cap unit) has been received within the reservoir receptacle.

The cap 1014 has a raised port end 1016 (for example, corresponding the port 6 end of the cap 4 in FIGS. 1 and 2). In particular embodiments, the cap 1014 may be any of the caps described herein (e.g., cap 4, 204, 404, 504, 704, 804, 904*a-e*, 964, 974, 984, 994, or 1004) or other suitable cap.

In the embodiment of FIGS. 78 and 79, the housing 33 of the infusion pump device covers both ends of the reservoir receptacle 32, in the axial direction A. In that regard, a portion 1018 of the housing 33 extends over (closes) the upper end of the reservoir receptacle 32. The reservoir receptacle 32 is also closed on its bottom end (not shown in FIGS. 78 and 79). However, the portion 1018 over the upper end of the reservoir receptacle 32 includes a slot-shaped opening 1020 that is open on one end to the side opening 1013 of the reservoir receptacle, and extends across the top of the reservoir receptacle 32.

In the illustrated embodiment, the slot-shaped opening 1020 extends across at least a portion of the diameter of the reservoir receptacle 32, and traverses the axis A of the reservoir receptacle 32. The slot-shaped opening 1020 has a width dimension that is smaller than its length dimension, so as to form an elongated, rectangular opening through the portion 1018 of the housing 33, into the reservoir receptacle 32. The slot-shaped opening 1020 is configured to receive the raised port end 1016 of the cap 1014, when the cap 1014 (or base/reservoir/cap unit) is received, through the side opening 1013, into the reservoir receptacle. As shown in FIG. 79, when the cap 1014 (or base/reservoir/cap unit) is received within the reservoir receptacle 32, the raised port end 1016 of the cap 1014 extends outward from the reservoir receptacle, through the slot-shaped opening 1020. In that arrangement, the port on the raised port end 1016 is readily accessible and unobstructed by the housing 33 of the infusion pump device 30, allowing for a greater flexibility in orientating the infusion set tubing for user comfort, or allowing for ready access for connection or disconnection of tubing from the raised port end 1016.

In embodiments as shown in FIGS. 78 and 79, the width dimension of the slot-shaped opening 1020 has a size that is able to receive the raised port end 1016, when the raised port end 1016 (and, thus, the cap 1014 and base/reservoir/cap unit) are aligned in a predefined rotational orientation relative to the axis A. However, the width dimension of the slot-shaped opening 1020 is smaller than the diameter of the cap 1014, thus inhibiting the cap 1014 from passing through the slot-shaped opening 1020, when the cap 1014 (or base/reservoir/cap unit) is located within the reservoir receptacle 32.

In such embodiments, a first face or dimension of the raised port end 1016 of the cap 1014 is wider than the width of the slot-shaped opening 1020, while the width of a second face or dimension of the raised port end 1016 is smaller than the width of the slot-shaped opening 1020. Accordingly, in such embodiments, the slot-shaped opening 1020 can help control the rotational or angular orientation of the cap 1014 (or base/reservoir/cap unit) relative to the axis A, when the cap 1014 (or base/reservoir/cap unit) is received within the reservoir receptacle 32. In addition, the portion 1018 of the housing 33 can help retain the cap 1014 (and base/reservoir/cap unit) from movement in the axial direction A relative to the housing 33 of the infusion pump device, when the cap 1014 (or base/reservoir/cap unit) is received within the reservoir receptacle 32.

Figure 80:
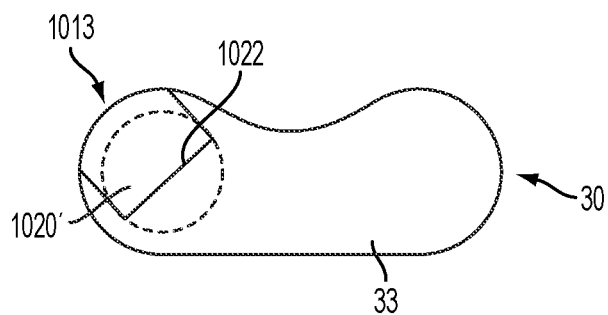
FIG. 80 is a top view of an infusion pump device having a side-entry reservoir receptacle according to another embodiment of the present invention.
Figure 81:
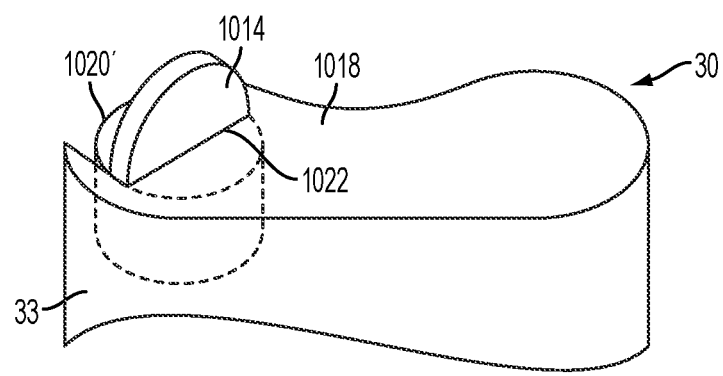
FIG. 81 is a partial perspective view of the infusion pump device of FIG. 80, with a portion of a cap extending through an opening in the infusion pump device housing.

In other embodiments as shown in FIGS. 80 and 81, the portion 1018 of the housing 33 is provided with a wider slot-shaped opening 1020', having sufficient width to allow the raised port end 1016 of the cap 1014 to fit through the open end of the slot-shaped opening 1020' while oriented with its wider face or dimension directed (facing) into the open end of the slot-shaped opening 1020' (i.e., facing toward the axis A). However, one or more dimensions of the slot-shaped opening 1020' is smaller than the diameter of the cap 1014, thus inhibiting the cap 1014 from passing through the slot-shaped opening 1020', when the cap 1014 (or base/reservoir/cap unit) is located within the reservoir receptacle 32. The slot-shaped opening 1020' includes an end surface 1022, against which the wider side or face of the raised port end 1016 of the cap 1014 abuts, when the cap 1014 (or base/reservoir/cap unit) is inserted into the reservoir receptacle 32 through the side opening of the reservoir receptacle 32. In particular embodiments, the end surface 1022 is located and oriented such that, when the raised port end 1016 of the cap 1014 is abutted against the end surface 1022, the cap 1014 (or base/reservoir/cap unit) is arranged in a properly installed position and orientation within the reservoir receptacle 32.

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

5. Vents on Caps or Infusion Pump Device

In further examples of any of the embodiments described herein, the cap (e.g., cap 4, 404, 504, 704, 804, 904*a-e*, 964, 974, 984, 994, 1004, 1014, or other suitable cap) is provided with one or more vent openings (such as vent openings 24 described above with respect to cap 4). The vent opening(s) 24 provide one or more air passages from the environment outside of the cap, to the interior volume of the cap body. Accordingly, when the cap (or base/reservoir/cap unit) is installed in a reservoir receptacle 32, the vent opening(s) provide an air flow passage or pressure equalization passage between the environment outside of the cap and infusion pump device, to the environment within the reservoir receptacle 32 (i.e., the volume between the base/reservoir/cap unit and the interior wall of the reservoir receptacle 32, when the base/reservoir/cap unit is received within the reservoir receptacle 32).

In particular embodiments, the vent opening(s) 24 include a hydrophobic material that inhibits the passage of water or other liquid through the vent opening(s). For example, the hydrophobic material may be provided as a membrane over one or both open ends (interior and exterior ends) of each vent opening, or within vent opening. In other embodiments, an absorbent material is provided in or adjacent each vent opening to absorb or wick away liquid that may drop or accumulate on the surface of the cap or the port of the reservoir receptacle 32.

In those or other embodiments, a wiper structure that wipes any residual liquid off of the surface of the reservoir when the reservoir is disengaged from a transfer guard (e.g., transfer guard 200 or 300 described herein), or engaged with a cap (e.g., any of the caps described herein).

An example embodiment of a vent configuration in a cap 1024 is described with reference to FIG. 82. In particular embodiments, the cap 1024 may be any of the caps described herein (e.g., cap 4, 204, 404, 504, 704, 804, 904*a-e*, 964, 974, 984, 994, 1004 or 1014) or other suitable cap.

Figure 82:
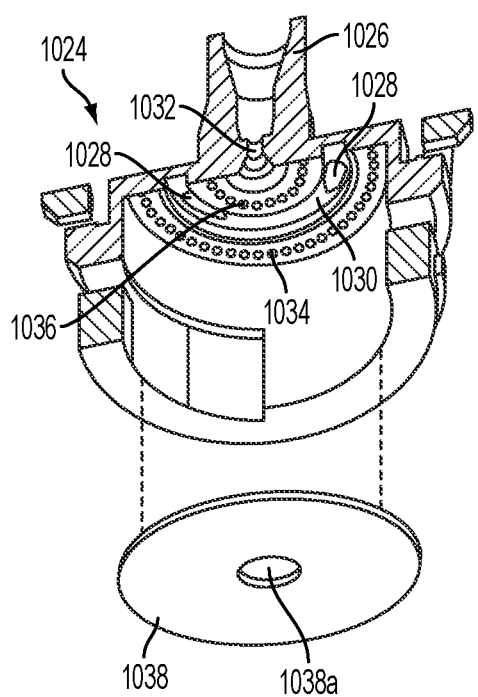
FIG. 82 is a partial perspective view of a cap of a reservoir connection interface apparatus according to an embodiment of the present invention.

A cut-away view of a cap 1024 is shown in FIG. 82, where the cap 1024 includes a plurality of vent openings 1028 (two of which are shown in view in FIG. 82). The vent openings 1028 are provided in a top wall of the cap 1024 and are arranged around the infusion set tubing port 1026 of the cap 1024. In the embodiment of FIG. 82, the inside surface of the cap 1024 (the surface facing the reservoir 1, when the cap 1024 is arranged on the reservoir 1) is provided with an annular groove 1030 that surrounds the inner opening 1032 to the port 1026. The vent openings 1028 are arranged within the annular groove 1030.

In addition, a first annular array of weld horns 1034 (or other attachment mechanisms) is provided around and concentric with the annular groove 1030. In particular embodiments, a second annular array of weld horns 1036 (or other attachment mechanisms) is provided between the annular groove 1030 and the inner port opening 1032, and concentric with the annular groove 1030 (and, thus, concentric with the first annular array 1036). In further embodiments, the second annular array of weld horns 1036 (or other attachment mechanisms) may be omitted.

The first and second annular arrays 1034 and 1036 secure a membrane 1038 to the inner surface of the cap 1024, over the annular groove 1030 and vent openings 1028. In particular, the first and second annular arrays 1034 and 1036 fix the membrane 1038 to the inner surface of the cap 1024 in two concentric, annular attachment zones on either side of the annular groove 1030. In particular embodiments, the membrane 1038 is made of (or coated with) a hydrophobic material that repels water, but allows the passage of air.

When affixed to the inner surface of the cap 1024, the membrane 1038 covers the groove 1030, but is separated from the vent openings 1028 by the depth of the annular groove 1030. Accordingly, the annular groove 1030 provides an unobstructed, annular air flow path between the membrane 1038 and the inner surface of the cap 1024. The vent openings 1028 are arranged around and in air flow communication with the annular air flow path in the annular groove 1030.

The membrane 1038 includes a central opening 1038*a* that aligns with the inner port opening 1032 when the membrane 1038 is attached to the inner surface of the cap 1024. In other embodiments, the central portion of the membrane 1038 does not include a central opening 1038*a*, but, instead, is configured to be pierced by a needle of the infusion set 50, when the infusion set tubing 52 is attached to the port 1026.

In particular embodiments, the first and second arrays of weld horns (or other attachment mechanisms) comprises arrays of ultrasonic weld horns. In such embodiments, the membrane is secured to the inner surface of the cap 1024 by pressing the membrane 1038 against the arrays of weld horns and applying ultrasonic energy to the weld horns sufficient to weld the membrane to the cap 1024. In other embodiments, other suitable attachment mechanisms may be employed including, but not limited to a glue or other adhesive material.

When secured to the inner surface of the cap 1024, the membrane 1038 allows the passage of air, but inhibits the passage of moisture through the vents 1028. The annular groove 1030 enhances the air flow through the vent openings 1028 and membrane 1038, by increasing the surface area of the membrane 1038 exposed to the air flow path (relative to a membrane arranged directly over the vent openings 1028).

While embodiments described above include vent openings and membranes located on caps (e.g., cap 1024), other embodiments described with reference to FIG. 83 include one or more vent openings (with or without membranes) on an upper ring member 1040 connected to (or connectable to) the housing 33 of the infusion pump device 30, over the open end of the reservoir receptacle 32. The upper ring member 1040 may be any of the upper ring members described herein (including, but not limited to upper ring member 94, 137, 910, 932, 990), or other suitable upper ring member.

Figure 83:
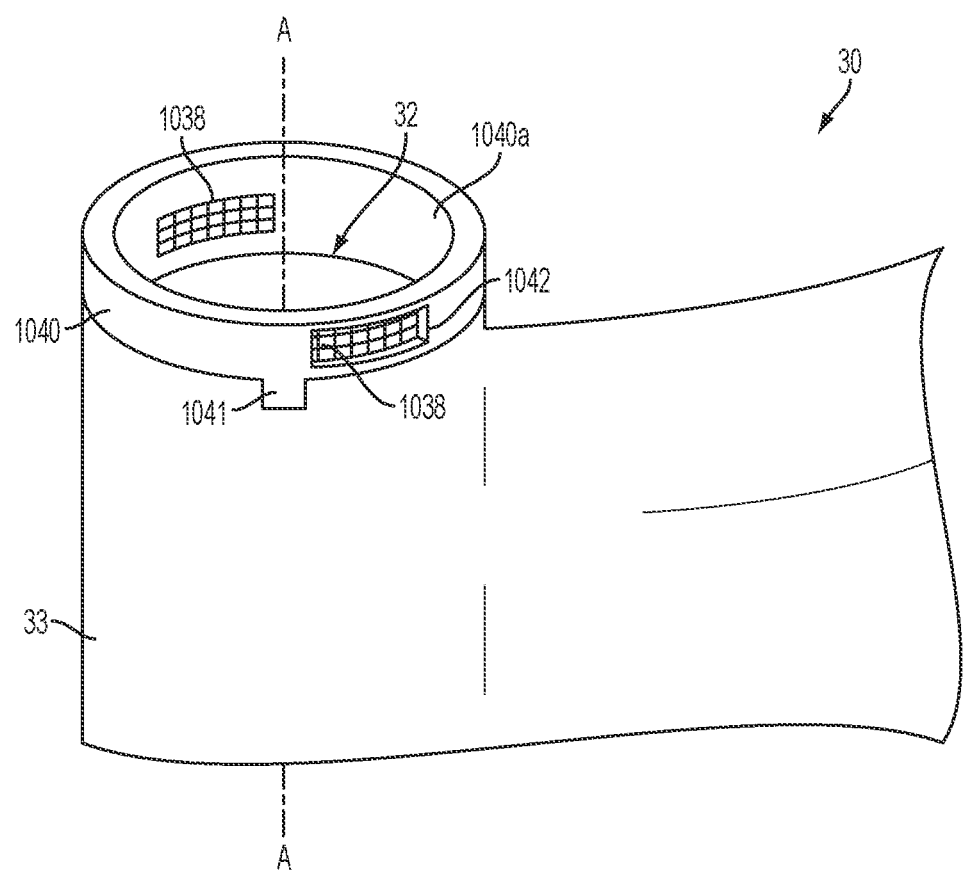
FIG. 83 is a partial perspective view of an upper ring member of a reservoir receptacle of an infusion pump device according to an embodiment of the present invention.

In the embodiment of FIG. 83, the upper ring member 1040 includes a central opening 1040*a* and one or more (or a plurality of) vent openings 1042 extending through the ring member 1040 to the interior of the reservoir receptacle 32. The upper ring member 1040 may also include one or more key tabs or protrusions 1041 that engage or fit within one or more corresponding key slots or recesses in the housing 33 of the infusion pump device 30, to inhibit rotation of the upper ring member 1040 relative to the housing 33 (or to properly position the upper ring member 1040 relative to the housing 33). In other embodiments, the positions of the key tab(s) or protrusion(s) and key slot(s) or recess(es) are reversed, such that the key tab(s) or protrusion(s) are on the housing 33 and the key slot(s) or recess(es) are on the upper ring member 1040.

In the drawing of FIG. 83, two vent openings 1042 are provided in the upper ring member 1040, through a side wall of the upper ring member on opposite sides of the axis A. In other embodiments, the upper ring member 1040 includes only one vent opening 1042. In other embodiments, the upper ring member 1040 includes more than two vent openings arranged around the circumference of the upper ring member (around the axis A). In yet further embodiments, one or more vent openings are provided through the free end surface (upward-facing surface in FIG. 83) of the upper ring member 1040.

In particular embodiments, each vent opening 1042 is covered with a membrane 1038, as described above. The membrane 1038 may be provided on the interior surface of the upper ring member 1040 (the surface facing into the central opening 1040*a*), and covering over the vent opening 1042. In other embodiments, the membrane 1038 is provided on the exterior surface of the upper ring member 1040 (the surface facing outward relative to the axis A), and covering over the outside of the vent opening 1042. In yet other embodiments, the membrane 1038 is provided inside of the vent opening 1038 flush with or recessed from one or both of the interior surface and exterior surface of the upper ring member 1040.

In various embodiments described above, the cap 4 (or cap 204, 404, 504, 704, 804, 904*a*-4, 1050, 974, 984, 994, 1004, 1014, 1024, or other cap as described herein) includes or operates with a hollow needle (such as needle 9) that pierces a septum in the reservoir 1, to provide a fluid flow path between the interior of the reservoir 1 and the tubing 52. Other embodiments employ a needle-free connection between the cap and the reservoir, an example of which is shown in FIGS. 84-86. In the embodiment of FIGS. 84-86, a cap 1050 is provided with a hollow, central channel or passage 1052 extending from a first open end 1052*a* at a port 1054 to a second open end 1052*b*. As described herein, the channel or passage 1052 provides a needle-free, fluid flow path from the port 1054, into the interior of a reservoir 1.

The cap 1050 includes a cap body having a rounded end portion 1050*a*. The rounded end portion 1050*a* of the cap body has an outer surface that has a semi-spherical or semi-spheroidal shape, with the second open end 1052*b* of the passage 1052 located at the apex of the semi-spherical or semi-spheroidal shape. The cap body has a port portion 1050*b* (the upper portion of the cap 1050 in FIGS. 84 and 85, on which the port 1054 is located. The port 1054 may be similar to the port 6 described above and may connect with a tubing 52 of an infusion set 50, as described above with respect to port 6. A ridge portion 1050*c* of the cap body extends around the cap body, between the rounded end portion 1050*a* and the port portion 1050*b* of the cap 1050. In particular embodiments, the cap body (including the rounded end portion 1050*a*, the port portion 1050*b* and the ridge portion 1050*c*) is formed as a single, unitary structure by, for example, but not limited to a single molded or machined structure, or the like. In other embodiments, the cap body (including the rounded end portion 1050*a*, the port portion 1050*b* or the ridge portion 1050*c*) are made of separate elements that are connected together to form the body of the cap 1050.

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

6. Pivotal Cap-To-Reservoir Connection

In the embodiment of FIGS. 84-86, the cap 1050 is configured to be selectively placed onto an open end of the body of a reservoir 1, with the rounded end portion 1050*a* of the cap body extending at least partially into the open end of the reservoir 1. When the cap 1050 is placed onto the open end of the reservoir 1, the rounded end portion 1050*a* of the cap 1050 is arranged to contact and seal against an annular seal structure 1054 located within the reservoir 1. The rounded (semi-spherical or semi-spheroidal) shape of the rounded end portion 1050*a* allows the surface of the rounded end portion 1050*a* to seal against the annular seal structure 1054, around the entire periphery of the cap 1050.

In particular embodiments, the annular seal structure 1054 includes an O-ring, band, or other suitable seal, made of silicon rubber or other suitable, flexible sealing material. The annular seal structure 1054 is arranged around the inner periphery of an inner surface of the reservoir 1, either at or a selected distance below the open end of the reservoir 1 (for example, in a head or neck portion of the reservoir 1, where the head or neck portion of the reservoir 1 has a smaller diameter than the rest of the body of the reservoir 1). In particular embodiments, the inner surface of the reservoir 1 (or of the head or neck portion of the reservoir 1) is provided with an annular groove 1056*a*, rib or ridge 1056*b*, or both (or other retaining surface) that abuts the annular seal structure 1054 and helps retain the annular seal structure 1054 in a fixed location within the reservoir 1.

In the embodiment of FIGS. 84-86, the cap 1050 is connected to the housing of the reservoir 1 (e.g., at the head or neck portion of the reservoir 1, or other location adjacent the open end of the reservoir 1) by a hinged or pivotal connection structure 1058. In the illustrated embodiment, the pivotal connection structure 1058 includes a first hinge portion 1058*a* on the cap 1050, a second hinge portion 1058*b* on the reservoir 1, and a pivot pin 1058*c* defining a pivot axis PA along its length. The first hinge portion 1058*a* connects with the second hinge portion 1058*b*, through the pivot pin 1058*c*, for pivotal rotation relative to each other (e.g., by extending the pivot pin 1058*c* through aligned openings in the first and second hinge portions 1058*a* and 1058*b* and fixing the pivot pin 1058*c* within those openings to allow one or both of the hinge portions 1058*a* and 1058*b* to rotate about the pivot axis PA of the pivot pin 1058*c*).

In this manner, the cap 1050 is pivotal between an open position in which the rounded end portion 1050*a* is located outside of the reservoir 1, and a closed position in which the rounded end portion 1050*a* is located at least partially within the reservoir 1 and abutted against the seal structure 1054. When in the closed position, the cap 1050 provides a fluid-tight seal with the seal structure 1054 in the reservoir 1, to seal the cap 1050 to the reservoir 1. In particular embodiments, one or more latches, clips or other securing mechanisms are provided on the cap 1050, the reservoir 1, or both, to selectively secure the cap 1050 in the closed position, to inhibit accidental or unauthorized opening of the cap 1050 from the closed position on the reservoir 1. In other embodiments, the rounded end portion 1050*a* and the seal structure 1054 provide a friction fit sufficient to retain the cap 1050 in a closed position.

In particular embodiments, the ridge portion 1050*c* of the body of the cap 1050 is configured to be located outside of the reservoir 1 (and, in some embodiments, to abut an upper edge of the reservoir 1 around the open end of the reservoir 1) when the cap 1050 is in a closed position relative to the reservoir 1. In such embodiments, the ridge portion 1050*c* has an outer peripheral edge with a diameter that is greater than the outer diameter of the opening in the open end of the reservoir 1, so that the ridge portion 1050*c* overlaps the upper edge of the reservoir 1, when the cap 1050 is in a closed position. In further embodiments, one or more seals may be arranged on one or both of the ridge portion 1050*c* and the upper edge of the reservoir 1, to provide a fluid seal between the ridge portion 1050*c* and the upper edge of the reservoir 1, when the cap 1050 is in a closed position.

In the embodiment of FIGS. 84 and 85, the first hinge portion 1058*a* is fixed to the ridge portion 1050*c* of the body of the cap 1050, so as to be located at a maximum distance, radially, from a center line of the cap 1050 (extending through the passage 1052). The second hinge portion 1058*b* is fixed to the body of the reservoir 1, for example at or near the upper edge of the reservoir 1. Thus, when the first and second hinge portions 1058*a* and 1058*b* are pivotally connected together by the hinge pin 1058*c*, the cap 1050 is able to be selectively pivoted in one direction a sufficient distance to an open position at which the rounded end portion 1050*a* of the body of the cap 1050 is fully outside of the reservoir 1. In addition, from the open position, the cap 1050 is able to be selectively pivoted in a second direction (opposite to the one direction) to a closed position at which the rounded end portion 1050*a* of the body of the cap 1050 is abutted against (and sealed against) the seal structure 1054. In the closed position, the cap 1050 is sealed with the reservoir 1, but provides a needle-free fluid flow path through the passage 1052, for example, to an infusion set tubing (such as tubing 52).

Moreover, in the representative drawing figures of embodiments of the present invention throughout this specification, the cap 4 may be illustrated without a reservoir 1 for sake of simplicity; however, it is known to those skilled in the art that the cap 4 may be coupled with the reservoir 1 according to embodiments of the present invention.

7. Transfer Guard with Cap Lock

In various embodiments described herein, a reservoir 1 may be filled (partially or completely) with an infusion media prior to being coupled with a cap (or in a base/reservoir/cap unit). The infusion media may be any suitable fluid capable of being dispensed from an infusion pump device (such as, but not limited to infusion pump device 30) or other delivery device. In particular embodiments, the infusion media includes insulin or an insulin formulation for treatment of diabetes. In other embodiments, the infusion media includes other suitable substances or formulations for medicinal, therapeutic, or other purposes including, but not limited to a formulation for treatment of cancer, human immunodeficiency virus (HIV), acquired immunodeficiency syndrome (AIDS), or other disease or condition.

In particular embodiments, a transfer guard device is employed to connect a vial or other container of infusion media to the reservoir, to transfer fluidic media from the vial or other container to the reservoir. An example embodiment of a transfer guard device 1060 is described with reference to FIGS. 87 and 88.

The transfer guard device 1060 is configured to selectively connect a vial 1062 or other container of fluidic media to a reservoir 1, to transfer fluidic media from the vial 1062 to the reservoir 1 (to fill the reservoir 1 partially or completely with the fluidic media). The vial 1062 or other container may contain any suitable fluidic media, including, but not limited to the examples of infusion media described herein.

The transfer guard device 1060 is configured to be connected to a reservoir 1 and to a vial 1062 or other container for and during a filling operation. In particular embodiments, the transfer guard device 1060 is configured to inhibit disconnection (accidental or unauthorized disconnection) of the transfer guard device 1060 from the reservoir, prior to completion of a filling operation. As such, accidental or unauthorized spilling of fluidic media from the vial 1062 or other container onto the top of the reservoir 1 (or elsewhere) can be avoided or minimized. The transfer guard device 1060 is configured to disconnect from the reservoir 1 (or from the reservoir 1 and the vial 1062), after completion of a fill operation, to allow the reservoir 1 to be coupled with a cap (for example, in a base/reservoir/cap unit) as described herein.

Figures 87, 88:
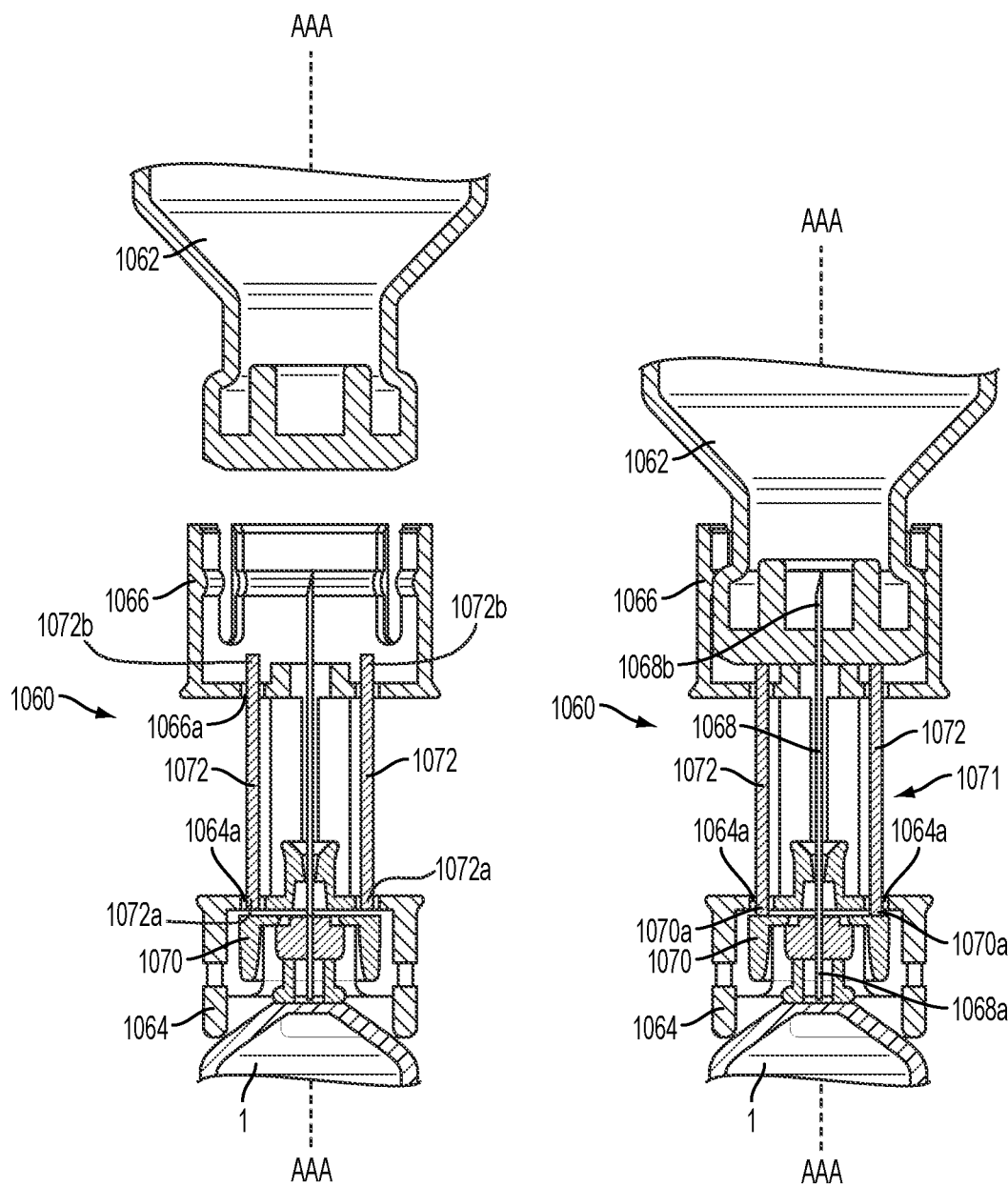
FIG. 87 is an enlarged, cross-section view of transfer guard connected with a cap, and an adjacent portion of a vial according to an embodiment of the present invention.
FIG. 88 is an enlarged, cross-section view of transfer guard connected with a cap with a vial of FIG. 87.

With reference to FIGS. 87 and 88, the transfer guard device 1060 includes a first end having a cup-shaped cap or enclosure 1064 configured to receive and at least partially enclose a port end of the reservoir 1. The transfer guard device 1060 includes a second end having a second cup-shaped cap or enclosure 1066 configured to receive and at least partially enclose a port end of the vial 1062 or other container of fluidic media.

The transfer guard 1060 also includes a fluid channel formed of one or more hollow needle or tube structures 1068 arranged to connect in fluid communication with the reservoir 1 and the vial 1062 or other container, when the port end of the reservoir 1 and the port end of the vial 1062 or other container are received in the first and second enclosures 1064 and 1066, respectively. In particular embodiments, the fluid channel includes a hollow needle structure having a first sharp end 1068*a* arranged to pierce a septum in the reservoir 1 and be in fluid flow communication with the interior of the reservoir 1, when the port end of the reservoir 1 is fully received within the first enclosure 1064.

The first enclosure 1064 fits over a base 1070 attached to the reservoir 1 (where the base 1070 may be similar to base 2 described herein, but with apertures as described below). In particular embodiments, the base 1070 is mounted to the port end of the reservoir 1 in a non-rotational manner (such that the base 1070 is not allowed to rotate relative to the reservoir 1). Also in particular embodiments, the first enclosure 1064 attaches to the port end of the reservoir 1, by a rotational motion (e.g., rotating in one direction, such as, but not limited to a clockwise direction) around the axis AAA. Similarly, the first enclosure 1064 detaches from the port end of the reservoir 1, by a rotational motion (e.g., rotating in a second direction, such as, but not limited to a counterclockwise direction) around the axis AAA. In such embodiments, the first enclosure 1064 and the port end of the reservoir 1 (or the base 1070 on the port end of the reservoir 1) is provided with a rotatable connection structure, such as, but not limited to screw threads, a slot and tab structure or other suitable structure that allows the first enclosure 1064 and the port end of the reservoir 1 to selectively connect and disconnect by relative rotary motion between those parts (i.e., rotary motion about the axis AAA).

The one or more hollow needle or tube structures 1068 of the fluid channel includes a second sharp end 1068*b* arranged to pierce a septum in the vial 1062 or other container, and be in fluid flow communication with the interior of the vial 1062 or other container when the port end of the vial 1062 or other container is fully received within the second enclosure 1066. In particular embodiments, the second enclosure 1066 fits over the port end of the vial 1062 or other container and is configured to connect to the port end of the vial 1062 or other container by snap or friction fit.

The transfer guard device 1060 includes a section 1071 connecting the first and second enclosures 1064 and 1066 together. The one or more hollow needle or tube structures 1068 of the fluid channel extends through the section 1071.

In addition, one or more (or a plurality) of movable members 1072 are arranged on or along the length of the section 1071. In particular embodiments, each moveable member 1072 includes a pin, post or plate of suitably rigid material that is supported by the first and second enclosures 1064 and 1066 for selective movement in the longitudinal direction of the axis AAA.

In the embodiment in FIGS. 87 and 88, each moveable member 1072 has a first end 1072a extending through an opening 1064a in the first enclosure 1064. In addition, each moveable member 1072 has a second end 1072b extending through an opening 1066a in the second enclosure 1066. The second end 1072b of each moveable member 1072 is arranged to be engaged and abutted by the port end of the vial 1062 or other container, when the port end of the vial 1062 or other container is received within the second enclosure 1066. In particular, as the port end of the vial 1062 or other container is being received within the second enclosure 1066, the port end of the vial 1062 or other container abuts and pushes against the second end 1072b of each movable member 1072 and causes each moveable member 1072 to move in the axial direction AAA from a first position to a second position (downward in the orientation of FIGS. 87 and 88).

More specifically, prior to the port end of the vial 1062 or other container being received within the second enclosure 1066 (as shown in FIG. 87), each moveable member 1072 is in a first position shown in FIG. 87. However, when the port end of the vial 1062 or other container is fully received within the second enclosure 1066 (as shown in FIG. 88), each moveable member 1072 is in a second position shown in FIG. 88. In the first position (FIG. 87) of the moveable member(s) 1072, the first end 1072a of each moveable member 1072 is separated from and outside of an opening 1070a in the base 1070. However, in the second position (FIG. 88) of the moveable member(s) 1072, the first end 1072a of each moveable member 1072 extends at least partially into a respective opening 1070a in the base 1070.

Accordingly, when each moveable member 1072 is in a first position shown in FIG. 87, the transfer guard 1060 is allowed to be rotated about the axis AAA relative to the reservoir 1 (and base 1070 attached to the reservoir 1). Thus, in the first position of the moveable member(s) 1072, the transfer guard 1060 can be rotated relative to the reservoir 1, to allow rotational connection (or disconnection) of the enclosure 1064 of the transfer guard 1060 from the port end of the reservoir 1. In that regard, prior to the port end of the vial 1062 or other container being received within the second enclosure 1066, or after removal of the port end of the vial 1062 or other container from the second enclosure 1066 (as shown in FIG. 87), the transfer guard 1060 is able to be selectively rotated relative to the reservoir 1, to allow selective connection or disconnection of the enclosure 1064 to or from the port end of the reservoir 1.

However, when the moveable members 1072 are in the second position shown in FIG. 88, moveable members 1072 extend at least partially into openings 1070a in the base 1070 and inhibit rotation of the transfer guard 1060 about the axis AAA relative to the base 1070 and reservoir 1. Thus, in the second position of the moveable member(s) 1072, the transfer guard 1060 is inhibited from being rotated relative to the reservoir 1, thus inhibiting disconnection of the enclosure 1064 of the transfer guard 1060 from the port end of the reservoir 1. In that regard, when the port end of the vial 1062 or other container is fully received within the second enclosure 1066 (as shown in FIG. 88), the transfer guard 1060 is inhibited from being rotated relative to the reservoir 1 and, thus, the enclosure 1064 is inhibited from being disconnected from the port end of the reservoir 1.

Therefore, accidental or unauthorized removal of the transfer guard 1060 from the reservoir 1 is inhibited, as long as the port end of the vial 1062 or other container is fully received within the enclosure 1066. The transfer guard 1060, thus, can provide additional safety and prevent undesired disconnection of the reservoir 1, while the vial 1062 or other container is connected in flow communication with the fluid channel 1068 in the transfer guard 1060.

The transfer guard device 1060 and components thereof may be made of any suitably rigid material having sufficient rigidity and strength to operate as described herein, including, but not limited to plastic, metal, ceramic, wood, composite material, or the like, or any combination thereof. While various embodiments described herein may employ a transfer guard 1060 to fill a reservoir prior to installation of the reservoir in an infusion pump device 30, other embodiments employ other suitable mechanisms and procedures for filling reservoirs, or employ pre-filled reservoirs.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. A connector interface system, comprising:
    a cap to connect to a reservoir to form a reservoir/cap unit for installation into an infusion pump device; and
    at least one magnetic detectable feature provided by a magnet on the cap for detection by at least one sensor element on the infusion pump device when the reservoir of the reservoir/cap unit is received in a reservoir receptacle of the infusion pump device,
    wherein the at least one magnetic detectable feature comprises a magnetic field angle of the magnet, wherein the magnet is attached to a housing of the cap, the magnetic field angle being an angle of orientation of a magnetic field of the magnet relative to three or more transverse axes of the at least one sensor element on the infusion pump device, when the reservoir of the reservoir/cap unit is received in the reservoir receptacle of the infusion pump device, wherein the magnet has a magnetic body having an axial dimension, and the magnetic field defines an axis that is at a non-parallel and non-perpendicular angle relative to the axial dimension of the magnetic body.

2. The connector interface system of claim 1, wherein the magnetic field angle of the at least one magnetic detectable feature is at least one detectable parameter that is associated with one or more predefined characteristics of one of the cap, the reservoir, a cannula, or a tubing connected between the cap and the cannula.

3. The connector interface system of claim 2, wherein the one or more predefined characteristics of the one of the cap, the reservoir, the cannula, or the tubing connected between the cap and the cannula comprises a type or an identity of a manufacturer of the one of the cap, the reservoir, the cannula or the tubing, or a size of the one of the cap, the reservoir, the cannula or the tubing.

4. The connector interface system of claim 1, wherein the magnetic field angle is at least one angle of orientation of the magnetic field of the magnet relative to one of a predefined surface or an axis of the cap or of the reservoir/cap unit.

5. The connector interface system of claim 1, wherein the at least one magnetic detectable feature is detected by the at least one sensor element when the reservoir or the cap of the reservoir/cap unit is in a fully installed position relative to the infusion pump device.

6. The connector interface system of claim 1, wherein the at least one magnetic detectable feature comprises a plurality of magnetic detectable features in locations that allow the magnetic detectable features to magnetically interact with the at least one sensor element to provide detectable signals for detection of axial or rotational motion or position of one of the cap or the reservoir relative to the reservoir receptacle, when the reservoir/cap unit is received in the reservoir receptacle.

7. The connector interface system of claim 1, wherein the at least one magnetic detectable feature comprises an additional magnetic field angle of at least one additional magnet included in the cap, wherein each magnetic field angle comprises an independently set angle β of the respective magnetic field relative to the three or more transverse axes in a sensor plane of the at least one sensor element on the infusion pump device.

8. The connector interface system of claim 7, wherein the magnetic field angles of the magnets are associated with one or more characteristics of one of the cap, the reservoir, a cannula, or a tubing connected between the cap and the cannula, wherein when the cap is received in the infusion pump device, the magnets create a magnetic field that uniquely identifies the one or more characteristics of the one of the cap, the reservoir, the cannula, or the tubing connected between the cap and the cannula.

9. The connector interface system of claim 8, wherein the magnets are arranged at a location on the cap to be detected by the at least one sensor element when the reservoir or the cap of the reservoir/cap unit is in a fully installed position relative to the infusion pump device.

10. The connector interface system of claim 7, wherein the magnetic field angles of the magnet and the at least one additional magnet are associated with one or more characteristics of one of the cap, the reservoir, a cannula, or a tubing connected between the cap and the cannula, wherein as the cap is rotated into the infusion pump device, the magnet and the at least one additional magnet create a magnetic field sequence that uniquely identifies the one or more characteristics of the one of the cap, the reservoir, the cannula, or the tubing.

11. The connector interface system as recited in claim 1, wherein the magnetic field angle comprises an angle β of the magnetic field relative to at least one of the three or more transverse axes, wherein the angle β is between 5° to 85°, 95° to 175°, 185° to 265°, or 275° to 355° relative to a side of the cap.

12. The connector interface system as recited in claim 1, wherein the magnetic field angle comprises an angle β of the magnetic field relative to at least one of the three or more transverse axes, wherein the angle β is between 2.5° to 87.5°, 92.5° to 177.5°, 182.5° to 267.5°, or 272.5° to 357.5° relative to a side of the cap.

13. The connector interface system as recited in claim 1, wherein the magnetic field angle comprises an angle β of the magnetic field relative to at least one of the three or more transverse axes, the angle β is between 10° to 80°, 100° to 170°, 180° to 260°, or 285° to 350° relative to a side of the cap.

14. A connector interface system, comprising:
  an infusion pump device having a reservoir receptacle and a sensor;
  a cap to connect to a reservoir to form a reservoir/cap unit for installation into the reservoir receptacle of the infusion pump device; and
  at least one magnetic detectable feature provided by a magnet on the cap for detection by the sensor of the infusion pump device when the reservoir of the reservoir/cap unit is received in the reservoir receptacle of the infusion pump device;
  wherein the at least one magnetic detectable feature comprises a magnetic field angle of the magnet, wherein the magnet is attached to a housing of the cap, the magnetic field angle being an angle of orientation of a magnetic field of the magnet relative to three or more transverse axes of the sensor of the infusion pump device, when the reservoir of the reservoir/cap unit is received in the reservoir receptacle of the infusion pump device;
  wherein the magnet has a magnetic body having an axial dimension, and the magnetic field defines an axis that is at a non-parallel and non-perpendicular angle relative to the axial dimension of the magnetic body.

15. The connector interface system of claim 14, wherein the magnetic field angle of the at least one magnetic detectable feature is at least one detectable parameter that is associated with one or more predefined characteristics of one of the cap, the reservoir, a cannula, or a tubing connected between the cap and the cannula.

16. The connector interface system of claim 15, wherein the one or more predefined characteristics of the one of the cap, the reservoir, the cannula, or the tubing connected between the cap and the cannula comprises a type or an identity of a manufacturer of the one of the cap, the reservoir, the cannula or the tubing, or a size of the one of the cap, the reservoir, the cannula or the tubing.

17. The connector interface system of claim 14:
  wherein the magnetic field angle of the magnet relative to the three or more transverse axes is in a sensor plane and is associated with one or more characteristics of one of the cap, the reservoir, a cannula, or a tubing connected between the cap and the cannula; and
  wherein when the cap is received in the infusion pump device, the magnetic field angle uniquely identifies the one of the one or more characteristics of the cap, the reservoir, the cannula, or the tubing connected between the cap and the cannula.

* * * * *